United States Patent
Endermann et al.

(10) Patent No.: US 7,446,102 B2
(45) Date of Patent: Nov. 4, 2008

(54) ANTIBACTERIAL AMIDE MACROCYCLES IV

(75) Inventors: Rainer Endermann, Wuppertal (DE); Kerstin Ehlert, Velbert (DE); Christoph Freiberg, Wuppertal (DE); Siegfried Raddatz, Cologne (DE); Martin Michels, West Haven, CT (US); Yolanda Cancho-Grande, Leverkusen (DE); Joachim Schuhmacher, Wuppertal (DE); Stefan Weigand, Penzberg (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 0 days.

(21) Appl. No.: 11/690,762

(22) Filed: Mar. 23, 2007

(65) Prior Publication Data

US 2008/0076745 A1    Mar. 27, 2008

Related U.S. Application Data

(63) Continuation of application No. PCT/EP2005/009912, filed on Sep. 15, 2005.

(30) Foreign Application Priority Data

Sep. 24, 2004  (DE) .................. 10 2004 046 307
Mar. 30, 2005  (DE) .................. 10 2005 014 240

(51) Int. Cl.
*C07K 5/08*      (2006.01)
*A61K 38/06*     (2006.01)
*A61P 31/04*     (2006.01)

(52) U.S. Cl. ....................... 514/183; 540/460
(58) Field of Classification Search ........... 540/460; 514/183

See application file for complete search history.

(56) References Cited

U.S. PATENT DOCUMENTS

2005/0256037 A1   11/2005  Lampe et al.

FOREIGN PATENT DOCUMENTS

WO   WO-03/106480      12/2003
WO   WO-2005/033129    4/2005

OTHER PUBLICATIONS

English Translation of the International Preliminary Report on Patentability for PCT/EP2005/009912, mailed May 3, 2007, 6 pages.
International Search Report for PCT/EP2005/009912, mailed on Oct. 31, 2005, 2 pages.

*Primary Examiner*—Bruck Kifle
(74) *Attorney, Agent, or Firm*—Morrison & Foerster LLP

(57) ABSTRACT

The invention relates to antibacterial amide macrocycles and processes for their preparation, their use for the treatment and/or prophylaxis of diseases and their use for the manufacture of medicaments for the treatment and/or prophylaxis of diseases, especially bacterial infections.

12 Claims, No Drawings

ANTIBACTERIAL AMIDE MACROCYCLES IV

CROSS REFERENCE TO RELATED APPLICATIONS

This application is a continuation of pending international application PCT/EP2005/009912, filed Sep. 15, 2005, designating US, which claims priority from German patent applications DE 10 2004 046 307.7, filed Sep. 24, 2004, and DE 10 2005 014 240.0, filed Mar. 30, 2005. The contents of the above-referenced applications are incorporated herein by this reference in their entirety.

BACKGROUND OF THE INVENTION

The invention relates to antibacterial amide macrocycles and methods for their preparation, their use for the treatment and/or prophylaxis of diseases, and their use for manufacturing medicaments for the treatment and/or prophylaxis of diseases, in particular of bacterial infections.

WO 03/106480 and WO 04/012816 describe macrocycles of the biphenomycin B type which have antibacterial activity and have amide and ester substituents respectively.

U.S. Pat. No. 3,452,136, thesis of R. U. Meyer, Stuttgart University, Germany (1991), thesis of V. Leitenberger, Stuttgart University, Germany (1991), Synthesis (1992) (10): 1025-1030, J. Chem. Soc., Perkin Trans. 1 (1992) (1):123-130, J. Chem. Soc., Chem. Commun. (1991) (10):744, Synthesis (1991) (5):409-413, J. Chem. Soc., Chem. Commun. (1991) (5):275-277, J. Antibiot. (1985) 38(11):1462-1468, J. Antibiot. (1985) 38(11):1453-1461 describe the natural product biphenomycin B as having antibacterial activity. Some steps in the synthesis of biphenomycin B are described in Synlett (2003), 4, 522-526.

Chirality (1995) 7(4):181-1892, J. Antibiot. (1991) 44(6):674-677, J. Am. Chem. Soc. (1989) 111(19):7323-7327, J. Am. Chem. Soc. (1989) 111(19):7328-7333, J. Org. Chem. (1987) 52(24):5435-5437, Anal. Biochem. (1987) 165(1):108-113, J. Org. Chem. (1985) 50(8):1341-1342, J. Antibiot. (1993) 46(3):C-2, J. Antibiot. (1993) 46(1):135-140, Synthesis (1992) (12):1248-1254, Appl. Environ. Microbiol. (1992) 58(12):3879-3888, J. Chem. Soc., Chem. Commun. (1992) (13):951-953 describe a structurally related natural product, biphenomycin A, which has a further substitution with a hydroxy group on the macrocycle.

The natural products in terms of their properties do not comply with the requirements for antibacterial medicaments. Although structurally different agents with antibacterial activity are available on the market, the development of resistance is a regular possibility. Novel agents for good and more effective therapy are therefore desirable.

SUMMARY OF THE INVENTION

One object of the present invention is therefore to provide novel and alternative compounds with the same or improved antibacterial effect for the treatment of bacterial diseases in humans and animals.

It has surprisingly been found that certain derivatives of these natural products in which the carboxyl group of the natural product is replaced by an amide group which comprises a basic group have antibacterial activity on biphenomycin-resistant $S.$ $aureus$ strains (RN4220Bi$^R$ and T17).

In addition, the derivatives show an improved spontaneous resistance rate for $S.$ $aureus$ wild-type strains and biphenomycin-resistant $S.$ $aureus$ strains.

The invention relates to compounds of formula

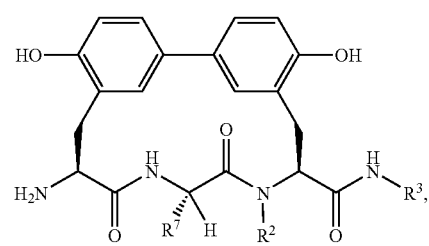

(I)

in which $R^7$ represents a group of formula

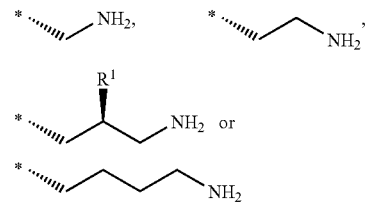

whereby $R^1$ represents hydrogen or hydroxy,

* is the linkage site to the carbon atom, $R^2$ represents hydrogen, methyl or ethyl, $R^3$ represents a group of formula

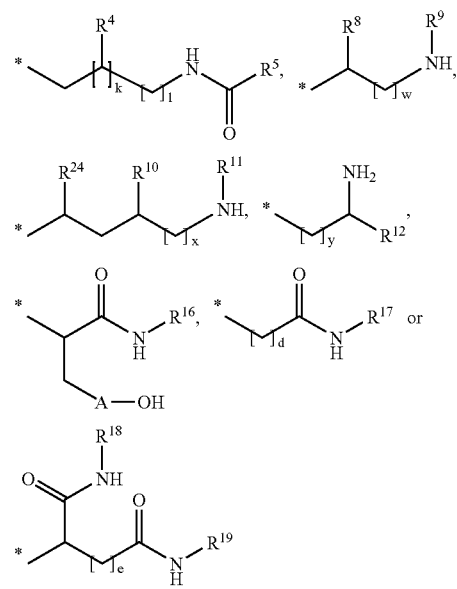

whereby

* is the linkage site to the nitrogen atom,

A represents a bond or phenyl, $R^4$ represents hydrogen, amino or hydroxy, $R^5$ represents a group of formula

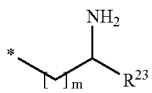

wherein
is the linkage site to the carbon atom,
$R^{23}$ represents hydrogen or a group of formula *—$(CH_2)_n$—OH or *—$(CH_2)_o$—$NH_2$,
wherein
* is the linkage site to the carbon atom,
n and o independently of one another are a number 1, 2, 3 or 4,
m is a number 0 or 1,
$R^8$ and $R^{12}$ independently of one another represent a group of formula *—$CONHR^{14}$ or *—$CH_2CONHR^{15}$,
wherein
is the linkage site to the carbon atom,
$R^{14}$ and $R^{15}$ independently of one another represent a group of formula

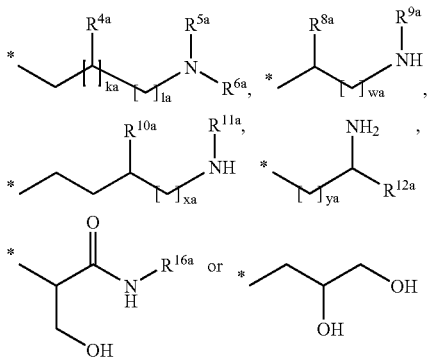

wherein
* is the linkage site to the nitrogen atom,
$R^{4a}$ represents hydrogen, amino or hydroxy,
$R^{5a}$ represents hydrogen, methyl or aminoethyl,
$R^{6a}$ represents hydrogen or aminoethyl, or
$R^{5a}$ and $R^{6a}$ together with the nitrogen atom to which they are bonded form a piperazine ring,
$R^{8a}$ and $R^{12a}$ independently of one another represent *—$(CH_2)_{Z1a}$—OH, *—$(CH_2)_{Z2a}$—$NHR^{13a}$, *—$CONHR^{14a}$ or *—$CH_2CONHR^{15a}$,
wherein
* is the linkage site to the carbon atom,
Z1a and Z2a independently of one another are a number 1, 2 or 3,
$R^{13a}$ represents hydrogen or methyl, and
$R^{14a}$ and $R^{15a}$ independently of one another represent a group of formula

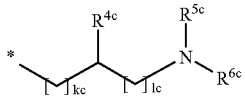

wherein
* is the linkage site to the nitrogen atom,
$R^{4c}$ represents hydrogen, amino or hydroxy,
$R^{5c}$ represents hydrogen, methyl or aminoethyl,
$R^{6c}$ represents hydrogen or aminoethyl,
kc is a number 0 or 1, and
lc is a number 1, 2, 3 or 4,
$R^{9a}$ and $R^{11a}$ independently of one another represent hydrogen or methyl,
$R^{10a}$ represents amino or hydroxy,
$R^{16a}$ represents a group of formula

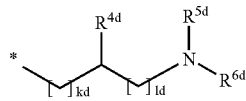

wherein
* is the linkage site to the nitrogen atom,
$R^{4d}$ represents hydrogen, amino or hydroxy,
$R^{5d}$ represents hydrogen, methyl or aminoethyl,
$R^{6d}$ represents hydrogen or aminoethyl,
kd is a number 0 or 1, and
ld is a number 1, 2, 3 or 4,
ka is a number 0 or 1, and
la, wa, xa and ya independently of one another are a number 1, 2, 3 or 4,
$R^9$ and $R^{11}$ independently of one another represent hydrogen, methyl, *—$C(NH_2)$=NH or a group of formula

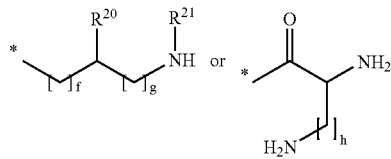

wherein
* is the linkage site to the nitrogen atom,
$R^{20}$ represents hydrogen or *—$(CH_2)_i$—$NHR^{22}$,
wherein
$R^{22}$ represents hydrogen or methyl, and
i is a number 1, 2 or 3,
$R^{21}$ represents hydrogen or methyl,
f is a number 0, 1, 2 or 3,
g is a number 1, 2 or 3, and
h is a number 1, 2, 3 or 4, or
$R^8$ represents *—$(CH_2)_{Z1}$—OH,
wherein
* is the linkage site to the carbon atom,
Z1 is a number 1, 2 or 3, and
$R^9$ represents a group of formula

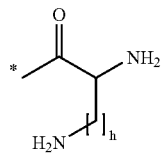

wherein
* is the linkage site to the nitrogen atom, and
h is a number 1, 2, 3 or 4,
$R^{10}$ represents amino or hydroxy,
$R^{16}$ and $R^{17}$ independently of one another represent a group of formula

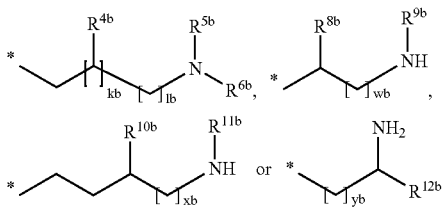

wherein
* is the linkage site to the nitrogen atom,
$R^{4b}$ represents hydrogen, amino or hydroxy,
$R^{5b}$ represents hydrogen, methyl or aminoethyl,
$R^{6b}$ represents hydrogen or aminoethyl, or
$R^{5b}$ and $R^{6b}$ together with the nitrogen atom to which they are bonded form a piperazine ring,
$R^{8b}$ and $R^{12b}$ independently of one another represent
*—$(CH_2)_{Z1b}$—OH, *—$(CH_2)_{Z2b}$—$NHR^{13b}$, *—$CONHR^{14b}$ or *—$CH_2CONHR^{15b}$,
wherein
* is the linkage site to the carbon atom,
$R^{3b}$ represents hydrogen or methyl, and
Z1b and Z2b independently of one another are a number 1, 2 or 3, and
$R^{14b}$ and $R^{15b}$ independently of one another represent a group of formula

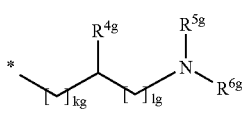

wherein
* is the linkage site to the nitrogen atom,
$R^{4g}$ represents hydrogen, amino or hydroxy,
$R^{5g}$ represents hydrogen, methyl or aminoethyl,
$R^{6g}$ represents hydrogen or aminoethyl,
kg is a number 0 or 1, and
lg is a number 1, 2, 3 or 4,
$R^{9b}$ and $R^{11b}$ independently of one another represent hydrogen or methyl,
$R^{10b}$ represents amino or hydroxy,
kb is a number 0 or 1,
lb, wb, xb and yb independently of one another are a number 1, 2, 3 or 4,
$R^{18}$ and $R^{19}$ independently of one another represent hydrogen or a group of formula

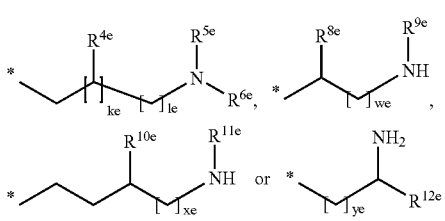

wherein
* is the linkage site to the nitrogen atom,
$R^{4e}$ represents hydrogen, amino or hydroxy,
$R^{5e}$ represents hydrogen, methyl or aminoethyl,
$R^{6e}$ represents hydrogen or aminoethyl, or
$R^{5e}$ and $R^{6e}$ together with the nitrogen atom to which they are bonded form a piperazine ring,
$R^{8e}$ and $R^{12e}$ independently of one another represent
*—$(CH_2)_{Z1e}$—OH or *—$(CH_2)_{Z2e}$—$NHR^{13e}$,
wherein
* is the linkage site to the carbon atom,
$R^{13e}$ represents hydrogen or methyl, and
Z1e and Z2e independently of one another are a number 1, 2 or 3,
$R^{9e}$ and $R^{11e}$ independently of one another represent hydrogen or methyl,
$R^{10e}$ represents amino or hydroxy,
ke is a number 0 or 1, and
le, we, xe and ye independently of one another are a number 1, 2, 3 or 4,
whereby $R^{18}$ and $R^{19}$ are not simultaneously hydrogen,
$R^{24}$ represents a group of formula *—$CONHR^{25}$,
wherein
* is the linkage site to the carbon atom,
$R^{25}$ represents a group of formula

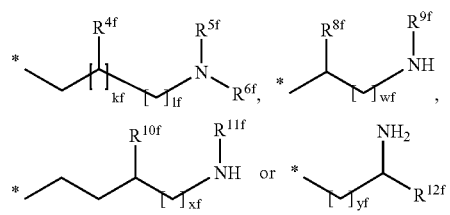

wherein
* is the point of linkage to the nitrogen atom,
$R^{4f}$ represents hydrogen, amino or hydroxy,
$R^{5f}$ represents hydrogen, methyl or aminoethyl,
$R^{6f}$ represents hydrogen or aminoethyl, or
$R^{5f}$ and $R^{6f}$ together with the nitrogen atom to which they are bonded form a piperazine ring,
$R^{8f}$ and $R^{12f}$ independently of one another represent
*—$(CH_2)_{Z1f}$—OH or *—$(CH_2)_{Z2f}$—$NHR^{13f}$,
wherein
* is the linkage site to the carbon atom,
$R^{3f}$ represents hydrogen or methyl, and
Z1f and Z2f independently of one another are a number 1, 2 or 3,
$R^{9f}$ and $R^{11f}$ independently of one another represent hydrogen or methyl,
$R^{10f}$ represents amino or hydroxy,
kf is a number 0 or 1, and
lf, wf, xf and yf independently of one another are a number 1, 2, 3 or 4,
d and e independently of one another are a number 1, 2 or 3,
k is a number 0 or 1,
l, w, x and y independently of one another are a number 1, 2, 3 or 4,

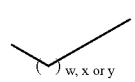

independently of one another may when w, x or y equals 3 carry a hydroxy group,
and their salts, their solvates and the solvates of their salts.

Compounds of the invention are the compounds of formula (I) and the salts, solvates and solvates of the salts thereof, and the compounds which are encompassed by formula (I) and are mentioned hereinafter as exemplary embodiment(s), and the salts, solvates and solvates of the salts, insofar as the compounds which are encompassed by formula (I) and are mentioned hereinafter are not already salts, solvates and solvates of the salts.

The compounds of the invention may, depending on their structure, exist in stereoisomeric forms (enantiomers, diastereomers). The invention therefore relates to the enantiomers or diastereomers and their respective mixtures. The stereoisomerically pure constituents can be isolated from such mixtures of enantiomers and/or diastereomers by known processes such as chromatography on a chiral phase or crystallization using chiral amines or chiral acids.

The invention also relates, depending on the structure of the compounds, to tautomers of the compounds.

Salts preferred for the purposes of the invention are physiologically acceptable salts of the compounds of the invention.

Physiologically acceptable salts of the compounds (I) include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid, trifluoroacetic acid and benzoic acid.

Physiologically acceptable salts of the compounds (I) also include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dihydroabietylamine, arginine, lysine, ethylenediamine and methylpiperidine.

Solvates for the purposes of the invention refer to those forms of the compounds which form a complex in the solid or liquid state through coordination with solvent molecules. Hydrates are a special form of solvates in which coordination takes place with water.

A symbol # on a carbon atom means that the compound is in enantiopure form in relation to the configuration at this carbon atom, meaning in the context of the present invention an enantiomeric excess of more than 90% (>90% ee).

In the formulae of the groups which $R^3$ can represent, the end point of the line beside which there is an * does not represent a carbon atom or a $CH_2$ group but is part of the bond to the nitrogen atom to which $R^3$ is bonded.

In the formulae of the groups which $R^7$ can represent, the end point of the line beside which there is an * does not represent a carbon atom or a $CH_2$ group but is part of the bond to the carbon atom to which $R^7$ is bonded.

Preference is given in the context of the present invention to compounds of formula (I) in which
$R^7$ represents a group of formula

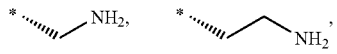

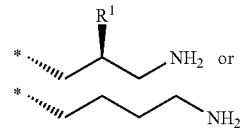

whereby
$R^1$ represents hydrogen or hydroxy,
* is the linkage site to the carbon atom,
$R^2$ represents hydrogen, methyl or ethyl,
$R^3$ represents a group of formula

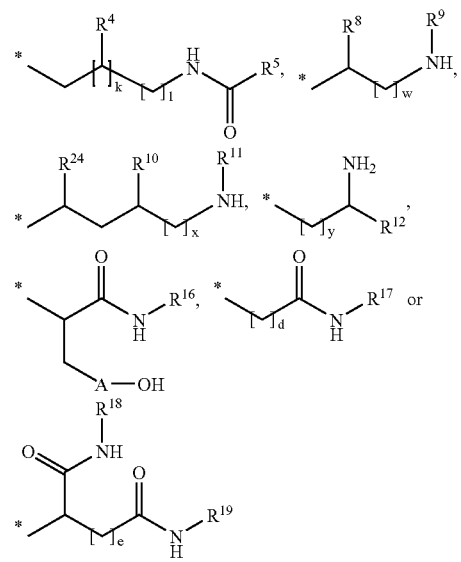

whereby
* is the linkage site to the nitrogen atom,
A represents a bond or phenyl,
$R^4$ represents hydrogen, amino or hydroxy,
$R^5$ represents a group of formula

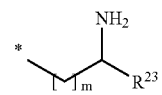

wherein
* is the linkage site to the carbon atom,
$R^{23}$ represents hydrogen or a group of formula *—$(CH_2)_n$—OH or *—$(CH_2)_o$—$NH_2$,
wherein
* is the linkage site to the carbon atom,
n and o independently of one another are a number 1, 2, 3 or 4,
m is a number 0 or 1,
$R^8$ and $R^{12}$ independently of one another represent a group of formula *—$CONHR^{14}$ or *—$CH_2CONHR^{15}$,
wherein
* is the linkage site to the carbon atom,
$R^{14}$ and $R^{15}$ independently of one another represent a group of formula

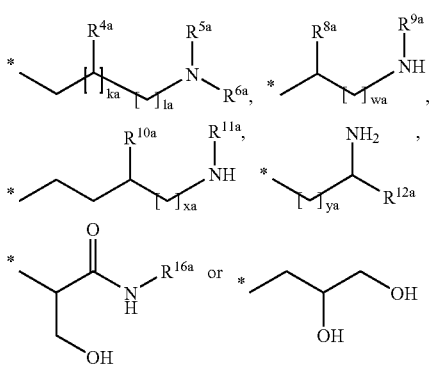

wherein
* is the linkage site to the nitrogen atom,
$R^{4a}$ represents hydrogen, amino or hydroxy,
$R^{5a}$ represents hydrogen, methyl or aminoethyl,
$R^{6a}$ represents hydrogen or aminoethyl, or
$R^{5a}$ and $R^{6a}$ together with the nitrogen atom to which they are bonded form a piperazine ring,
$R^{8a}$ and $R^{12a}$ independently of one another represent $*-(CH_2)_{Z1a}-OH$, $*-(CH_2)_{Z2a}-NHR^{13a}$, $*-CONHR^{14a}$ or $*-CH_2CONHR^{15a}$,
wherein
* is the point of the linkage to the carbon atom,
Z1a and Z2a independently of one another are a number 1, 2 or 3,
$R^{13a}$ represents hydrogen or methyl, and
$R^{14a}$ and $R^{15a}$ independently of one another are a group of formula

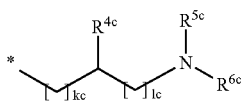

wherein
* is the linkage site to the nitrogen atom,
$R^{4c}$ represents hydrogen, amino or hydroxy,
$R^{5c}$ represents hydrogen, methyl or aminoethyl,
$R^{6c}$ represents hydrogen or aminoethyl,
kc is a number 0 or 1, and
lc is a number 1, 2, 3 or 4,
$R^{9a}$ and $R^{11a}$ independently of one another represent hydrogen or methyl,
$R^{10a}$ represents amino or hydroxy,
$R^{16a}$ represents a group of formula

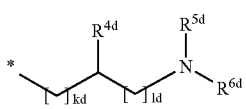

wherein
* is the linkage site to the nitrogen atom,
$R^{4d}$ represents hydrogen, amino or hydroxy,
$R^{5d}$ represents hydrogen, methyl or aminoethyl,
$R^{6d}$ represents hydrogen or aminoethyl,
kd is a number 0 or 1, and
ld is a number 1, 2, 3 or 4, ka is a number 0 or 1, and
la, wa, xa and ya independently of one another are a number 1, 2, 3 or 4,
$R^9$ and $R^{11}$ independently of one another represent hydrogen, methyl, $*-C(NH_2)=NH$ or a group of formula

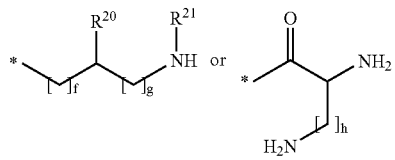

wherein
* is the linkage site to the nitrogen atom,
$R^{20}$ represents hydrogen or $*-(CH_2)_i-NHR^{22}$,
wherein
$R^{22}$ represents hydrogen or methyl, and
i is a number 1, 2 or 3,
$R^{21}$ represents hydrogen or methyl,
f is a number 0, 1, 2 or 3,
g is a number 1, 2 or 3, and
h is a number 1, 2, 3 or 4, or
$R^8$ represents $*-(CH_2)_{Z1}-OH$,
wherein
* is the linkage site to the carbon atom,
Z1 is a number 1, 2 or 3, and
$R^9$ represents a group of formula

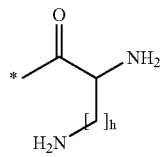

wherein
* is the linkage site to the nitrogen atom, and
h is a number 1, 2, 3 or 4,
$R^{10}$ represents amino or hydroxy,
$R^{16}$ and $R^{17}$ independently of one another represent a group of formula

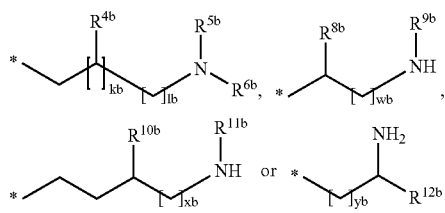

wherein
* is the linkage site to the nitrogen atom,
$R^{4b}$ represents hydrogen, amino or hydroxy,
$R^{5b}$ represents hydrogen, methyl or aminoethyl,
$R^{6b}$ represents hydrogen or aminoethyl, or
$R^{5b}$ and $R^{6b}$ together with the nitrogen atom to which they are bonded form a piperazine ring,
$R^{8b}$ and $R^{12b}$ independently of one another represent $*-(CH_2)_{Z1b}-OH$ or $*-(CH_2)_{Z2b}-NHR^{13b}$,
wherein
* is the linkage site to the carbon atom, $R^{13b}$ represents hydrogen or methyl, and Z1b and Z2b independently of one another are a number 1, 2 or 3, $R^{9b}$ and $R^{11b}$ independently of one another represent hydrogen or methyl, $R^{10b}$ represents amino or hydroxy, kb is a number 0 or 1, lb, wb, xb and yb independently of one another are a number 1, 2, 3 or 4, $R^{18}$ and $R^{19}$ independently of one another represent hydrogen or a group of formula

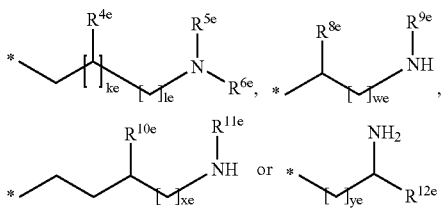

wherein

* is the linkage site to the nitrogen atom, $R^{4e}$ represents hydrogen, amino or hydroxy, $R^{5e}$ represents hydrogen, methyl or aminoethyl, $R^{6e}$ represents hydrogen or aminoethyl, or $R^{5e}$ and $R^{6e}$ together with the nitrogen atom to which they are bonded form a piperazine ring, $R^{8e}$ and $R^{12e}$ independently of one another represent *—$(CH_2)_{Z1e}$—OH or *—$(CH_2)_{Z2e}$—$NHR^{13e}$, wherein

* is the linkage site to the carbon atom, $R^{13e}$ represents hydrogen or methyl, and Z1e and Z2e independently of one another are a number 1, 2 or 3, $R^{9e}$ and $R^{11e}$ independently of one another represent hydrogen or methyl, $R^{10e}$ represents amino or hydroxy, ke is a number 0 or 1, and le, we, xe and ye independently of one another are a number 1, 2, 3 or 4, whereby $R^{18}$ and $R^{19}$ are not simultaneously hydrogen, $R^{24}$ represents a group of formula *—$CONHR^{25}$, wherein

* is the linkage site to the carbon atom, $R^{25}$ represents a group of formula

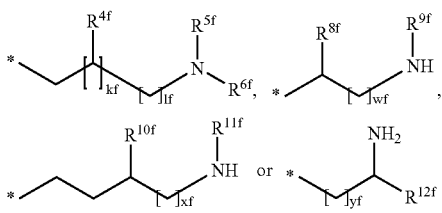

wherein

* is the linkage site to the nitrogen atom, $R^{4f}$ represents hydrogen, amino or hydroxy, $R^{5f}$ represents hydrogen, methyl or aminoethyl, $R^{6f}$ represents hydrogen or aminoethyl, or $R^{5f}$ and $R^{6f}$ together with the nitrogen atom to which they are bonded form a piperazine ring, $R^{8f}$ and $R^{12f}$ independently of one another represent *—$(CH_2)_{Z1f}$—OH or *—$(CH_2)_{Z2f}$—$NHR^{13f}$, wherein

* is the linkage site to the carbon atom, $R^{3f}$ represents hydrogen or methyl, and Z1f and Z2f independently of one another are a number 1, 2 or 3, $R^{9f}$ and $R^{11f}$ independently of one another represent hydrogen or methyl, $R^{10f}$ represents amino or hydroxy, kf is a number 0 or 1, and lf, wf, xf and yf independently of one another are a number 1, 2, 3 or 4, d and e independently of one another are a number 1, 2 or 3, k is a number 0 or 1, l, w, x and y independently of one another are a number 1, 2, 3 or 4,

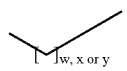

independently of one another may when w, x or y equals 3 carry a hydroxy group, and their salts, their solvates and the solvates of their salts.

Preference is also given in the context of the present invention to compounds of formula

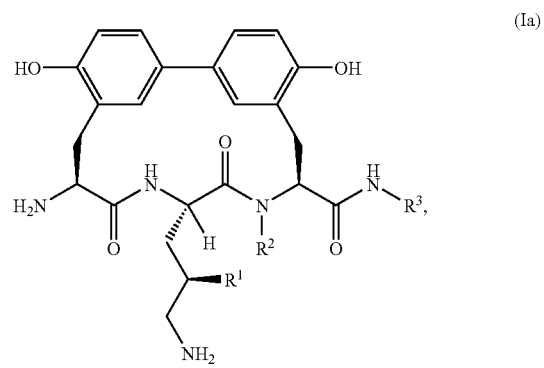

(Ia)

in which $R^1$ represents hydrogen or hydroxy, $R^2$ represents hydrogen, methyl or ethyl, $R^3$ is as defined above, and their salts, their solvates and the solvates of their salts.

Preference is also given in the context of the present invention to compounds of formula (I) or (Ia) in which $R^3$ represents a group of formula

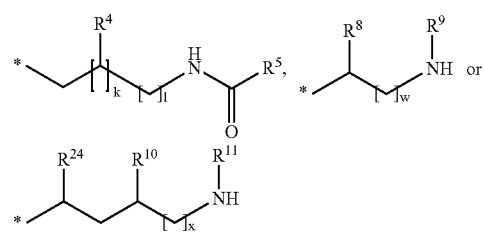

whereby

* is the linkage site to the nitrogen atom,
$R^4$ represents hydrogen, amino or hydroxy,
$R^5$ represents a group of formula

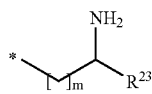

wherein
* is the linkage site to the carbon atom,
$R^{23}$ represents hydrogen or a group of formula *—$(CH_2)_n$—OH or *—$(CH_2)_o$—$NH_2$,
wherein
* is the linkage site to the carbon atom,
n and o independently of one another are a number 1, 2, 3 or 4,
m is a number 0 or 1,
$R^8$ represents a group of formula *—$CONHR^{14}$ or *—$CH_2CONHR^{15}$,
wherein
* is the linkage site to the carbon atom,
$R^{14}$ and $R^{15}$ independently of one another represent a group of formula

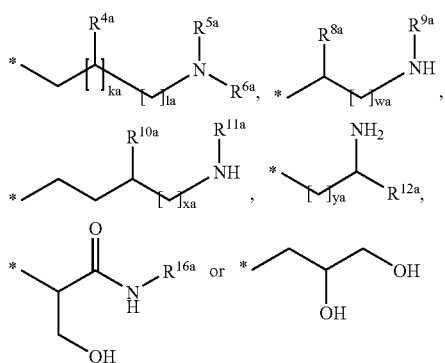

wherein
* is the linkage site to the nitrogen atom,
$R^{4a}$ represents hydrogen, amino or hydroxy,
$R^{5a}$ represents hydrogen, methyl or aminoethyl,
$R^{6a}$ represents hydrogen or aminoethyl, or
$R^{5a}$ and $R^{6a}$ together with the nitrogen atom to which they are bonded form a piperazine ring,
$R^{8a}$ and $R^{12a}$ independently of one another represent *—$(CH_2)_{Z1a}$—OH, *—$(CH_2)_{Z2a}$—$NHR^{13a}$, *—$CONHR^{14a}$ or *—$CH_2CONHR^{15a}$,
wherein
* is the linkage site to the carbon atom,
Z1a and Z2a independently of one another are a number 1, 2 or 3,
$R^{13a}$ represents hydrogen or methyl, and
$R^{14a}$ and $R^{15a}$ independently of one another represent a group of formula

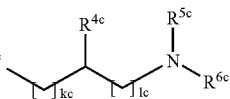

wherein
* is the linkage site to the nitrogen atom,
$R^{4c}$ represents hydrogen, amino or hydroxy,
$R^{5c}$ represents hydrogen, methyl or aminoethyl,
$R^{6c}$ represents hydrogen or aminoethyl,
kc is a number 0 or 1, and
lc is a number 1, 2, 3 or 4,
$R^{9a}$ and $R^{11a}$ independently of one another represent hydrogen or methyl,
$R^{10a}$ represents amino or hydroxy,
$R^{16a}$ represents a group of formula

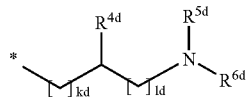

wherein
* is the linkage site to the nitrogen atom,
$R^{4d}$ represents hydrogen, amino or hydroxy,
$R^{5d}$ represents hydrogen, methyl or aminoethyl,
$R^{6d}$ represents hydrogen or aminoethyl,
kd is a number 0 or 1, and
ld is a number 1, 2, 3 or 4,
ka is a number 0 or 1, and
la, wa, xa and ya independently of one another are a number 1, 2, 3 or 4,
$R^9$ and $R^{11}$ independently of one another represent hydrogen, methyl, *—$C(NH_2)$=NH or a group of formula

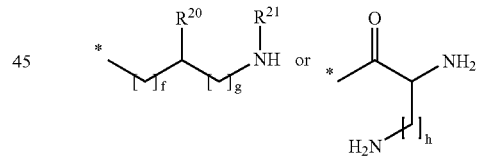

wherein
* is the linkage site to the nitrogen atom,
$R^{20}$ represents hydrogen or *—$(CH_2)_i$—$NHR^{22}$,
wherein
$R^{22}$ represents hydrogen or methyl, and
i is a number 1, 2 or 3,
$R^{21}$ represents hydrogen or methyl,
f is a number 0, 1, 2 or 3,
g is a number 1, 2 or 3, and
h is a number 1, 2, 3 or 4, or
$R^8$ represents *—$(CH_2)_{Z1}$—OH
wherein
* is the linkage site to the carbon atom,
Z1 is a number 1, 2 or 3, and
$R^9$ represents a group of formula

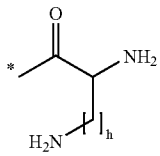

wherein
* is the linkage site to the nitrogen atom, and
h is a number 1, 2, 3 or 4,
$R^{10}$ represents amino or hydroxy,
$R^{24}$ represents a group of formula *—$CONHR^{25}$,
wherein
* is the linkage site to the carbon atom,
$R^{25}$ represents a group of formula

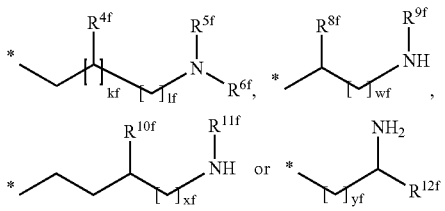

wherein
* is the linkage site to the nitrogen atom,
$R^{4f}$ represents hydrogen, amino or hydroxy,
$R^{5f}$ represents hydrogen, methyl or aminoethyl,
$R^{6f}$ represents hydrogen or aminoethyl, or
$R^{5f}$ and $R^{6f}$ together with the nitrogen atom to which they are bonded form a piperazine ring,
$R^{8f}$ and $R^{12f}$ independently of one another represent
*—$(CH_2)_{Z1f}$—OH or *—$(CH_2)_{Z2f}$—$NHR^{13f}$,
wherein
* is the linkage site to the carbon atom,
$R^{13f}$ represents hydrogen or methyl, and
Z1f and Z2f independently of one another are a number 1, 2 or 3,
$R^{9f}$ and $R^{11f}$ independently of one another represent hydrogen or methyl,
$R^{10f}$ represents amino or hydroxy,
kf is a number 0 or 1, and
lf, wf, xf and yf independently of one another are a number 1, 2, 3 or 4,
k is a number 0 or 1,
l, w, and x independently of one another are a number 1, 2, 3 or 4,

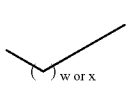

independently of one another may when w or x equals 3 carry a hydroxy group,
and their salts, their solvates and the solvates of their salts.
Particular preference is given in the context of the present invention to compounds of formula (I) or (Ia) in which
$R^3$ represents a group of formula

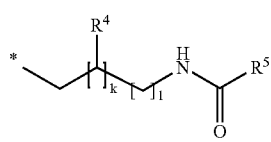

whereby
* is the linkage site to the nitrogen atom,
$R^4$ represents hydrogen, amino or hydroxy,
$R^5$ represents a group of formula

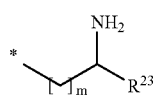

wherein
* is the linkage site to the carbon atom,
$R^{23}$ represents hydrogen or a group of formula *—$(CH_2)_n$—OH or *—$(CH_2)_o$—$NH_2$,
wherein
* is the linkage site to the carbon atom,
n and o independently of one another are a number 1, 2, 3 or 4,
m is a number 0 or 1,
k is a number 0 or 1,
l is a number 1, 2, 3 or 4,
and their salts, their solvates and the solvates of their salts.
Particular preference is also given in the context of the present invention to compounds of formula (I) or (Ia) in which
$R^3$ represents a group of formula

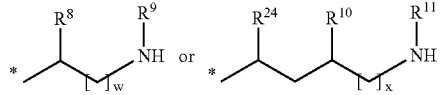

whereby
* is the linkage site to the nitrogen atom,
$R^8$ represents a group of formula *—$CONHR^{14}$ or *—$CH_2CONHR^{15}$,
wherein
* is the linkage site to the carbon atom,
$R^{14}$ and $R^{15}$ independently of one another represent a group of formula

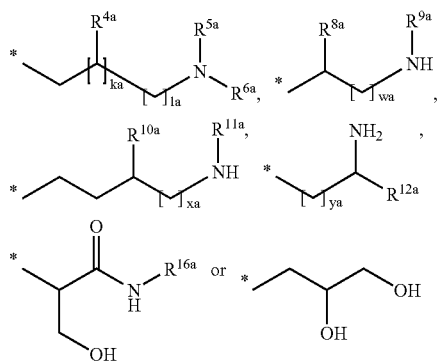

wherein
* is the linkage site to the nitrogen atom,
$R^{4a}$ represents hydrogen, amino or hydroxy,
$R^{5a}$ represents hydrogen, methyl or aminoethyl,
$R^{6a}$ represents hydrogen or aminoethyl, or
$R^{5a}$ and $R^{6a}$ together with the nitrogen atom to which they are bonded form a piperazine ring,
$R^{8a}$ and $R^{12a}$ independently of one another represent *—$(CH_2)_{Z1a}$—OH, *—$(CH_2)_{Z2a}$—$NHR^{13a}$, *—$CONHR^{14a}$ or *—$CH_2CONHR^{15a}$,
wherein
* is the linkage site to the carbon atom,
Z1a and Z2a independently of one another are a number 1, 2 or 3,
$R^{13a}$ represents hydrogen or methyl, and
$R^{14a}$ and $R^{15a}$ independently of one another represent a group of formula

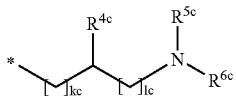

wherein
* is the linkage site to the nitrogen atom,
$R^{4c}$ represents hydrogen, amino or hydroxy,
$R^{5c}$ represents hydrogen, methyl or aminoethyl,
$R^{6c}$ represents hydrogen or aminoethyl,
kc is a number 0 or 1, and
lc is a number 1, 2, 3 or 4,
$R^{9a}$ and $R^{11a}$ independently of one another represent hydrogen or methyl,
$R^{10a}$ represents amino or hydroxy,
$R^{16a}$ represents a group of formula

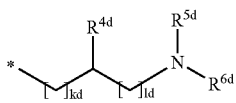

wherein
* is the linkage site to the nitrogen atom,
$R^{4d}$ represents hydrogen, amino or hydroxy,
$R^{5d}$ represents hydrogen, methyl or aminoethyl,
$R^{6d}$ represents hydrogen or aminoethyl,
kd is a number 0 or 1, and
ld is a number 1, 2, 3 or 4,
ka is a number 0 or 1, and
la, wa, xa and ya independently of one another are a number 1, 2, 3 or 4,
$R^9$ and $R^{11}$ independently of one another represent hydrogen, methyl, *—$C(NH_2)$=NH or a group of formula

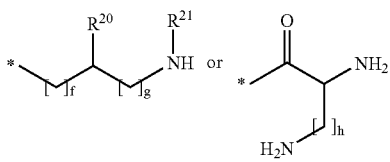

wherein
* is the linkage site to the nitrogen atom,
$R^{20}$ represents hydrogen or *—$(CH_2)_i$—$NHR^{22}$, wherein
$R^{22}$ represents hydrogen or methyl, and
i is a number 1, 2 or 3,
$R^{21}$ represents hydrogen or methyl,
f is a number 0, 1, 2 or 3,
g is a number 1, 2 or 3, and
h is a number 1, 2, 3 or 4, or
$R^8$ represents *—$(CH_2)_{Z1}$—OH,
wherein
* is the linkage site to the carbon atom,
Z1 is a number 1, 2 or 3, and
$R^9$ represents a group of formula

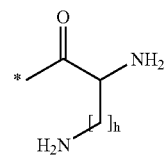

wherein
* is the linkage site to the nitrogen atom, and
h is a number 1, 2, 3 or 4,
$R^{10}$ represents amino or hydroxy,
$R^{24}$ represents a group of formula *—$CONHR^{25}$,
wherein
* is the linkage site to the carbon atom,
$R^{25}$ represents a group of formula

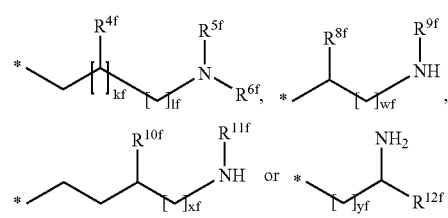

wherein
* is the linkage site to the nitrogen atom,
$R^{4f}$ represents hydrogen, amino or hydroxy,
$R^{5f}$ represents hydrogen, methyl or aminoethyl,
$R^{6f}$ represents hydrogen or aminoethyl, or
$R^{5f}$ and $R^{6f}$ together with the nitrogen atom to which they are bonded form a piperazine ring,
$R^{8f}$ and $R^{12f}$ independently of one another represent *—$(CH_2)_{Z1f}$—OH or *—$(CH_2)_{Z2f}$—$NHR^{13f}$,
wherein
* is the linkage site to the carbon atom,
$R^{13f}$ represents hydrogen or methyl, and
Z1f and Z2f independently of one another are a number 1, 2 or 3,
$R^{9f}$ and $R^{11f}$ independently of one another represent hydrogen or methyl,
$R^{10f}$ represents amino or hydroxy,
kf is a number 0 or 1, and
lf, wf, xf and yf independently of one another are a number 1, 2, 3 or 4,
w and x independently of one another are a number 1, 2, 3 or 4,

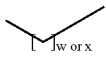

independently of one another may when w or x equals 3 carry a hydroxy group, and their salts, their solvates and the solvates of their salts.

Preference is also given in the context of the present invention to compounds of formula (I) or (Ia) in which $R^3$ represents a group of formula

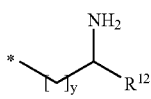

whereby

* is the linkage site to the nitrogen atom, $R^{12}$ represents a group of formula *—CONHR$^{14}$ or *—CH$_2$CONHR$^{15}$, wherein

* is the linkage site to the carbon atom, $R^{14}$ and $R^{15}$ independently of one another represent a group of formula

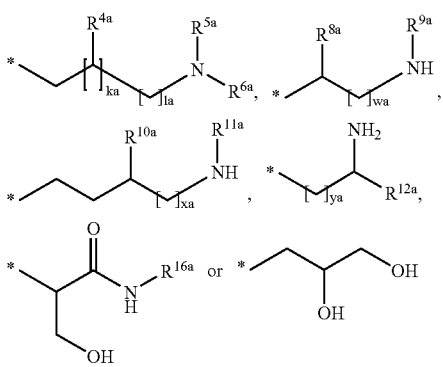

wherein

* is the linkage site to the nitrogen atom, $R^{4a}$ represents hydrogen, amino or hydroxy, $R^{5a}$ represents hydrogen, methyl or aminoethyl, $R^{6a}$ represents hydrogen or aminoethyl, or $R^{5a}$ and $R^{6a}$ together with the nitrogen atom to which they are bonded form a piperazine ring, $R^{8a}$ and $R^{12a}$ independently of one another represent *—(CH$_2$)$_{Z1a}$—OH, *—(CH$_2$)$_{Z2a}$—NHR$^{13a}$, *—CONHR$^{14a}$ or *—CH$_2$CONHR$^{15a}$, wherein

* is the linkage site to the carbon atom,

Z1a and Z2a independently of one another are a number 1, 2 or 3, $R^{13a}$ represents hydrogen or methyl, and $R^{14a}$ and $R^{15a}$ independently of one another represent a group of formula

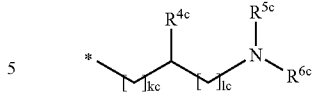

wherein

* is the linkage site to the nitrogen atom, $R^{4c}$ represents hydrogen, amino or hydroxy, $R^{5c}$ represents hydrogen, methyl or aminoethyl, $R^{6c}$ represents hydrogen or aminoethyl, kc is a number 0 or 1, and lc is a number 1, 2, 3 or 4, $R^{9a}$ and $R^{11a}$ independently of one another represent hydrogen or methyl, $R^{10a}$ represents amino or hydroxy, $R^{16a}$ represents a group of formula

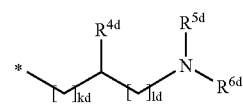

wherein

* is the linkage site to the nitrogen atom, $R^{4d}$ represents hydrogen, amino or hydroxy, $R^{5d}$ represents hydrogen, methyl or aminoethyl, $R^{6d}$ represents hydrogen or aminoethyl, kd is a number 0 or 1, and ld is a number 1, 2, 3 or 4, ka is a number 0 or 1, and la, wa, xa and ya independently of one another are a number 1, 2, 3 or 4, y is a number 1, 2, 3 or 4,

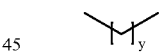

may when y equals 3 carry a hydroxy group, and their salts, their solvates and the solvates of their salts.

Preference is also given in the context of the present invention to compounds of formula (I) or (Ia) in which $R^3$ represents a group of formula

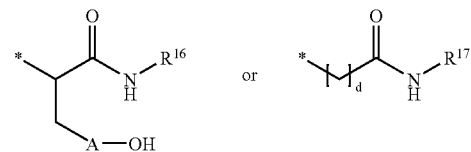

whereby

* is the linkage site to the nitrogen atom,

A represents a bond or phenyl, $R^{16}$ and $R^{17}$ independently of one another represent a group of formula

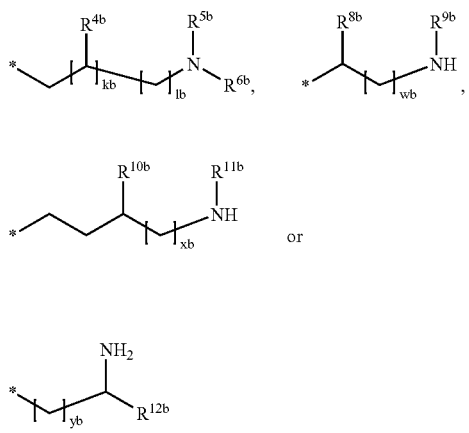

wherein
* is the linkage site to the nitrogen atom,
$R^{4b}$ represents hydrogen, amino or hydroxy,
$R^{5b}$ represents hydrogen, methyl or aminoethyl,
$R^{6b}$ represents hydrogen or aminoethyl, or
$R^{5b}$ and $R^{6b}$ together with the nitrogen atom to which they are bonded form a piperazine ring,
$R^{8b}$ and $R^{12b}$ independently of one another represent *—$(CH_2)_{Z1b}$—OH or *—$(CH_2)_{Z2b}$—$NHR^{13b}$,
wherein
* is the linkage site to the carbon atom,
$R^{13b}$ represents hydrogen or methyl, and
Z1b and Z2b independently of one another are a number 1, 2 or 3,
$R^{9b}$ and $R^{11b}$ independently of one another represent hydrogen or methyl,
$R^{10b}$ represents amino or hydroxy,
kb is a number 0 or 1,
lb, wb, xb and yb independently of one another are a number 1, 2, 3 or 4,
d is a number 1, 2 or 3,
and their salts, their solvates and the solvates of their salts.

Among these, particularly preferred compounds are those in which $R^3$ represents a group of formula

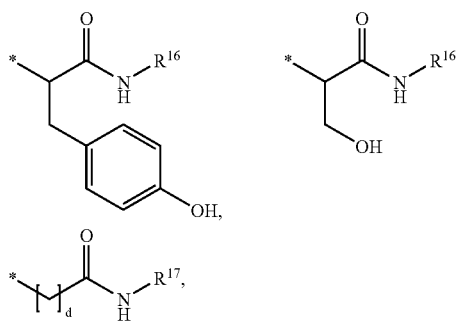

in particular a group of formula

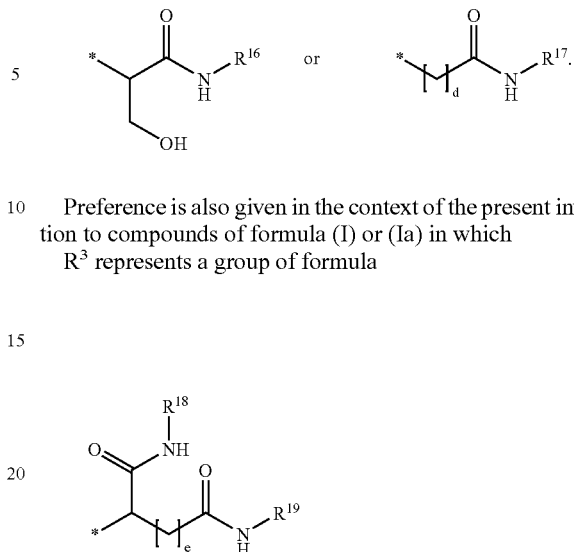

Preference is also given in the context of the present invention to compounds of formula (I) or (Ia) in which
$R^3$ represents a group of formula

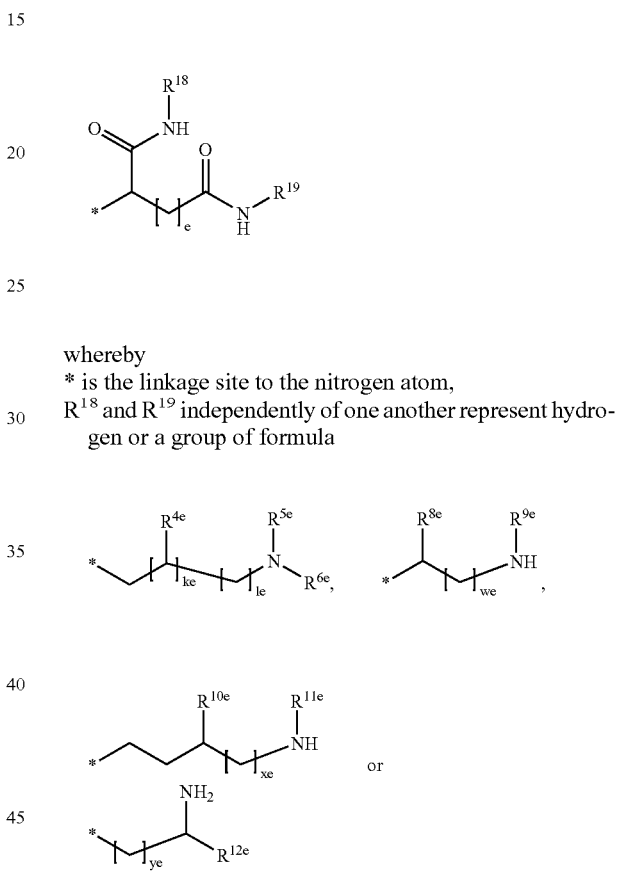

whereby
* is the linkage site to the nitrogen atom,
$R^{18}$ and $R^{19}$ independently of one another represent hydrogen or a group of formula wherein
* is the linkage site to the nitrogen atom,
$R^{4e}$ represents hydrogen, amino or hydroxy,
$R^{5e}$ represents hydrogen, methyl or aminoethyl,
$R^{6e}$ represents hydrogen or aminoethyl, or
$R^{5e}$ and $R^{6e}$ together with the nitrogen atom to which they are bonded form a piperazine ring,
$R^{8e}$ and $R^{12e}$ independently of one another represent *—$(CH_2)_{Z1e}$—OH or *—$(CH_2)_{Z2e}$—$NHR^{13e}$,
wherein
* is the linkage site to the carbon atom,
$R^{13e}$ represents hydrogen or methyl, and
Z1e and Z2e independently of one another are a number 1, 2 or 3,
$R^{9e}$ and $R^{11e}$ independently of one another represent hydrogen or methyl,
$R^{10e}$ represents amino or hydroxy,
ke is a number 0 or 1, and le, we, xe and ye independently of one another are a number 1, 2, 3 or 4,
whereby $R^{18}$ and $R^{19}$ are not simultaneously hydrogen,
e is a number 1, 2 or 3,
and their salts, their solvates and the solvates of their salts.

The invention further relates to a process for preparing the compounds of formula (I) or their salts, their solvates or the solvates of their salts, whereby according to process

[A] compounds of formula

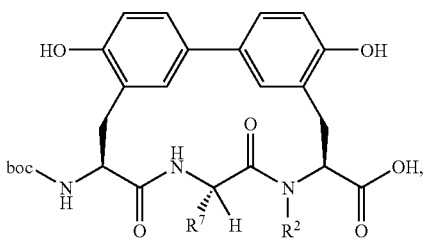

(II)

wherein $R^2$ and $R^7$ have the meaning mentioned above, and boc is tert-butoxycarbonyl,
are reacted in a two-stage process firstly in the presence of one or more dehydrating reagents with compounds of formula

H$_2$NR$^3$ (III), wherein $R^3$ has the meaning mentioned above,
and subsequently with an acid and/or by hydrogenolysis, or

[B] compounds of formula

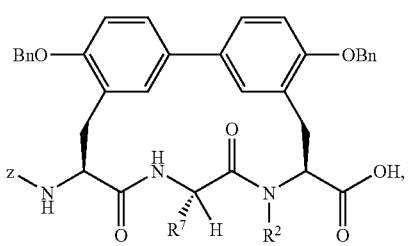

(IV)

wherein $R^2$ and $R^7$ have the meaning mentioned above, and Z is benzyloxycarbonyl,
are reacted in a two-stage process firstly in the presence of one or more dehydrating reagents with compounds of formula

H$_2$NR$^3$ (III), wherein $R^3$ has the meaning mentioned above,
and subsequently with an acid or by hydrogenolysis.

The free base of the salts can for example be obtained by chromatography on a reversed phase column using an acetonitrile-water gradient with the addition of a base, in particular by using an RP18 Phenomenex Luna C18(2) column and diethylamine as base.

The invention further relates to a process for preparing the compounds of formula (I) or their solvates as claimed in claim 1 in which salts of the compounds or solvates of the salts of the compounds are converted by chromatography with addition of a base into the compounds.

The hydroxy group on $R^1$ is protected where appropriate during the reaction with compounds of formula (III) with a tert-butyldimethylsilyl group which is removed in the second reaction step.

Reactive functionalities in the radical $R^3$ of compounds of formula (III) are introduced into the synthesis already protected, with preference for acid-labile protective groups (e.g. boc). After the reaction has taken place to give compounds of formula (I), the protective groups can be removed by a deprotection reaction. This takes place by standard methods of protective group chemistry. Deprotection reactions under acidic conditions or by hydrogenolysis are preferred.

The reaction in the first stage of processes [A] and [B] generally takes place in inert solvents, where appropriate in the presence of a base, preferably in a temperature range from 0° C. to 40° C. under atmospheric pressure.

Examples of suitable dehydrating reagents in this connection include carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or mixtures thereof, or mixtures thereof together with bases.

Examples of bases include alkali metal carbonates such as, for example, sodium or potassium carbonate, or sodium or potassium bicarbonate, or organic bases such as trialkylamines, e.g. triethylamine, N-methylmorpholine, N-methylpiperidine, 4-dimethylaminopyridine or diisopropylethylamine.

The condensation with HATU is preferably carried out in the presence of a base, in particular diisopropylethylamine, or with EDC and HOBt in the presence of a base, in particular triethylamine.

Examples of inert solvents include halohydrocarbons such as dichloromethane or trichloromethane, hydrocarbon such as benzene, or nitromethane, dioxane, dimethylformamide or acetonitrile. It is likewise possible to employ mixtures of the solvents. Dimethylformamide is particularly preferred.

The reaction with an acid in the second stage of processes [A] and [B] preferably takes place in a temperature range from 0° C. to 40° C. under atmospheric pressure.

Suitable acids in this connection include hydrogen chloride in dioxane, hydrogen bromide in acetic acid or trifluoroacetic acid in methylene chloride.

The hydrogenolysis in the second stage of process [B] generally takes place in a solvent in the presence of hydrogen and palladium on activated carbon, preferably in a temperature range from 0° C. to 40° C. under atmospheric pressure.

Examples of solvents include alcohols such as methanol, ethanol, n-propanol or isopropanol, in a mixture with water and glacial acetic acid, with preference for a mixture of ethanol, water and glacial acetic acid.

The compounds of formula (III) are known or can be prepared in analogy to known processes.

The compounds of formula (II) are known or can be prepared by reacting compounds of formula

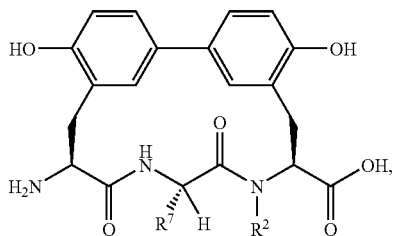

(V)

wherein $R^2$ and $R^7$ have the meaning mentioned above,
with di(tert-butyl)dicarbonate in the presence of a base.

The reaction generally takes place in a solvent, preferably in a temperature range from 0° C. to 40° C. under atmospheric pressure.

Examples of bases include alkali metal hydroxides such as sodium or potassium hydroxide, or alkali metal carbonates such as cesium carbonate, sodium or potassium carbonate, or other bases such as DBU, triethylamine or diisopropylethylamine, with preference for sodium hydroxide or sodium carbonate.

Examples of solvents include halohydrocarbons such as methylene chloride or 1,2-dichloroethane, alcohols such as methanol, ethanol or isopropanol, or water.

The reaction is preferably carried out with sodium hydroxide in water or sodium carbonate in methanol.

The compounds of formula (V) are known or can be prepared by reacting compounds of formula

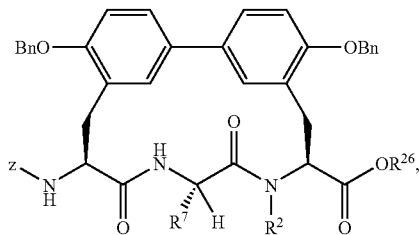

(VI)

wherein $R^2$ and $R^7$ have the meaning mentioned above, and $R^{26}$ represents benzyl, methyl or ethyl,
with an acid or by hydrogenolysis as described for the second stage of process [B], where appropriate by subsequent reaction with a base to hydrolyse the methyl or ethyl ester.

The hydrolysis can take place for example as described for the reaction of compounds of formula (VI) to give compounds of formula (IV).

The compounds of formula (IV) are known or can be prepared by hydrolysing the benzyl, methyl or ethyl ester in compounds of formula (VI).

The reaction generally takes place in a solvent in the presence of a base, preferably in a temperature range from 0° C. to 40° C. under atmospheric pressure.

Examples of bases include alkali metal hydroxide such as lithium, sodium or potassium hydroxide, with preference for lithium hydroxide.

Examples of solvents include halohydrocarbons such as dichloromethane or trichloromethane, ethers, such as tetrahydrofuran or dioxane, or alcohols such as methanol, ethanol or isopropanol, or dimethylformamide. It is likewise possible to employ mixtures of the solvents or mixtures of the solvents with water. Tetrahydrofuran or a mixture of methanol and water are particularly preferred.

The compounds of formula (VI) are known or can be prepared by reacting compounds of formula

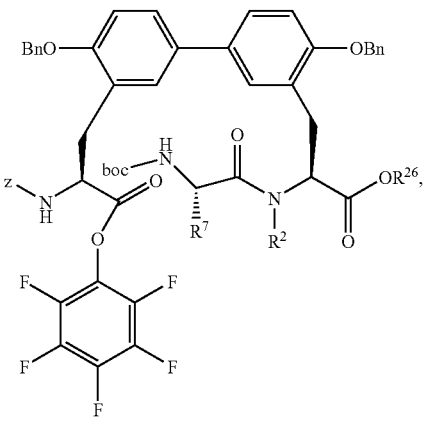

(VII)

wherein $R^2$, $R^7$ and $R^{26}$ have the meaning mentioned above,
in the first stage with acids as described for the second stage of processes [A] and [B], and in the second stage with bases.

The reaction with bases in the second stage generally takes place in a solvent, preferably in a temperature range from 0° C. to 40° C. under atmospheric pressure.

Examples of bases include alkali metal hydroxides such as sodium or potassium hydroxide, or alkali metal carbonates such as cesium carbonate, sodium or potassium carbonate, or other bases such as DBU, triethylamine or diisopropylethylamine, with preference for triethylamine.

Examples of solvents include halohydrocarbons such as chloroform, methylene chloride or 1,2-dichloroethane, or tetrahydrofuran, or mixtures of the solvents, with preference for methylene chloride or tetrahydrofuran.

The compounds of formula (VII) are known or can be prepared by reacting compounds of formula

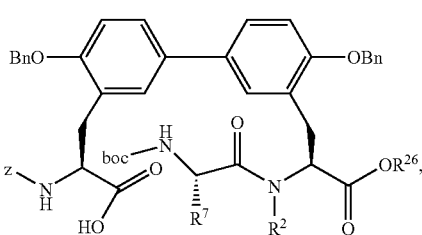

(VIII)

wherein $R^2$, $R^7$ and $R^{26}$ have the meaning mentioned above,
with pentafluorophenol in the presence of dehydrating reagents as described for the first stage of processes [A] and [B].

The reaction preferably takes place with DMAP and EDC in dichloromethane in a temperature range from −40° C. to 40° C. under atmospheric pressure.

The compounds of formula (VIII) are known or can be prepared by reacting compounds of formula

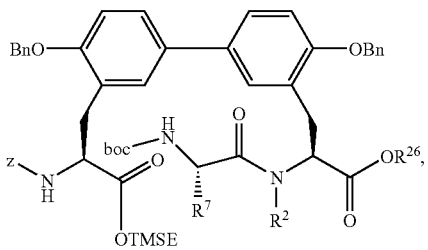

(IX)

wherein $R^2$, $R^7$ and $R^{26}$ have the meaning mentioned above, with fluoride, in particular with tetrabutylammonium fluoride.

The reaction generally takes place in a solvent, preferably in a temperature range from −10° C. to 30° C. under atmospheric pressure.

Examples of inert solvents include halohydrocarbons such as dichloromethane, or hydrocarbons such as benzene or toluene, or ethers such as tetrahydrofuran or dioxane, or dimethylformamide. It is likewise possible to employ mixtures of the solvents. Tetrahydrofuran and dimethylformamide are preferred solvents.

The compounds of formula (IX) are known or can be prepared by reacting compounds of formula

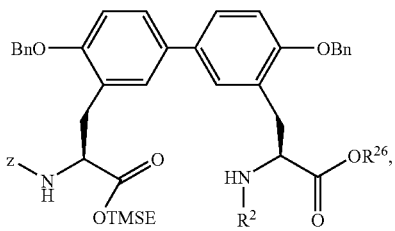

(X)

wherein $R^2$ and $R^{26}$ have the meaning mentioned above, with compounds of formula

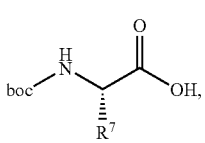

(XI)

wherein $R^7$ has the meaning mentioned above, in the presence of dehydrating reagents as described for the first stage of processes [A] and [B].

The compounds of formula (X) are known or can be prepared in analogy to the processes described in the examples section.

The compounds of formula (XI) are known or can be prepared in analogy to known processes.

The compounds of the invention show a valuable range of pharmacological and pharmacokinetic effects which could not have been predicted.

They are therefore suitable for use as medicaments for the treatment and/or prophylaxis of diseases in humans and animals.

The compounds of the invention can, due to their pharmacological properties, be employed alone or in combination with other active ingredients for the treatment and/or prophylaxis of infectious diseases, especially of bacterial infections.

For example, it is possible to treat and/or prevent local and/or systemic diseases caused by the following pathogens or by mixtures of the following pathogens: gram-positive cocci, e.g. staphylococci (*Staph. aureus, Staph. epidermidis*) and streptococci (*Strept. agalactiae, Strept. faecalis, Strept. pneumoniae, Strept. pyogenes*); gram-negative cocci (*neisseria gonorrhoeae*) and gram-negative rods such as enterobacteriaceae, e.g. *Escherichia coli, Haemophilus influenzae, Citrobacter* (*Citrob. freundii, Citrob. divernis*), *Salmonella* and *Shigella*; also klebsiellas (*Klebs. pneumoniae, Klebs. oxytocy*), *Enterobacter* (*Ent. aerogenes, Ent. agglomerans*), *Hafnia, Serratia* (*Serr. marcescens*), *Proteus* (*Pr. mirabilis, Pr. rettgeri, Pr. vulgaris*), *Providencia, Yersinia*, and the genus *Acinetobacter*. The antibacterial range additionally includes the genus *Pseudomonas* (*Ps. aeruginosa, Ps. maltophilia*) and strictly anaerobic bacteria such as *Bacteroides fragilis*, representatives of the genus *Peptococcus, Peptostreptococcus*, and the genus *Clostridium*; also mycoplasmas (*M. pneumoniae, M. hominis, M. urealyticum*) and mycobacteria, e.g. *Mycobacterium tuberculosis*.

The above list of pathogens is merely by way of example and is by no means to be interpreted as limiting. Examples which may be mentioned of diseases which are caused by the pathogens mentioned or mixed infections and can be prevented, improved or healed by preparations of the invention, which can be used topically, are:

infectious diseases in humans such as, for example, septic infections, bone and joint infections, skin infections, postoperative wound infections, abscesses, phlegmon, wound infections, infected burns, burn wounds, infections in the oral region, infections after dental operations, septic arthritis, mastitis, tonsillitis, genital infections and eye infections.

Apart from humans, bacterial infections can also be treated in other species. Examples which may be mentioned are:

Pigs: coli diarrhea, enterotoxemia, sepsis, dysentery, salmonellosis, metritis-mastitis-agalactiae syndrome, mastitis;

Ruminants (cattle, sheep, goats): diarrhea, sepsis, bronchopneumonia, salmonellosis, pasteurellosis, mycoplasmosis, genital infections;

Horses: bronchopneumonias, joint ill, puerperal and post-puerperal infections, salmonellosis;

Dogs and cats: bronchopneumonia, diarrhea, dermatitis, otitis, urinary tract infections, prostatitis;

Poultry (chickens, turkeys, quail, pigeons, ornamental birds and others): mycoplasmosis, *E. coli* infections, chronic airway diseases, salmonellosis, pasteurellosis, psittacosis.

It is likewise possible to treat bacterial diseases in the rearing and management of productive and ornamental fish, in which case the antibacterial spectrum is extended beyond the pathogens mentioned above to further pathogens such as, for example, *Pasteurella, Brucella, Campylobacter, Listeria, Erysipelothris, corynebacteria, Borellia, Treponema, Nocardia, Rikettsie, Yersinia*.

The present invention further relates to the use of the compounds of the invention for the treatment and/or prophylaxis of diseases, preferably of bacterial diseases, especially of bacterial infections.

The present invention further relates to the use of the compounds of the invention for the treatment and/or prophylaxis of diseases, especially of the aforementioned diseases.

The present invention further relates to the use of the compounds of the invention for the production of a medicament for the treatment and/or prophylaxis of diseases, especially of the aforementioned diseases.

The present invention further relates to a method for the treatment and/or prophylaxis of diseases, especially of the aforementioned diseases, using an antibacterially effective amount of the compounds of the invention.

The compounds of the invention may act systemically and/or locally. For this purpose, they can be administered in a suitable way such as, for example, orally, parenterally, pulmonarily, nasally, sublingually, lingually, buccally, rectally, dermally, transdermally, conjuctivally or otically or as implant or stent.

The compounds of the invention can be administered in administration forms suitable for these administration routes.

Suitable for oral administration are administration forms which function according to the prior art and deliver the compounds of the invention rapidly and/or in modified fashion, and which contain the compounds of the invention in crystalline and/or amorphized and/or dissolved form, such as, for example, tablets (uncoated or coated tablets, for example having coatings which are resistant to gastric juice or are insoluble or dissolve with a delay and control the release of the compound of the invention), tablets or films/wafers, which disintegrate rapidly in the mouth, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilisates or sterile powders.

Suitable for the other administration routes are, for example, pharmaceutical forms for inhalation (inter alia powder inhalers, nebulizers), nasal drops, solutions, sprays; tablets, films/wafers or capsules for lingual, sublingual or buccal administration, suppositories, preparations for the ears or eyes, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

The compounds of the invention can be converted into the stated administration forms. This can take place in a manner known per se by mixing with inert, nontoxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and taste and/or odor corrigents.

The present invention further relates to medicaments which comprise at least one compound of the invention, normally together with one or more inert, nontoxic, pharmaceutically suitable excipients, and to the use thereof for the aforementioned purposes.

It has generally proved advantageous on parenteral administration to administer amounts of about 5 to 250 mg/kg of body weight per 24 h to achieve effective results. The amount on oral administration is about 5 to 100 mg/kg of body weight per 24 h.

It may nevertheless be necessary where appropriate to deviate from the stated amounts, in particular as a function of the body weight, administration route, individual behavior towards the active ingredient, nature of the preparation and time or interval over which administration takes place. Thus, it may be sufficient in some cases to make do with less than the aforementioned minimum amount, whereas in other cases the stated upper limit must be exceeded. Where larger amounts are administered, it may be advisable to divide these into a plurality of single doses over the day.

The percentage data in the following tests and examples are percentages by weight unless otherwise indicated; parts are parts by weight. Solvent ratios, dilution ratios and concentration data for liquid/liquid solutions are in each case based on volume.

DETAILED DESCRIPTION OF PREFERRED EMBODIMENTS

A. EXAMPLES

Abbreviations Used:
abs. Absolute
aq. aqueous
Bn benzyl
boc tert-butoxycarbonyl
$CDCl_3$ chloroform
CH cyclohexane
d doublet (in $^1$H NMR)
dd doublet of doublets (in $^1$H NMR)
DCC dicyclohexylcarbodiimide
DIC diisopropylcarbodiimide
DIEA diisopropylethylamine (Hünig's base)
DMSO dimethylsulfoxide
DMAP 4-N,N-dimethylaminopyridine
DMF dimethylformamide
EA ethyl acetate (acetic acid ethyl ester)
EDC N'-(3-dimethylaminopropyl)-N-ethylcarbodiimide×HCl
ESI electrospray ionization (in MS)
Fmoc 9-fluorenylmethoxycarbonyl
HATU O-(7-azabenzotriazol-1-yl)-N,N,N',N'-tetramethyluronium hexafluorophosphate
HBTU O-(benzotriazol-1-yl)-N,N,N',N'-tetramethyluronium hexafluorophosphate
HOBt 1-hydroxy-1H-benzotriazole×$H_2O$
h hour(s)
HPLC high pressure, high performance liquid chromatography
LC-MScoupled liquid chromatography-mass spectroscopy
m multiplet (in $^1$H NMR)
min minute
MS mass spectroscopy
NMR nuclear magnetic resonance spectroscopy
MTBE methyl tert-butyl ether
Pd/C palladium/carbon
q quartet (in $^1$H NMR)
$R_f$ retention index (in TLC)
RP reverse phase (in HPLC)
RT room temperature
$R_t$ retention time (in HPLC)
s singlet (in $^1$H NMR)
sat saturated t triplet (in ¹H NMR)
TBS tert-butyldimethylsilyl
TFA trifluoroacetic acid
THF tetrahydrofuran
TLC thin-layer chromatography
TMSE 2-(trimethylsilyl)ethyl
TPTU 2-(2-oxo-1(2H)-pyridyl)-1,1,3,3,-tetramethyluronium tetrafluoroborate
Z benzyloxycarbonyl LC-MS and HPLC Methods:

Method 1 (HPLC): Instrument: HP 1100 with DAD detection; column: Kromasil RP-18, 60 mm×2 mm, 3.5 µm; eluent A: 5 ml of perchloric acid/l of water, eluent B: acetonitrile; gradient: 0 min 2% B, 0.5 min 2% B, 4.5 min 90% B, 6.5 min 90% B; flow rate: 0.75 ml/min; oven: 30° C.; UV detection: 210 nm.

Method 2 (LC-MS): Instrument: Micromass Platform LCZ; column: Symmetry C18, 50 mm×2.1 mm, 3.5 µm; temperature: 40° C.; flow rate: 0.5 ml/min; eluent A: acetonitrile+0.1% formic acid, eluent B: water+0.1% formic acid, gradient: 0.0 min 10% A→4 min 90% A→6 min 90% A.

Method 3 (LC-MS): Instrument: Waters Alliance 2790 LC; column: Symmetry C18, 50 mm×2.1 mm, 3.5 µm; eluent A: water+0.1% formic acid, eluent B: acetonitrile+0.1% formic acid; gradient: 0.0 min 5% B→5.0 min 10% B→6.0 min 10% B; temperature: 50° C.; flow rate: 1.0 ml/min; UV detection: 210 nm.

Method 4 (LC-MS): ZMD Waters; column: Inertsil ODS3 50 mm×2.1 mm, 3 µm; temperature: 40° C.; flow rate: 0.5 ml/min; eluent A: water+0.05% formic acid, eluent B: acetonitrile+0.05% formic acid, gradient: 0.0 min 5% B→12 min→100% B→15 min 100% B.

Method 5 (LC-MS): MAT 900, Finnigan MAT, Bremen; column: X-terra 50 mm×2.1 mm, 2.5 µm; temperature: 25° C.; flow rate: 0.5 ml/min; eluent A: water+0.01% formic acid, eluent B: acetonitrile+0.01% formic acid, gradient: 0.0 min 10% B→15 min→90% B→30 min 90% B.

Method 6 (LC-MS): TSQ 7000, Finnigan MAT, Bremen; column: Inertsil ODS3 50 mm×2.1 mm, 3 µm; temperature: 25° C.; flow rate: 0.5 ml/min; eluent A: water+0.05% formic acid, eluent B: acetonitrile+0.05% formic acid, gradient: 0.0 min 15% B→15 min→100% B→30 min 100% B.

Method 7 (LC-MS): 7 Tesla Apex II with external electrospray ion source, Bruker Daltronics; column: X-terra C18 50 mm×2.1 mm, 2.5 µm; temperature: 25° C.; flow rate: 0.5 ml/min; eluent A: water+0.1% formic acid, eluent B: acetonitrile+0.1% formic acid, gradient: 0.0 min 5% B→13 min→100% B→15 min 100% B.

Method 8 (LC-MS): MS instrument type: Micromass ZQ; HPLC instrument type: Waters Alliance 2795; column: Merck Chromolith SpeedROD RP-18e 50×4.6 mm; eluent A: water+500 µl of 50% formic acid/l; eluent B: acetonitrile+500 µl of 50% formic acid/l; gradient: 0.0 min 10% B→2.0 min 95% B→4.0 min 95% B; oven: 35° C.; flow rate: 0.0 min 1.0 ml/min→2.0 min 3.0 ml/min→4.0 min 3.0 ml/min; UV detection: 210 nm.

Method 9 (LC-MS): Instrument: Micromass Platform LCZ with HPLC Agilent series 1100; column: Grom-SIL1200DS-4 HE, 50 mm×2.0 mm, 3 µm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 210 nm.

Method 10 (LC-MS): MS instrument type: Micromass ZQ; HPLC instrument type: Waters Alliance 2795; column: Merck Chromolith SpeedROD RP-18e 50×4.6 mm; eluent A: water+500 µl of 50% formic acid/l; eluent B: acetonitrile+500 µl of 50% formic acid/l; gradient: 0.0 min 10% B→3.0 min 95% B→4.0 min 95% B; oven: 35° C.; flow rate: 0.0 min 1.0 ml/min→3.0 min 3.0 ml/min→4.0 min 3.0 ml/min; UV detection: 210 nm.

Method 11 (LC-MS): MS instrument type: Micromass ZQ; HPLC instrument type: Waters Alliance 2790; column: Uptisphere C 18, 50 mm×2.0 mm, 3.0 µm; eluent B: acetonitrile+0.05% formic acid, eluent A: water+0.05% formic acid; gradient: 0.0 min 5% B→2.0 min 40% B→4.5 min 90% B→5.5 min 90% B; oven: 45° C.; flow rate: 0.0 min 0.75 ml/min→4.5 min 0.75 ml/min→5.5 min 1.25 ml/min; UV detection: 210 nm.

Method 12 (LC-MS): MS instrument type: Micromass ZQ; HPLC instrument type: Waters Alliance 2795; column: Phenomenex Synergi 2µ Hydro-RP Mercury 20×4 mm; eluent A: 1 l of water+0.5 ml of 50% formic acid, eluent B: 1 l of acetonitrile+0.5 ml of 50% formic acid; gradient: 0.0 min 90% A (flow rate: 1 ml/min)→2.5 min 30% A (flow rate: 2 ml/min)→3.0 min 5% A (flow rate: 2 ml/min)→4.5 min 5% A (flow rate: 2 ml/min); oven: 50° C.; UV detection: 210 nm.

Method 13 (LC-MS): MS instrument type: Micromass ZQ; HPLC instrument type: HP 1100 series; UV DAD; column: Grom-Sil 1200DS-4 HE 50×2 mm, 3.0 µm; eluent A: water+500 µl of 50% formic acid/l, eluent B: acetonitrile+500 µl of 50% formic acid/l; gradient: 0.0 min 70% B→4.5 min 90% B; oven: 50° C., flow rate: 0.8 ml/min, UV detection: 210 nm.

Method 14 (LC-MS): Instrument: Micromass Quattro LCZ, with HPLC Agilent series 1100; column: Grom-SIL1200DS-4 HE, 50 mm×2.0 mm, 3 µm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 15 (LC-MS): MS instrument type: Micromass ZQ; HPLC instrument type: Waters Alliance 2790; column: Grom-Sil 1200DS-4 HE 50×2 mm, 3.0 µm; eluent A: water+500 µl of 50% formic acid, eluent B: acetonitrile+500 µl of 50% formic acid/l; gradient: 0.0 min 5% B→2.0 min 40% B→4.5 min 90% B→5.5 min 90% B; oven: 45° C.; flow rate: 0.0 min 0.75 ml/min→4.5 min 0.75 ml 5.5 min→5.5 min 1.25 ml; UV detection: 210 nm.

Method 16 (HPLC): Instrument: HP 1100 with DAD detection; column: Kromasil RP-18, 60 mm×2 mm, 3.5 µm; eluent A: 5 ml of perchloric acid/l of water, eluent B: acetonitrile; gradient: 0 min 2% B, 0.5 min 2% B, 4.5 min 90% B, 15 min 90% B; flow rate: 0.75 ml/min; oven: 30° C.; UV detection: 210 nm.

Method 17 (LC-MS): MS instrument type: Micromass ZQ; HPLC instrument type: HP 1100 series; UV DAD; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 18 (LC-MS): Instrument: Micromass Platform LCZ with HPLC Agilent series 1100; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 19 (LC-MS): Instrument: Micromass Quattro LCZ with HPLC Agilent series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 20 (LC-MS): Instrument: Micromass Platform LCZ with HPLC Agilent series 1100; column: ThermoHypersil-Keystone HyPurity Aquastar, 50 mm×2.1 mm, 3 μm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 210 nm.

Method 21 (preparative HPLC/RP-HPLC): column: RP18 Phenomenex Luna C18(2) (New Column), 250 mm×21.2 mm, 5 μm (Phenomenex, Aschaffenburg, Germany), eluent: acetonitrile-water gradient with addition of 0.2% diethylamine.

Method 22 (HPLC): Instrument: HP 1100 with DAD detection; column: Kromasil RP-18, 60 mm×2 mm, 3.5 μm; eluent A: 5 ml of perchloric acid/l of water, eluent B: acetonitrile; gradient: 0 min 2% B, 0.5 min 2% B, 4.5 min 90% B, 9 min 90% B; flow rate: 0.75 ml/min; oven: 30° C.; UV detection: 210 nm.

Method 23 (LC-MS): Instrument: Micromass Platform LCZ with HPLC agilent series 1100; column: Thermo Hypersil GOLD-3μ 20×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Chemical Synthesis of the Examples
Synthesis of the Starting Compounds:

Synthesis of substituted phenylalanine derivatives using (−)-3-(2-benzyloxy-5 iodophenyl)-2(S)-tert-butoxycarbonylaminopropionic acid [(−)-6A] as example Synthesis of protected hydroxyornithine derivatives using 5-benzyloxycarbonylamino-2(S)-tert-butoxycarbonylamino-4(R)-(tert-butyldimethylsilyloxy) pentanoic acid (14A) as example

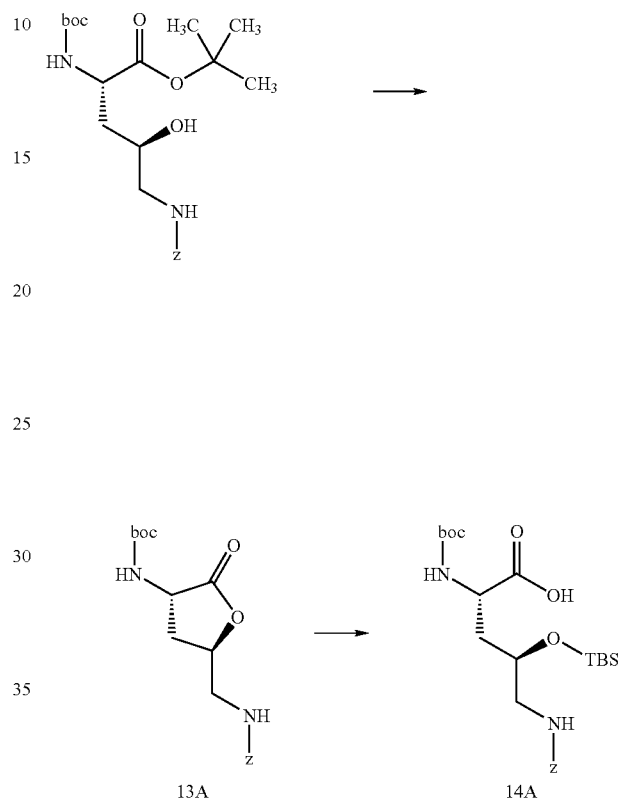

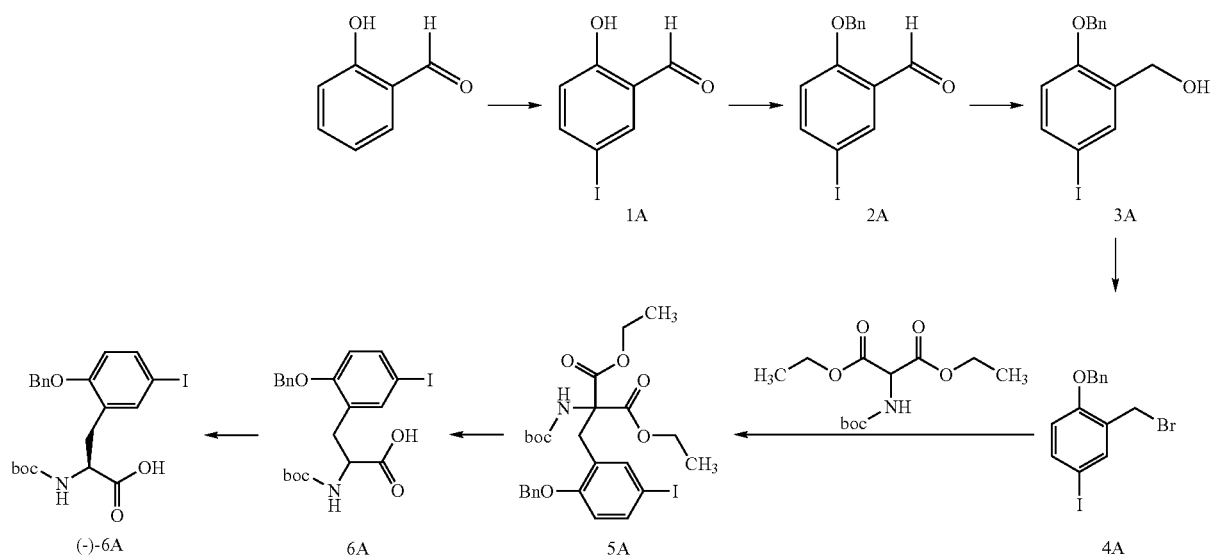

Synthesis of substituted phenylalanine derivatives using methyl 2-(benzyloxy)-N-[(benzyloxy)carbonyl]-5-bromo-L-phenylalaninate] (56A) as example
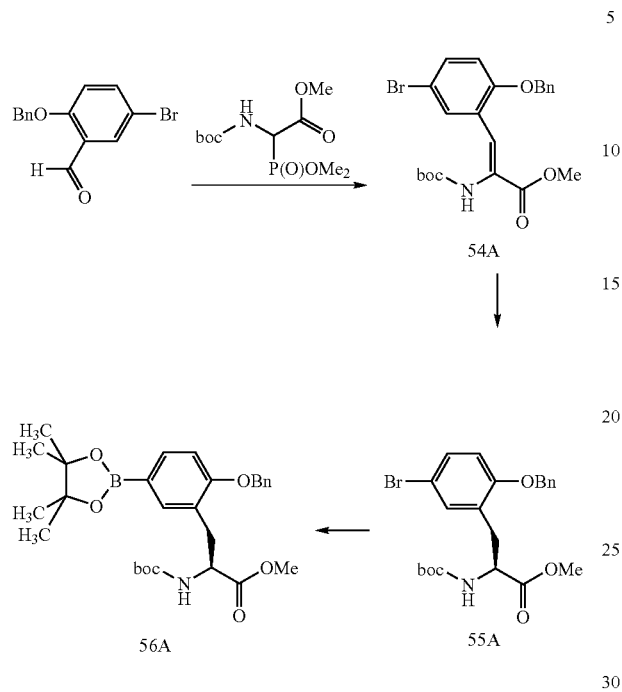
Synthesis of protected biphenylbisamino acids using 2(S)-trimethylsilanylethyl 2(S)-benzyloxycarbonylamino-3-[4,4'-bis-benzyloxy-3'-(2(S)-benzyloxycarbonyl-2(S)-tert-butoxycarbonylaminoethyl)biphenyl-3-yl]propionate (12A) as example
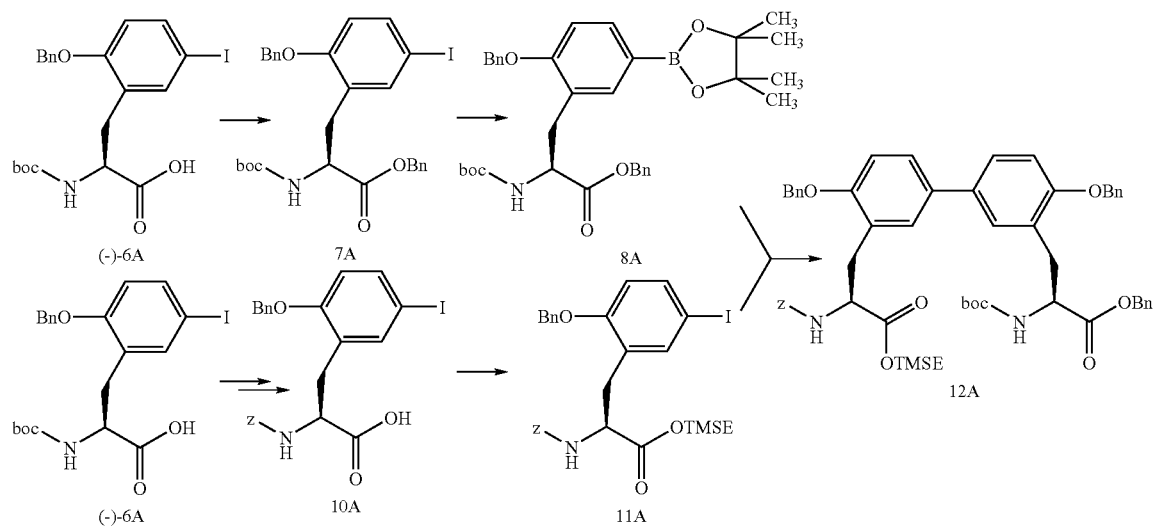

Cyclization of the Biphenylbisamino Acids
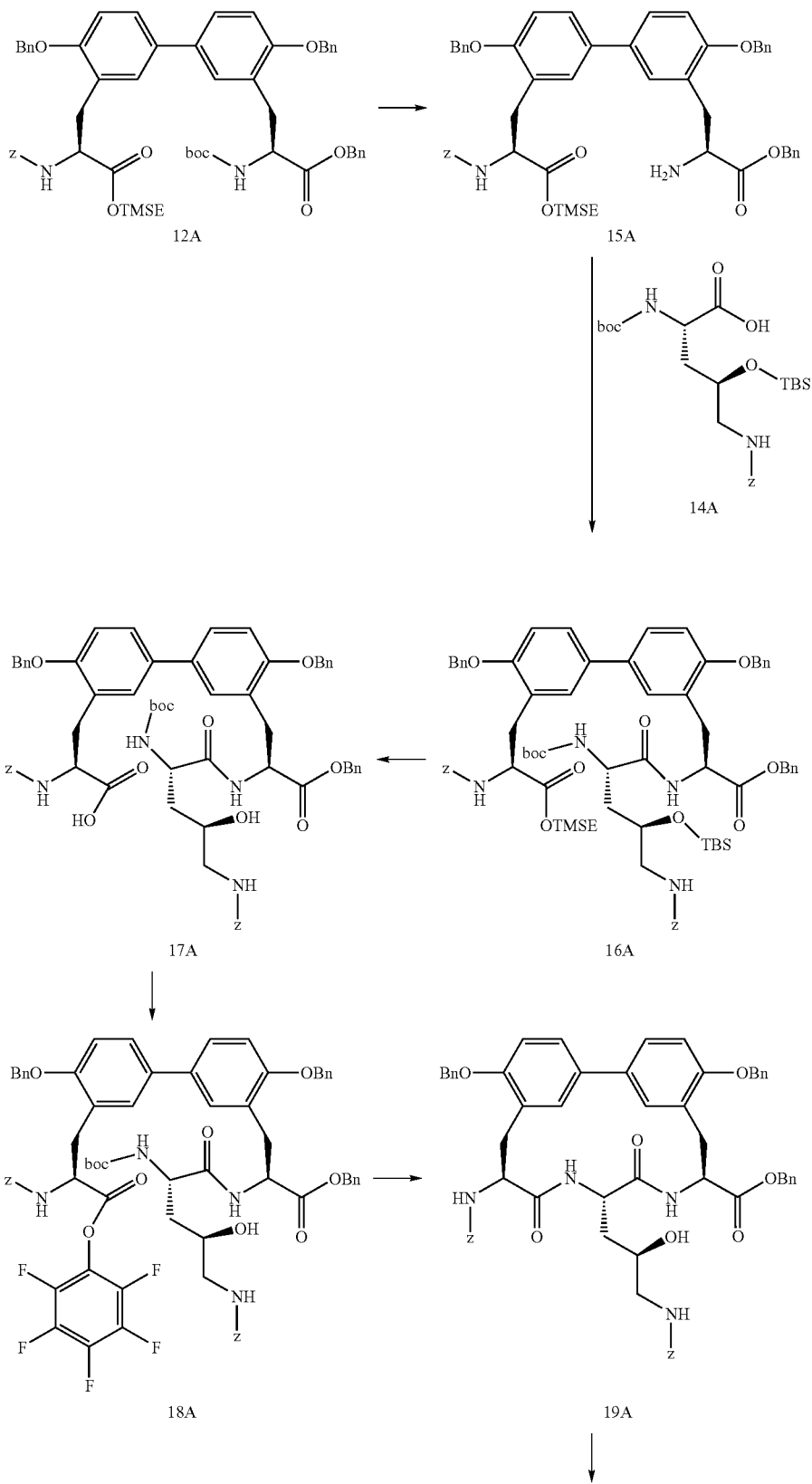

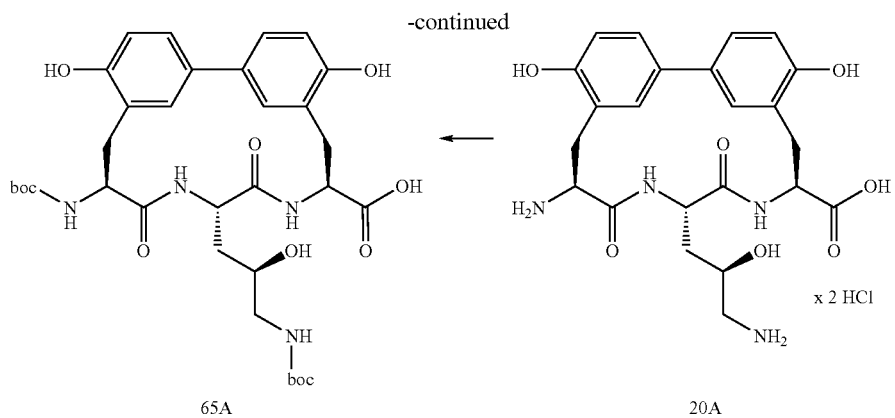

65A ← 20A · 2 HCl

Starting Compounds

Example 1A

2-Hydroxy-5-iodobenzaldehyde

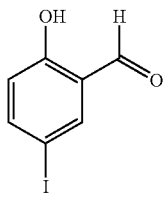

A solution of 250 g (1.54 mol) of iodine chloride in 600 ml of anhydrous dichloromethane is added dropwise over the course of 2 h to a solution of 188 g (1.54 mol) of salicylaldehyde in 1 l of anhydrous dichloromethane in a heat-dried flask under argon. After stirring at RT for 3 days, a saturated aqueous sodium sulfite solution is added with vigorous stirring. The organic phase is separated, washed once with water and a saturated aqueous sodium chloride solution and dried over sodium sulfate. The solvent is evaporated and the residue is recrystallized from ethyl acetate. 216 g (57% of theory) of product are obtained.

LC-MS (ESI, Method 4): m/z=246 (M−H)⁻.

¹H-NMR (400 MHz, CDCl₃): δ=6.7 (d, 1H), 7.77 (dd, 1H), 7.85 (d, 1H), 9.83 (s, 1H), 10.95 (s, 1H).

Example 2A

2-Benzyloxy-5-iodobenzaldehyde

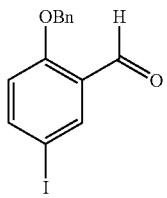

67.2 g (0.48 mol) of potassium carbonate are added to a solution of 100 g (0.40 mol) of 2-hydroxy-5-iodobenzaldehyde (Example 1A) in 1.5 l of dimethylformamide and, after a few minutes, 51 ml (0.44 mol) of benzyl chloride are added. The reaction mixture is stirred under reflux at 120° C. for 24 h. After stirring at RT for a further 24 h and the addition of 1.5 l of water, a solid crystallizes out. The precipitate is collected by suction filtration, washed twice with water and dried in vacuo. The solid is recrystallized from 230 ml of ethanol. 122.9 g (90% of theory) of product are obtained.

LC-MS (ESI, Method 4): m/z=338 (M+H)⁺.

¹H-NMR (400 MHz, CDCl₃): δ=5.18 (s, 2H), 6.84 (d, 1H), 7.33-7.45 (m, 5H), 7.78 (dd, 1H), 8.12 (d, 1H), 10.4 (s, 1H).

Example 3A (2-Benzyloxy-5-iodophenyl)methanol

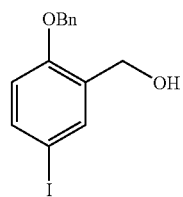

100 ml of a 1M diisobutylaluminum hydride solution in dichloromethane are added to a solution, cooled to 0° C., of 33.98 g (100.5 mmol) of 2-benzyloxy-5-iodobenzaldehyde (Example 2A) in 200 ml of dichloromethane. After stirring at 0° C. for 2 h, a saturated potassium sodium tartrate solution is added while cooling (highly exothermic reaction), and the reaction mixture is stirred for a further 2 h. After the separation of the phases, the organic phase is washed twice with water and once with a saturated aqueous sodium chloride solution and dried over sodium sulfate. The solvent is evaporated in vacuo. 31.8 g (93% of theory) of product are obtained.

¹H-NMR (400 MHz, CDCl₃): δ=2.17 (t, 1H), 4.68 (d, 2H), 5.1 (s, 2H), 6.72 (d, 1H), 7.32-7.42 (m, 5H), 7.54 (dd, 1H), 7.63 (d, 1H).

Example 4A

1-Benzyloxy-2-bromomethyl-4-iodobenzene

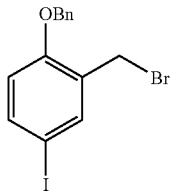

3.3 ml (35 mmol) of phosphorus tribromide are added dropwise to a solution of 35 g (103 mmol) of (2-benzyloxy-5-iodophenyl)methanol (Example 3A) in 350 ml of toluene at 40° C. The temperature of the reaction mixture is raised to 100° C. over the course of 15 min and the reaction mixture is stirred at this temperature for a further 10 min. After cooling, the two phases are separated. The organic phase is washed twice with distilled water and once with a saturated aqueous sodium chloride solution. The organic phase is dried over sodium sulfate and evaporated. The yield amounts to 41 g (99% of theory).

$^1$H-NMR (300 MHz, CDCl$_3$): δ=4.45 (s, 2H), 5.06 (s, 2H), 7.30 (m, 8H).

Example 5A

Diethyl 2-(2-benzyloxy-5-iodobenzyl)-2-tert-butoxycarbonylaminomalonate

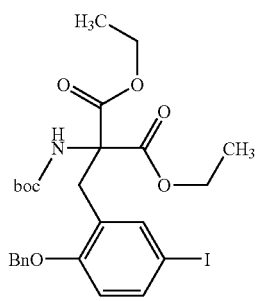

41 g (101.7 mmol) of 1-benzyloxy-2-bromomethyl-4-iodobenzene (Example 4A) are added to a solution of 28 g (101.7 mmol) of diethyl 2-[N-(tert-butoxycarbonyl)amino]malonate and 7.9 ml (101.7 mmol) of sodium ethoxide in 300 ml of ethanol. After stirring at RT for 3 h, the precipitated product is collected by suction filtration. After drying in vacuo, 55 g (90% of theory) of product are isolated.

$^1$H-NMR (400 MHz, CDCl$_3$): δ=1.12 (t, 6H), 1.46 (s, 9H), 3.68 (s, 2H), 3.8-3.9 (m, 2H), 4.15-4.25 (m, 2H), 5.0 (s, 2H), 5.7 (s, 1H), 6.58 (d, 1H), 7.28-7.4 (m, 6H), 7.4 (dd, 1H).

Example 6A (+/−)-3-(2-Benzyloxy-5-iodophenyl)-2-tert-butoxycarbonylaminopropionic acid

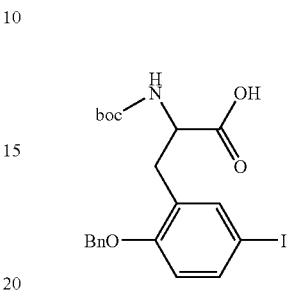

400 ml of a 1N sodium hydroxide solution are added to a suspension of 58 g (97 mmol) of diethyl 2-(2-benzyloxy-5-iodobenzyl)-2-tert-butoxycarbonylaminomalonate (Example 5A) in 800 ml of a mixture of ethanol and water (7:3). After 3 h under reflux and after cooling to room temperature, the pH of the reaction mixture is adjusted to about pH 2 with conc. hydrochloric acid. The reaction mixture is evaporated. The residue is taken up in MTBE and water. The aqueous phase is extracted three times with MTBE. The combined organic phases are dried over sodium sulfate, filtered and concentrated. After drying in vacuo 47 g (97% of theory) of product are obtained.

$^1$H-NMR (400 MHz, DMSO-d$_6$): δ=1.32 (s, 9H), 2.68 (dd, 1H), 3.18 (dd, 1H), 4.25 (m, 1H), 5.15 (s, 2H), 6.88 (d, 1H), 7.08 (d, 1H), 7.30-7.40 (m, 3H), 7.45-7.55 (m, 3H).

Example (−)-6A 3-(2-Benzyloxy-5-iodophenyl)-2(S)-tert-butoxycarbonylaminopropionic acid

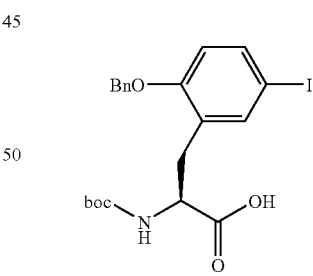

The racemate from Example 6A [(+/−)-3-(2-benzyloxy-5-iodophenyl)-2(S)-tert-butoxycarbonylaminopropionic acid] is separated on a chiral stationary silica gel phase based on the selector from poly(N-methacryloyl-L-leucine dicyclopropylmethylamide) using an i-hexane/ethyl acetate mixture as eluent. The enantiomer eluted first (98.9% ee) is dextrorotatory in dichloromethane ([α]$_D^{21}$: +3.0°, c=0.54, dichloromethane) and corresponds to the (R) enantiomer Example (+)-6A, as was determined by single-crystal X-ray structural analysis. The purity of the second, levorotatory enantiomer Example (−)-6A, i.e. the (S) enantiomer, is >99% ee.

Example 7A

Benzyl 3-(2-benzyloxy-5-iodophenyl)-2(S)-tert-butoxycarbonylaminopropionate

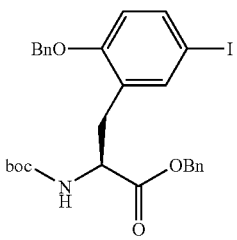

Under argon, 10 g (20.11 mmol) of (−)-3-(2-benzyloxy-5-iodophenyl)-2(S)-tert-butoxycarbonylaminopropionic acid (Example (−)-6A) are dissolved in 200 ml of acetonitrile. To this are added 246 mg (2.01 mmol) of 4-dimethylaminopyridine and 4.16 ml (40.22 mmol) of benzyl alcohol. The mixture is cooled to −10° C., and 4.63 g (24.13 mmol) of EDC are added. The mixture is allowed slowly to reach RT and is stirred overnight. After about 16 h, the mixture is concentrated on a rotary evaporator in vacuo, and the residue is purified by column chromatography on silica gel (mobile phase: dichloromethane). Yield: 10.65 g (88% of theory).

HPLC (Method 1): $R_t$=6.03 min; LC-MS (Method 3): $R_t$=4.70 min

MS (DCI): m/z=605 (M+NH$_4$)$^+$.

$^1$H-NMR (200 MHz, CDCl$_3$): δ=1.38 (s, 9H), 2.97 (dd, 1H), 3.12 (dd, 1H), 4.50-4.70 (m, 1H), 5.00-5.10 (m, 4H), 5.22 (d, 1H), 6.64 (d, 1H), 7.28-7.36 (m, 7H), 7.37-7.52 (m, 5H).

Example 8A

Benzyl 3-[2-benzyloxy-5-(4,4,5,5-tetramethyl[1,3,2]dioxaborolan-2-yl)phenyl]-2(S)-tert-butoxycarbonylaminopropionate

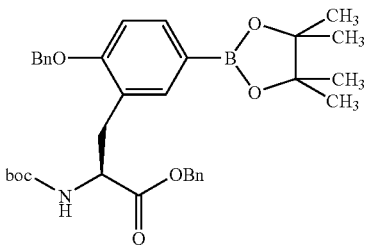

5.15 g (52.60 mmol) of potassium acetate are added to a solution of 10.30 g (17.53 mol) of benzyl 3-(2-benzyloxy-5-iodophenyl)-2(S)-tert-butoxycarbonylaminopropionate (Example 7A) in 70 ml of DMSO. The mixture is deoxygenated by passing argon through the vigorously stirred solution for 15 min. Then 5.17 g (20.16 mmol) of bis(pinacolato)diborane and 515 mg (0.70 mmol) of bis(diphenylphosphino)ferrocenepalladium(II) chloride are added. The mixture is then heated to 80° C. under a gentle stream of argon and after 6 h is cooled again. The mixture is filtered through silica gel (mobile phase: dichloromethane). The residue is purified by column chromatography on silica gel (mobile phase: cyclohexane:ethyl acetate 4:1).

Yield: 8.15 g (79% of theory)

HPLC (Method 1): $R_t$=6.26 min

LC-MS (Method 2): $R_t$=5.93 and 6.09 min

MS (EI): m/z=588 (M+H)$^+$ $^1$H-NMR (200 MHz, CDCl$_3$): δ=1.26 (s, 6H), 1.33 (s, 9H), 1.36 (s, 6H), 2.91-3.10 (m, 1H), 3.12-3.28 (m, 1H), 4.49-4.68 (m, 1H), 5.05 (dd, 2H), 5.11 (dd, 2H), 5.30 (d, 1H), 6.90 (d, 1H), 7.27-7.37 (m, 7H), 7.38-7.42 (m, 3H), 7.55-7.62 (m, 1H), 7.67 (dd, 1H).

Example 9A

2(S)-Amino-3-(2-benzyloxy-5-iodophenyl)propionic acid hydrochloride

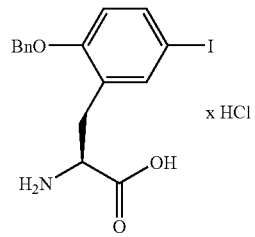

12 g (24.13 mmol) of 3-(2-benzyloxy-5-iodophenyl)-2(S)-tert-butoxycarbonylaminopropionic acid (Example (−)-6A) are added under argon into 60 ml of a 4M solution of hydrogen chloride in dioxane and stirred at RT for 2 h. The reaction solution is concentrated and dried under high vacuum.

Yield: 10.47 g (100% of theory)

HPLC (Method 1): $R_t$=4.10 min

MS (EI): m/z=398 (M+H−HCl)$^+$ $^1$H-NMR (200 MHz, CDCl$_3$): δ=3.17-3.31 (m, 1H), 3.33-3.47 (m, 1H), 4.22 (t, 1H), 5.13 (s, 2H), 6.69 (d, 1H), 7.24-7.40 (m, 2H), 7.41-7.45 (m, 2H), 7.48 (d, 1H), 7.52 (d, 1H), 7.60 (d, 1H), 8.66 (br. s, 2H).

Example 10A

2(S)-Benzyloxycarbonylamino-3-(2-benzyloxy-5-iodophenyl)propionic acid

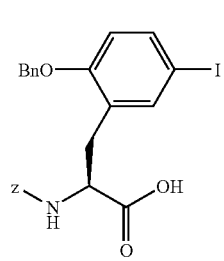

9.25 ml (53.09 mol) of N,N-diisopropylethylamine are added to a solution of 10.46 g (24.13 mmol) of 2(S)-amino-3-(2-benzyloxy-5-iodophenyl)propionic acid hydrochloride (Example 9A) in DMF. 6.615 g (26.54 mmol) of N-(benzyloxycarbonyl)succinimide (Z-OSuc) are added thereto. The resulting solution is stirred overnight and then concentrated on a rotary evaporator in vacuo. The residue is taken up in dichloromethane and extracted twice each with a 0.1N hydrochloric acid solution and a saturated aqueous sodium chloride solution. The organic phase is dried, filtered and concentrated. The mixture is purified by column chromatography on silica gel (mobile phase: cyclohexane/diethyl ether 9:1 to 8:2).

Yield: 8.30 g (65% of theory)
HPLC (Method 1): $R_t$=5.01 min
MS (EI): m/z=532 (M+H)$^+$
$^1$H-NMR (200 MHz, DMSO-d$_6$): δ=3.14-3.3 (m, 2H), 4.25-4.45 (m, 1H), 4.97 (s, 2H), 5.14 (s, 2H), 6.88 (d, 1H), 7.20-7.56 (m, 12H), 7.62 (d, 1H), 12.73 (br. s, 1H).

Example 11A (2-Trimethylsilyl)ethyl 2(S)-benzyloxycarbony-lamino-3-(2-benzyloxy-5-iodophenyl)-propionate

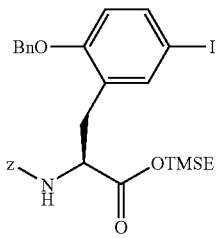

8.35 g (15.7 mmol) of 2(S)-benzyloxycarbonylamino-3-(2-benzyloxy-5-iodophenyl)propionic acid (Example 10A) are provided in 150 ml of THF, and 2.14 g (18.07 mmol) of 2-trimethylsilylethanol and 250 mg (2.04 mmol) of 4-dimethylaminopyridine are added. The mixture is cooled to 0° C., and 2.38 g (2.95 ml, 18.86 mmol) of N,N'-diisopropylcarbo-diimide dissolved in 40 ml of THF are added. The mixture is stirred at RT overnight and concentrated on a rotary evaporator in vacuo for the work-up. The residue is taken up in dichloromethane and extracted twice each with a 0.1N hydrochloric acid solution and a saturated aqueous sodium chloride solution. The organic phase is dried, filtered and concentrated. The mixture is purified by column chromatography (silica gel, mobile phase: cyclohexane/diethyl ether 9:1 to 8:2).

Yield: 8.2 g (83% of theory)
HPLC (Method 1): $R_t$=6.42 min
MS (EI): m/z=532 (M+H)$^+$
$^1$H-NMR (300 MHz, CDCl$_3$): δ=0.01 (s, 9H), 0.88 (t, 2H), 2.96 (dd, 1H), 3.13 (dd, 1H), 4.04-4.17 (m, 2H), 4.51-4.62 (m, 1H), 4.95-5.05 (m, 4H), 5.44 (d, 1H), 6.64 (d, 1H), 7.25-7.33 (m, 7H), 7.37 (dd, 4H), 7.45 (dd, 1H).

Example 12A 2-(Trimethylsilyl)ethyl 2(S)-benzyloxycarbony-lamino-3-[4,4'-bisbenzyloxy-3'-(2(S)-benzyloxycar-bonyl-2-tert-butoxycarbonylaminoethyl)biphenyl-3-yl]propionate

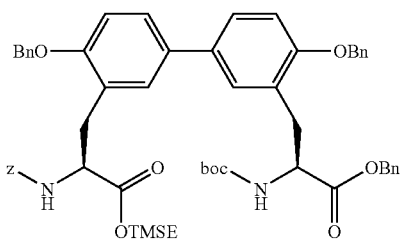

45.8 mg (0.05 mmol) of bis(diphenylphosphino)ferrocene-palladium(II) chloride (PdCl$_2$(dppf)) and 0.325 g (1.0 mmol) of cesium carbonate are added to a solution of 0.316 g (0.5 mmol) of (2-trimethylsilyl)ethyl 2(S)-benzyloxycarbony-lamino-3-(2-benzyloxy-5-iodophenyl)propionate (Example 11A) in 2.5 ml of degassed DMF under argon at RT. The reaction mixture is heated to 40° C. Over the course of 30 min, a solution of 0.294 g (0.5 mmol) of benzyl 3-[2-benzyloxy-5-(4,4,5,5-tetramethyl-[1,3,2]dioxaborolan-2-yl)phenyl]-2 (S)-tert-butoxycarbonylaminopropionate (Example 8A) in 2.5 ml of degassed DMF is added dropwise. The reaction mixture is stirred at 40° C. for 4 h and at 50° C. for a further 2 h. The solvent is evaporated and the residue is taken up in ethyl acetate. The organic phase is extracted twice with water, dried over sodium sulfate and concentrated. The crude product is purified by chromatography on silica gel with dichloromethane/ethyl acetate (30/1). 0.320 g (66% of theory) of product are obtained.

HPLC (Method 1): $R_t$=7.65 min
MS (EI): m/z=987 (M+Na), 965 (M+H)$^+$
$^1$H-NMR (200 MHz, CDCl$_3$): δ=0.00 (s, 9H), 0.90 (t, 2H), 1.37 (s, 9H), 3.02-3.35 (m, 4H) 4.06-4.25 (m, 2H), 4.55-4.73 (m, 2H), 4.98-5.18 (m, 8H), 5.40 (d, 1H), 5.63 (d, 1H), 6.88-7.00 (m, 2H), 7.19-7.39 (m, 20H), 7.42-7.53 (m, 4H).

Example 13A

Benzyl({(2R,4S)-4-[(tert-butoxycarbonyl)amino]-5-oxotetrahydrofuran-2-yl}methyl)carbamate

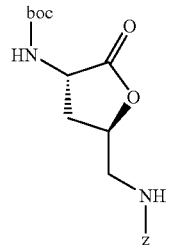

A solution of 7.60 g (17.3 mmol) of tert-butyl 5-benzy-loxycarbonylamino-2(S)-tert-butoxycarbonylamino-4(R)-hydroxypentanoate (Org. Lett. (2001) 3, 20:3153-3155) in 516 ml of dichloromethane and 516 ml of trifluoroacetic acid is stirred at RT for 2 h. The solvent is evaporated. The remaining crude product is dissolved in 2.6 l of anhydrous methanol and, while stirring at 0° C., 6.3 g (28.8 mmol) of di-tert-butyl dicarbonate and 7.3 ml (52.43 mmol) of triethylamine are added. After 15 h, the reaction solution is evaporated and the residue is taken up in 1 l of ethyl acetate. After the phases have separated, the organic phase is extracted twice with a 5% citric acid solution, twice with water and once with a saturated aqueous sodium chloride solution, dried over sodium sulfate and concentrated. The crude product is purified by chromatography on silica gel with toluene/acetone (5/1). 4.92 g (78% of theory) of product are obtained.

LC-HR-FT-ICR-MS (Method 7): calc. for $C_{18}H_{28}N_3O_6$ (M+NH$_4$)$^+$ 382.19726. found 382.19703.
$^1$H-NMR (400 MHz, CDCl$_3$): δ=1.45 (s, 9H), 2.3-2.4 (m, 1H), 2.45-2.55 (m, 1H), 3.3-3.4 (m, 1H), 3.5-3.6 (m, 1H), 4.17-4.28 (m, 1H), 4.7-4.8 (m, 1H), 5.0-5.15 (m, 4H), 7.3-7.4 (m, 5H).

Example 14A

5-Benzyloxycarbonylamino-2(S)-tert-butoxycarbonylamino-4(R)-(tert-butyldimethylsilanyloxy)pentanoic acid

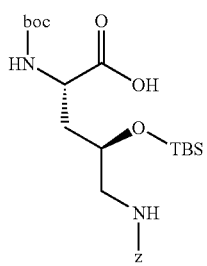

Method A:

2 ml of a 1M sodium hydroxide solution are added to a solution of 0.73 g (2 mmol) of the compound from Example 13A in 50 ml of 1,4-dioxane at 0° C. The reaction solution is stirred for 2 h and then evaporated. The residue is taken up in 50 ml of dichloromethane. 1.12 ml (8 mmol) of triethylamine are added to this solution and, after a short time, 1.38 ml (6 mmol) of tert-butyldimethylsilyl trifluoromethanesulfonate are added dropwise. After stirring at RT for 3 h, the reaction mixture is diluted with dichloromethane. The organic phase is washed with a 1N sodium bicarbonate solution, dried over sodium sulfate and evaporated. The crude product is dissolved in 7.4 ml of 1,4-dioxane, and 36.2 ml of a 0.1N sodium hydroxide solution are added. After stirring at RT for 3 h, the reaction solution is evaporated, and the residue is taken up in water and ethyl acetate. The organic phase is extracted three times with ethyl acetate. The combined organic phases are dried over sodium sulfate and evaporated. 0.90 g (90% of theory) of product are obtained.

Method B:

A solution of 14.0 g (38 mmol) of benzyl 2(S)-tert-butoxycarbonylamino-4(R)-hydroxy-5-nitropentanoate (Example 22A) in 840 ml of ethanol/water 9/1 is mixed with 1.96 g of palladium on carbon (10%) and hydrogenated under atmospheric pressure at RT for 24 h. The mixture is filtered through kieselguhr, and the filtrate is mixed with 14.7 g (114 mmol) of diisopropylethylamine. Then 11.4 g (45.6 mmol) of N-(benzyloxycarbonyloxy)succinimide are added, and the mixture is stirred at RT for 4 h. The solution is concentrated, and the residue is taken up in dichloromethane and extracted twice with 0.1N hydrochloric acid. The organic phase is separated and made alkaline with 14.7 g (114 mmol) of diisopropylamine. The solution is cooled to 0° C., 30.1 g (114 mmol) of dimethyl-tert-butylsilyl trifluoromethanesulfonate are added, and the mixture is stirred at RT for 2.5 h. The organic phase is washed with a saturated sodium bicarbonate solution, dried over sodium sulfate and evaporated. The residue is dissolved in 50 ml of dioxane, mixed with 200 ml of a 0.1N sodium hydroxide solution and stirred at RT for 3 h. The mixture is extracted several times with ethyl acetate, the collected organic phases are dried over sodium sulfate and concentrated in vacuo. The residue is chromatographed on silica gel (mobile phase: dichloromethane/ethanol 20/1, 9/1). 8.11 g (43% of theory) of product are obtained.

MS (ESI): m/z=497 (M+H)$^+$ $^1$H-NMR (300 MHz, DMSO-d$_6$): δ=0.00 (s, 6H), 0.99 (s, 9H), 1.33 (s, 9H), 1.59 (m, 1H), 1.80 (m, 1H), 2.75-3.15 (m, 2H), 3.81 (m, 1H), 3.98 (m, 1H), 4.96 (m, 2H), 7.04 (d, 1H), 7.19 (m, 1H), 7.30 (m, 5H), 12.37 (br. s, 1H).

Example 15A 2-(Trimethylsilyl)ethyl 3-[3'-2(S)-amino-2-benzyloxycarbonylethyl)-4,4'-bisbenzyloxybiphenyl-3-yl]-2(S)-benzyloxycarbonylaminopropionate hydrochloride

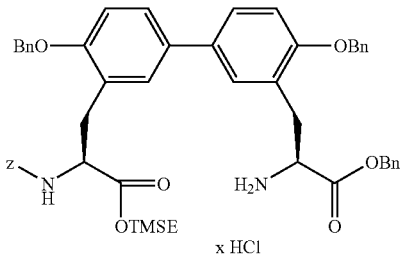

50 ml of a 4M solution of hydrogen chloride in dioxane are added over the course of about 20 min to a solution, cooled to 0° C., of 2.65 g (2.75 mmol) of 2-(trimethylsilyl)ethyl 2(S)-benzyloxycarbonylamino-3-[4,4'-bisbenzyloxy-3'-(2(S)-benzyloxycarbonyl-2-tert-butoxycarbonylaminoethyl)biphenyl-3-yl]propionate (Example 12A) in 50 ml of anhydrous dioxane. After stirring for 3 h, the reaction solution is evaporated and dried under high vacuum.

Yield: 100% of theory

HPLC (Method 1): R$_t$=5.96 min

MS (EI): m/z=865 (M+H)$^+$

Example 16A

Benzyl 2(S)-[5-benzyloxycarbonylamino-2(S)-tert-butoxycarbonylamino-4(R)-(tert-butyldimethylsilyloxy)pentanoylamino]-3-{4,4'-bisbenzyloxy-3'-[2(S)-benzyloxycarbonylamino-2-(2-trimethylsilylethoxycarbonyl)ethyl]biphenyl-3-yl}propionate

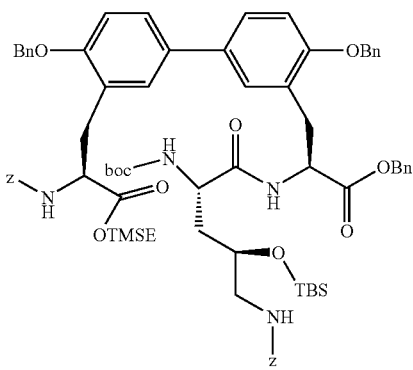

0.219 g (0.58 mmol) of HATU and 0.082 g (0.63 mmol) of N,N-diisopropylethylamine are added to a solution, cooled to 0° C., of 0.520 g (0.58 mmol) of (2-trimethylsilyl)ethyl 3-[3'-(2(S)-amino-2-benzyloxycarbonylethyl)-4,4'-bisbenzyloxy-biphenyl-3-yl]-2(S)-benzyloxycarbonylaminopropionate hydrochloride (Example 15A) and 0.287 g (0.58 mmol) of 5-benzyloxycarbonylamino-2(S)-tert-butoxycarbonyl-lamino-4(R)-(tert-butyldimethylsilyloxy)pentanoic acid (Example 14A) in 7.3 ml of anhydrous DMF. After stirring at 0° C. for 30 min, an additional 0.164 g (1.26 mmol) of N,N-diisopropylethylamine are added. The reaction mixture is stirred at RT for 15 h. The solvent is then evaporated, and the residue is taken up in ethyl acetate. The organic phase is washed three times with water and once with a saturated aqueous sodium chloride solution, dried over sodium sulfate and concentrated. The crude product is purified by chromatography on silica gel with dichloromethane/ethyl acetate (gradient 30/1→20/1→10/1). 533 mg (66% of theory) of product are obtained.

LC-MS (ESI, Method 6): m/z=1342 (M+H)$^+$, 1365 (M+Na)$^+$

Example 17A

2(S)-Benzyloxycarbonylamino-3-{4,4'-bisbenzy-loxy-3'-[2(S)-benzyloxycarbonyl-2-(5-benzyloxycar-bonylamino-2(S)-tert-butoxycarbonylamino-4(R)-hydroxypentanoylamino)ethyl]biphenyl-3-yl}propionic acid

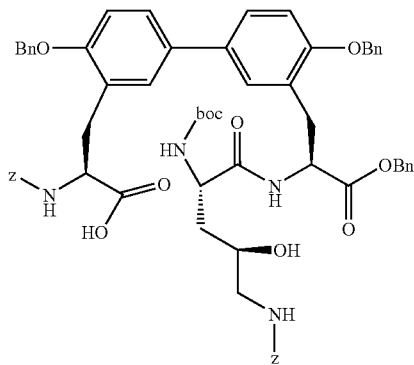

1.8 ml of 1N tetrabutylammonium fluoride in THF are added dropwise to a solution of 800 mg (0.6 mmol) of benzyl 2(S)-[5-benzyloxycarbonylamino-2(S)-tert-butoxycarbony-lamino-4(R)-(tert-butyldimethylsilyloxy)pentanoylamino]-3-{4,4'-bisbenzyloxy-3'-[2(S)-benzyloxycarbonylamino-2-(2-trimethylsilylethoxycarbonyl)ethyl]biphenyl-3-yl}propionate (Example 16A) in 26 ml of absolute DMF at RT. After 25 min at RT, the mixture is cooled to 0° C. and a large amount of ice-water is added. Ethyl acetate and a little 1N hydrochloric acid solution are immediately added; the organic phase is dried with magnesium sulfate, concentrated and dried under high vacuum for 1 h. The crude product is reacted without further purification.

LC-MS (ESI, Method 4): m/z=1129 (M+H)$^+$

LC-HR-FT-ICR-MS (Method 7): calc. for $C_{65}$; $H_{69}N_4$; $O_{14}$; (M+H)$^+$1129.48048. found: 1129.48123.

Example 18A

Benzyl 2(S)-(5-benzyloxycarbonylamino-2(S)-tert-butoxycarbonylamino-4(R)-hydroxypentanoy-lamino)-3-[4,4'-bisbenzyloxy-3'-(2(S)-benzyloxycar-bonylamino-2-pentafluorophenyloxycarbonylethyl)biphenyl-3-yl]propionate

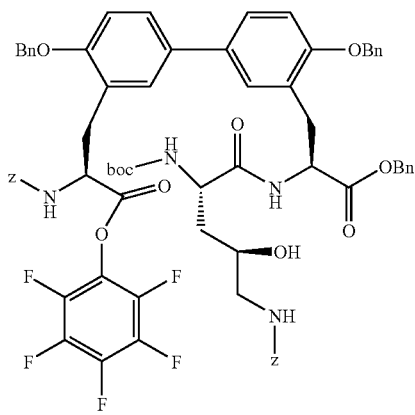

691 mg (crude mixture, approx. 0.6 mmol) of 2(S)-benzy-loxycarbonylamino-3-{4,4'-bisbenzyloxy-3'-[2(S)-benzy-loxycarbonyl-2-(5-benzyloxycarbonylamino-2(S)-tert-bu-toxycarbonylamino-4(R)-hydroxypentanoylamino)ethyl]biphenyl-3-yl}propionic acid (Example 17A) are provided in 25 ml of dichloromethane, and 547.6 mg (2.98 mmol) of pentafluorophenol, dissolved in 6 ml of dichloromethane, are added. 7.3 mg (0.06 mmol) of DMAP are added, and the mixture is cooled to −25° C. (ethanol/carbon dioxide bath). At −25° C., 148 mg (0.774 mmol) of EDC are added. The mixture slowly warms to RT overnight. The reaction mixture is concentrated in vacuo and briefly dried under high vacuum. The crude product is reacted without further purification.

LC-MS (ESI, Method 5): m/z=1317 (M+Na)$^+$, 1295 (M+H)$^+$

LC-HR-FT-ICR-MS (Method 7): calc. for $C_{71}$; $H_{68}$; $F_5$; $N_4$; $O_{14}$; (M+H)$^+$1295.46467. found: 1295.46430.

Example 19A

Benzyl 5,17-bisbenzyloxy-14(S)-benzyloxycarbony-lamino-11(S)-(3-benzyloxycarbonylamino-2(R)-hydroxypropyl)-10,13-dioxo-9,12-diazatricyclo [14.3.1.1$^{2,6}$]henicosa-1(19),2,4,6(21),16(20),17-hexaene-8(S)-carboxylate

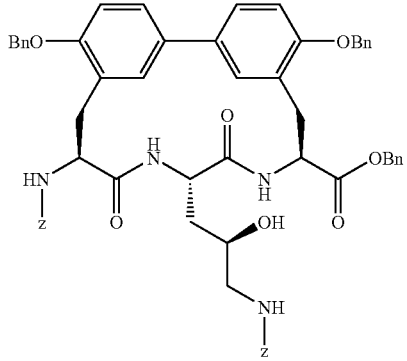

Method A:

4 ml of a 4M solution of hydrogen chloride in dioxane are added to a solution of 119.3 mg of benzyl 2(S)-(5-benzyloxy-carbonylamino-2(S)-tert-butoxycarbonylamino-4(R)-hydroxypentanoylamino)-3-[4,4'-bisbenzyloxy-3'-(2(S)-benzyloxycarbonylamino-2-pentafluorophenyloxycarbonylethyl)biphenyl-3-yl] propionate (Example 18A) in 2.7 ml of 1,4-dioxane. Until the reaction is complete, a further 1.5 ml of a 4M solution of hydrogen chloride in dioxane are added. The reaction solution is evaporated and codistilled with chloroform twice. The crude product (LC-HR-FT-ICR-MS, Method 7: calc. for $C_{66}H_{60}F_5N_4O_{12}$ (M+H)$^+$1195.41224, found 1195.41419) is dissolved in 100 ml of chloroform and added dropwise over the course of 3 h to a very strongly stirred suspension of 200 ml of chloroform and 100 ml of a saturated aqueous sodium bicarbonate solution. The reaction mixture is vigorously stirred for 2 h. After the two phases have separated, the aqueous phase is extracted with chloroform. The combined organic phases are washed with a 5% aqueous citric acid solution, dried over magnesium sulfate and evaporated to dryness. The crude product is washed with acetonitrile and dried under high vacuum.

Yield: 60.5 mg (65% of theory)
LC-MS (ESI, Method 5): m/z=101 (M+H)$^+$

Method B:

771 mg (0.595 mmol) of benzyl 2(S)-(5-benzyloxycarbonylamino-2(S)-tert-butoxycarbonylamino-4(R)-hydroxypentanoylamino)-3-[4,4'-bisbenzyloxy-3'-(2(S)-benzyloxycarbonylamino-2-pentafluorophenyloxycarbonylethyl)biphenyl-3-yl]propionate (Example 18A) are dissolved in 8 ml of dioxane and then, at 0° C., 16 ml of a 4N solution of hydrogen chloride in dioxane are added dropwise. After 45 min, 6 ml of a 4N solution of hydrogen chloride in dioxane are again added, and after 15 min a further 8 ml are added. The mixture is stirred at 0° C. for 30 min before the reaction solution is concentrated under mild conditions, codistilled with chloroform (twice) and briefly dried under high vacuum. The crude product (732 mg, 0.59 mmol) is dissolved in 1000 ml of chloroform, and a solution of 6 ml of triethylamine in 50 ml of chloroform is added dropwise. The mixture is stirred at RT overnight. For the work-up the mixture is concentrated under mild conditions on a rotary evaporator in vacuo and the residue is stirred in acetonitrile. The resulting crystals are collected by suction filtration, washed with acetonitrile and dried under high vacuum.

Yield: 360 mg (60% of theory)
MS (EI): m/z=101 (M+H)$^+$
HPLC (Method 1): R$_t$=5.59 min
$^1$H-NMR (400 MHz, DMSO-d$_6$): δ=1.52-1.65 (m, 1H), 1.73-1.84 (m, 1H), 2.82-3.01 (m, 3H), 3.02-3.11 (m, 1H), 3.46 (s, 1H), 3.57-3.68 (m, 1H), 4.47-4.56 (m, 1H), 4.64-4.71 (m, 1H), 4.73-4.85 (m, 2H), 4.88-5.00 (m, 4H), 5.09 (s, 2H), 5.14-5.20 (m, 4H), 6.29 (d, 1H), 7.00-7.11 (m, 4H), 7.21-7.40 (m, 20H), 7.41-7.48 (m, 9H), 8.77 (d, 1H), 8.87 (d, 1H).

Example 20A

14(S)-Amino-11(S)-(3-amino-2(R)-hydroxypropyl)-5,17-dihydroxy-10,13-dioxo-9,12-diazatricyclo[14.3.1.1$^{2,6}$]henicosa-1(19),2,4,6(21),16(20),17-hexaene-8(S)-carboxylic acid dihydrochloride (biphenomycin B)

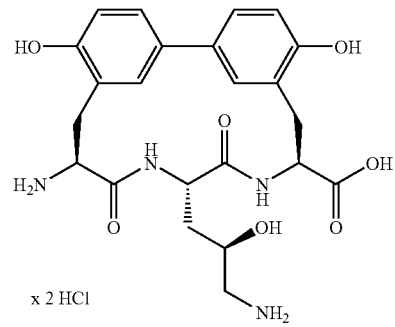

200 mg (0.20 mmol) of benzyl 5,17-bisbenzyloxy-14(S)-benzyloxycarbonylamino-1(S)-(3-benzyloxycarbonylamino-2(R)-hydroxypropyl)-10,13-dioxo-9,12-diazatricyclo[14.3.1.1$^{2,6}$]henicosa-1(19),2,4,6(21),16(20),17-hexaene-8(S)-carboxylate (Example 19A) are added to 220 ml of an acetic acid/water/ethanol 4:1:1 mixture (ethanol can be replaced by THF). 73 mg of 10% palladium/carbon (10% Pd/C) are added, and the mixture is hydrogenated under atmospheric pressure for 15 h. The reaction mixture is filtered through prewashed kieselguhr, and the filtrate is concentrated on a rotary evaporator in vacuo. The residue is mixed with 4.95 ml of 0.1N aqueous hydrochloric acid and concentrated. The residue is stirred with 10 ml of diethyl ether and decantered. The remaining solid is dried under high vacuum.

Yield: 103 mg (95% of theory).
HPLC (Method 1): R$_t$=3.04 min
LC-MS (Method 2): R$_t$=0.38 min
MS (EI): m/z=473 (M+H)$^+$
$^1$H-NMR (400 MHz, D$_2$O): δ=2.06-2.20 (m, 1H), 2.74-2.89 (m, 1H), 2.94-3.05 (m, 1H), 3.12-3.25 (m, 2H), 3.53 (d, 1H), 3.61-3.72 (m, 1H), 3.97-4.07 (m, 1H), 4.53 (s, 1H), 4.61 (d, 1H), 4.76-4.91 (m, 2H), 7.01-7.05 (m, 2H), 7.07 (s, 1H), 7.40-7.45 (m, 2H), 7.51 (d, 1H).

Example 21A

Benzyl 2(S)-tert-butoxycarbonylamino-5-nitro-4-oxopentanoate

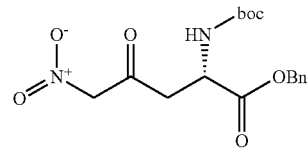

A solution A of 10 g (30.9 mmol) of 2(S)-tert-butoxycarbonylaminosuccinic acid 1-benzyl ester and 5.27 g (32.5 mmol) of 1,1'-carbonyldiimidazole in 100 ml of tetrahydrofuran is stirred at RT for 5 h. 18.8 g (30.9 mmol) of nitromethane are added dropwise to a solution B of 3.2 g (34.2 mmol) of potassium tert-butoxide in 100 ml of tetrahydrofuran at 0° C. Solution B is stirred while warming to RT, and then solution A is added dropwise at RT. The resulting mixture is stirred at RT for 16 h and adjusted to pH 2 using 20% hydrochloric acid. The solvent is evaporated. The remaining crude product is taken up in ethyl acetate/water. After separation of the phases, the organic phase is extracted twice with water, dried over sodium sulfate and concentrated. 13 g (99% of theory) of product are obtained.

MS (ESI): m/z=334 (M+H)$^+$ $^1$H-NMR (300 MHz, DMSO-d$_6$): δ=1.37 (s, 9H), 2.91 (m, 1H), 3.13 (m, 1H), 4.44 (m, 1H), 5.12 (s, 2H), 5.81 (m, 2H), 7.2-7.5 (m, 5H).

Example 22A

Benzyl 2(S)-tert-butoxycarbonylamino-4(R)-hydroxy-5-nitropentanoate

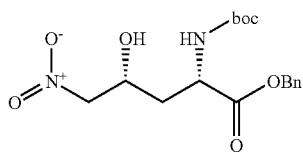

A solution of 11.3 g (30.8 mmol) of benzyl 2(S)-tert-butoxycarbonylamino-5-nitro-4-oxopentanoate in 300 ml of tetrahydrofuran is cooled to −78° C., 30.8 ml of a 1M solution of L-Selectride® in tetrahydrofuran are added dropwise, and the mixture is stirred at −78° C. for 1 h. After warming to RT, a saturated ammonium chloride solution is cautiously added to the solution. The reaction solution is concentrated, and the residue is taken up in water and ethyl acetate. The aqueous phase is extracted three times with ethyl acetate. The combined organic phases are dried over sodium sulfate and evaporated. The crude product is prepurified on silica gel 60 (mobile phase: cyclohexane/ethyl acetate 10/1), and the collected fractions are concentrated and stirred with cyclohexane/ethyl acetate 5/1. The remaining crystals are collected by suction filtration and dried. 2.34 g (21% of theory) of the desired diastereomer are obtained. Chromatographic separation of the mother liquor on Lichrospher Diol 10 µm (mobile phase: ethanol/isohexane 5/95) results in a further 0.8 g (6.7% of theory) of the product.

MS (ESI): m/z=369 (M+H)$^+$ $^1$H-NMR (300 MHz, DMSO-d$_6$): δ=1.38 (s, 9H), 1.77 (m, 1H), 1.97 (m, 1H), 4.10-4.44 (m, 3H), 4.67 (m, 1H), 5.12 (m, 2H), 5.49 (d, 1H), 7.25-7.45 (m, 5H).

Example 23A

Benzyl 2(S)-[S-benzyloxycarbonylamino-2(S)-tert-butoxycarbonylaminopentanoylamino]-3-{4,4'-bisbenzyloxy-3'-[2(S)-benzyloxycarbonylamino-2-(2-trimethylsilylethoxycarbonyl)ethyl]biphenyl-3-yl}propionate

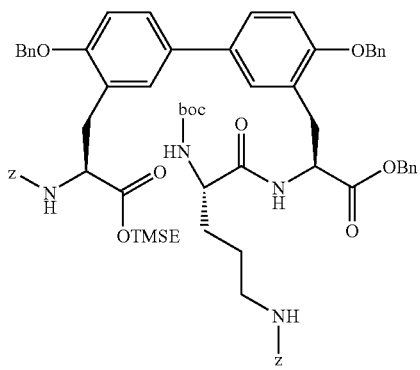

Preparation takes place in analogy to Example 16A from 0.47 g (0.51 mmol) of the compound from Example 15A and 0.19 g (0.51 mmol) of N$^5$-[(benzyloxy)carbonyl]-N$^2$-(tert-butoxycarbonyl)-L-ornithine with 0.19 g (0.51 mmol) of HATU and 0.35 ml (1.65 mmol) of N,N-diisopropylethylamine in 5.55 ml of dry DMF.

Yield: 0.58 g (92% of theory)

LC-MS (Method 10): R$_t$=3.46 min

MS (ESI): m/z=1212 (M+H)$^+$

Example 24A

2(S)-Benzyloxycarbonylamino-3-{4,4'-bisbenzyloxy-3'-[2(S)-benzyloxycarbonyl-2-(5-benzyloxycarbonylamino)-2(S)-tert-butoxycarbonylaminopentanoylamino)ethyl]biphenyl 3-yl}-propionic acid

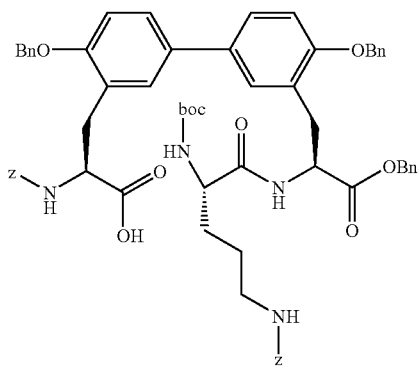

Preparation takes place in analogy to Example 17A from 0.82 g (0.68 mmol) of the compound from Example 23A with 2 equivalents (1.3 ml) of tetrabutylammonium fluoride (1M in THF) in 30 ml of dry DMF.

Yield: 772 mg (94% of theory)

LC-MS (Method 11): R$_t$=1.62 min

MS (ESI): m/z=1112 (M+H)$^+$

Example 25A

Benzyl 2(S)-(5-benzyloxycarbonylamino-2(S)-tert-butoxycarbonylaminopentanoylamino)-3-[4,4'-bis-benzyloxy-3'-(2(S)-benzyloxycarbonylamino-2-pentafluorophenyloxycarbonylethyl)biphenyl-3-yl]propionate

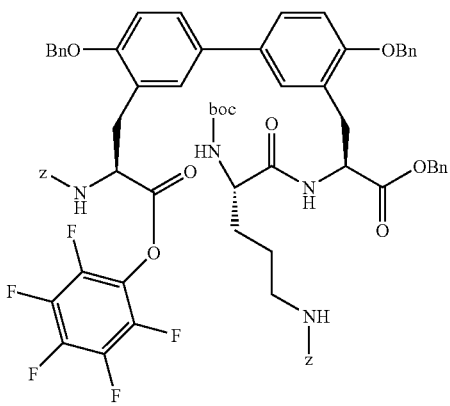

Preparation takes place in analogy to Example 18A from 422 mg (0.38 mmol) of the compound from Example 24A and 349 mg (1.9 mmol) of pentafluorophenol with 80 mg (0.42 mmol) of EDC and 4.63 mg (0.04 mmol) of DMAP in 4 ml of dichloromethane.

Yield: 502 mg (95% of theory)
LC-MS (Method 11): $R_t$=3.13 min
MS (ESI): m/z=1278 (M+H)$^+$

Example 26A

Benzyl 2(S)-(5-benzyloxycarbonylamino-2(S)-aminopentanoylamino)-3-[4,4'-bisbenzyloxy-3'-(2(S)-benzyloxycarbonylamino-2-pentafluorophenyloxycarbonylethyl)biphenyl-3-yl]propionate hydrochloride

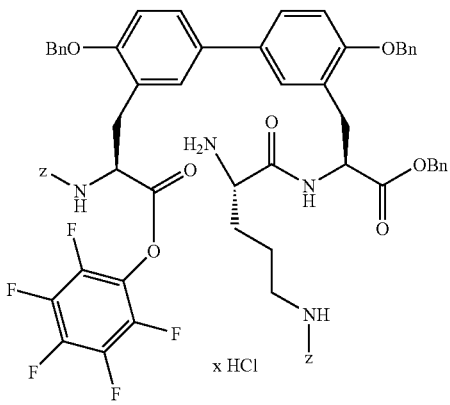

5 ml of a 4N solution of hydrogen chloride in dioxane are added to 215 mg (0.17 mmol) of the compound from Example 25A while stirring in an ice bath. The mixture is stirred for one hour and evaporated to constant weight in vacuo.

Yield: 200 mg (92% of theory)
LC-MS (Method 11): $R_t$=4.25 min
MS (ESI): m/z=1178 (M−HCl+H)$^+$

Example 27A

Benzyl 5,17-bisbenzyloxy-14(S)-benzyloxycarbonylamino-11(S)-(3-benzyloxycarbonylamiopropyl)-10,13-dioxo-9,12-diazatricyclo[14.3.1.1$^{2,6}$]henicosa-1(19),2,4,6(21),16(20),17-hexaene-8(S)-carboxylate

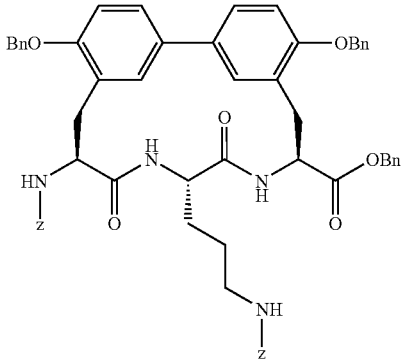

1.35 g (0.91 mmol) of the compound from Example 26A are provided in 3 l of chloroform and, while stirring vigorously, 2.54 ml (18.2 mmol) of triethylamine in 50 ml of chloroform are added at RT over the course of 20 min. The mixture is stirred overnight and evaporated to dryness in vacuo. The residue is stirred with 5 ml of acetonitrile and filtered, and the residue is dried to constant weight.

Yield: 890 mg (93% of theory)
LC-MS (Method 11): $R_t$=5.10 min
MS (ESI): m/z=994 (M+H)$^+$

Example 28A (8S,11S,14S)-14-Amino-11-(3-aminopropyl)-5,17-dihydroxy-10,13-dioxo-9,12-diazatricyclo[14.3.1.1$^{2,6}$]henicosa-1(20),2(21),3,5,6,18-hexaene-8-carboxylic acid dihydrochloride

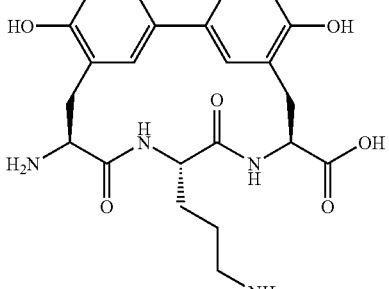

50 mg (0.05 mmol) of the compound from Example 27A are suspended in 50 ml of glacial acetic acid/water/ethanol (4/1/1), 30 mg of Pd/C (10%) catalyst are added, and the mixture is hydrogenated at RT for 20 hours. After removal of the catalyst by filtration through kieselguhr, the filtrate is evaporated to dryness in vacuo and, while stirring, 2.5 ml of 0.1N hydrochloric acid are added. The mixture is evaporated to dryness in vacuo and dried to constant weight.
Yieid: 17 mg (63% of theory)
TLC (methanol/dichloromethane/25% ammonia=5/3/2): $R_f$=0.6
LC-MS (Method 3): $R_t$=0.28 min
MS (ESI): m/z=457 (M−2HCl+H)$^+$ Example 29A (8S,11S,14S)-14-[(tert-Butoxycarbonyl)amino-11-[3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaene-8-carboxylic acid

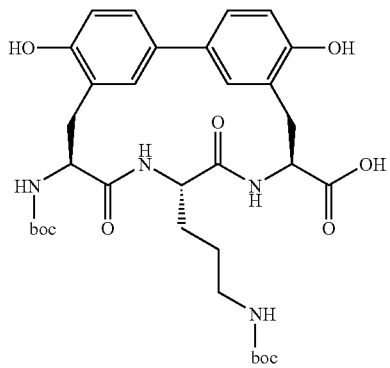

600 mg (1.13 mmol) of the compound from Example 28A are dissolved in 6 ml (5.66 mmol) of a 1N sodium hydroxide solution and, while stirring at room temperature, 740.8 mg (3.39 mmol) of di-tert-butyl dicarbonate, dissolved in 5 ml of methanol, are added. The reaction is complete after one hour (TLC check, mobile phase: dichloromethane/methanol/ammonia=80/20/2). The pH is adjusted to 3 by dropwise addition of 0.1N hydrochloric acid. The mixture is extracted three times with 20 ml of ethyl acetate each time, dried with sodium sulfate and evaporated to constant weight in vacuo.
Yieid: 622 mg (84% of theory)
LC-MS (Method 10): $R_t$=1.96 min
MS (ESI): m/z=656 (M+H)$^+$ Example 30A 2-(Benzyloxy)-N-(tert-butoxycarbonyl)-5-iodo-N-methyl-L-phenylalanine

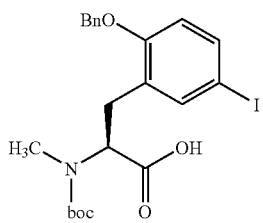

Under an argon atmosphere, 500 mg (1 mmol) of the compound from Example (−)-6A are dissolved in 20 ml of THF,
90.5 mg (3.02 mmol) of sodium hydride and 0.51 ml (141.6 mg; 8.04 mmol) of methyl iodide (80% pure) are added, and the mixture is stirred at room temperature overnight. The mixture is diluted with 25 ml of ethyl acetate and 25 ml of water and adjusted to pH=9 with 0.1N hydrochloric acid. The mixture is concentrated to a small volume in vacuo. 10 ml of ethyl acetate and 10 ml of water are added, the mixture is shaken vigorously, and the organic phase is separated. Drying with sodium sulfate and concentration in vacuo result in 140 mg of product (19% of theory). The aqueous phase is acidified (pH=3) and extracted three times with 20 ml of ethyl acetate. Concentration in vacuo and drying in vacuo result in 351 mg of product (68% of theory).
LC-MS (Method 9): $R_t$=3.9 min
MS (EI): m/z=511 (M+H)$^+$ Example 31A Benzyl 2-(benzyloxy)-N-(tert-butoxycarbonyl)-5-iodo-N-methyl-L-phenylalaninate

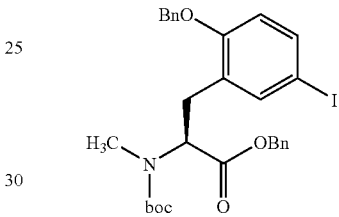

Preparation takes place in analogy to Example 7A from 350 mg (0.68 mmol) of the compound from Example 30A, 8.29 mg (0.07 mmol) of DMAP, 148 mg (1.37 mmol) of benzyl alcohol and 157.46 mg (0.82 mmol) of EDC in 3 ml of acetonitrile.
Yield: 382 mg (93% of theory)
LC-MS (Method 9): $R_t$=4.8 min
MS (EI): m/z=601 (M+H)$^+$ Example 32A Benzyl 2-(benzyloxy)-N-(tert-butoxycarbonyl)-N-methyl-5-(4,4,5,5-tetramethyl-1,3,2-dioxaborolan-2-yl)-L-phenylalaninate

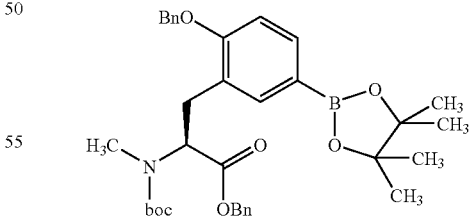

In analogy to Example 8A, 380 mg (0.63 mmol) of the compound from Example 31A are provided in 4 ml of DMF in a heat-dried flask and, while stirring at room temperature, 184.5 mg (0.73 mmol) of 4,4,4',4',5,5,5',5'-octamethyl-2,2'-bi-1,3,2-dioxaborolane, 186 mg (1.9 mmol) of potassium acetate and 23.15 mg (0.03 mmol) of bis(diphenylphosphino)ferrocenepalladium(II) chloride are added. Reaction is allowed to take place at 80° C. for 4 h. The product is obtained after workup and chromatography (silica gel 60, mobile phase: cyclohexane/ethyl acetate=4/1).

Yield: 196 mg
LC-MS (Method 9): R$_t$=4.9 min
MS (EI): m/z=601 (M+H)$^+$

Example 33A 2-(Trimethylsilyl)ethyl 2(S)-benzyloxycarbonylamino-3-[4,4'-bisbenzyloxy-3'-(2(S)-benzyloxycarbonyl-(2-tert-butoxycarbonyl-2-methyl)aminoethyl)biphenyl-3-yl]propionate

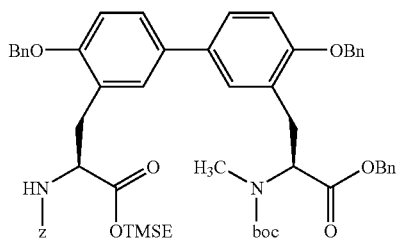

Preparation takes place in analogy to Example 12A from 190 mg (0.32 mmol) of the compound from Example 32A, 199.5 mg (0.32 mmol) of the compound from Example 11A, 195.5 mg (0.63 mmol) of cesium carbonate and 23.15 mg (0.03 mmol) of bis(diphenylphosphino)ferrocenepalladium (II) chloride in 1.5 ml of DMF under an argon atmosphere.

Yield: 212 mg (66% of theory)
LC-MS (Method 13): R$_t$=4.86 min
MS (EI): m/z=978 (M+H)$^+$ Example 34A 2-(Trimethylsilyl)ethyl 2(S)-benzyloxycarbonylamino-3-[4,4'-bisbenzyloxy-3'-(2(S)-benzyloxycarbonyl-2-methylaminoethylbiphenyl-3-yl]propionate hydrochloride

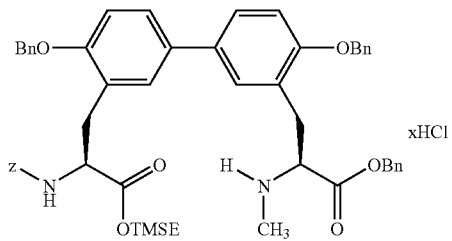

Preparation takes place in analogy to Example 15A from 930 mg (0.95 mmol) of the compound from Example 33A and 22.14 ml of a 4M solution of hydrogen chloride in dioxane, in 15 ml of dioxane.

Yield: 915 mg (78% of theory)
LC-MS (Method 13): R$_t$=2.53 min
MS (EI): m/z=878 (M−HCl+H)$^+$ Example 35A Benzyl 2(S)-{Methyl-[5-benzyloxycarbonylamino-2(S)-tert-butoxycarbonylamino-4(R)-(tert-butyldimethylsilyloxy)pentanoyl]amino}-3-{4,4'-bisbenzyloxy-3'-[12(S)-benzyloxycarbonylamino-2-(2-trimethylsilylethoxycarbonyl)ethyl]biphenyl 3-yl}propionate

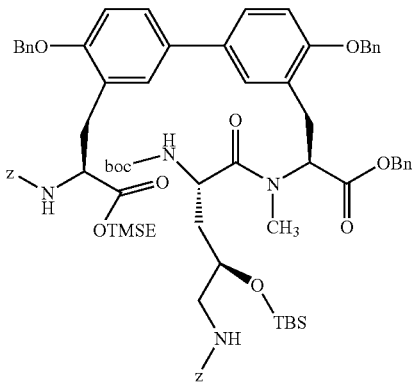

Preparation takes place in analogy to Example 16A from 922 mg (1.01 mmol) of the compound from Example 34A, 0.5 g (1.01 mmol) of the compound from Example 14A, 421 mg (1.11 mmol) of HATU and 0.7 ml (518 mg; 3.27 mmol) of DIEA in 4.2 ml of DMF.

Yield: 703 mg (51% of theory)
LC-MS (Method 8): R$_t$=3.17 min
MS (EI): m/z=1356 (M+H)$^+$ Example 36A 2(S)-Benzyloxycarbonylamino-3-{4,4'-bisbenzyloxy-3'-[2(S)-benzyloxycarbonyl-2-{methyl-(5-benzyloxycarbonylamino-2(S)-tert-butoxycarbonylamino-4(R)-hydroxypentanoyl)amino}ethyl]biphenyl-3-yl}propionic acid

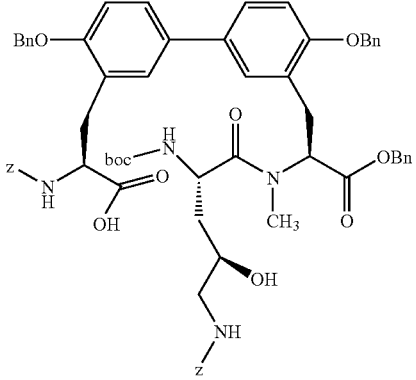

Preparation takes place in analogy to Example 17A from 360 mg (0.27 mmol) of the compound from Example 35A and 0.8 ml (3 equivalents) of a 1M tetrabutylammonium fluoride solution (THF) in 20 ml of DMF.

Yield: 159 mg (53% of theory)
LC-MS (Method 12): R$_t$=3.19 min
MS (EI): m/z=1142 (M+H)$^+$

Example 37A

Benzyl 2(S)-[methyl-(5-benzyloxycarbonylamino)-2(S)-tert-butoxycarbonylamino-4(R)-hydroxypentanoyl]amino-3-[4,4'-bisbenzyloxy-3'-(2(S)-benzyloxycarbonylamino-2-pentafluorophenyloxycarbonylethyl)biphenyl-3-yl]propionate

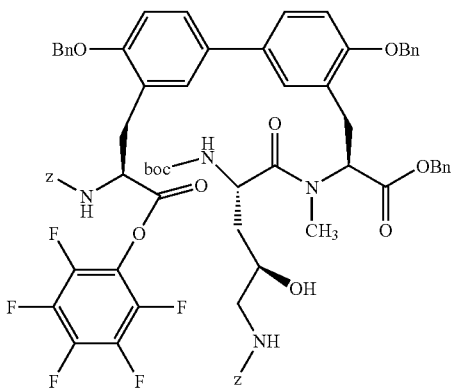

Preparation takes place in analogy to Example 18A from 330 mg (0.29 mmol) of the compound from Example 36A, 265.6 mg (1.44 mmol) of pentafluorophenol, 3.53 mg (0.03 mmol) of DMAP and 60.87 mg (0.32 mmol) of EDC in 10 ml of dichloromethane.

Yield: 271 mg (69% of theory)
LC-MS (Method 12): $R_t$=3.38 min
MS (EI): m/z=1308 (M+H)$^+$

Example 38A

Benzyl 2(S)-[methyl-(5-benzyloxycarbonylamino)-2(S)-amino-4(R)-hydroxy-pentanoyl]amino-3-[4,4'-bisbenzyloxy-3'-(2(S)-benzyloxycarbonylamino-2-pentafluorophenyloxycarbonylethyl)biphenyl-3-yl]propionate hydrochloride

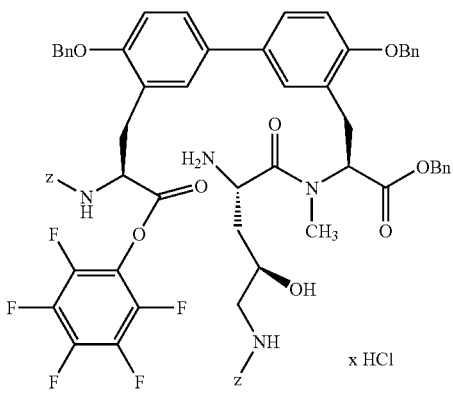

130 mg (0.1 mmol) of the compound from Example 37A are dissolved in 0.5 ml of dioxane, and 5 ml of a 4N solution of hydrogen chloride in dioxane are cautiously added (ice bath). After 30 minutes, the reaction is allowed to continue at room temperature for a further 2 h. The mixture is evaporated to dryness in vacuo and dried to constant weight under high vacuum.

Yield: 130 mg (70% of theory)
LC-MS (Method 15): $R_t$=2.68 min
MS (EI): m/z=1208 (M−HCl+H)$^+$

Example 39A

Benzyl(8S,11S,14S)-5,17-bis(benzyloxy)-14-{[(benzyloxy)carbonyl]amino}-11-((2R)-3-{[(benzyloxy)carbonyl]amino}-2-hydroxypropyl-9-methyl-10,13-dioxo-9,12-diazatricyclo[14.3.1.1$^{2,6}$]henicosa-1(20),2(21),3,5,16,18-hexaene-8-carboxylate

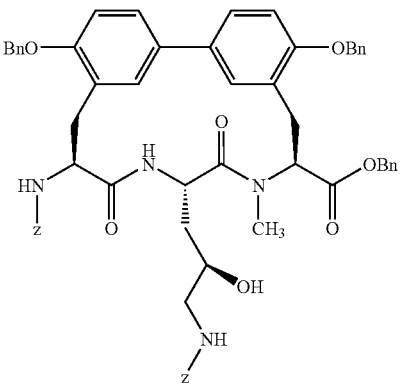

130 mg (0.1 mmol) of the compound from Example 38A are provided in 220 ml of dry chloroform. While stirring at room temperature, 23 ml (20 eq.) of triethylamine in 5 ml of dichloromethane are added over the course of 20 minutes. The mixture is stirred overnight. The mixture is then evaporated to dryness in vacuo. The residue is stirred with acetonitrile. After drying of the residue 44 mg of product are obtained. Further product (30 mg) is obtained from the mother liquor by RP-HPLC.

Yield: 74 mg (69% of theory)
LC-MS (Method 15): $R_t$=3.13 min
MS (EI): m/z=1024 (M+H)$^+$

Example 40A (8S,11S,14S)-14-Amino-11-[(2R)-3-amino-2-hydroxypropyl]-5,17-dihydroxy-9-methyl-10,13-dioxo-9,12-diazatricyclo[14.3.1.1$^{2,6}$]henicosa-1(20),2(21),3,5,16,18-hexaene-carboxylic acid di(hydrotrifluoroacetate)

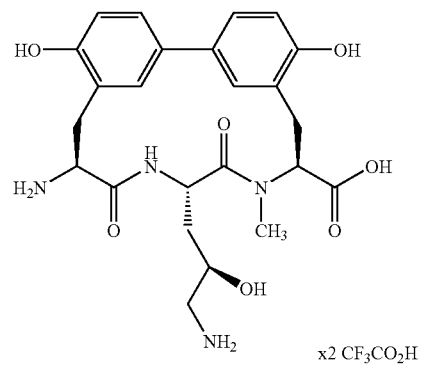

33 mg (0.032 mmol) of the compound from Example 39A are cautiously treated with dilute trifluoroacetic acid. The resulting clear solution is subsequently lyophilized.

Yield: 23 mg (quantitative)
LC-MS (Method 15): $R_t$=0.92 min
MS (EI): m/z=486 (M−2CF$_3$CO$_2$H+H)$^+$

Example 41A (8S,11S,14S)-5,17-Bis(benzyloxy)-14-{[benzyloxycarbonyl]amino}-11-(2R)-3-{[benzyloxycarbonyl]amino}-2-hydroxypropyl-9-methyl-10,13-dioxo-9,12-diazatricyclo[14.3.1.1²,⁶]henicosa-1(20),2(21),3,5,16,18-hexaene-8-carboxylic acid

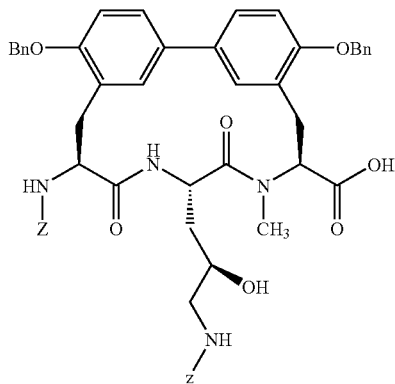

37 mg (0.04 mmol) of the compound from Example 39A are dissolved in 2 ml of THF, 0.14 ml of a 1N lithium hydroxide solution are added, and the mixture is stirred at room temperature for 3 h. The mixture is then acidified with 1N hydrochloric acid and evaporated to dryness under high vacuum.

Yield: 33 mg (71% of theory)

LC-MS (Method 12): $R_t$=2.90 min

MS (EI): m/z=934 (M+H)$^+$

Examples 42A to 48A listed in the following table are prepared from the appropriate starting materials in analogy to the methods detailed above:

| Ex. No. | Structure | Prepared in analogy to | Analytical data |
|---|---|---|---|
| 42A | 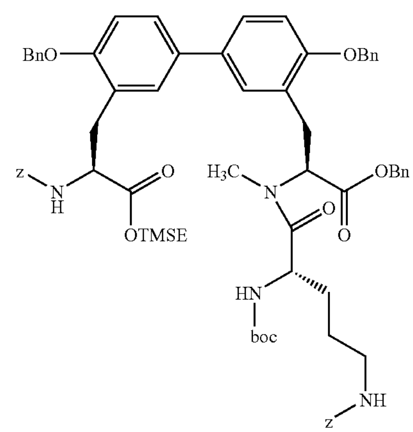 | 16A with N⁵-[(benzyloxy)-carbonyl]-N²-(tert-butoxy-carbonyl)-L-ornithine | LC-MS (Method 13): $R_t$ = 4.85 min. MS (EI): m/z = 1226 (M + H)$^+$ |
| 43A | 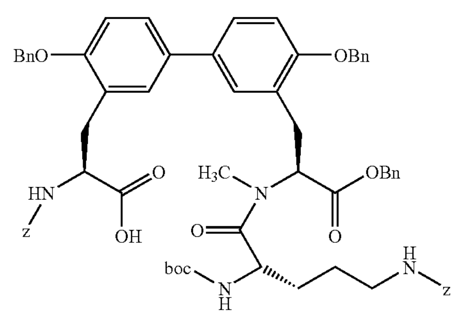 | 17A | LC-MS (Method 13): $R_t$ = 2.04 min. MS (EI): m/z = 1126 (M + H)$^+$ |

-continued

| Ex. No. | Structure | Prepared in analogy to | Analytical data |
|---|---|---|---|
| 44A | 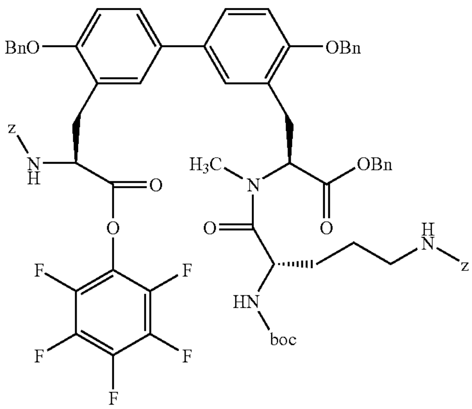 | 18A | LC-MS (Method 13): $R_t$ = 3.79 min. MS (EI): m/z = 1292 (M + H)$^+$ |
| 45A | 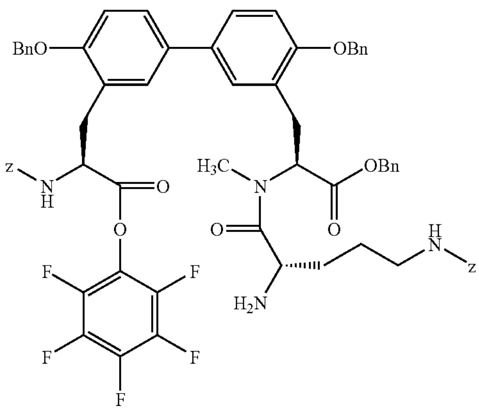 | 26A | LC-MS (Method 13): $R_t$ = 3.72 min. MS (EI): m/z = 1192 (M − HCl + H)$^+$ |
| 46A | 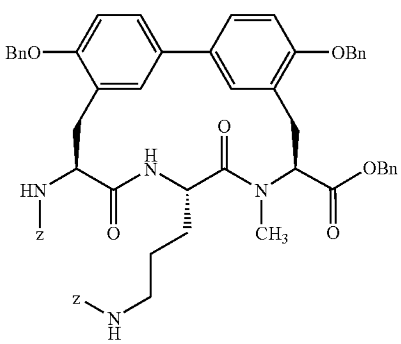 | 39A | LC-MS (Method 13): $R_t$ = 4.39 min. MS (EI): m/z = 1008 (M + H)$^+$ |
| 47A | 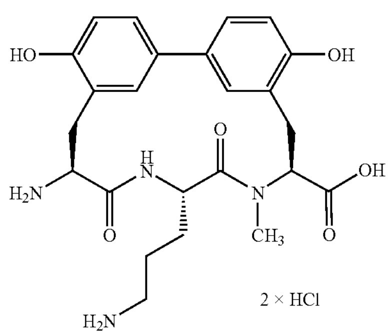 | 40A | LC-MS (Method 12): $R_t$ = 0.53 min. MS (EI): m/z = 470 (M − 2HCl + H)$^+$ |

| Ex. No. | Structure | Prepared in analogy to | Analytical data |
|---|---|---|---|
| 48A | -continued | 41A | LC-MS (Method 14): $R_t$ = 3.64 min. MS (EI): m/z = 918 (M + H)$^+$ |

Example 49A 2-(Trimethylsilyl)ethyl(2Z)-3-[2-(benzyloxy)-5-bromophenyl]-2-{[(benzyloxy)carbonyl]amino}acrylate

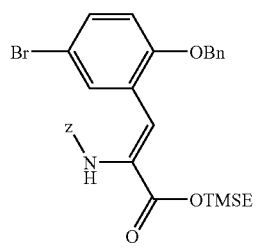

7.5 g (25.8 mmol) of 2-(benzyloxy)-5-bromobenzaldehyde (*Synthesis* (1992) 10: 1025-1030) and 11.8 g (28.3 mmol) of 2-(trimethylsilyl)ethyl{[(benzyloxy)carbonyl]amino}(dimethoxyphosphoryl)acetate (*Tetrahedron* (1999) 55:10527-10536) are provided in 150 ml of THF and, while cooling at −78° C. in acetone/dry ice, 3.26 g (28.3 mmol) of 1,1,3,3-tetramethylguanidine are added. The mixture is slowly warmed to RT and stirred at RT for a further 12 h. The solvent is distilled off in vacuo, and the crude product is taken up in ethyl acetate and washed once each with a saturated sodium bicarbonate solution and a saturated sodium chloride solution. The organic phase is dried over magnesium sulfate, filtered and concentrated to dryness in vacuo. The crude product is recrystallized from ethyl acetate/cyclohexane (1:20).

Yield: 13 g (88% of theory)
HPLC (Method 16): $R_t$=6.06 min
MS (DCI(NH$_3$)): m/z=599 (M+NH$_4$)$^+$

Example 50A (8S,11S,14S)-5,17-Bis(benzyloxy)-14-{[(benzyloxy)carbonyl]amino}-11-(3-{[(benzyloxy)carbonyl]amino}propyl)-10,13-dioxo-9,12-diazatricyclo[14.3.1.1$^{2,6}$]henicosa-1(20),2(21),3,5,16,18-hexaene-8-carboxylic acid

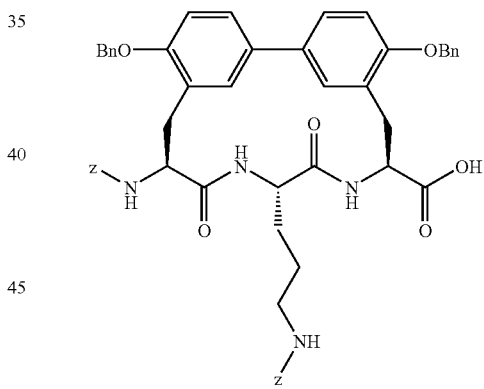

200 mg (0.2 mmol) of the compound from Example 27A are provided in 8 ml of THF and 4 ml of DMF and, while stirring, 0.8 ml of a 1M aqueous lithium hydroxide solution (4 equivalents) are added. A gel is formed after stirring at room temperature for 2 h. 0.8 ml of 1N hydrochloric acid and a little water are added. The mixture is then evaporated to dryness in vacuo, stirred with water, and the precipitate is filtered and dried.

Yield: 140 mg (77% of theory)
LC-MS (Method 10): $R_t$=2.83 min
MS (EI): m/z=904 (M+H)$^+$

Example 51A (8S,11S,14S)-14-[(tert-Butoxycarbonyl)amino]-11-{3-[(tert-butoxycarbonyl)amino]propyl}-5,17-dihydroxy-9-methyl-10,13-dioxo-9,12-diazatricyclo[14.3.1.1$^{2,6}$]henicosa-1(20),2(21),3,5,16,18-hexaene-8-carboxylic acid

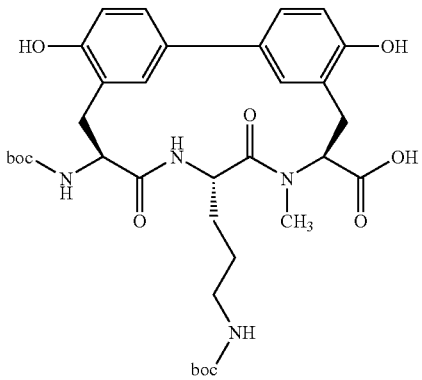

11 mg (0.02 mmol) of the compound from Example 47A are dissolved in 0.5 ml of water, 12.27 mg (0.08 mmol) of sodium carbonate are added, the mixture is cooled in an ice bath and, while stirring, 13.25 mg (0.06 mmol) of di-tert-butyl dicarbonate in 0.2 ml of methanol are added. The mixture is stirred at RT overnight, evaporated to dryness in vacuo, dissolved in 0.5 ml of water and acidified to pH=2 with 1N hydrochloric acid, and the resulting suspension is extracted with ethyl acetate. Drying with sodium sulfate is followed by evaporation to dryness in vacuo.

Yield: 10 mg (51% of theory)
LC-MS (Method 12): $R_t$=1.92 min
MS (EI): m/z=670 (M+H)$^+$

Example 52A (8S,11S,14S)-14-[(tert-Butoxycarbonyl)amino]-11-{(2R)-3-[(tert-butoxycarbonyl)amino]-2-hydroxypropyl}-5,17-dihydroxy-9-methyl-10,13-dioxo-9,12-diazatricyclo[14.3.1.1$^{2,6}$]henicosa-1(20),2(21),3,5,16,18-hexaene-8-carboxylic acid

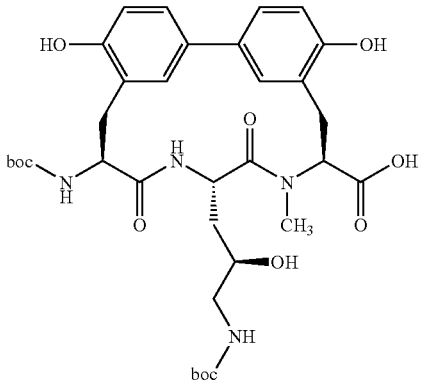

90 mg (0.16 mmol) of the compound from Example 40A are dissolved in 2.5 ml of water, 85.3 mg (0.8 mmol) of sodium carbonate are added, the mixture is cooled in an ice bath, and 105.3 mg (0.48 mmol) of di-(tert-butyl)dicarbonate in 1.2 ml of methanol are added. The mixture is stirred at room temperature overnight, concentrated in vacuo to a small volume and acidified to pH=2 with 1N hydrochloric acid. The resulting precipitate is collected by filtration and dried.

Yield: 89 mg (73% of theory)
LC-MS (Method 12): $R_t$=1.8 min
MS (EI): m/z=686 (M+H)$^+$

Example 53A 2-(Trimethylsilyl)ethyl 2-(benzyloxy)-N-[(benzyloxy)carbonyl]-5-bromo-L-phenylalaninate

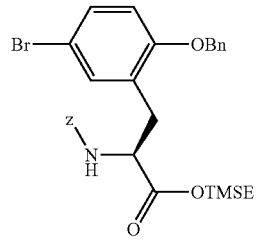

930 mg (1.6 mmol) of the compound from Example 49A are dissolved in 100 ml of ethanol and 10 ml of dioxane. Under an argon atmosphere, 20 mg of (+)-1,2-bis((2S,5S)-2,5-diethylphospholano)benzene(cyclooctadiene)rhodium(I) trifluoromethanesulfonate are added, and the solution is left in an ultrasonic bath for 15 min. The mixture is then hydrogenated under a hydrogen pressure of 3 bar for 5 d. The mixture is filtered through silica gel and carefully washed with ethanol. The filtrate is concentrated in vacuo, and the crude product is dried under high vacuum.

Yield: 900 mg (96% of theory)
ee=98.8% (Chiralcel OD (Daicel); eluent: i-hexane and ethanol (5/1 vol/vol) with addition of 0.2% by volume diethylamine)
HPLC (Method 16): $R_t$=6.08 min
MS (DCI(NH$_3$)): m/z=601 (M+NH$_4$)$^+$

Example 54A

Methyl(2Z)-3-[2-(benzyloxy)-5-bromophenyl]-2-{[(benzyloxy)carbonyl]amino}acrylate

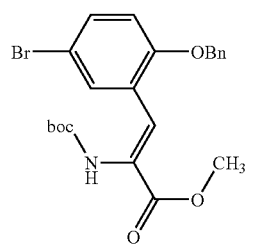

Preparation takes place in analogy to Example 49A from 7.5 g (25.8 mmol) of 2-(benzyloxy)-5-bromobenzaldehyde and 8.4 g (28.3 mmol) of 2-(trimethylsilyl)ethyl{[benzyloxy)carbonyl]amino}(dimethoxyphosphoryl)acetate (*J. Prakt. Chem.* (2000) 342: 736-744) with 3.3 g (28.3 mmol) of 1,1,3,3-tetramethylguanidine in 150 ml of THF.

Yield: 10 g (87% of theory)
HPLC (Method 16): $R_t$=5.42 min
MS (DCI(NH$_3$)): m/z=479 (M+NH$_4$)$^+$

Example 55A

Methyl 2-(benzyloxy)-N-[(benzyloxy)carbonyl]-5-bromo-L-phenylalaninate

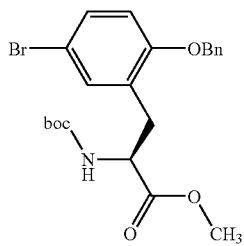

Preparation takes place in analogy to Example 53A from 1.96 g (4.2 mmol) of the compound from Example 54A and 15 mg of (+)-1,2-bis((2S,5S)-2,5-diethylphospholano)benzene(cyclooctadiene)rhodium(I) trifluoromethanesulfonate in 100 ml of ethanol and 20 ml of dioxane.

Yield: 1.96 g (99% of theory)

ee=97.6% (Chiralcel OD (Daicel); eluent: i-hexane and ethanol (5/1 vol/vol) with addition of 0.2% by volume diethylamine)

LC-MS (Method 17): $R_t$=3.05 min

MS (DCI(NH$_3$)): m/z=481 (M+NH$_4$)$^+$ $^1$H-NMR (300 MHz, DMSO-d$_6$): δ=1.32 (s, 9H), 2.72 (m$_c$, 1H), 3.17 (m$_c$, 1H), 3.60 (s, 3H), 4.32 (m$_c$, 1H), 5.13 (s, 2H), 7.01 (m$_c$, 1H), 7.22 (m$_c$, 1H), 7.28-7.58 (m$_c$, 6H).

Example 56A

Methyl 2-(benzyloxy)-N-(tert-butoxycarbonyl)-5-(4,4,5,5-tetramethyl-1,3,2-dioxaborolan-2-yl)-L-phenylalaninate

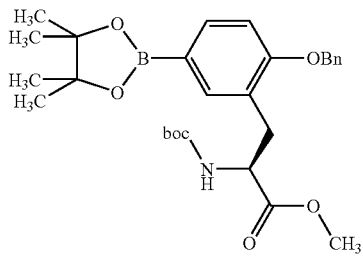

0.23 g (2.31 mmol) of potassium acetate and 4 mg (0.08 mmol) of potassium hydroxide are added to a solution of 0.36 g (0.77 mmol) of the compound from Example 55A in 5 ml of DMF. The mixture is deoxygenated by passing argon through the vigorously stirred solution for 15 min. Then 0.25 g (1.0 mmol) of 4,4,4',4',5,5,5',5'-octamethyl-2,2'-bi-1,3,2-dioxaborolane and 0.023 g (0.03 mmol, 0.04 equivalents) of bis(diphenylphosphino)ferrocenepalladium(II) chloride are added. The mixture is heated under a gentle stream of argon to 60° C. and stirred at this temperature for 1.5 h. The mixture is subsequently stirred at 80° C. for 30 min and then cooled to RT. The solvent is distilled off in vacuo, and the crude product is taken up with ethyl acetate and washed twice with a saturated sodium chloride solution. The organic phase is dried over magnesium sulfate, filtered and evaporated to dryness in vacuo. The residue is purified by chromatography (RP-HPLC, acetonitrile, water).

Yield: 0.219 g (56% of theory)

MS (EI): m/z=512 (M+H)$^+$ $^1$H-NMR (400 MHz, DMSO-d$_6$): δ=1.27 (m$_c$, 12H), 1.29 (s, 9H), 2.75 (m$_c$, 1H), 3.19 (m$_c$, 1H), 3.57 (s, 3H), 4.30 (m$_c$, 1H), 5.19 (m$_c$, 2H), 7.04 (m$_c$, 1H), 7.24 (m$_c$, 1H), 7.28-7.58 (m, 6H).

Example 57A 2-(Trimethylsilyl)ethyl 2-(benzyloxy)-N-[(benzyloxy)carbonyl]-5-(4,4,5,5-tetramethyl-1,3,2-dioxaborolan-2-yl)-L-phenylalaninate

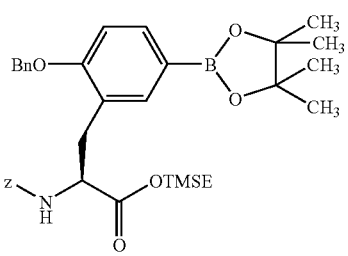

Preparation takes place in analogy to Example 8A from 2.0 g (3.17 mmol) of the compound from Example 11A, 0.924 g (3.64 mmol) of 4,4,4',4',5,5,5',5'-octamethyl-2,2'-bi-1,3,2-dioxaborolane, 0.932 g (9.50 mmol) of potassium acetate and 0.116 g (0.160 mmol, 0.05 equivalents) of bis(diphenylphosphino)ferrocenepalladium(II) chloride in 30 ml of dimethyl sulfoxide.

Yield: 1.12 g (56% of theory)

LC-MS (Method 13): $R_t$=4.50 min

MS (EI): m/z=632 (M+H)$^+$ $^1$H-NMR (200 MHz, CDCl$_3$): δ=0.92 (dd, 2H), 1.31 (s, 12H), 2.95-3.95 (m, 2H), 4.11 (m$_c$, 2H), 4.55 (11 (m$_c$, 1H), 4.99 (s, 2H), 5.08 (s, 2H), 5.53 (d, 1H), 6.90 (d, 1H), 7.15-7.47 (m, 10H), 7.58 (d, 1H), 7.67 (dd, 1H).

Example 58A 2-(Trimethylsilyl)ethyl(2S)-2-{[(benzyloxyl)carbonyl]amino}-3-(4,4'-bis(benzyloxy)-3'-{(2S)-2-[(tert-butoxycarbonyl)amino]-3-methoxy-3-oxopropyl}biphenyl-3-yl)propanoate

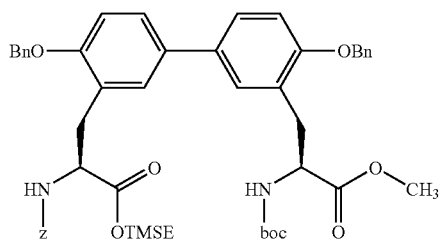

Method A:

Preparation takes place in analogy to Example 12A from 0.46 g (0.79 mmol) of the compound from Example 53A, 0.41 g (0.79 mmol) of the compound from Example 56A, 0.52 g (1.58 mmol) of cesium carbonate and 0.023 g (0.032 mmol, 0.04 equivalents) of bis(diphenylphosphino)ferrocenepalladium(II) chloride in 12 ml of DMF.

Yield: 0.34 g (48% of theory)

Method B:

Preparation takes place in analogy to Example 53A from 0.59 g (0.67 mmol) of the compound from Example 69A and 10 mg of (+)-1,2-bis((2S,5S)-2,5-diethylphospholano)benzene(cyclooctadiene)rhodium(I) trifluoromethanesulfonate in 100 ml of ethanol and 30 ml of dioxane.

Yield: 0.60 g (99% of theory)

ee=99.5% (chiral stationary silica gel phase, based on the selector poly(N-methacryloyl-L-leucine L-menthylamide); eluent: i-hexane and ethyl acetate (2/1 vol/vol))

HPLC (Method 16): $R_t$=6.54 min

MS (EI): m/z=890 (M+H)$^+$ $^1$H-NMR (400 MHz, DMSO-d$_6$): δ=0.00 (s, 9H), 0.83 (m$_c$, 2H), 1.31 (s, 9H), 2.86 (m, 2H), 3.25 (m, 2H), 3.62 (s, 3H), 4.09 (m, 2H), 4.41 (m$_c$, 1H), 4.98 (m$_c$, 2H), 5.22 (m, 4H), 7.12 (m, 2H), 7.29 (m, 2H), 7.33-7.59 (m, 20H), 7.78 (d, 1H).

Examples 59A to 64A listed in the following table are prepared from the appropriate starting materials in analogy to the methods detailed above:

| Ex. No. | Structure | Prepared in analogy to | Analytical data |
|---|---|---|---|
| 59A | 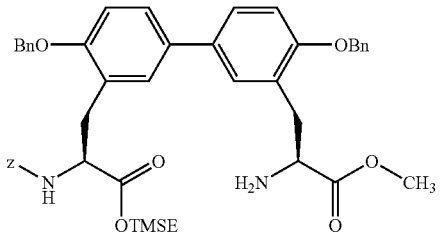 | 15A | LC-MS (Method 12):<br>$R_t$ = 2.50 min.<br>MS (EI): m/z = 789<br>(M − HCl + H)$^+$ |
| 60A | 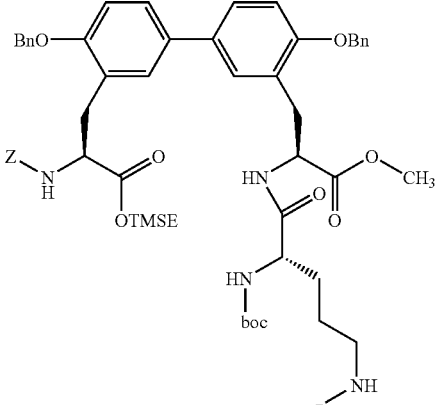 | 16A | LC-MS (Method 13):<br>$R_t$ = 3.51 min.<br>MS (EI): m/z = 1137<br>(M + H)$^+$ |
| 61A | 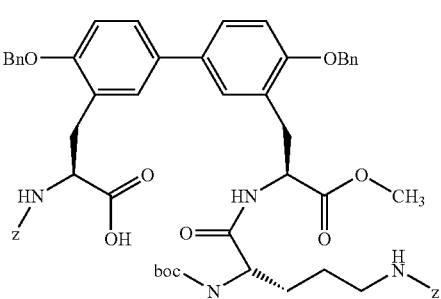 | 17A | LC-MS (Method 13):<br>$R_t$ = 3.20 min.<br>MS (EI): m/z = 1037<br>(M + H)$^+$ |

-continued

| Ex. No. | Structure | Prepared in analogy to | Analytical data |
|---|---|---|---|
| 62A | (structure) | 18A | LC-MS (Method 19): $R_t$ = 3.43 min. MS (EI): m/z = 1203 $(M + H)^+$ |
| 63A | (structure) | 26A | LC-MS (Method 12): $R_t$ = 2.83 min. MS (EI): m/z = 1103 $(M - HCl + H)^+$ |
| 64A | (structure) | 39A | LC-MS (Method 12): $R_t$ = 3.10 min. MS (EI): m/z = 919 $(M + H)^+$ |

Example 65A (8S,11S,14S)-14-[(tert-Butoxycarbonyl)amino]-11-{(2R)-3-[(tert-butoxycarbonyl)amino]-2-hydroxypropyl}-5,17-dihydroxy-10,13-dioxo-9,12-diazatricyclo[14.3.1.1$^{2,6}$]henicosa-1(20),2(21),3,5,16,18-hexaene-8-carboxylic acid

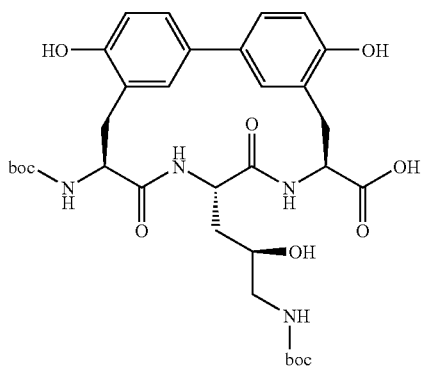

50 mg (0.09 mmol) of the compound from Example 20A are provided in 8 ml of a methanol/water (9:1) mixture. 1 ml of a 1N sodium bicarbonate solution and then 80 mg (0.37 mmol) of di-tert-butyl dicarbonate in 2 ml of methanol/water (9:1) are added. The mixture is stirred at RT overnight. For the work-up 60 ml of ethyl acetate and 30 ml of water are added to the solution. The organic phase is washed once with 0.1N hydrochloric acid, dried and concentrated on a rotary evaporator in vacuo.

Yield: 49 mg (79% of theory)
LC-MS (Method 3): $R_t$=2.56 min
MS (EI): m/z=673 (M+H)$^+$
LC-HR-FT-ICR-MS: calc. for $C_{33}$; $H_{44}$; $N_4$; $O_{11}$ ; (M+H)$^+$ 673.3079.
found: 673.3082.

Example 66A

Benzyl(8S,11S,14S)-5,17-bis(benzyloxy)-14-{[(benzyloxy)carbonyl]amino}-11-((2R)-3-{[(benzyloxy)carbonyl]amino}-2-{[tert-butyl(dimethyl)silyl]oxy}propyl)-10,13-dioxo-9, 12-diazatricyclo[14.3.1.1$^{2,6}$]henicosa-1(20),2(21),3,5,16,18-hexaene-8-carboxylate

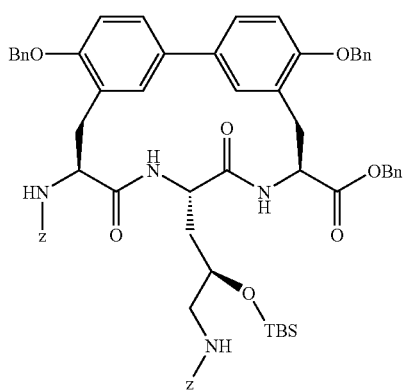

200 mg (0.20 mmol) of the compound from Example 19A are dissolved in 50 ml of absolute DMF and, at 0° C., 210 mg (0.79 mmol) of tert-butyldimethylsilyl trifluoromethanesulfonate, 0.11 ml (0.79 mmol) of triethylamine and 20 mg (0.20 mmol) of DMAP are added. The mixture is stirred at RT for 2 d. After the addition of 20 ml of dichloromethane, the solution is cautiously washed with 10 ml of a saturated sodium bicarbonate solution and 10 ml of water. The organic phase is concentrated to dryness, and the residue is dried under high vacuum.

Yield: 215 mg (96% of theory)
LC-MS (Method 12): $R_t$=3.43 min
MS (EI): m/z=1125 (M+H)$^+$

Example 67A (8S,11S,14S)-5,17-Bis(benzyloxy)-14-{[(benzyloxy)carbonyl]amino}-11-((2R)-3-{[(benzyloxy)carbonyl]amino}-2-{[tert-butyl(dimethyl)silyl]oxy}propyl)-10,13-dioxo-9,12-diazatricyclo[14.3.1.1$^{2,6}$]henicosa-1(20),2(21),3,5,16,18-hexaene-8-carboxylic acid

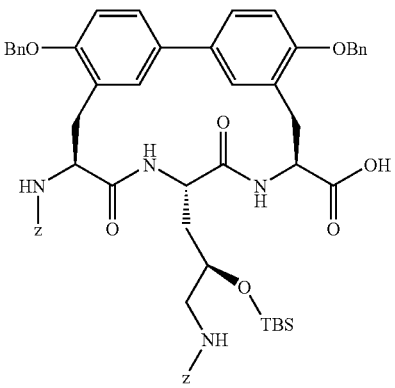

210 mg (0.19 mmol) of the compound from Example 66A are dissolved in 2 ml of THF, and 1 ml each of water and methanol are added. After the addition of 13 mg (0.56 mmol) of lithium hydroxide the mixture is stirred at RT for 12 h. The reaction solution is then diluted with 30 ml of water and adjusted to pH=3 by adding 1N hydrochloric acid. The precipitate is collected by filtration and dried under high vacuum.

Yield: 192 mg (99% of theory)
LC-MS (Method 12): $R_t$=3.24 min
MS (EI): m/z=1135 (M+H)$^+$

Example 68A

Methyl(2Z)-3-[2-(benzyloxy)-5-(4,4,5,5-tetramethyl-1,3,2-dioxaborolan-2-yl)phenyl]-2-[(tert-butoxycarbonyl)amino]acrylate

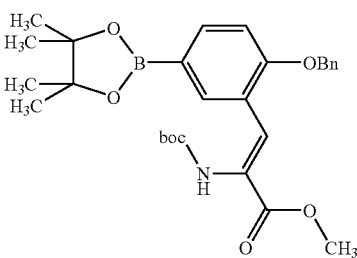

Preparation takes place in analogy to Example 8A from 1.0 g (2.16 mmol) of the compound from Example 54A, 0.63 g (2.5 mmol) of 4,4,4',4',5,5,5',5'-octamethyl-2,2'-bi-1,3,2-dioxaborolane, 0.64 g (6.50 mmol) of potassium acetate and 0.063 g (0.087 mmol, 0.04 equivalents) of bis(diphenylphosphino)ferrocenepalladium(II) chloride in 14 ml of dimethylsulfoxide.

Yield: 0.832 g (76% of theory)
LC-MS (Method 12): $R_t$=2.96 min.
MS (EI): m/z=510 (M+H)$^+$ Example 69A 2-(Trimethylsilyl)ethyl-(2Z)-2-{[(benzyloxy)carbonyl]amino}-3-(4,4'-bis(benzyloxy)-3'-{(1Z)-2-[(tert-butoxycarbonyl)amino]-3-methoxy-3-oxoprop-1-en-1-yl}biphenyl-3-yl)acrylate

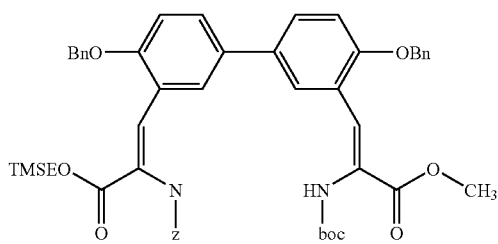

Preparation takes place in analogy to Example 12A from 0.42 g (0.82 mmol) of the compound from Example 68A, 0.48 g (0.82 mmol) of the compound from Example 49A, 0.54 g (1.65 mmol) of cesium carbonate and 0.024 g (0.033 mmol, 0.04 equivalents) of bis(diphenylphosphino)ferrocenepalladium(II) chloride in 12 ml of DMF.

Yield: 0.47 g (64% of theory)
HPLC (Method 16): $R_t$=6.57 min
MS (EI): m/z=886 (M+H)$^+$ Example 70A 2-(Benzyloxy)-N-(tert-butoxycarbonyl)-5-iodo-N-ethyl-L-phenylalanine

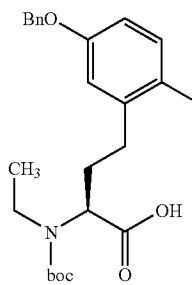

Under an argon atmosphere, 1.0 g (2.01 mmol) of the compound from Example (–)-6A is dissolved in 40 ml of THF, and 241 mg (6.03 mmol) of sodium hydride (60% dispersion in mineral oil), 1.0 g (6.03 mmol) of potassium iodide and 1.29 ml (2509 mg; 16.1 mmol) of ethyl iodide are added, and the mixture is stirred at room temperature overnight. The mixture is concentrated in vacuo. The crude product is taken up in ethyl acetate, and the organic phase is washed several times with water, dried over sodium sulfate and concentrated in vacuo. The crude product is purified by RP-HPLC chromatography (mobile phase acetonitrile/water gradient).

Yield: 470 mg (44% of theory).
LC-MS (Method 12): $R_t$=2.79 min.
MS (EI): m/z=526 (M+H)$^+$ Example 71A Benzyl 2-(benzyloxy)-N-(tert-butoxycarbonyl)-5-iodo-N-ethyl-L-phenylalaninate

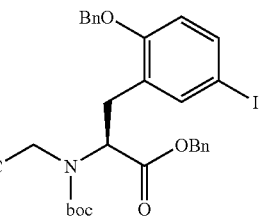

Preparation takes place in analogy to Example 7A from 420 mg (0.68 mmol) of the compound from Example 70A, 9.77 mg (0.08 mmol) of DMAP, 173 mg (1.6 mmol) of benzyl alcohol and 184 mg (0.96 mmol) of EDC in 8 ml of acetonitrile.

Yield: 375 mg (76% of theory)
LC-MS (Method 12): $R_t$=3.26 min.
MS (EI): m/z=616 (M+H)$^+$
$^1$H-NMR (300 MHz, CDCl$_3$): δ=0.80 (m$_c$, 3H), 1.4 (m$_c$, 9H) 2.75 (m$_c$, 1H), 3.07 (m$_c$, 1H), 3.22 (m$_c$, 1H), 3.47 (m$_c$, 1H), 4.23 (m$_c$, 1H), 5.06 (s, 2H), 5.15 (m$_c$, 2H), 6.65 (d, 1H), 7.25-7.5 (m, 12H).

Example 72A 2-(Trimethylsilyl)ethyl 2(S)-benzyloxycarbonylamino-3-[4,4'-bis-benzyloxy-3'-(2(S)-benzyloxycarbonyl-(2-tert-butoxycarbonyl-2-ethyl)aminoethyl) biphenyl 3-yl]propionate

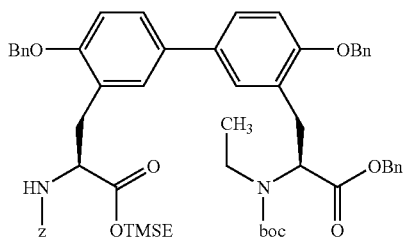

Preparation takes place in analogy to Example 12A from 343 mg (0.54 mmol) of the compound from Example 57A, 334 mg (0.54 mmol) of the compound from Example 71A, 354 mg (1.09 mmol) of cesium carbonate and 40 mg (0.05 mmol) of bis(diphenylphosphino)ferrocenepalladium(II) chloride in 8 ml of DMF under an argon atmosphere.

Yield: 216 mg (40% of theory)
LC-MS (Method 12): $R_t$=3.54 min.
MS (EI): m/z=893 (M−boc+H)$^+$

Example 73A 2-(Trimethylsilyl)ethyl 2(S)-benzyloxycarbonylamino-3-[4,4'-bis-benzyloxy-3'-(2(S)-benzyloxycarbonyl-2-ethylaminoethylbiphenyl-3-yl]propionate hydrochloride

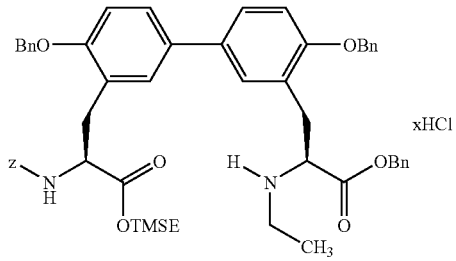

Preparation takes place in analogy to Example 15A from 210 mg (0.211 mmol) of the compound from Example 72A and 15 ml of a 4N solution of hydrogen chloride in dioxane in 4 ml of dioxane.

Yield: quantitative

LC-MS (Method 12): Rt=3.01 min.

MS (EI): m/z=893 (M−HCl+H)+

Examples 74A to 78A listed in the following table are prepared from the appropriate starting materials in analogy to the methods detailed above:

| Ex. No. | Structure | Prepared in analogy to | Analytical data |
|---|---|---|---|
| 74A | (structure) | 16A with $N^5$-[(benzyloxy)-carbonyl]-$N^2$-(tert-butoxy-carbonyl)-L-ornithine | LC-MS (Method 17): $R_t$ = 3.63 min. MS (EI): m/z = 1241 (M + H)+ |
| 75A | (structure) | 17A | LC-MS (Method 17): $R_t$ = 3.38 min. MS (EI): m/z = 1149 (M + H)+ |

-continued

| Ex. No. | Structure | Prepared in analogy to | Analytical data |
|---|---|---|---|
| 76A | 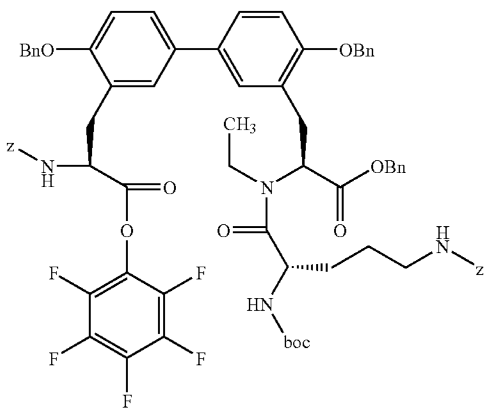 | 18A | LC-MS (Method 17): $R_t$ = 3.58 min. MS (EI): m/z = 1315 $(M + H)^+$ |
| 77A | 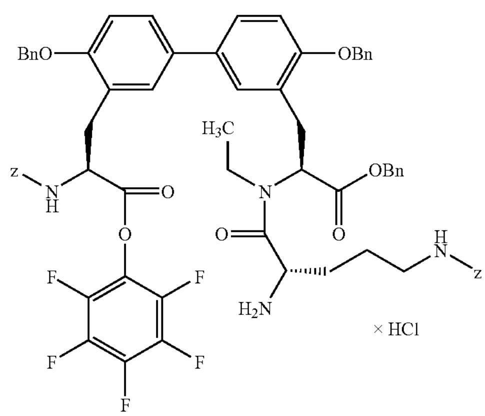 | 26A | |
| 78A | 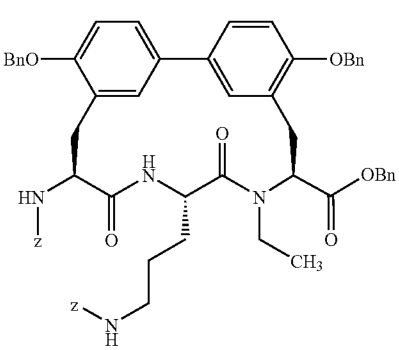 | 39A | LC-MS (Method 17): $R_t$ = 3.39 min. MS (EI): m/z = 931 $(M + H)^+$ |

Example 79A

Benzyl{(1S)-4-[(tert-butoxycarbonyl)amino]-1-[({2-[(tert-butoxycarbonyl)amino]ethyl}amino)carbonyl]butyl}carbamate

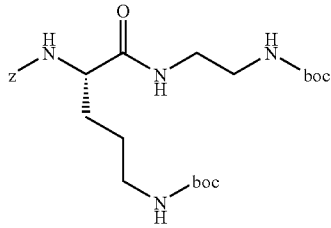

Under argon, 300 mg (0.82 mmol) of $N^2$-[(benzyloxy)carbonyl]-$N^5$-(tert-butoxycarbonyl)-L-ornithine and 171 mg (1.06 mmol) of tert-butyl-(2-aminoethyl)carbamate are dissolved in 6 ml of dimethylformamide. Then, at 0° C. (ice bath), 204 mg (1.06 mmol) of EDC and 33 mg (0.25 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is dried under high vacuum.

Yield: 392 mg (94% of theory)
LC-MS (Method 17): $R_t$=2.36 min.
MS (EI): m/z=509 (M+H)$^+$

Example 80A

Benzyl{(1S)-4-[(tert-butoxycarbonyl)amino]-1-[({3-[(tert-butoxycarbonyl)amino]-2-hydroxypropyl}amino)carbonyl]butyl}carbamate

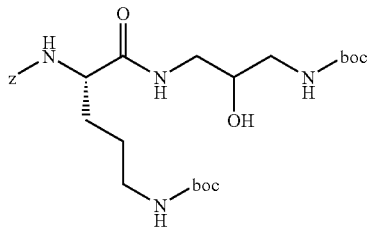

Preparation takes place in analogy to Example 79A from 300 mg (0.82 mmol) of $N^2$-[(benzyloxy)carbonyl]-$N^5$-(tert-butoxycarbonyl)-L-ornithine and 202 mg (1.06 mmol) of tert-butyl(3-amino-2-hydroxypropyl)carbamate in 6 ml of dimethylformamide with the addition of 204 mg (1.06 mmol) of EDC and 33 mg (0.25 mmol) of HOBt.

Yield: 412 mg (93% of theory)
LC-MS (Method 19): $R_t$=2.23 min.
MS (EI): m/z=539 (M+H)$^+$

Example 81A $N^5$-(tert-Butoxycarbonyl)-N-{2-[(tert-butoxycarbonyl)amino]ethyl}-L-ornithinamide

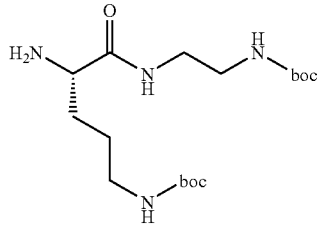

A solution of 390 mg (0.77 mmol) of benzyl{(1S)-4-[(tert-butoxycarbonyl)amino]-1-[({2-[(tert-butoxycarbonyl)amino]ethyl}amino)carbonyl]butyl}carbamate (Example 79A) in 50 ml of ethanol is hydrogenated after the addition of 40 mg of palladium on activated carbon (10%) at RT under atmospheric pressure for 4 h. The mixture is filtered through kieselguhr, and the residue is washed with ethanol. The filtrate is evaporated to dryness in vacuo. The product is reacted without further purification.

Yield: 263 mg (91% of theory)
MS (ESI): m/z=375 (M+H)$^+$; 397 (M+Na)$^+$.

Example 82A $N^5$-(tert-Butoxycarbonyl)-N-{3-[(tert-butoxycarbonyl)amino]-2-hydroxypropyl}-L-ornithinamide

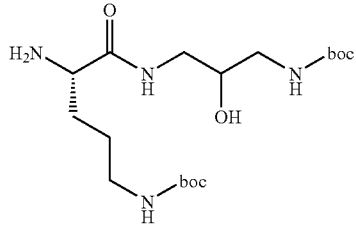

Preparation takes place in analogy to Example 81A from 412 mg (0.76 mmol) of benzyl{(1S)-4-[(tert-butoxycarbonyl)amino]-1-[({3-[(tert-butoxycarbonyl)amino]-2-hydroxypropyl}amino)carbonyl]butyl}carbamate (Example 80A) in 50 ml of ethanol with the addition of 41 mg of palladium on activated carbon (10%). The product is reacted without further purification.

Yield: 306 mg (99% of theory)
MS (ESI): m/z=405 (M+H)$^+$.

Example 83A tert-Butyl[(1S)-4-[(tert-butoxycarbonyl)amino]-1-(hydroxymethyl)butyl]carbamate

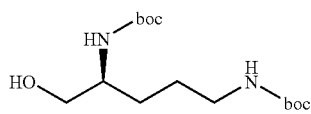

91 mg (0.90 mmol) of 4-methylmorpholine and 98 mg (0.90 mmol) of ethyl chloroformate are added to a solution of 300 mg (0.90 mmol) of $N^2,N^5$-bis(tert-butoxycarbonyl)-L-ornithine in 10 ml of tetrahydrofuran at −10° C., and the mixture is stirred for 30 min. At this temperature, 1.81 ml (1.81 mmol) of a 1M solution of lithium aluminum hydride in tetrahydrofuran are slowly added dropwise. The mixture is slowly warmed to RT and stirred at RT for 12 h. While cooling in ice, 0.1 ml of water and 0.15 ml of a 4.5% sodium hydroxide solution are cautiously added, and the mixture is stirred at RT for a further 3 h. The mixture is filtered and the filtrate is concentrated in vacuo. The residue is dissolved in ethyl acetate, washed with water, dried over magnesium sulfate and again evaporated to dryness in vacuo. The product is reacted without further purification.

Yield: 239 mg (83% of theory)

MS (ESI): m/z=319 (M+H)$^+$; 341 (M+Na)$^+$.

Example 84A (2S)-2,5-Bis[(tert-butoxycarbonyl)amino]pentyl methanesulfonate

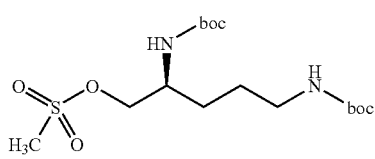

103 mg (0.90 mmol) of methanesulfonyl chloride and 0.21 ml (1.5 mmol) of triethylamine are added to a solution of 240 mg (0.75 mmol) of tert-butyl[(1S)-4-[(tert-butoxycarbonyl)amino]-1-(hydroxymethyl)butyl]carbamate (Example 83A) in 20 ml of dichloromethane, and the mixture is stirred at RT for 16 h. The mixture is diluted with dichloromethane and washed twice with 0.1N hydrochloric acid. The organic phase is dried over magnesium sulfate and evaporated to dryness in vacuo. The product is reacted without further purification.

Yield: 218 mg (73% of theory)

MS (ESI): m/z=419 (M+Na)$^+$.

Example 85A tert-Butyl-{(4S)-5-azido-4-[(tert-butoxycarbonyl)amino]pentyl}carbamate

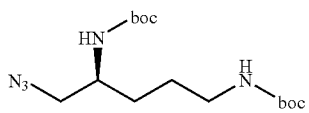

A solution of 218 mg (0.55 mmol) of (2S)-2,5-bis[(tert-butoxycarbonyl)amino]pentyl methanesulfonate (Example 84A) in 15 ml of dimethylformamide is mixed with 36 mg (0.55 mmol) of sodium azide and stirred at 70° C. for 12 h. Most of the solvent is removed by distillation in vacuo, and the residue is diluted with ethyl acetate. The mixture is washed several times with a saturated sodium bicarbonate solution, dried over magnesium sulfate and evaporated to dryness in vacuo. The product is reacted without further purification.

Yield: 188 mg (99% of theory)

MS (ESI): m/z=344 (M+H)$^+$.

Example 86A tert-Butyl{(4S)-5-amino-4-[(tert-butoxycarbonyl)amino]pentyl}carbamate

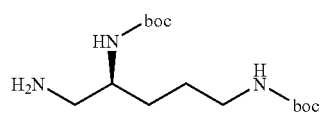

A solution of 188 mg (0.55 mmol) of tert-butyl{(4S)-5-azido-4-[(tert-butoxycarbonyl)amino]pentyl}carbamate (Example 85A) in ethanol is hydrogenated after the addition of 20 mg of palladium on activated carbon (10%) at RT under atmospheric pressure for 12 h. The mixture is filtered through kieselguhr, and the residue is washed with ethanol. The filtrate is evaporated to dryness in vacuo. The product is reacted without further purification.

Yield: 102 mg (59% of theory)

MS (ESI): m/z=318 (M+H)$^+$; 340 (M+Na)$^+$.

Example 87A

Benzyl[(1S)-3-[(tert-butoxycarbonyl)amino]-1-(hydroxymethyl)propyl]carbamate

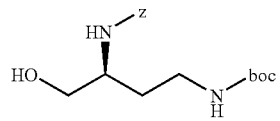

Preparation takes place in analogy to Example 83A from 300 mg (0.85 mmol) of (2S)-2-{[(benzyloxy)carbonyl]amino}-4-[(tert-butoxycarbonyl)amino]butanoic acid in 10 ml of tetrahydrofuran with 86 mg (0.85 mmol) of 4-methylmorpholine, 92 mg (0.85 mmol) of ethyl chloroformate and 1.7 ml (1.70 mmol) of a 1M solution of lithium aluminum hydride in tetrahydrofuran. The product is reacted without further purification.

Yield: 229 mg (80% of theory)

LC-MS (Method 12): R$_t$=1.83 min.

MS (EI): m/z=339 (M+H)$^+$; 239 (M-C$_5$H$_8$O$_2$+H)$^+$.

Example 88A tert-Butyl[(3S)-3-amino-4-hydroxybutyl]carbamate hydrochloride

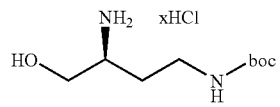

Preparation takes place in analogy to Example 81A from 229 mg (0.68 mmol) of benzyl[(1S)-3-[(tert-butoxycarbonyl)amino]-1-(hydroxymethyl)propyl]carbamate (Example 87A) in 50 ml of ethanol with the addition of 23 mg of palladium on activated carbon (10%). The crude product is stirred in 1 ml of 1N hydrochloric acid and evaporated in vacuo and dried to constant weight under high vacuum.

Yieid: 183 mg (90% of theory)

MS (ESI): m/z=205 (M–HCl+H)+.

Example 89A tert-Butyl{(3S)-3-[(tert-butoxycarbonyl)amino]-4-hydroxybutyl}carbamate

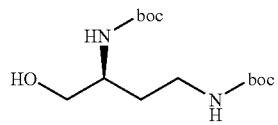

Preparation takes place in analogy to Example 83A from 300 mg (0.60 mmol) of (2S)-2,4-bis[(tert-butoxycarbonyl)amino]butanoic acid-N-cyclohexylcyclohexanamine (1:1) in 10 ml of tetrahydrofuran with 61 mg (0.60 mmol) of 4-methylmorpholine, 65 mg (0.60 mmol) of ethyl chloroformate and 1.2 ml (1.20 mmol) of a 1M solution of lithium aluminum hydride in tetrahydrofuran. The product is reacted without further purification.

Yieid: 174 mg (95% of theory)

MS (ESI): m/z=305 (M+H)+.

Example 90A (2S)-2,4-Bis[(tert-butoxycarbonyl)amino]butyl methanesulfonate

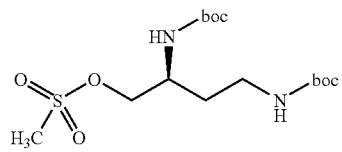

Preparation takes place in analogy to Example 84A from 250 mg (0.81 mmol) of tert-butyl{(3S)-3-[(tert-butoxycarbonyl)amino]-4-hydroxybutyl}carbamate (Example 89A) in 20 ml of dichloromethane with 110 mg (0.97 mmol) of methanesulfonyl chloride and 0.23 ml (1.6 mmol) of triethylamine. The product is reacted without further purification.

Yieid: 200 mg (64% of theory)

MS (ESI): m/z=383 (M+H)+; 400 (M+Na)+.

Example 91A tert-Butyl{(3S)-4-azido-3-[(tert-butoxycarbonyl)amino]butyl}carbamate

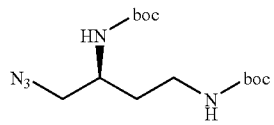

Preparation takes place in analogy to Example 85A from 200 mg (0.52 mmol) of (2S)-2,4-bis[(tert-butoxycarbonyl)amino]butyl methanesulfonate (Example 90A) in 15 ml of dimethylformamide with 34 mg (0.52 mmol) of sodium azide. The product is reacted without further purification.

Yieid: 171 mg (99% of theory)

Example 92A tert-Butyl{(3S)-4-amino-3-[(tert-butoxycarbonyl)amino]butyl}carbamate

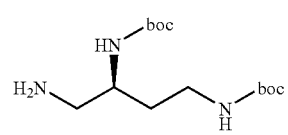

Preparation takes place in analogy to Example 86A from 171 mg (0.52 mmol) of tert-butyl{(3S)-4-azido-3-[(tert-butoxycarbonyl)amino]butyl}carbamate (Example 91A) in 10 ml of ethanol with the addition of 20 mg of palladium on activated carbon (10%). The product is reacted without further purification.

Yieid: 117 mg (75% of theory)

MS (ESI): m/z=304 (M+H)+; 326 (M+Na)+.

Example 93A

Benzyl((4S)-4-[(tert-butoxycarbonyl)amino]-5-{[(1S)-3-[(tert-butoxycarbonyl)amino]-1-(hydroxymethyl)propyl]amino}-5-oxopentyl)carbamate

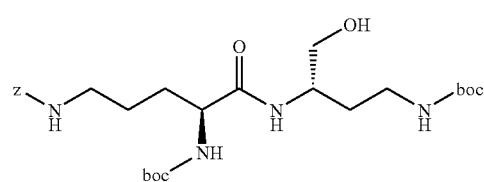

Preparation takes place in analogy to Example 79A from 140 mg (0.38 mmol) of $N^5$-[(benzyloxy)carbonyl]-$N^2$-(tert-butoxycarbonyl)-L-ornithine and 120 mg (0.50 mmol) of tert-butyl [(3S)-3-amino-4-hydroxybutyl]carbamate hydrochloride (Example 88A) in 6 ml of dimethylformamide with the addition of 96 mg (0.50 mmol) of EDC, 16 mg (0.12 mmol) of HOBt and 0.17 ml (1.00 mmol) of diisopropylethylamine. The product is purified by preparative RP-HPLC (mobile phase water/acetonitrile gradient: 90:10→10:90).

Yieid: 50 mg (23% of theory)

LC-MS (Method 19): $R_t$=2.24 min.

MS (EI): m/z=553 (M+H)+

Example 94A

N²-(tert-Butoxycarbonyl)-N-[(1S)-3-[(tert-butoxycarbonyl)amino]-1-(hydroxymethyl)propyl]-L-ornithinamide

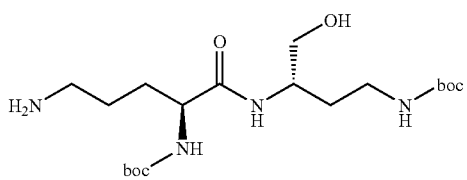

Preparation takes place in analogy to Example 81A from 50 mg (0.09 mmol) of benzyl((4S)-4-[(tert-butoxycarbonyl)amino]-5-{[(1S)-3-[(tert-butoxycarbonyl)amino]-1-(hydroxymethyl)propyl]amino}-5-oxopentyl)carbamate (Example 93A) in 50 ml of ethanol with the addition of 5 mg of palladium on activated carbon (10%). The product is reacted without further purification.

Yield: 37 mg (98% of theory)
MS (ESI): m/z=419 (M+H)⁺

Example 95A

Benzyl{2-[((2S,4R)-5-{[(benzyloxy)carbonyl]amino}-2-[(tert-butoxycarbonyl)amino]-4-{[tert-butyl(dimethyl)silyl]oxy}pentanoyl)amino]ethyl}carbamate

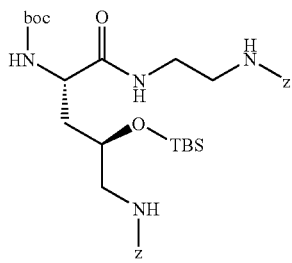

85 mg (0.17 mmol) of 5-benzyloxycarbonylamino-2 (S)-tert-butoxycarbonylamino-4 (R)-(tert-butyldimethylsilanyloxy)pentanoic acid (Example 14A), 67.1 mg (0.29 mmol) of benzyl-(2-aminoethyl)carbamate hydrochloride and 0.05 ml (0.29 mmol) of diisopropylethylamine are dissolved in 3 ml of DMF and cooled to 0° C. 55.8 mg (0.29 mmol) of EDC and 7.6 mg (0.06 mmol) of HOBT are added, and the mixture is allowed to warm to room temperature and is stirred overnight.

The mixture is then concentrated in vacuo and purified by chromatography on silica gel (dichloromethane/methanol 20:1)

Yield: 73 mg (59% of theory).
LC-MS (Method 12): $R_t$=3.04 min.
MS (EI): m/z=673 (M+H)⁺.

Example 96A

Benzyl{2-[((2S,4R)-2-amino-5-{[(benzyloxy)carbonyl]amino}-4-{[tert-butyl(dimethyl)silyl]oxy}pentanoyl)amino]ethyl}carbamate hydrochloride

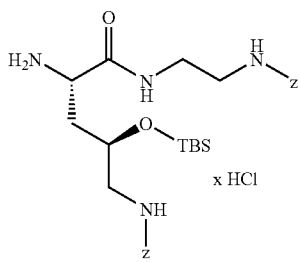

53 mg (0.08 mmol) of the compound from Example 95A are cooled to 0° C., and 1 ml of 4N hydrogen chloride in dioxane is added. After 1 h, concentration in vacuo results in the title compound.

Yield: 41 mg (90% of theory).
LC-MS (Method 17): $R_t$=1.60 min.
MS (EI): m/z=459 (M−HCl+H)⁺.

Example 97A (2S)-2-{[(Benzyloxy)carbonyl]amino}-4-[(tert-butoxycarbonyl)amino]butanoic acid

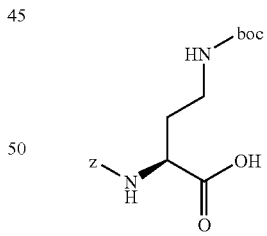

500 mg (1.98 mmol) of (2S)-4-amino-2-{[(benzyloxy)carbonyl]amino}butanoic acid are dissolved in 5 ml of water and 5 ml of a 1N sodium hydroxide solution. 649 mg (2.97 mmol) of di-tert-butyl dicarbonate in 2 ml of methanol are added. The mixture is briefly heated to 30° C. in a water bath and stirred at room temperature overnight. After concentration in vacuo, purification by chromatography on silica gel (dichloromethane/methanol/concentrated ammonia solution 85:15:3) results in the title compound.

Yield: 740 mg (99% of theory).
LC-MS (Method 17): $R_t$=2.08 min.
MS (EI): m/z=353 (M+H)⁺.

Example 98A

Benzyl{(1S)-3-[(tert-butoxycarbonyl)amino]-1-[({3-[(tert-butoxycarbonyl)amino]-2-hydroxypropyl}amino)carbonyl]propyl}carbamate

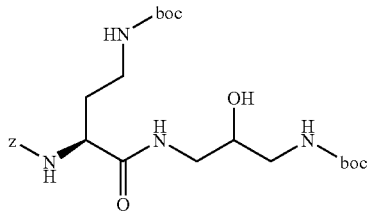

44 mg (0.12 mmol) of the compound from Example 97A and 40 mg (0.21 mmol) of tert-butyl(3-amino-2-hydroxypropyl)carbamate are dissolved in 1 ml of DMF and cooled to 0° C., and 40.3 mg (0.21 mmol) of EDC and 5.51 mg (0.04 mmol) of HOBt are successively added. The mixture is allowed to warm to room temperature and is stirred overnight. After concentration in vacuo, purification by chromatography on silica gel (dichloromethane/methanol 20:1) results in the title compound.

Yieid: 38 mg (59% of theory).
LC-MS (Method 17): $R_t$=2.25 min.
MS (EI): m/z=525 (M+H)$^+$.

Example 99A tert-Butyl[3-({(2S)-2-amino-4-[(tert-butoxycarbonyl)amino]butanoyl}amino)-2-hydroxypropyl]carbamate

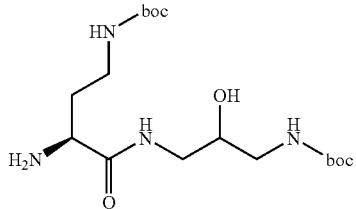

38 mg (0.12 mmol) of the compound from Example 98A are dissolved in 10 ml of methanol, and 10 mg of palladium on activated carbon (10%) are added. The mixture is hydrogenated under atmospheric pressure for 2 h and filtered through kieselguhr, and the mother liquor is concentrated in vacuo.

Yieid: 26 mg (75% of theory).
LC-MS (Method 12): $R_t$=1.10 min.
MS (EI): m/z=391 (M+H)$^+$.

Example 100A

Benzyl[(1S)-2-({3-[(tert-butoxycarbonyl)amino]-2-hydroxypropyl}amino)-1-(hydroxymethyl)-2-oxoethyl]carbamate

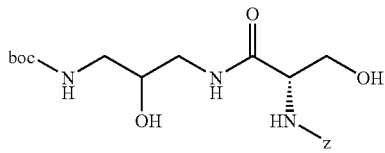

362.8 mg (0.954 mmol) of HATU and 123.3 mg (0.954 mmol) of N,N-diisopropylethylamine are added to a solution of 207.5 mg (0.867 mmol) of N-[(benzyloxy)carbonyl]-L-serine in 10 ml of anhydrous DMF. After stirring at RT for 15 min, 165 mg (0.867 mmol) of tert-butyl(3-amino-2-hydroxypropyl)carbamate are added. The reaction mixture is stirred at RT for 15 h. The solvent is then evaporated and the residue is taken up in dichloromethane. The organic phase is washed with water, dried over magnesium sulfate and concentrated. The crude product is purified by preparative HPLC.

Yield 175 mg (49% of theory)
LC-MS (Method 12): $R_t$=1.56 min.
MS (EI): m/z=412 (M+H)$^+$.

Example 101A

N-{3-[(tert-Butoxycarbonyl)amino]-2-hydroxypropyl}-L-serinamide

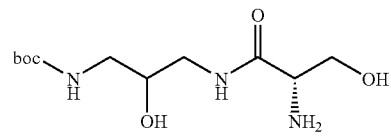

131 mg (0.318 mmol) of benzyl[(1S)-2-({3-[(tert-butoxycarbonyl)amino]-2-hydroxypropyl}amino)-1-(hydroxymethyl)-2-oxoethyl]carbamate (Example 100A) are dissolved in 20 ml of ethanol. 20 mg of palladium on activated carbon (10%) are added thereto, and the mixture is hydrogenated under atmospheric pressure for 15 h. The reaction mixture is filtered through prewashed kieselguhr, and the filtrate is concentrated in vacuo on a rotary evaporator. The crude product is reacted without further purification.

Yieid: 63 mg (71% of theory).
LC-MS (Method 19): $R_t$=0.53 min
MS (EI): m/z=278 (M+H)$^+$.

Example 102A

Benzyl(2-{[N$^5$-[{[(benzyloxy)carbonyl]amino}(imino)methyl]-N$^2$-(tert-butoxycarbonyl)-L-ornithyl]amino}ethyl)carbamate

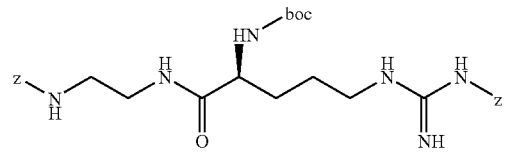

419.3 mg (1.1 mmol) of HATU and 258.5 mg (2 mmol) of N,N-diisopropylethylamine are added to a solution of 408.4 mg (1 mmol) of N$^5$-[{[(benzyloxy)carbonyl]amino}(imino)methyl]-N$^2$-(tert-butoxycarbonyl)-L-ornithine in 15 ml of anhydrous DMF. After stirring at RT for 15 min, 253.76 mg (1.1 mmol) of benzyl (2-aminoethyl)carbamate hydrochloride are added. The reaction mixture is stirred at RT for 15 h. The solvent is then evaporated and the residue is taken up in dichloromethane. The organic phase is washed with water, dried over magnesium sulfate and concentrated. The crude product is purified by preparative HPLC.

Yieid: 334 mg (41% of theory)
LC-MS (Method 17): $R_t$=1.94
MS (EI): m/z=585 (M+H)$^+$.

Example 103A

Benzyl[(6S)-6-amino-7,12-dioxo-14-phenyl-13-oxa-2,8,11-triazatetradecan-1-imidoyl]carbamate hydrochloride

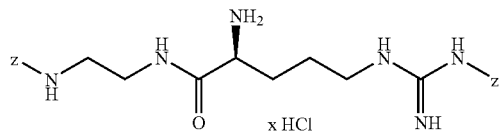

A mixture of 334 mg (0.417 mmol) of benzyl (2-{[N$^5$-[{[(benzyloxy)carbonyl]amino}(imino)methyl]-N$^2$-(tert-butoxycarbonyl)-L-ornithyl]amino}ethyl)carbamate (Example 102A) and 17 ml of a 4M solution of hydrogen chloride in dioxane is stirred at RT for 4 h. The reaction solution is concentrated, coevaporated with dichloromethane several times, and dried under high vacuum. The crude product is reacted without further purification.

Yield: quant.
LC-MS (Method 12): R$_t$=1.05 min.
MS (EI): m/z=485 (M−HCl+H)$^+$.

Example 104A

Benzyl[2-({(3S)-3-{[(benzyloxy)carbonyl]amino}-6-[(tert-butoxycarbonyl)amino]hexanoyl}amino)ethyl]carbamate

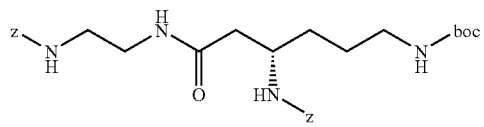

549.7 mg (1.446 mmol) of HATU and 339.7 mg (2.629 mmol) of N,N-diisopropylethylamine are added to a solution of 500 mg (1.31 mmol) of (3S)-3-{[(benzyloxy)carbonyl]amino}-6-[(tert-butoxycarbonyl)amino]hexanoic acid in 25 ml of anhydrous DMF. After stirring at RT for 15 min, 333.5 mg (1.446 mmol) of benzyl (2-aminoethyl)carbamate hydrochloride are added. The reaction mixture is stirred at RT for 15 h. The solvent is then evaporated and the residue is taken up in dichloromethane. The organic phase is washed with water, dried over magnesium sulfate and concentrated. The crude product is purified by preparative HPLC.

Yield 556.6 mg (44% of theory)
LC-MS (Method 17): R$_t$=2.41 min.
MS (EI): m/z=557 (M+H)$^+$.

Example 105A

Benzyl((1S)-4-amino-1-{2-[(2-{[(benzyloxy)carbonyl]amino}ethyl)amino]-2-oxoethyl}butyl)carbamate hydrochloride

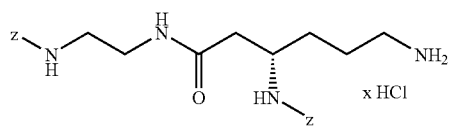

8 ml of a 4M solution of hydrogen chloride in dioxane are added to a solution of 320 mg (0.287 mmol) of benzyl[2-({(3S)-3-{[(benzyloxy)carbonyl]amino}-6-[(tert-butoxycarbonyl)amino]hexanoyl}amino)ethyl]carbamate (Example 104A) in 2 ml of dioxane at 0° C. After 1 h at RT, the reaction solution is concentrated in vacuo, coevaporated with dichloromethane several times and dried under high vacuum. The crude product is reacted without further purification.

Yield: quant.
LC-MS (Method 20): R$_t$=2.84 min.
MS (EI): m/z=457 (M−HCl+H)$^+$.

Example 106A

Benzyl{2-[((3S)-3-{[(benzyloxy)carbonyl]amino}-6-{[N$^5$-[(benzyloxy)carbonyl]-N$^2$-(tert-butoxycarbonyl)-L-ornithyl]amino}hexanoyl)amino]ethyl}carbamate

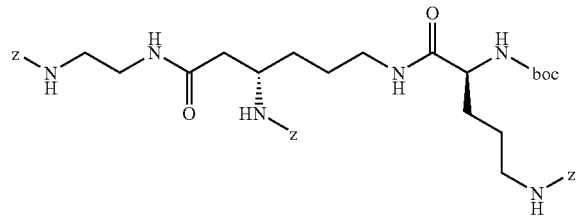

89.5 mg (0.235 mmol) of HATU and 55.3 mg (0.428 mmol) of N,N-diisopropylethylamine are added to a solution of 78.4 mg (0.214 mmol) of N$^5$-[(benzyloxy)carbonyl]-N$^2$-(tert-butoxycarbonyl)-L-ornithine in 5 ml of anhydrous DMF. After stirring at RT for 15 min, a solution of 116 mg (0.235 mmol) of benzyl((1S)-4-amino-1-{2-[(2-{[(benzyloxy)carbonyl]amino}ethyl)amino]-2-oxoethyl}butyl)carbamate hydrochloride (Example 105A) in 5 ml of anhydrous DMF is added. The reaction mixture is stirred at RT for 15 h. The solvent is then evaporated and the residue is taken up in dichloromethane. The organic phase is washed with water, dried over magnesium sulfate and concentrated. The crude product is purified by preparative HPLC.

Yield 48 mg (28% of theory)
LC-MS (Method 12): R$_t$=2.33 min.
MS (EI): m/z=805 (M+H)$^+$.

Example 107A

Benzyl((4S,10S)-4-amino-10-{[(benzyloxy)carbonyl]amino}-5,12,17-trioxo-19-phenyl-18-oxa-6,13,16-triazanonadec-1-yl)carbamate hydrochloride

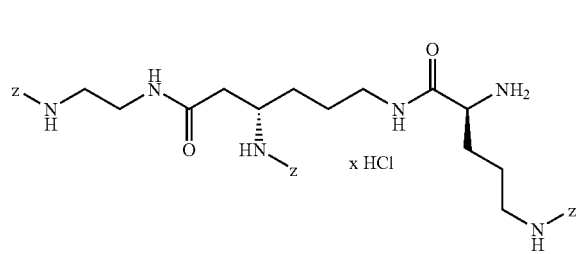

2.5 ml of a 4M solution of hydrogen chloride in dioxane are added to a solution of 48 mg (0.060 mmol) of benzyl{2-[((3S)-3-{[(benzyloxy)carbonyl]amino}-6-{[N$^5$-[(benzyloxy)carbonyl]-N$^2$-(tert-butoxycarbonyl)-L-ornithyl]amino}hexanoyl)amino]ethyl}carbamate (Example 106A) in 1 ml of dioxane at RT. After 4 h at RT, the reaction solution is concentrated in vacuo, coevaporated with dichloromethane several times and dried under high vacuum. The crude product is reacted without further purification.

Yield: quant.
LC-MS (Method 12): $R_t$=1.69 min.
MS (EI): m/z=705 (M–HCl+H)$^+$.

Example 108A

Benzyl{(4S)-4-[(tert-butoxycarbonyl)amino]-5-[(2,3-dihydroxypropyl)amino]-5-oxopentyl}carbamate

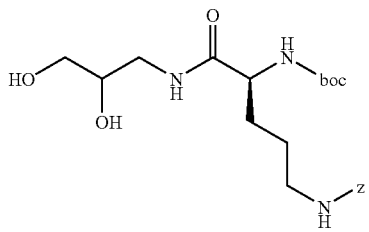

658.5 mg (1.8 mmol) of HATU and 129.2 mg (1 mmol) of N,N-diisopropylethylamine are added to a solution of 366 mg (1 mmol) of $N^5$-[(benzyloxy)carbonyl]-$N^2$-(tert-butoxycarbonyl)-L-ornithine in 15 ml of anhydrous DMF. After stirring at RT for 15 min, 182.2 mg (1 mmol) of 3-aminopropane-1,2-diol are added. The reaction mixture is stirred at RT for 15 h. The solvent is then evaporated and the residue is taken up in dichloromethane. The organic phase is washed with water, dried over magnesium sulfate and concentrated. The crude product is purified by preparative HPLC.

Yield 135 mg (30% of theory)
LC-MS (Method 12): $R_t$=1.79 min.
MS (EI): m/z=440 (M+H)$^+$.

Example 109A

Benzyl{(4S)-4-amino-5-[(2,3-dihydroxypropyl)amino]-5-oxopentyl}carbamate hydrochloride

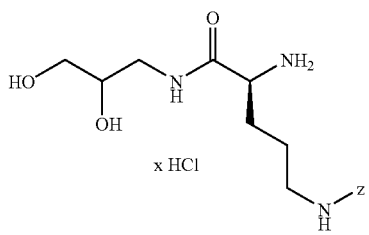

4 ml of a 4M solution of hydrogen chloride in dioxane are added to a solution of 135 mg (0.31 mmol) of benzyl{(4S)-4-[(tert-butoxycarbonyl)amino]-5-[(2,3-dihydroxypropyl)amino]-5-oxopentyl}carbamate (Example 108A) in 0.5 ml of dioxane at 0° C. After 1 h at RT, the reaction solution is concentrated in vacuo, coevaporated with dichloromethane several times and dried under high vacuum. The crude product is reacted without further purification.

Yield: quant.
LC-MS (Method 12): $R_t$=1.01 min.
MS (EI): m/z=340 (M–HCl+H)$^+$.

Example 110A

Benzyl[2-({(2S)-4-{[(benzyloxy)carbonyl]amino}-2-[(tert-butoxycarbonyl)amino]butanoyl}amino)ethyl]carbamate

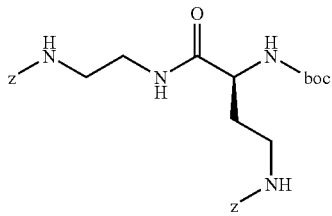

321.9 mg (0.847 mmol) of HATU and 199.3 mg (1.534 mmol) of N,N-diisopropylethylamine are added to a solution of 410.8 mg (0.770 mmol) of (2S)-4-{[(benzyloxy)carbonyl]amino}-2-[(tert-butoxycarbonyl)amino]butanoic acid —N-cyclohexylcyclohexanamine (1:1) in 25 ml of anhydrous DMF. After stirring at RT for 15 min, 195.3 mg (0.847 mmol) of benzyl(2-aminoethyl)carbamate hydrochloride are added. The reaction mixture is stirred at RT for 15 h. The solvent is then evaporated and the residue is taken up in dichloromethane. The organic phase is washed with water, dried over magnesium sulfate and concentrated. The crude product is purified by preparative HPLC.

Yield 270 mg (66% of theory)
LC-MS (Method 12): $R_t$=2.19 min.
MS (EI): m/z=529 (M+H)$^+$.

Example 111A

Benzyl{2-[((2S)-2-amino-4-{[(benzyloxy)carbonyl]amino}butanoyl)amino]ethyl}carbamate hydrochloride

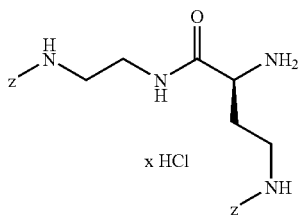

A mixture of 270 mg (0.511 mmol) of benzyl-[2-({(2S)-4-{[(benzyloxy)carbonyl]amino}-2-[(tert-butoxycarbonyl)amino]butanoyl}amino)ethyl]carbamate (Example 110A) and 9 ml of a 4M solution of hydrogen chloride in dioxane is stirred at RT for 2 h. The reaction solution is concentrated, coevaporated with dichloromethane several times and dried under high vacuum. The crude product is reacted without further purification.

Yield: quant.
LC-MS (Method 17): $R_t$=1.58 min.
MS (EI): m/z=429 (M–HCl+H)$^+$.

Example 112A

Benzyl{2-[((2S)-4-{[(benzyloxy)carbonyl]amino}-2-{[N$^5$-(benzyloxy)carbonyl]-N$^2$-(tert-butoxycarbonyl)-L-ornithyl]amino}butanoyl)amino]ethyl}carbamate

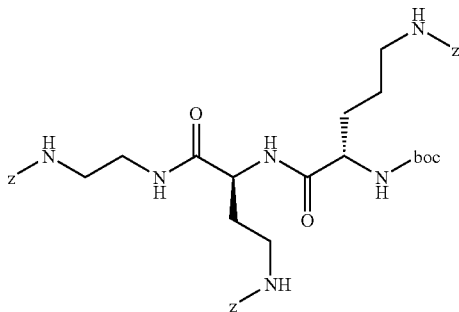

217.0 mg (0.467 mmol) of HATU and 109.7 mg (1.534 mmol) of N,N-diisopropylethylamine are added to a solution of 155.4 mg (0.770 mmol) of N$^5$-[(benzyloxy)carbonyl]-N$^2$-(tert-butoxycarbonyl)-L-ornithine in 5 ml of anhydrous DMF. After stirring at RT for 15 min, a solution of 195.3 mg (0.849 mmol) of benzyl{2-[((2S)-2-amino-4-{[(benzyloxy)carbonyl]amino}butanoyl)amino]ethyl}carbamate hydrochloride (Example 111A) in 5 ml of anhydrous DMF is added. The reaction mixture is stirred at RT for 15 h. The solvent is then evaporated and the residue is taken up in dichloromethane. The organic phase is washed with water, dried over magnesium sulfate and concentrated. The crude product is purified by preparative HPLC.

Yield 71 mg (21% of theory)
LC-MS (Method 12): R$_t$=2.42 min.
MS (EI): m/z=777 (M+H)$^+$

Example 113A

Benzyl[(4S,7S)-4-amino-7-(2-{[(benzyloxy)carbonyl]amino}ethyl)-5,8,13-trioxo-15-phenyl-14-oxa-6,9,12-triazapentadec-1-yl]carbamate hydrochloride

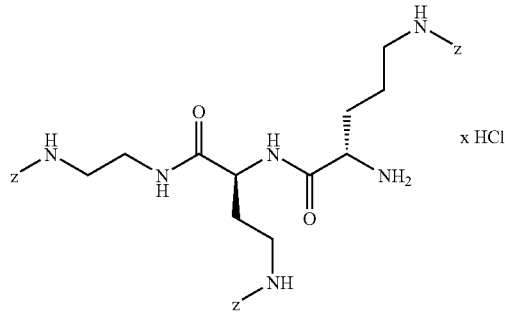

3.7 ml of a 4M solution of hydrogen chloride in dioxane are added to a solution of 71 mg (0.091 mmol) of benzyl{2-[((2S)-4-{[(benzyloxy)carbonyl]amino}-2-{[N$^5$-[(benzyloxy)carbonyl]-N$^2$-(tert-butoxycarbonyl)-L-ornithyl]amino}butanoyl)amino]ethyl}carbamate (Example 112A) in 1.5 ml of dioxane at RT. After 4 h at RT, the reaction solution is concentrated in vacuo, coevaporated with dichloromethane several times and dried under high vacuum. The crude product is reacted without further purification.

Yield: quant.
LC-MS (Method 12): R$_t$=1.70 min.
MS (EI): m/z=677 (M−HCl+H)$^+$

Example 114A

Benzyl{(1S)-4-[(tert-butoxycarbonyl)amino]-1-[2-({2-[(tert-butoxycarbonyl)amino]ethyl}amino)-2-oxoethyl]butyl}carbamate

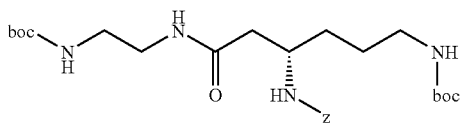

836.5 mg (2.2 mmol) of HATU and 517.0 mg (4 mmol) of N,N-diisopropylethylamine are added to a solution of 760.9 mg (2 mmol) of (3S)-3-{[(benzyloxy)carbonyl]amino}-6-[(tert-butoxycarbonyl)amino]hexanoic acid in 25 ml of anhydrous DMF. After stirring at RT for 45 min 352.5 mg (2.2 mmol) of tert-butyl (2-aminoethyl)carbamate hydrochloride are added. The reaction mixture is stirred at RT for 15 h. The solvent is then evaporated and the residue is taken up in dichloromethane. The organic phase is washed with water, dried over magnesium sulfate and concentrated. The crude product is purified by preparative HPLC.

Yield 400 mg (38% of theory)
LC-MS (Method 19): R$_t$=2.33 min.
MS (EI): m/z=523 (M+H)$^+$.

Example 115A tert-Butyl[(4S)-4-amino-6-({2-[(tert-butoxycarbonyl)amino]ethyl}amino)-6-oxohexyl]carbamate

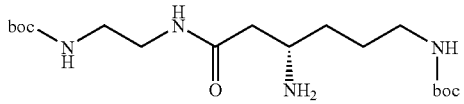

400 mg (0.765 mmol) of benzyl{(1S)-4-[(tert-butoxycarbonyl)amino]-1-[2-({2-[(tert-butoxycarbonyl)amino]ethyl}amino)-2-oxoethyl]butyl}carbamate (Example 114A) are dissolved in 50 ml of ethanol. 80 mg of palladium on activated carbon (10%) are added thereto, and the mixture is then hydrogenated under atmospheric pressure for 15 h. The reaction mixture is filtered through prewashed kieselguhr, and the filtrate is concentrated on a rotary evaporator in vacuo. The crude product is reacted without further purification.

Yield: quant.
LC-MS (Method 17): R$_t$=1.42 min
MS (EI): m/z=389 (M+H)$^+$.

Examples 116A and 117A detailed in the following table are prepared from the appropriate starting compounds in analogy to the method of Example 83A detailed above:

| Ex. No. | Structure | Prepared in analogy to | Analytical data |
|---|---|---|---|
| 116A | 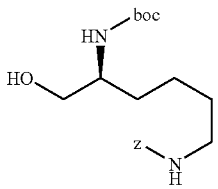 | N⁶-[(Bezyloxy)-carbonyl]-N²-(tert-butoxycarbonyl)-L-lysine | LC-MS (Method 12): $R_t$ = 1.94 min. MS (EI): m/z = 367 (M + H)+ |
| 117A | 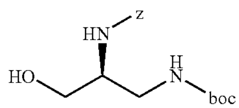 | N-[(Benzyloxy)-carbonyl]-3-[(tert-butoxycarbonyl)-amino]-L-alanine | LC-MS (Method 19): $R_t$ = 1.98 min. MS (EI): m/z = 325 (M + H)+ |

Example 118A

Benzyl[(1S)-2-amino-1-(hydroxymethyl)ethyl]carbamate hydrochloride

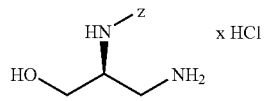

A mixture of 269 mg (0.83 mmol) of benzyl tert-butyl [(2S)-3-hydroxypropane-1,2-diyl]biscarbamate (Example 117A) and 5 ml of a 4M solution of hydrogen in dioxane chloride is stirred at RT for 2 h. The reaction solution is concentrated, coevaporated with dichloromethane several times and dried under high vacuum. The crude product is reacted without further purification.

Yield: 212 mg (98% of theory)
LC-MS (Method 12): $R_t$=0.55 min.
MS (EI): m/z=225 (M−HCl+H)+.

Example 119A

Benzyl{(1S)-1-[({(2S)-2,5-bis[(tert-butoxycarbonyl) amino]pentyl}amino)carbonyl]-4-[(tert-butoxycarbonyl)amino]butyl}carbamate

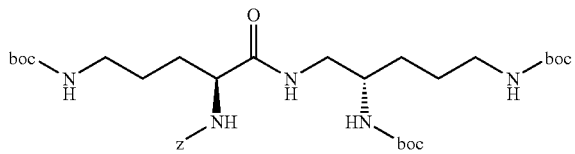

Preparation takes place in analogy to Example 79A from 120 mg (0.33 mmol) of N⁵-(tert-butoxycarbonyl)-N²-[(benzyloxy)carbonyl]-L-ornithine and 136 mg (0.43 mmol) of tert-butyl{(4S)-5-amino-4-[(tert-butoxycarbonyl)amino] pentyl}carbamate (Example 86A) in 6 ml of dimethylformamide with the addition of 82 mg (0.43 mmol) of EDC and 13 mg (0.1 mmol) of HOBt. The product is purified by preparative RP-HPLC (mobile phase water/acetonitrile gradient: 90:10→5:95).

Yield: 132 mg (61% of theory)
LC-MS (Method 17): $R_t$=2.68 min.
MS (EI): m/z=666 (M+H)+

Example 120A tert-Butyl[(4S)-4-amino-5-({(2S)-2,5-bis[(tert-butoxycarbonyl)amino]pentyl}amino)-5-oxopentyl] carbamate

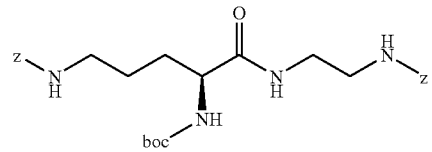

Preparation takes place in analogy to Example 81A from 132 mg (0.20 mmol) of benzyl{(1S)-1-[({(2S)-2,5-bis[(tert-butoxycarbonyl)amino]pentyl}amino)carbonyl]-4-[(tert-butoxycarbonyl)amino]butyl}carbamate (Example 119A) in 50 ml of ethanol with the addition of 13 mg of palladium on activated carbon (10%). The product is reacted without further purification.

Yield: quant.
MS (ESI): m/z=532 (M+H)+

Example 121A

Benzyl[2-({(2S)-5-{[(benzyloxy)carbonyl]amino}-2-[(tert-butoxycarbonyl)amino]pentanoyl}amino)ethyl] carbamate Preparation takes place in analogy to Example 79A from 300 mg (0.82 mmol) of N⁵-[(benzyloxy)carbonyl]-N-(tert-butoxycarbonyl)-L-ornithine and 246 mg (1.06 mmol) of benzyl (2-aminoethyl)carbamate hydrochloride in 6 ml of dimethylformamide with the addition of 204 mg (1.06 mmol) of EDC, 33 mg (0.25 mmol) of HOBt and 148 mg (1.15 mmol) of N,N-diisopropylethylamine.

Yield: 397 mg (89% of theory)
LC-MS (Method 12): $R_t$=2.20 min.
MS (EI): m/z=543 (M+H)$^+$

Example 122A

Benzyl{(4S)-4-amino-5-[(2-{[(benzyloxy)carbonyl]amino}ethyl)amino]-5-oxopentyl}carbamate hydrochloride

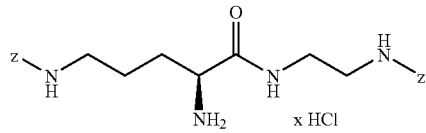

A mixture of 400 mg (0.73 mmol) of benzyl[2-({(2S)-5-{[(benzyloxy)carbonyl]amino}-2-[(tert-butoxycarbonyl)amino]pentanoyl}amino)ethyl]carbamate (Example 121A) and 1 ml of a 4M solution of hydrogen chloride in dioxane is stirred at RT for 2 h. The reaction solution is concentrated, coevaporated with dichloromethane several times and dried under high vacuum. The crude product is reacted without further purification.

Yield: quant
LC-MS (Method 19): $R_t$=1.61 min.
MS (EI): m/z=443 (M–HCl+H)$^+$.

Example 123A

N$^5$-[(Benzyloxy)carbonyl]-N$^2$-(tert-butoxycarbonyl)-L-ornithyl-N$^5$-[(benzyloxy)carbonyl]-N-(2-{[(benzyloxy)carbonyl]amino}ethyl)-L-ornithinamide

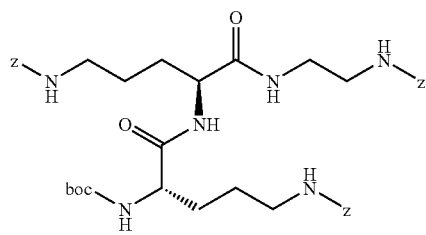

350 mg (0.92 mmol) of HATU and 330 mg (2.56 mmol) of N,N-diisopropylethylamine are added to a solution of 320 mg (0.88 mmol) of N$^5$-[(benzyloxy)carbonyl]-N$^2$-(tert-butoxycarbonyl)-L-ornithine and 350 mg (0.73 mmol) of benzyl{(4S)-4-amino-5-[(2-{[(benzyloxy)carbonyl]amino}ethyl)amino]-5-oxopentyl}carbamate (Example 122A) in 5 ml of anhydrous DMF at 0° C. The reaction mixture is stirred at RT for 15 h. The solvent is then evaporated and the residue is stirred with water, collected by filtration and dried under high vacuum.

Yield 480 mg (68% of theory)
LC-MS (Method 19): $R_t$=2.61 min.
MS (EI): m/z=791 (M+H)$^+$.

Example 124A

N$^5$-[(Benzyloxy)carbonyl]-L-ornithyl-N$^5$-[(benzyloxy)carbonyl]-N-(2-{[(benzyloxy)carbonyl]amino}ethyl)-L-ornithinamide hydrochloride

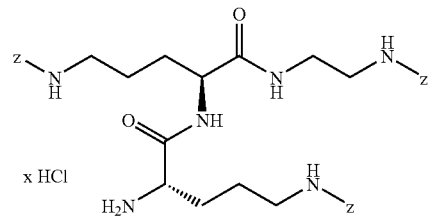

Preparation takes place in analogy to Example 122A from 70 mg (0.09 mmol) of N$^5$-[(benzyloxy)carbonyl]-N$^2$-(tert-butoxycarbonyl)-L-ornithyl-N$^5$-[(benzyloxy)carbonyl]-N-(2-{[(benzyloxy)carbonyl]amino}ethyl)-L-ornithinamide (Example 123A) in 0.68 ml of a 4M solution of hydrogen chloride in dioxane.

Yield: 65 mg (98% of theory)
MS (ESI): m/z=691 (M–HCl+H)$^+$

Example 125A

Benzyl[2-({(2S)-2,5-bis[(tert-butoxycarbonyl)amino]pentyl}amino)-2-oxoethyl]carbamate

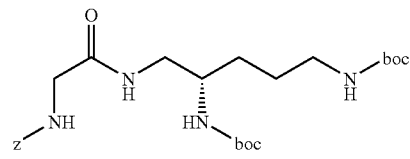

Preparation takes place in analogy to Example 79A from 92 mg (0.44 mmol) of N-[(benzyloxy)carbonyl]glycine and 181 mg (0.57 mmol) of tert-butyl{(4S)-5-amino-4-[(tert-butoxycarbonyl)amino]pentyl}carbamate (Example 86A) in 6 ml of dimethylformamide with the addition of 110 mg (0.57 mmol) of EDC and 18 mg (0.13 mmol) of HOBt. The product is purified by preparative RP-HPLC (mobile phase water/acetonitrile gradient: 90:10→5:95).

Yield: 105 mg (47% of theory)
LC-MS (Method 12): $R_t$=2.12 min.
MS (EI): m/z=509 (M+H)$^+$

Example 126A tert-Butyl{(4S)-5-[(aminoacetyl)amino]-4-[(tert-butoxycarbonyl)amino]pentyl}carbamate

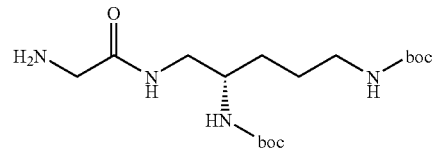

Preparation takes place in analogy to Example 81A from 105 mg (0.21 mmol) of benzyl[2-({(2S)-2,5-bis[(tert-butoxycarbonyl)amino]pentyl}amino)-2-oxoethyl]carbamate (Example 125A) in 50 ml of ethanol with the addition of 11 mg of palladium on activated carbon (10%). The product is reacted without further purification.

Yield: 64 mg (83% of theory)
MS (ESI): m/z=375 (M+H)$^+$

Example 127A

Benzyl[(1S)-1-[(benzyloxy)methyl]-2-({(2S)-2,5-bis[(tert-butoxycarbonyl)amino]pentyl}amino)-2-oxoethyl]carbamate

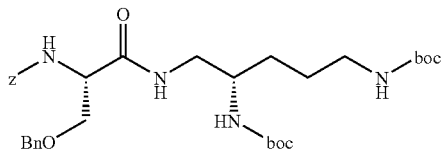

Preparation takes place in analogy to Example 79A from 150 mg (0.46 mmol) of O-benzyl-N-[(benzyloxy)carbonyl]-L-serine and 188 mg (0.59 mmol) of tert-butyl{(4S)-5-amino-4-[(tert-butoxycarbonyl)amino]pentyl}carbamate (Example 86A) in 6 ml of dimethylformamide with the addition of 114 mg (0.57 mmol) of EDC and 18 mg (0.13 mmol) of HOBt. The product is purified by preparative RP-HPLC (mobile phase water/acetonitrile gradient: 90:10→5:95).

Yield: 129 mg (45% of theory)
LC-MS (Method 17): R$_t$=2.81 min.
MS (EI): m/z=629 (M+H)$^+$

Example 128A tert-Butyl{(4S)-5-{[(2S)-2-amino-3-hydroxypropanoyl]amino}-4-[(tert-butoxycarbonyl)amino]pentyl}carbamate

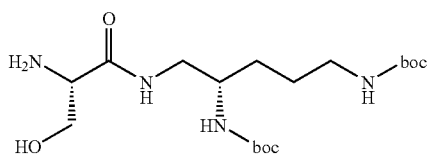

A solution of 128 mg (0.77 mmol) of benzyl[(1S)-1-[(benzyloxy)methyl]-2-({(2S)-2,5-bis[(tert-butoxycarbonyl)amino]pentyl}amino)-2-oxoethyl]carbamate (Example 127A) in 50 ml of ethanol is hydrogenated after the addition of 13 mg of palladium on activated carbon (10%) at RT under atmospheric pressure for 48 h. The mixture is filtered through kieselguhr and the residue is washed with ethanol. The filtrate is evaporated to dryness in vacuo. The product is purified by preparative RP-HPLC (mobile phase water/acetonitrile gradient: 90:10→5:95).

Yield: 22 mg (27% of theory)
LC-MS (Method 19): R$_t$=1.43 min.
MS (EI): m/z=405 (M+H)$^+$

Example 129A

9H-Fluoren-9-ylmethyl{(1S)-4-amino-1-[({(2S)-2,5-bis[(tert-butoxycarbonyl)amino]pentyl}amino)carbonyl]-4-oxobutyl}carbamate

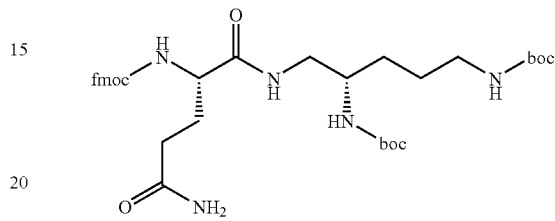

129 mg (0.34 mmol) of HATU and 133 mg (0.95 mmol) of N,N-diisopropylethylamine are added to a solution of 100 mg (0.27 mmol) of N$^2$-[(9H-fluoren-9-ylmethoxy)carbonyl]-L-glutamine and 112 mg (0.35 mmol) of tert-butyl{(4S)-5-amino-4-[(tert-butoxycarbonyl)amino]pentyl}carbamate (Example 86A) in 5 ml of anhydrous DMF at 0° C. The reaction mixture is stirred at RT for 15 h. The solvent is then evaporated and the residue is stirred with water, collected by filtration and dried under high vacuum.

Yield 45 mg (25% of theory)
LC-MS (Method 12): R$_t$=2.27 min.
MS (EI): m/z=668 (M+H)$^+$.

Example 130A tert-Butyl[(1S)-4-[(tert-butoxycarbonyl)amino]-1-({[(2S)-2,5-diamino-5-oxopentanoyl]amino}methyl)butyl]carbamate

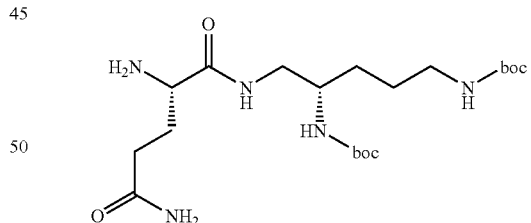

A solution of 33 mg (0.05 mmol) of 9H-fluoren-9-ylmethyl{(1S)-4-amino-1-[({(2S)-2,5-bis[(tert-butoxycarbonyl)amino]pentyl}amino)carbonyl]-4-oxobutyl}carbamate (Example 129A) in 1 ml of dimethylformamide is stirred after the addition of 4 mg (0.05 mmol) of piperidine at room temperature for 45 min. The solvent is evaporated and the crude product is reacted without further purification.

Yield: quant.
MS (ESI): m/z=446 (M+H)$^+$

Examples 131A to 135 listed in the following table are prepared from the appropriate starting materials in analogy to the method of Example 79A detailed above:

| Ex. No. | Structure | Prepared in analogy to | Analytical data |
|---|---|---|---|
| 131A | 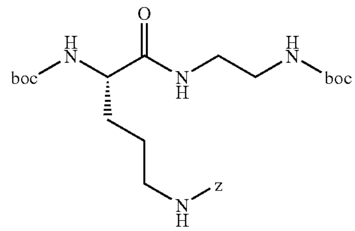 | $N^5$-[(Benzyloxy)-carbonyl]-$N^2$-(tert-butoxycarbonyl)-L-ornithine and tert-butyl (2-aminoethyl)-carbamate | LC-MS (Method 19): $R_t$ = 2.33 min. MS (EI): m/z = 509 $(M + H)^+$ |
| 132A | 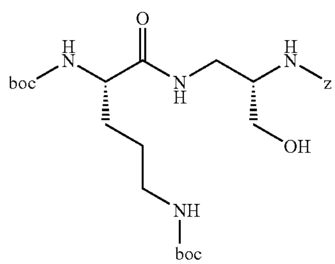 | $N^2,N^5$-Bis(tert-butoxycarbonyl)-L-ornithine and Example 118A | LC-MS (Method 19): $R_t$ = 2.20 min. MS (EI): m/z = 539 $(M + H)^+$ |
| 133A | 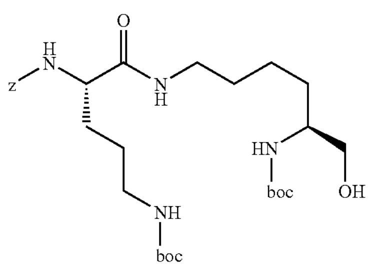 | $N^2$-[(benzyloxy)-carbonyl]-$N^5$-(tert-butoxycarbonyl)-L-ornithine and Example 142A | LC-MS (Method 19): $R_t$ = 2.31 min. MS (EI): m/z = 581 $(M + H)^+$ |
| 134A | 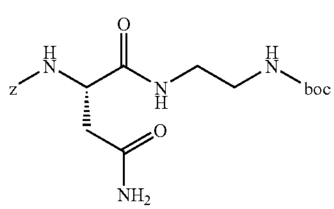 | $N^2$-[(Benzyloxy)-carbonyl]-L-asparagine and tert-butyl (2-aminoethyl)-carbamate | LC-MS (Method 19): $R_t$ = 1.75 min. MS (EI): m/z = 409 $(M + H)^+$ |
| 135A | 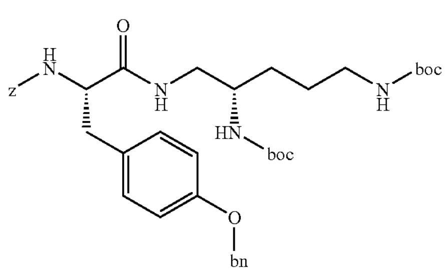 | O-Benzyl-N-[(benzyl-oxy)carbonyl]-L-tyrosine and Example 86A | LC-MS (Method 12): $R_t$ = 2.79 min. MS (EI): m/z = 705 $(M + H)^+$ |

Examples 136A to 141A listed in the following table are prepared from the appropriate starting materials in analogy to the method of Example 129A detailed above:

| Ex. No. | Structure | Prepared in analogy to | Analytical data |
|---|---|---|---|
| 136A | (structure) | N²-[(9H-Fluoren-9-ylmethoxy)-carbonyl]-L-alpha-asparagine and tert-butyl (3-amino-2-hydroxy-propyl)carbamate | LC-MS (Method 17): R$_t$ = 2.09 min. MS (EI): m/z = 527 (M + H)$^+$ |
| 137A | (structure) | N²-[(Benzyloxy)-carbonyl]-L-alpha glutamine and Example 86A | LC-MS (Method 12): R$_t$ = 1.93 min. MS (EI): m/z = 580 (M + H)$^+$ |
| 138A | (structure) | N²-[(9H-Fluoren-9-ylmethoxy)-carbonyl]-L-asparagine and tert-butyl (3-amino-2-hydroxy-propyl)carbamate | LC-MS (Method 12): R$_t$ = 1.88 min. MS (EI): m/z = 527 (M + H)$^+$ |
| 139A | (structure) | N-[(9H-Fluoren-9-ylmethoxy)carbonyl]-L-glutaminic acid and tert-butyl-(2-aminoethyl)-carbamate | LC-MS (Method 12): R$_t$ = 2.31 min. MS (EI): m/z = 654 (M + H)$^+$ |
| 140A | (structure) | N-[(9H-Fluoren-9-ylmethoxy)carbonyl]-L-asparaginic acid and tert-butyl (2-aminoethyl)-carbamate | LC-MS (Method 19): R$_t$ = 2.52 min. MS (EI): m/z = 640 (M + H)$^+$ |
| 141A | (structure) | N²-[(9H-Fluoren-9-ylmethoxy)-carbonyl]-L-asparagine and Example 92A | LC-MS (Method 17): R$_t$ = 2.46 min. MS (EI): m/z = 640 (M + H)$^+$ |

Examples 142A to 148A listed in the following table are prepared from the appropriate starting materials in analogy to the method of Example 81A detailed above:

| Ex. No. | Structure | Prepared in analogy to | Analytical data |
|---|---|---|---|
| 142A | 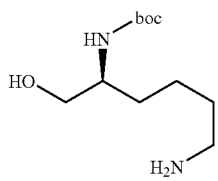 | Example 116A | MS (ESI): m/z = 233 (M + H)+ |
| 143A | 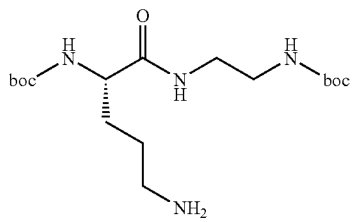 | Example 131A | MS (ESI): m/z = 375 (M + H)+ |
| 144A | 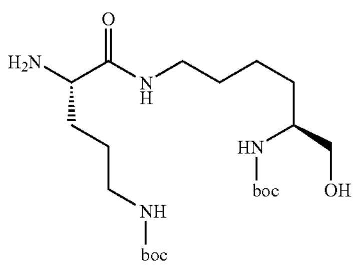 | Example 133A | MS (ESI): m/z = 447 (M + H)+ |
| 145A | 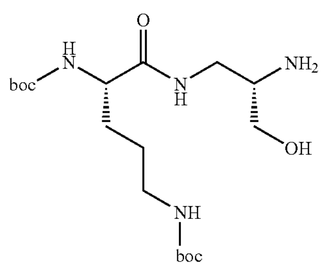 | Example 132A | MS (ESI): m/z = 405 (M + H)+ |
| 146A | 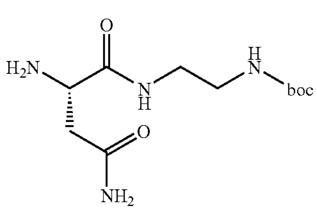 | Example 134A | LC-MS (Method 12): $R_t$ = 0.41 min. MS (EI): m/z = 275 (M + H)+ |
| 147A | 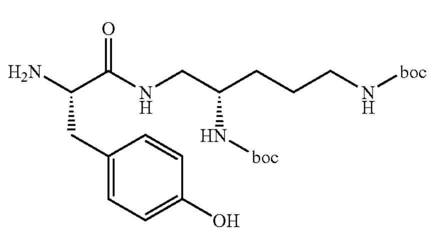 | Example 135A | LC-MS (Method 17): $R_t$ = 1.67 min. MS (EI): m/z = 481 (M + H)+ |

-continued

| Ex. No. | Structure | Prepared in analogy to | Analytical data |
|---|---|---|---|
| 148A | 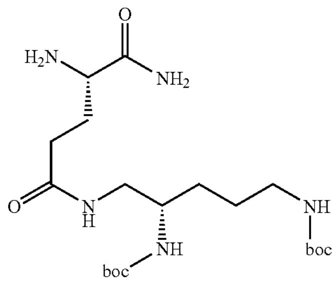 | Example 137A | MS (ESI): m/z = 289 (M + H)+ |

Examples 149A to 153A listed in the following table are prepared from the appropriate starting materials in analogy to the method of Example 130A detailed above:

| Ex. No. | Structure | Prepared in analogy to | Analytical data |
|---|---|---|---|
| 149A | 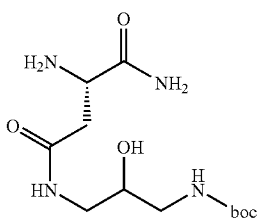 | Example 136A | MS (ESI): m/z = 305 (M + H)+ |
| 150A | 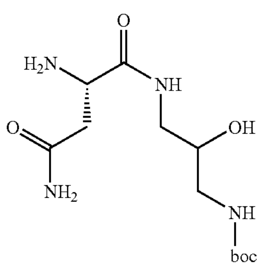 | Example 138A | MS (ESI): m/z = 305 (M + H)+ |
| 151A | 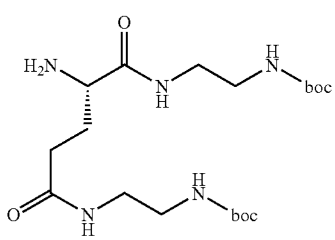 | Example 139A | MS (ESI): m/z = 432 (M + H)+ |
| 152A | 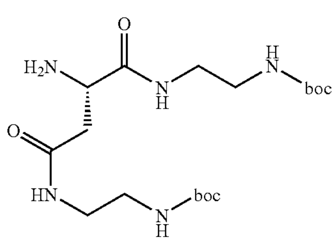 | Example 140A | MS (ESI): m/z = 418 (M + H)+ |

| Ex. No. | Structure | Prepared in analogy to | Analytical data |
|---|---|---|---|
| 153A | 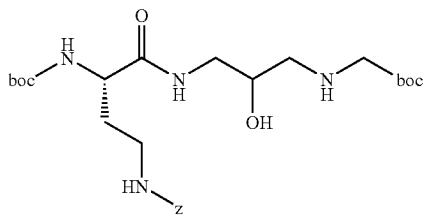 | Example 141A | MS (ESI): m/z = 418 (M + H)+ |

Example 154A

Benzyl[(3S)-[(tert-butoxycarbonyl)amino]-4-({3-[tert-butoxycarbonyl)amino]-2-hydroxypropyl}amino)-4-oxybutyl]carbamate

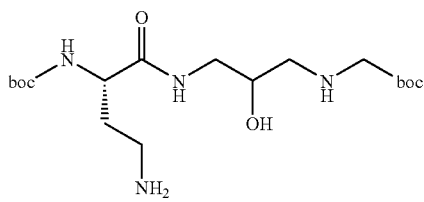

104.5 mg (0.275 mmol) of HATU and 64.6 mg (0.500 mmol) of N,N-diisopropylethylamine are added to a solution of 133.4 mg (0.25 mmol) of (2S)-4-{[(benzyloxy)carbonyl]amino}-2-[(tert-butoxycarbonyl)amino]butanoic acid-N-cyclohexylcyclohexanamine (1:1) in 10 ml of anhydrous DMF. After stirring at RT for 15 min, 52.3 mg (0.275 mmol) of tert-butyl(3-amino-2-hydroxypropyl)carbamate are added. The reaction mixture is stirred at RT for 15 h. The solvent is then evaporated and the residue is taken up in dichloromethane. The organic phase is washed with water, dried over magnesium sulfate and concentrated. The crude product is purified by preparative HPLC.

Yield 25 mg (19% of theory)
LC-MS (Method 17): $R_t$=2.23 min.
MS (EI): m/z=525 (M+H)+

Example 155A tert-Butyl[3-({(2S)-4-amino-2-[(tert-butoxycarbonyl)amino]butanoyl}amino)-2-hydroxypropyl]carbamate

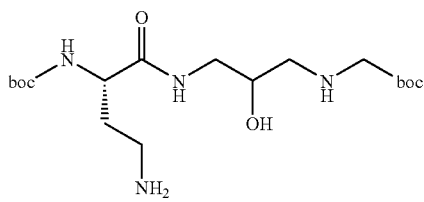

25 mg (0.048 mmol) of benzyl[(3S)-3-[(tert-butoxycarbonyl)amino]-4-({3-[(tert-butoxycarbonyl)amino]-2-hydroxypropyl}amino)-4-oxobutyl]carbamate (Example 154A) are dissolved in 10 ml of ethanol. 10 mg of palladium on activated carbon (10%) are added thereto, and the mixture is then hydrogenated under atmospheric pressure for 15 h. The reaction mixture is filtered through prewashed kieselguhr, and the filtrate is concentrated on a rotary evaporator in vacuo. The crude product is reacted without further purification.

Yield: quant.
LC-MS (Method 12): $R_t$=1.10 min
MS (EI): m/z=391 (M+H)+

Example 156A

Di-tert-butyl[2-({(2S)-4-{[(benzyloxy)carbonyl]amino}-2-[(tert-butoxycarbonyl)amino]butanoyl}amino)propane-1,3-diyl]biscarbamate

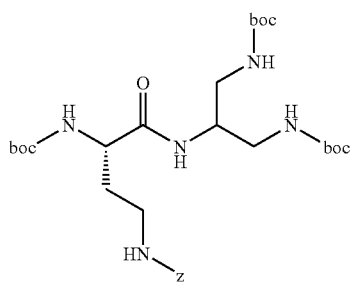

11.9 mg (0.294 mmol) of HATU and 64.1 mg (0.535 mmol) of N,N-diisopropylethylamine are added to a solution of 142.7 mg (0.267 mmol) of (2S)-4-{[(benzyloxy)carbonyl]amino}-2-[(tert-butoxycarbonylamino]butanoic acid-N-cyclohexylcyclohexanamine (1:1) in 10 ml of anhydrous DMF. After stirring at RT for 15 min, 100 mg (0.294 mmol) of di-tert-butyl(2-aminopropane-1,3-diyl)biscarbamate hydrochloride are added. The reaction mixture is stirred at RT for 15 h. The solvent is then evaporated and the residue is taken up in dichloromethane. The organic phase is washed with water, dried over magnesium sulfate and concentrated. The crude product is purified by preparative HPLC.

Yield 116 mg (70% of theory)
LC-MS (Method 19): $R_t$=2.71 min.
MS (EI): m/z=624 (M+H)+

Example 157A

Di-tert-butyl[2-({(2S)-4-amino-2-[(tert-butoxycarbonyl)amino]butanoyl}amino)propane-1,3-diyl]biscarbamate

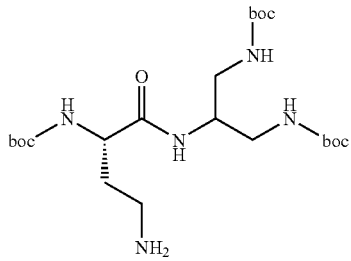

116 mg (0.186 mmol) of di-tert-butyl[2-({(2S)-4-{[(benzyloxy)carbonyl]amino}-2-[(tert-butoxycarbonyl)amino]butanoyl}amino)propane-1,3-diyl]biscarbamate (Example 156A) are dissolved in 20 ml of ethanol. 30 mg of palladium on activated carbon (10%) are added thereto, and the mixture is then hydrogenated under atmospheric pressure for 15 h. The reaction mixture is filtered through prewashed kieselguhr and the filtrate is concentrated on a rotary evaporator in vacuo. The crude product is reacted without further purification.

Yield: 72 mg (80% of theory)
LC-MS (Method 17): $R_t$=1.75 min
MS (EI): m/z=490 (M+H)$^+$

Example 158A

Benzyl(2-{[N-(tert-butoxycarbonyl)-L-seryl]amino}ethyl)carbamate

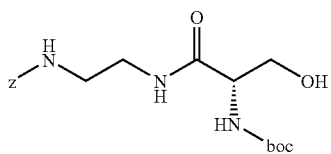

627.4 mg (1.650 mmol) of HATU and 387.7 mg (3.0 mmol) of N,N-diisopropylethylamine are added to a solution of 307.8 mg (1.50 mmol) of N-(tert-butoxycarbonyl)-L-serine in 25 ml of anhydrous DMF. After stirring at RT for 15 min, 380.6 mg (1.650 mmol) of benzyl(2-aminoethyl)carbamate hydrochloride are added. The reaction mixture is stirred at RT for 15 h. The solvent is then evaporated and the residue is taken up in dichloromethane. The organic phase is washed with water, dried over magnesium sulfate and concentrated. The crude product is purified by preparative HPLC.

Yield: 49 mg (7% of theory)
LC-MS (Method 17): $R_t$=1.83 min.
MS (EI): m/z=382 (M+H)$^+$

Example 159A

Benzyl[2-(L-serylamino)ethyl]carbamate hydrochloride

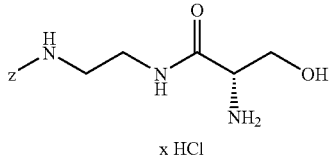

1.5 ml of a 4M solution of hydrogen chloride in dioxane are added to a solution of 49 mg (0.128 mmol) of benzyl(2-{[N-(tert-butoxycarbonyl)-L-seryl]amino}ethyl)carbamate (Example 158A) in 1 ml of dioxane. The mixture is stirred at RT for 2 h. The reaction solution is concentrated, coevaporated with dichloromethane several times and dried under high vacuum. The crude product is reacted without further purification.

Yield: 33 mg (91% of theory)
LC-MS (Method 19): $R_t$=0.89 min.
MS (EI): m/z=282 (M−HCl+H)$^+$

Example 160A

Benzyl{(1S)-5-{[(benzyloxy)carbonyl]amino}-1-[2-({3-[(tert-butoxycarbonyl)amino]-2-hydroxypropyl}amino)-2-oxoethyl]pentyl}carbamate

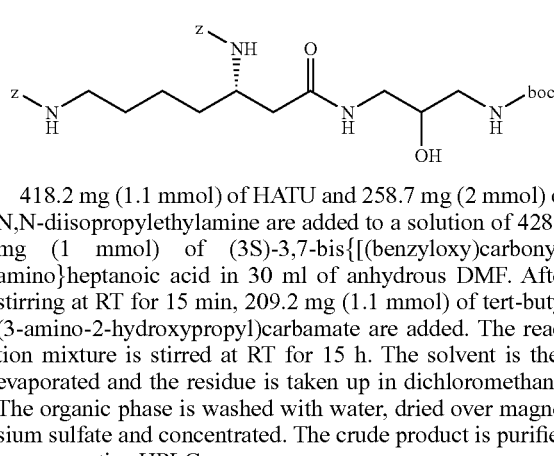

418.2 mg (1.1 mmol) of HATU and 258.7 mg (2 mmol) of N,N-diisopropylethylamine are added to a solution of 428.5 mg (1 mmol) of (3S)-3,7-bis{[(benzyloxy)carbonyl]amino}heptanoic acid in 30 ml of anhydrous DMF. After stirring at RT for 15 min, 209.2 mg (1.1 mmol) of tert-butyl (3-amino-2-hydroxypropyl)carbamate are added. The reaction mixture is stirred at RT for 15 h. The solvent is then evaporated and the residue is taken up in dichloromethane. The organic phase is washed with water, dried over magnesium sulfate and concentrated. The crude product is purified by preparative HPLC.

Yield 310 mg (47% of theory)
LC-MS (Method 17): $R_t$=2.38 min.
MS (EI): m/z=601 (M+H)$^+$

Example 161A

Benzyl((5S)-7-[(3-amino-2-hydroxypropyl)amino]-5-{[(benzyloxy)carbonyl]amino}-7-oxoheptyl)carbamate hydrochloride

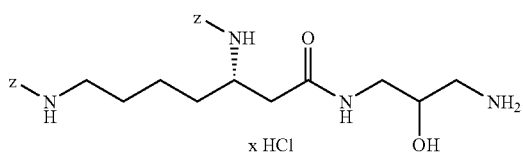

11 ml of a 4M solution of hydrogen chloride in dioxane are added to a solution of 160 mg (0.267 mmol) of benzyl{(1S)-5-{[(benzyloxy)carbonyl]amino}-1-[2-({3-[(tert-butoxycarbonyl)amino]-2-hydroxypropyl}amino)-2-oxoethyl]pentyl}carbamate (Example 160A) in 5.5 ml of dioxane at 0° C. The mixture is stirred at RT for 1 h. The reaction solution is concentrated, coevaporated with dichloromethane several times and dried under high vacuum. The crude product is reacted without further purification.

Yield: quant.
LC-MS (Method 17): $R_t$=1.77 min.
MS (EI): m/z=501 (M−HCl+H)$^+$.

Example 162A

Benzyl[(1S)-2-({2-[(tert-butoxycarbonyl)amino]ethyl}amino)-1-(hydroxymethyl)-2-oxoethyl]carbamate

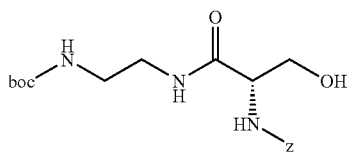

1.05 g (2.759 mmol) of HATU and 648.3 mg (5.016 mmol) of N,N-diisopropylethylamine are added to a solution of 600 mg (2.5 mmol) of N-[(benzyloxy)carbonyl]-L-serine in 25 ml of anhydrous DMF. After stirring at RT for 15 min, 442.0 mg (2.76 mmol) of tert-butyl(2-aminoethyl)carbamate are added. The reaction mixture is stirred at RT for 15 h. The solvent is then evaporated and the residue is taken up in dichloromethane. The organic phase is washed with water, dried over magnesium sulfate and concentrated. The crude product is purified by preparative HPLC.

Yield 295 mg (31% of theory)
LC-MS (Method 12): $R_t$=1.63 min.
MS (EI): m/z=382 (M+H)$^+$ Example 163A Benzyl[(1S)-2-[(2-aminoethyl)amino]-1-(hydroxymethyl)-2-oxoethyl]carbamate hydrochloride

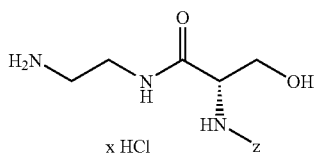

A mixture of 58 mg (0.152 mmol) of benzyl[(1S)-2-({2-[(tert-butoxycarbonyl)amino]ethyl}amino)-1-(hydroxymethyl)-2-oxoethyl]carbamate (Example 162A) in 25 ml of dioxane of a 4M solution of hydrogen chloride in dioxane is stirred at RT for 2 h. The reaction solution is concentrated, coevaporated with dichloromethane several times and dried under high vacuum. The crude product is reacted without further purification.

Yield: 42 mg (65% of theory)
LC-MS (Method 17): $R_t$=0.59 min.
MS (EI): m/z=282 (M−HCl+H)$^+$.

Example 164A

N$^5$-[(Benzyloxy)carbonyl]-N$^2$-(tert-butoxycarbonyl)-L-ornithyl-N-(2-{[(benzyloxy)carbonyl]amino}ethyl)-L-serinamide

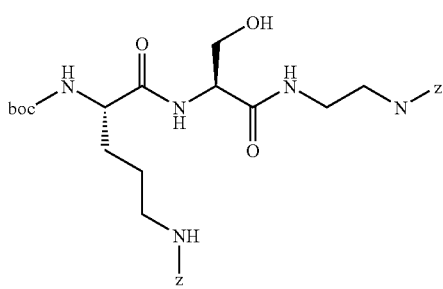

2.76 g (7.27 mmol) of HATU and 1.71 g (13.22 mmol) of N,N-diisopropylethylamine are added to a solution of 2.42 g (6.61 mmol) of N$^5$-[(benzyloxy)carbonyl]-N-(tert-butoxycarbonyl)-L-ornithine in 10 ml of anhydrous DMF at 0° C. After stirring at RT for 15 min, 2.1 g (6.61 mmol) of benzyl [2-(L-serylamino)ethyl]carbamate hydrochloride (Example 159A) are added. The reaction mixture is stirred at RT for 15 h. The solvent is then evaporated and the residue is taken up in dichloromethane. The organic phase is washed with water, dried over magnesium sulfate and concentrated. The crude product is purified by preparative HPLC.

Yield 122 mg (3% of theory)
LC-MS (Method 17): $R_t$=2.25 min.
MS (EI): m/z=630 (M+H)$^+$ Example 165A N$^5$-[(Benzyloxy)carbonyl]-L-ornithyl-N-(2-{[(benzyloxy)carbonyl]amino}ethyl)-L-serinamide hydrochloride

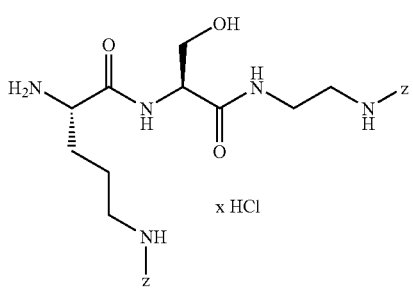

10 ml of a 4M solution of hydrogen chloride in dioxane are added to a solution of 120 mg (0.191 mmol) of N$^5$-[(benzyloxy)carbonyl]-N$^2$-(tert-butoxycarbonyl)-L-ornithyl-N-(2-{[(benzyloxy)carbonyl]amino}ethyl)-L-serinamide (Example 164A) in 5 ml of dioxane at RT. The mixture is stirred at RT for 1 h. The reaction solution is concentrated, coevaporated with dichloromethane several times and dried under high vacuum. The crude product is reacted without further purification.

Yield: quant.
LC-MS (Method 19): $R_t$=1.63 min.
MS (EI): m/z=530 (M−HCl+H)$^+$.

Example 166A tert-Butyl(3-{[(2S)-5-[(tert-butoxycarbonyl)amino]-2-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)pentanoyl]amino}-2-hydroxypropyl)carbamate

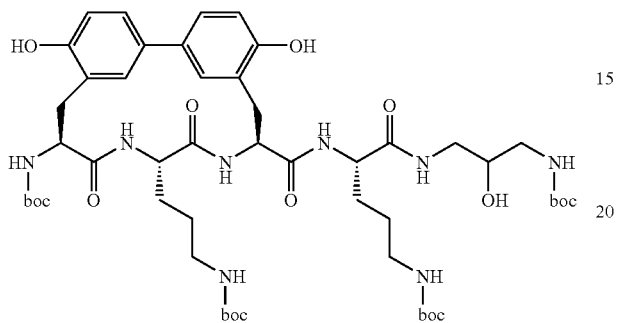

Under argon, 50 mg (0.076 mmol) of the compound from Example 29A and 40 mg (0.10 mmol) of N$^5$-(tert-butoxycarbonyl)-N-{3-[(tert-butoxycarbonyl)amino]-2-hydroxypropyl}-L-ornithinamide (Example 82A) are dissolved in 1.7 ml of dimethylformamide. Then, at 0° C. (ice bath), 19 mg (0.10 mmol) of EDC and 3.1 mg (0.023 mmol) of HOBt are added. The mixture is slowly warmed to RT and stirred at RT for 12 h. The solution is concentrated in vacuo, and the residue is stirred with water. The remaining solid is collected by suction filtration and purified by chromatography on silica gel (mobile phase dichloromethane/isopropanol 30:1 to 10:1).

Yield: 47 mg (48% of theory)
LC-MS (Method 17): R$_t$=2.40 min.
MS (EI): m/z=1043 (M+H)$^+$

Example 167A tert-Butyl(2-{[(2S)-5-[(tert-butoxycarbonyl)amino]-2-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)pentanoyl]amino}ethyl)carbamate

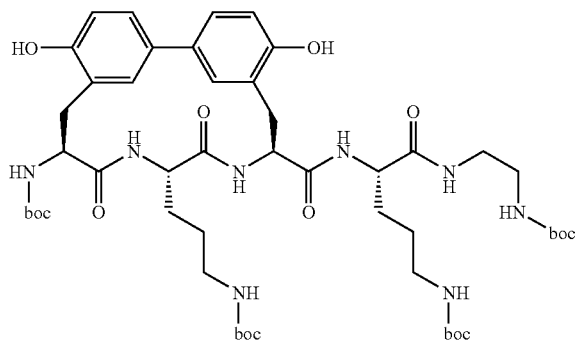

Under argon, 50 mg (0.076 mmol) of the compound from Example 29A and 37 mg (0.10 mmol) of N$^5$-(tert-butoxycarbonyl)-N-{2-[(tert-butoxycarbonyl)amino]ethyl}-L-ornithinamide (Example 81A) are dissolved in 1.7 ml of dimethylformamide. Then, at 0° C. (ice bath), 19 mg (0.10 mmol) of EDC and 3.1 mg (0.023 mmol) of HOBT are added. The mixture is slowly warmed to RT and stirred at RT for 12 h. The solution is concentrated in vacuo, and the residue is stirred with water. The remaining solid is collected by suction filtration and purified by chromatography on silica gel (mobile phase dichloromethane/isopropanol 30:1 to 10:1).

Yield: 43 mg (55% of theory)
LC-MS (Method 12): R$_t$=2.29 min.
MS (EI): m/z=1013 (M+H)$^+$

Example 168A tert-Butyl((3S)-3-{[(2S)-2-[(tert-butoxycarbonyl)amino]-5-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)pentanoyl]amino}-4-hydroxybutyl)carbamate

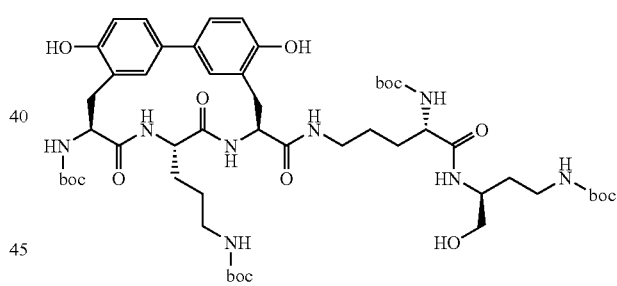

Under argon, 50 mg (0.076 mmol) of the compound from Example 29A and 42 mg (0.10 mmol) of N$^2$-(tert-butoxycarbonyl)-N-[(1S)-3-[(tert-butoxycarbonyl)amino]-1-(hydroxymethyl)propyl]-L-ornithinamide (Example 94A) are dissolved in 1.7 ml of dimethylformamide. Then, at 0° C. (ice bath), 19 mg (0.10 mmol) of EDC and 3.1 mg (0.023 mmol) of HOBT are added. The mixture is slowly warmed to RT and stirred at RT for 12 h. The solution is concentrated in vacuo, and the residue is stirred with water. The remaining solid is collected by suction filtration and purified by chromatography on silica gel (mobile phase dichloromethane/isopropanol 30:1 to 10:1).

Yield: 25 mg (31% of theory)
LC-MS (Method 12): R$_t$=2.18 min.
MS (EI): m/z=1057 (M+H)$^+$

Example 169A (8S,11S,14S)-14-Amino-11-(3-aminopropyl)-9-ethyl-5,17-dihydroxy-10,13-dioxo-9,12-diazatricyclo[14.3.1.1$^{2,6}$]henicosa-1(20),2(21),3,5,16,18-hexaene-8-carboxylic acid dihydrochloride

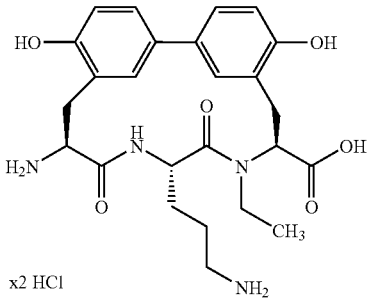

930 mg (0.91 mmol) of the compound from Example 78A are suspended in 260 ml of glacial acetic acid/water/ethanol (4/1/1), mixed with 270 mg of palladium on activated carbon (10%) and hydrogenated under atmospheric pressure at room temperature for 24 h. Removal of the catalyst by filtration through kieselguhr is followed by evaporation of the filtrate to dryness in vacuo and addition of 36.5 ml of 0.1N hydrochloric acid with stirring. The mixture is evaporated to dryness in vacuo and dried to constant weight.

Yield: 500 mg (98% of theory)
LC-MS (Method 20): $R_f$=2.45 min.
MS (ESI): m/z=485 (M−2HCl+H)$^+$

Example 170A (8S,11S,14S)-14-[(tert-Butoxycarbonyl)amino]-11-{3-[(tert-butoxycarbonyl)amino]propyl}-9-ethyl-5,17-dihydroxy-10,13-dioxo-9,12-diazatricyclo[14.3.1.1$^{2,6}$]henicosa-1(20),2(21),3,5,16,18-hexaene-8-carboxylic acid

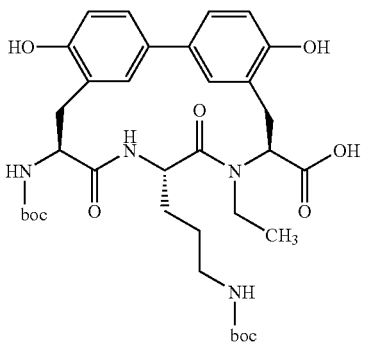

710 mg (1.27 mmol) of the compound from Example 169A are dissolved in 15 ml of water and 6.5 ml (6.5 mmol) of a 1N sodium hydroxide solution and, while stirring at room temperature, 834 mg (3.82 mmol) of di-tert-butyl dicarbonate dissolved in 5.5 ml of methanol are added. The reaction is complete after one hour (check by analytical RP-HPLC, mobile phase: acetonitrile/water). The pH is adjusted to 3 by dropwise addition of 0.1N hydrochloric acid. Extraction three times with 20 ml of ethyl acetate each time is followed by drying with sodium sulfate and evaporation to constant weight in vacuo.

Yield: 770 mg (88% of theory)
LC-MS (Method 19): $R_f$=2.16 min.
MS (ESI): m/z=685 (M+H)$^+$

Example 171A

Benzyl(2-{[(2S,4R)-5-{[(benzyloxy)carbonyl]amino}-2-({[(8S,11S,14S)-14-[(tert-butoxycarbonyl)amino]-11-{(2R)-3-[(tert-butoxycarbonyl)amino]-2-hydroxypropyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)-4-hydroxypentanoyl]amino}ethyl)carbamate

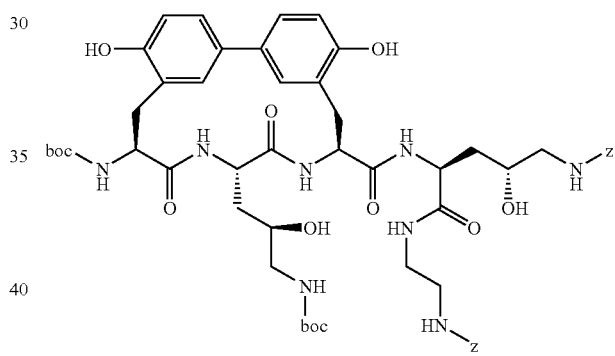

44 mg (0.07 mmol) of (8S,11S,14S)-14-[(tert-butoxycarbonyl)amino]-11-{(2R)-3-[(tert-butoxycarbonyl)amino]-2-hydroxypropyl}-5,17-dihydroxy-10,13-dioxo-9,12-diazatricyclo[14.3.1.126]henicosa-1(20),2(21),3,5,16,18-hexaene-8-carboxylic acid (Example 65A) are dissolved in 3 ml of DMF, and 38.9 mg (0.08 mmol) of the compound from Example 96A are added. The mixture is cooled to 0° C. and 29.8 mg (0.08 mmol) of HATU and 13 mg (0.1 mmol) of diisopropylethylamine are successively added. After 30 min at 0° C., the mixture is allowed to warm to room temperature and, after the addition of a further 26 mg (0.2 mmol) of diisopropylethylamine, stirred overnight. Concentration in vacuo is followed by purification by chromatography on silica gel (dichloromethane/methanol 9:1) and then by preparative HPLC.

Yield: 14 mg (20% of theory).
LC-MS (Method 19): $R_f$=2.42 min.
MS (EI): m/z=1114 (M+H)$^+$.

Example 172A tert-Butyl{(2R)-3-[(8S,11S,14S)-8-{[((1S,3R)-4-amino-1-{[(2-aminoethyl)amino]carbonyl}-3-hydroxybutyl)amino]carbonyl}-14-[(tert-butoxycarbonyl)amino]-5,17-dihydroxy-10,13-dioxo-9,12-diazatricyclo[14.3.1.1²,⁶]henicosa-1(20),2(21),3,5,16,18-hexaen-11-yl]-2-hydroxypropyl}carbamate dihydrochloride

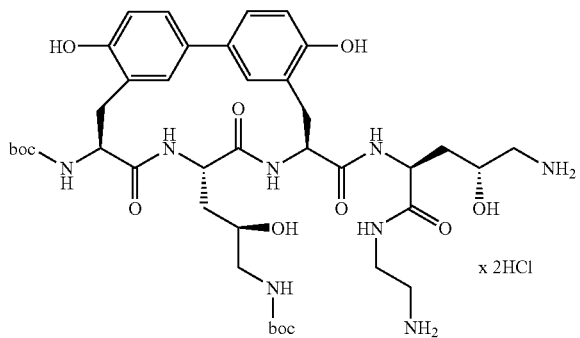

23 mg (0.02 mmol) of the compound from Example 171A are dissolved in 20 ml of a glacial acetic acid/methanol/water mixture (4/1/1), and 12 mg of palladium on activated carbon (10%) are added. The mixture is hydrogenated under atmospheric pressure for 4 h and then the catalyst is removed by filtration. The mother liquor obtained in this way is evaporated to dryness in vacuo, stirred with 2 ml of 0.1N hydrochloric acid and again evaporated to dryness. The crude product obtained in this way is reacted without further purification.

Yield: 16 mg (83% of theory).
LC-MS (Method 12): $R_t$=1.23 min.
MS (EI): m/z=845 (M−2HCl+H)⁺.

Example 173A tert-Butyl(3-{[(2S)-4-[(tert-butoxycarbonyl)amino]-2-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1²,⁶]henicosa-1(20),2(21),3,5,16,18-hexaen-8-yl]carbonyl}amino)butanoyl]amino}-2-hydroxypropyl)carbamate

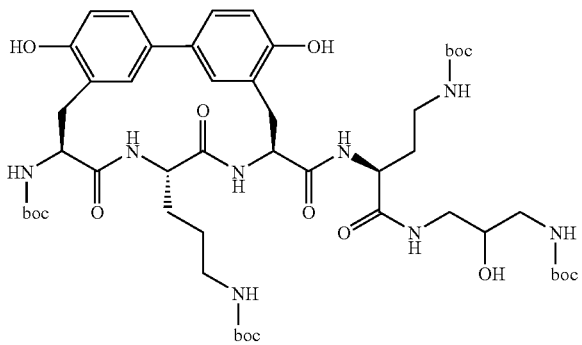

36 mg (0.06 mmol) of (8S,11S,14S)-14-[(tert-butoxycarbonyl)amino-11-[3-[(tert-butoxycarbonyl)amino]propyl}-5,17-dihydroxy-10,13-dioxo-9,12-diazatricyclo[14.3.1.1²,⁶]-henicosa-1(20),2(21),3,5,16,18-hexaene-8-carboxylic acid (Example 29A) and 26 mg (0.07 mmol) of tert-butyl[3-({(2S)-2-amino-4-[(tert-butoxycarbonyl)amino]butanoyl}amino)-2-hydroxypropyl]carbamate (Example 99A) are dissolved in 1 ml of DMF and cooled to 0° C., and 18 mg (0.09 mmol) of EDC and 2 mg (0.02 mmol) of HOBt are successively added. The mixture is allowed to warm to room temperature and is stirred overnight. The residue is stirred in water, and the precipitate resulting therefrom is collected by filtration, dried and purified by chromatography on silica gel (dichloromethane/methanol 100:7).

Yield: 9 mg (14% of theory).
LC-MS (Method 12): $R_t$=2.22 min.
MS (EI): m/z=1029 (M+H)⁺.

Example 174A

Benzyl(2-{[(2S,4R)-5-{[(benzyloxy)carbonyl]amino}-2-({[(8S,11S,14S)-14-[(tert-butoxycarbonyl)amino]-11-{3-[(tert-butoxycarbonyl)aminopropyl]}-5,17-dihydroxy-10,13-dioxo-9,12-diazatricyclo[14.3.1.1²,⁶]henicosa-1(20),2(21),3,5,16,18-hexaen-8-yl]carbonyl}amino)-4-hydroxypentanoyl]amino}ethyl)carbamate

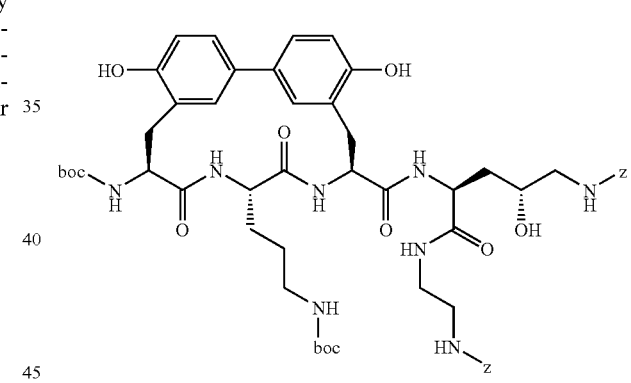

30 mg (0.05 mmol) of (8S,11S,14S)-14-[(tert-butoxycarbonyl)aminopropyl]-11-{3-[(tert-butoxycarbonyl)amino]}-5,17-dihydroxy-10,13-dioxo-9,12-diazatricyclo[14.3.1.1²,⁶]henicosa-1(20),2(21),3,5,16,18-hexaene-8-carboxylic acid (Example 29A) are dissolved in 1 ml of DMF, and 27 mg (0.05 mmol) of the compound from Example 96A are added. The mixture is cooled to 0° C., and 21 mg (0.05 mmol) of HATU and 10 mg (0.07 mmol) of diisopropylethylamine are successively added. After 30 min at 0° C., the mixture is allowed to warm to room temperature and, after the addition of a further 0.20 mg (0.14 mmol) of diisopropylethylamine, stirred overnight. Concentration in vacuo is followed by purification by chromatography on silica gel (dichloromethane/methanol/concentrated ammonia solution 90:10:1). After concentration of the fractions, the residue is stirred in acetonitrile and the precipitate is collected by filtration and dried in vacuo.

Yield: 16 mg (30% of theory).
LC-MS (Method 17): $R_t$=2.52 min.
MS (EI): m/z=1197 (M+H)⁺.

Example 175A tert-Butyl{3-[(8S,11S,14S)-8-{[((1S,3R)-4-amino-1-{[(2-aminoethyl)amino]carbonyl}-3-hydroxybutyl)amino]carbonyl}-14-[(tert-butoxycarbonyl)amino]-5,17-dihydroxy-10,13-dioxo-9,12-diazatricyclo[14.3.1.1²,⁶]henicosa-1(20),2(21),3,5,16,18-hexaen-1-yl]propyl}carbamate

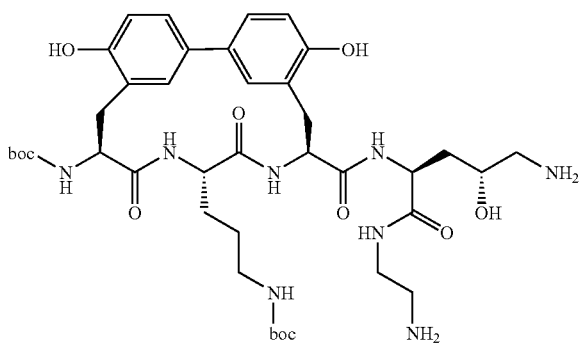

16 mg (0.01 mmol) of the compound from Example 174A are dissolved in 10 ml of methanol, and 8 mg of palladium on activated carbon (10%) are added. The mixture is hydrogenated under atmospheric pressure for 4 h, and then the catalyst is removed by filtration. The mother liquor obtained in this way is evaporated to dryness in vacuo. The crude product obtained in this way is reacted without further purification.

Yield: 10 mg (74% of theory).
LC-MS (Method 12): $R_t$=1.18 min.
MS (EI): m/z=829 (M+H)⁺.

Example 176A

Benzyl(2-{[(3S)-3-{[(benzyloxy)carbonyl]amino}-6-({[(8S,11S,14S)-14-[(tert-butoxycarbonyl)amino]-11-{3-[(tert-butoxycarbonyl)amino]propyl}-9-ethyl-5,17-dihydroxy-10,13-dioxo-9,12-diazatricyclo[14.3.1.1²,⁶]henicosa-1(20),2(21),3,5,16,18-hexaen-8-yl]carbonyl}amino)hexanoyl]-amino}ethyl)carbamate

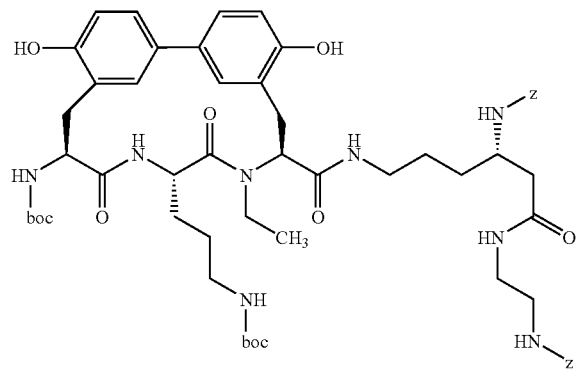

Under argon, 30 mg (0.044 mmol) of (8S,11S,14S)-14-[(tert-butoxycarbonyl)amino]-11-{3-[(tert-butoxycarbonyl)amino]propyl}-9-ethyl-5,17-dihydroxy-10,13-dioxo-9,12-diazatricyclo-[14.3.1.1²,⁶]henicosa-1(20),2(21),3,5,16,18-hexaene-8-carboxylic acid (Example 170A) and 80 mg (0.162 mmol) of benzyl-((1S)-4-amino-1-{2-[(2-{[(benzyloxy)carbonyl]amino}ethyl)amino]-2-oxoethyl}butyl)carbamate hydrochloride (Example 105A) are dissolved in 2 ml of dimethylformamide. Then, at 0° C. (ice bath), 31.16 mg (0.162 mmol) of EDC and 1.95 mg (0.014 mmol) of HOBt are added. The mixture is slowly warmed to RT and stirred at 50° C. for 3 days. The solution is concentrated in vacuo and the residue is purified by preparative HPLC.

Yield: 14.5 mg (30% of theory)
LC-MS (Method 17): $R_t$=2.55 min.
MS (EI): m/z=1123 (M+H)⁺.

Example 177A tert-Butyl[(4S)-5-({(2S)-2,5-bis[(tert-butoxycarbonyl)amino]pentyl}amino)-4-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1²,⁶]henicosa-1(20),2(21),3,5,16,18-hexaen-8-yl]carbonyl}amino)-5-oxopentyl]carbamate

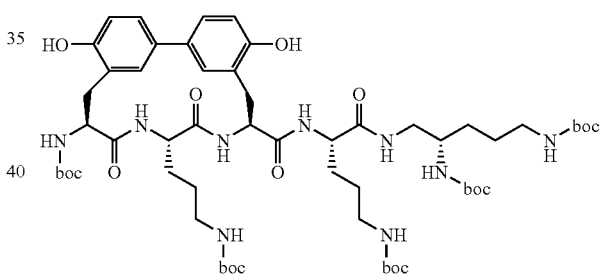

Under argon, 50 mg (0.076 mmol) of the compound from Example 29A and 53 mg (0.10 mmol) of tert-butyl[(4S)-4-amino-5-({(2S)-2,5-bis[(tert-butoxycarbonyl)amino]pentyl}amino)-5-oxopentyl]carbamate (Example 120A) are dissolved in 1.7 ml of dimethylformamide. Then, at 0° C. (ice bath), 19 mg (0.10 mmol) of EDC and 3.1 mg (0.023 mmol) of HOBt are added. The mixture is slowly warmed to RT and stirred at RT for 12 h. The solution is concentrated in vacuo and the residue is stirred with water. The remaining solid is collected by suction filtration and purified by preparative HPLC (Kromasil, mobile phase: acetonitrile/0.2% aqueous trifluoroacetic acid 5:95→95:5).

Yield: 40 mg (45% of theory)
LC-MS (Method 12): $R_t$=2.46 min.
MS (EI): m/z=1170 (M+H)⁺

Example 178A tert-Butyl[(1S)-4-[(tert-butoxycarbonyl)amino]-1-({[({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)acetyl]amino}methyl)butyl]carbamate

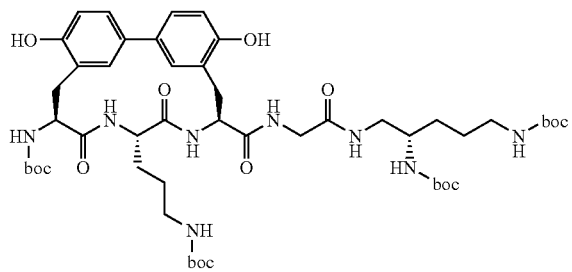

Under argon, 43 mg (0.066 mmol) of the compound from Example 29A and 32 mg (0.085 mmol) of tert-butyl{(4S)-5-[(aminoacetyl)amino]-4-[(tert-butoxycarbonyl)amino]pentyl}carbamate (Example 126A) are dissolved in 1.7 ml of dimethylformamide. Then, at 0° C. (ice bath), 16 mg (0.085 mmol) of EDC and 2.7 mg (0.02 mmol) of HOBt are added. The mixture is slowly warmed to RT and stirred at RT for 12 h. The solution is concentrated in vacuo and the residue is stirred with water. The remaining solid is collected by suction filtration and purified by preparative HPLC (Kromasil, mobile phase: acetonitrile/0.2% aqueous trifluoroacetic acid 5:95→95:5).

Yield: 11.5 mg (17% of theory)

LC-MS (Method 19): $R_t$=2.47 min.

MS (EI): m/z=1013 (M+H)$^+$

Example 179A tert-Butyl[(1S)-4-[(tert-butoxycarbonyl)amino]-1-({[(2S)-2-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)-3-hydroxypropanoyl]amino}methyl)butyl]carbamate

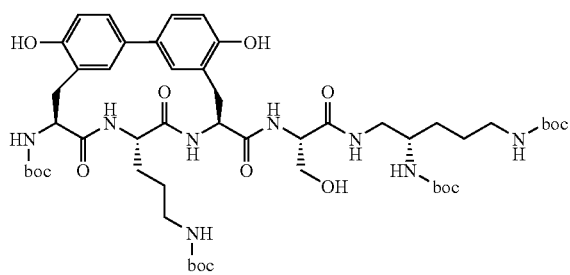

Under argon, 28 mg (0.042 mmol) of the compound from Example 29A and 22 mg (0.055 mmol) of tert-butyl{(4S)-5-{[(2S)-2-amino-3-hydroxypropanoyl]amino}-4-[(tert-butoxycarbonyl)amino]pentyl}carbamate (Example 128A) are dissolved in 1.7 ml of dimethylformamide. Then, at 0° C. (ice bath), 11 mg (0.055 mmol) of EDC and 1.7 mg (0.013 mmol) of HOBt are added. The mixture is slowly warmed to RT and stirred at RT for 12 h. The solution is concentrated in vacuo and the residue is stirred with water. The remaining solid is collected by suction filtration and purified by chromatography (Sephadex LH20, mobile phase: methanol/acetic acid (0.25%)).

Yield: 18.4 mg (42% of theory)

LC-MS (Method 17): $R_t$=2.43 min.

MS (EI): m/z=1043 (M+H)$^+$

Example 180A tert-Butyl{(1S)-1-({[(2S)-5-amino-2-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]-henicosa-1(20),2(21),3,5,16,18-hexaen-8-yl]carbonyl}amino)-5-oxopentanoyl]amino}methyl)-4-[(tert-butoxycarbonyl)amino]butyl}carbamate

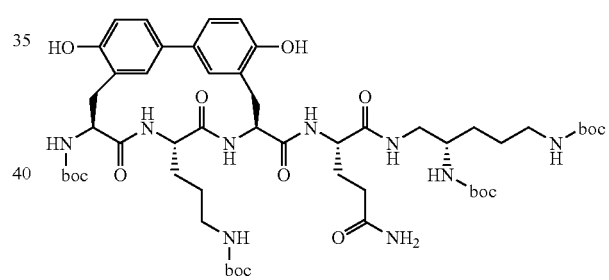

Under argon, 27 mg (0.042 mmol) of the compound from Example 29A and 21 mg (0.047 mmol) of tert-butyl[(1S)-4-[(tert-butoxycarbonyl)amino]-1-({[(2S)-2,5-diamino-5-oxopentanoyl]amino}methyl)butyl]carbamate (Example 130A) are dissolved in 2 ml of dimethylformamide. Then, at 0° C. (ice bath), 10 mg (0.053 mmol) of EDC and 1.7 mg (0.013 mmol) of HOBt are added. The mixture is slowly warmed to RT and stirred at RT for 12 h. The solution is concentrated in vacuo and the residue is stirred with water. The remaining solid is collected by suction filtration and purified by chromatography (Sephadex LH20, mobile phase: methanol/acetic acid (0.25%)).

Yield: 16 mg (36% of theory)

LC-MS (Method 19): $R_t$=2.38 min.

MS (EI): m/z=1084 (M+H)$^+$

Example 181

$N^5$-[(Benzyloxy)carbonyl]-$N^2$-{[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}-L-ornithyl-$N^5$-[(benzyloxy)carbonyl]-N-(2-{[(benzyloxy)carbonyl]amino}ethyl)-L-ornithinamide

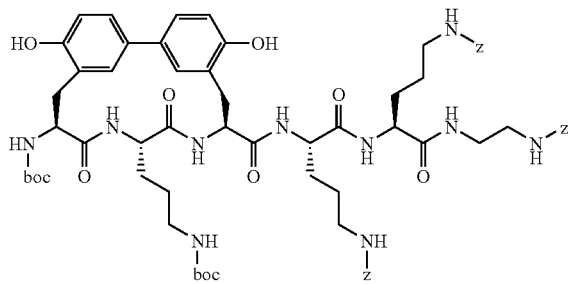

Under argon, 40 mg (0.061 mmol) of the compound from Example 29A and 66 mg (0.091 mmol) of $N^5$-[(benzyloxy)carbonyl]-L-ornithyl-$N^5$-[(benzyloxy)carbonyl]-N-(2-{[(benzyloxy)carbonyl]amino}ethyl)-L-ornithinamide (Example 124A) are dissolved in 2 ml of dimethylformamide. Then, at 0° C. (ice bath), 15 mg (0.079 mmol) of EDC and 2.5 mg (0.018 mmol) of HOBt are added. The mixture is slowly warmed to RT and stirred at RT for 12 h. The solution is concentrated in vacuo and the residue is stirred with water. The remaining solid is collected by suction filtration and purified by preparative HPLC (mobile phase: acetonitrile/water gradient).

Yield: 25 mg (26% of theory)
LC-MS (Method 17): $R_t$=2.73 min.
MS (EI): m/z=1330 (M+H)$^+$

Example 182A tert-Butyl(2-{[2-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)ethyl]amino}-2-oxoethyl)carbamate

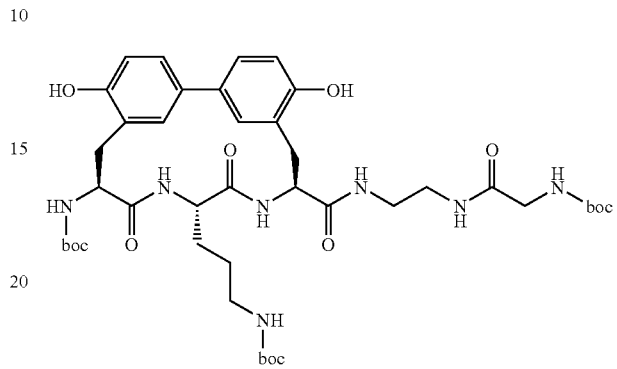

Under argon, 34 mg (0.052 mmol) of the compound from Example 29A and 17 mg (0.078 mmol) of tert-butyl{2-[(2-aminoethyl)amino]-2-oxoethyl}carbamate (*Russ. J. Bioorg. Chem.* (1994) 20:397-405) are dissolved in 2 ml of dimethylformamide. Then, at 0° C. (ice bath), 13 mg (0.068 mmol) of EDC and 2.1 mg (0.016 mmol) of HOBt are added. The mixture is slowly warmed to RT and stirred at RT for 12 h. The solution is concentrated in vacuo and the residue is stirred with water. The remaining solid is collected by suction filtration and purified by chromatography (Sephadex LH20, mobile phase: methanol/acetic acid (0.25%)).

Yield: 23 mg (50% of theory)
LC-MS (Method 19): $R_t$=2.16 min.
MS (EI): m/z=856 (M+H)$^+$ Examples 183A to 203A listed in the following table are prepared from the appropriate starting materials in analogy to the method of Example 166A:

| Ex. No. | Starting material example | Structure | Analytical data |
|---|---|---|---|
| 183A | 29A and methyl glycinate | ![structure] | LC-MS (Method 12): $R_t$ = 1.90 min. MS (EI): m/z = 728 (M + H)$^+$ |

-continued
| Ex. No. | Starting material example | Structure | Analytical data |
|---|---|---|---|
| 184A | 29A and 143A | 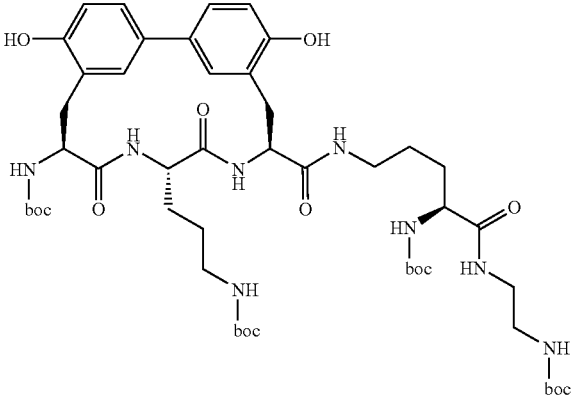 | LC-MS (Method 19): $R_t$ = 2.42 min. MS (EI): m/z = 1013 $(M + H)^+$ |
| 185A | 29A and 144A | 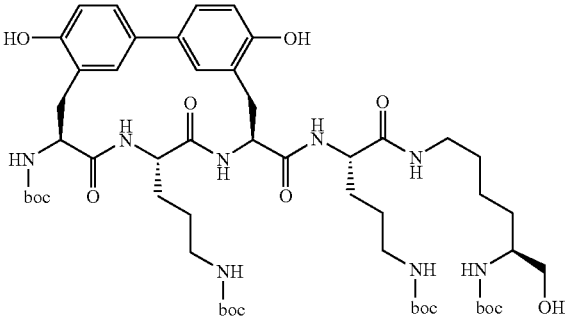 | LC-MS (Method 17): $R_t$ = 2.42 min. MS (EI): m/z = 1086 $(M + H)^+$ |
| 186A | 29A and 145A | 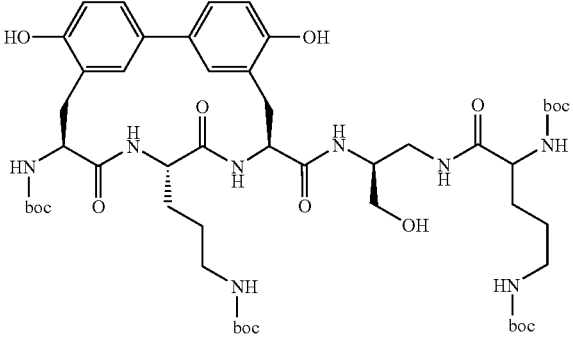 | LC-MS (Method 17): $R_t$ = 2.41 min. MS (EI): m/z = 1043 $(M + H)^+$ |
| 187A | 29A and 146A | 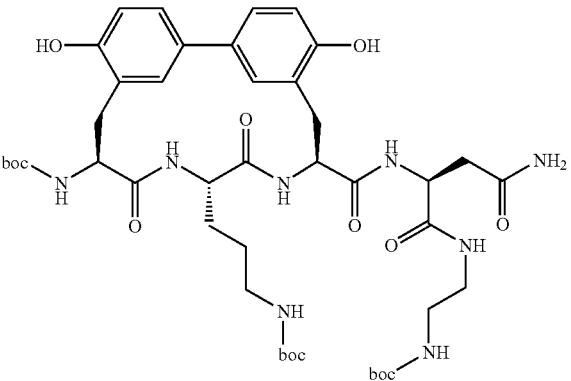 | LC-MS (Method 12): $R_t$ = 1.94 min. MS (EI): m/z = 913 $(M + H)^+$ |

-continued

| Ex. No. | Starting material example | Structure | Analytical data |
|---|---|---|---|
| 188A | 29A and 101A | 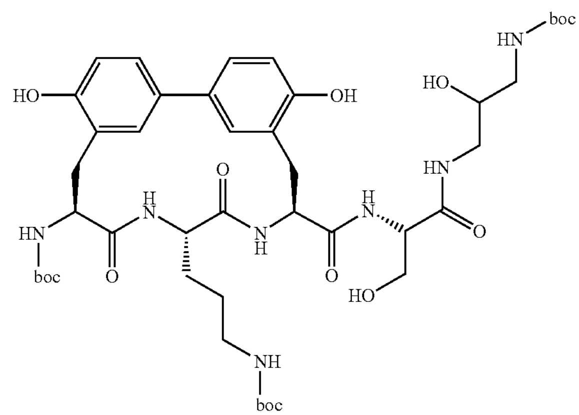 | LC-MS (Method 12): $R_t$ = 1.91 min. MS (EI): m/z = 916 (M + H)$^+$ |
| 189A | 29A and 107A | 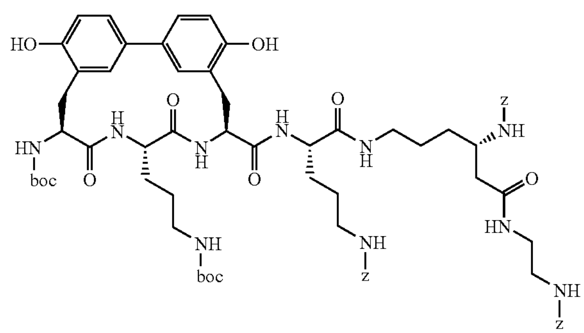 | LC-MS (Method 17): $R_t$ = 2.65 min. MS (EI): m/z = 1344 (M + H)$^+$ |
| 190A | 29A and 105A | 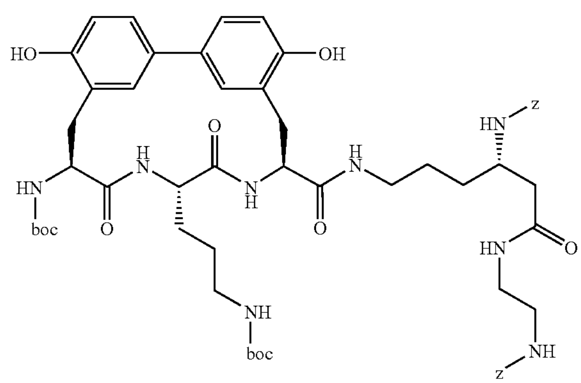 | LC-MS (Method 12): $R_t$ = 2.35 min. MS (EI): m/z = 1095 (M + H)$^+$ |
| 191A | 29A and 111A | 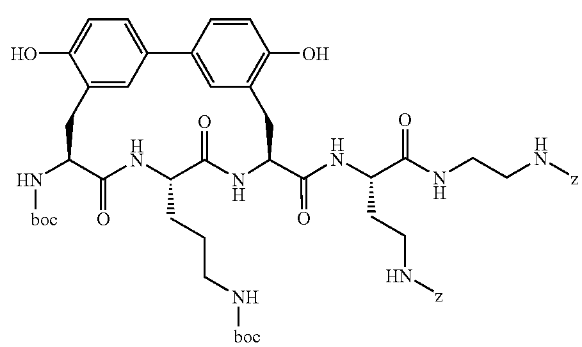 | LC-MS (Method 19): $R_t$ = 2.53 min. MS (EI): m/z = 1067 (M + H)$^+$ |

| Ex. No. | Starting material example | Structure | Analytical data |
|---|---|---|---|
| 192A | 29A and 113A | 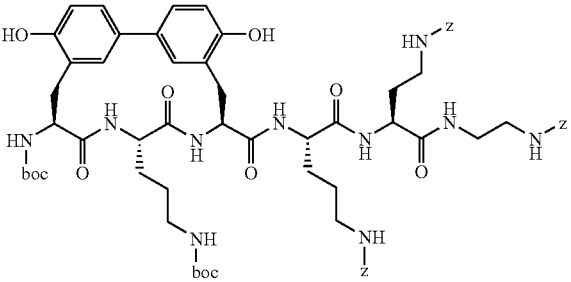 | LC-MS (Method 19): $R_t$ = 2.70 min. MS (EI): m/z = 1315 (M + H)$^+$ |
| 193A | 29A and 115A | 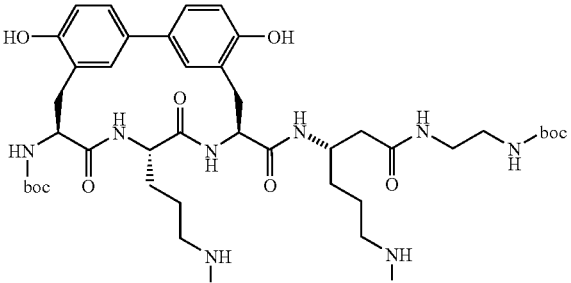 | LC-MS (Method 19): $R_t$ = 2.42 min. MS (EI): m/z = 1027 (M + H)$^+$ |
| 194A | 29A and 103A | 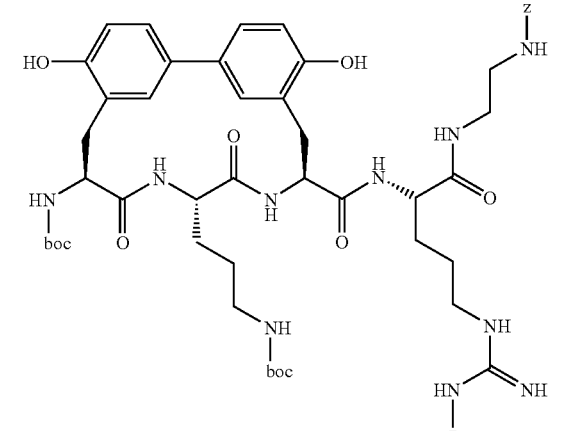 | LC-MS (Method 19): $R_t$ = 2.17 min. MS (EI): m/z = 1123 (M + H)$^+$ |
| 195A | 29A and 155A | 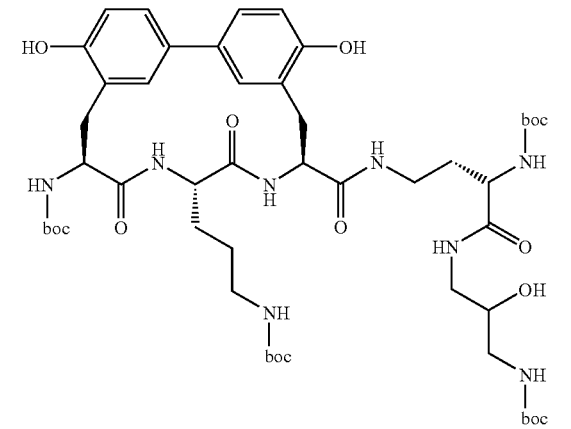 | LC-MS (Method 12): $R_t$ = 2.15 min. MS (EI): m/z = 1029 (M + H)$^+$ |

-continued
| Ex. No. | Starting material example | Structure | Analytical data |
|---|---|---|---|
| 196A | 29A and 157A | 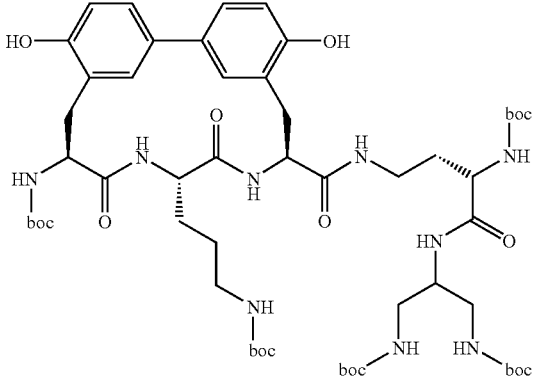 | LC-MS (Method 19): $R_t$ = 2.63 min. MS (EI): m/z = 1128 $(M + H)^+$ |
| 197A | 29A and 149A | 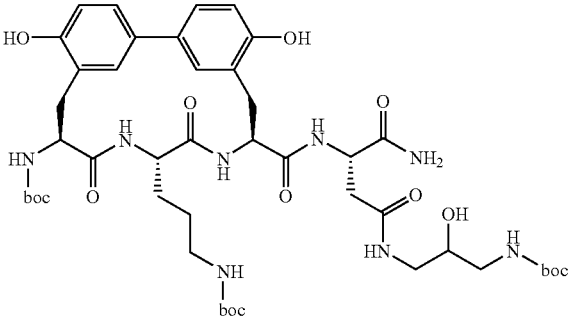 | LC-MS (Method 19): $R_t$ = 2.07 min. MS (EI): m/z = 943 $(M + H)^+$ |
| 198A | 29A and 148A | 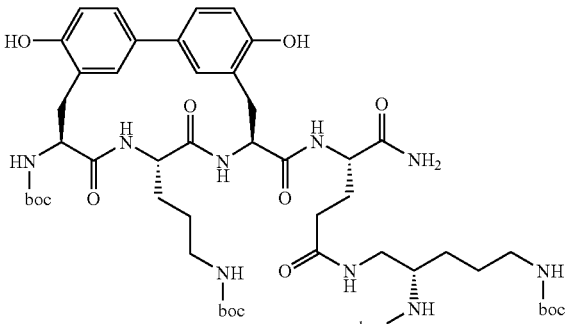 | LC-MS (Method 12): $R_t$ = 2.17 min. MS (EI): m/z = 1084 $(M + H)^+$ |
| 199A | 29A and 147A | 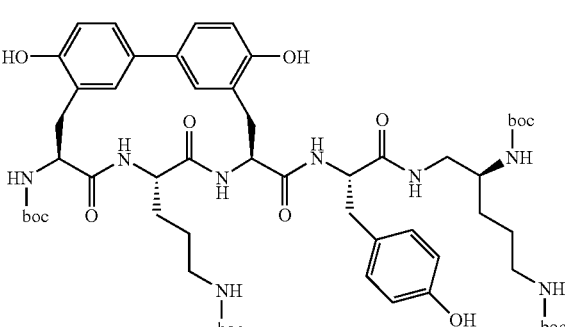 | LC-MS (Method 19): $R_t$ = 2.54 min. MS (EI): m/z = 1119 $(M + H)^+$ |

-continued

| Ex. No. | Starting material example | Structure | Analytical data |
|---|---|---|---|
| 200A | 29A and 150A | 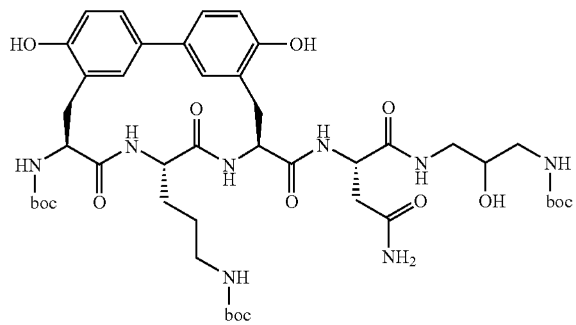 | LC-MS (Method 17): R$_t$ = 2.11 min. MS (EI): m/z = 943 (M + H)$^+$ |
| 201A | 29A and 151A | 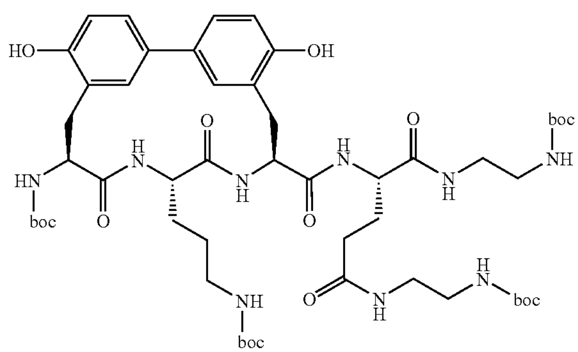 | LC-MS (Method 17): R$_t$ = 2.39 min. MS (EI): m/z = 1070 (M + H)$^+$ |
| 202A | 29A and 152A | 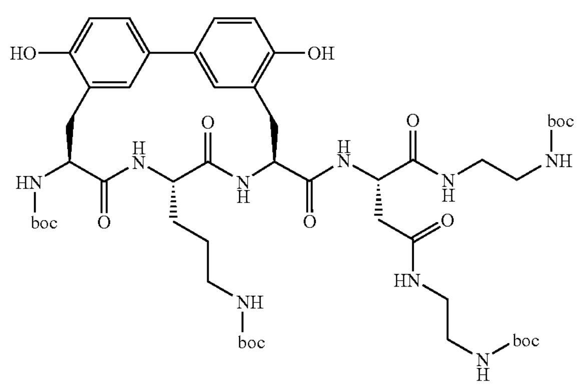 | LC-MS (Method 17): R$_t$ = 2.44 min. MS (EI): m/z = 1056 (M + H)$^+$ |
| 203A | 29A and 153A | 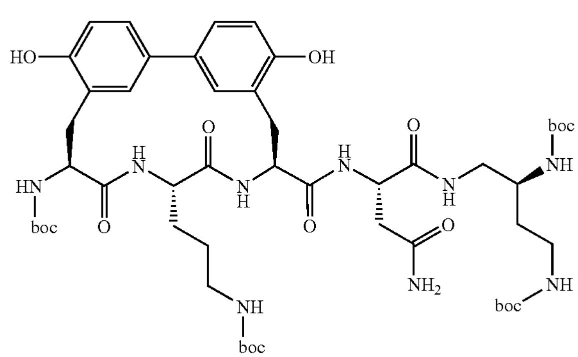 | LC-MS (Method 17): R$_t$ = 2.40 min. MS (EI): m/z = 1056 (M + H)$^+$ |

Example 204A tert-Butyl{3-[(8S,11S,14S)-8-[({(4S)-4-amino-6-[(2-aminoethyl)amino]-6-oxohexyl}amino)carbonyl]-14-[(tert-butoxycarbonyl)amino]-9-ethyl-5,17-dihydroxy-10,13-dioxo-9,12-diazatricyclo[14.3.1.1$^{2,6}$]henicosa-1(20),2(21),3,5,16,18-hexaen-11-yl]propyl}carbamate

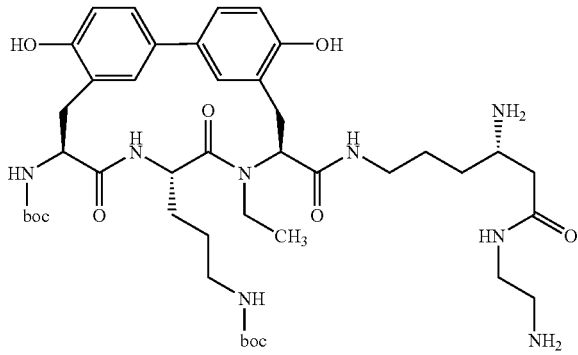

14.5 mg (0.013 mmol) of benzyl(2-{[(3S)-3-{[(benzyloxy)carbonyl]amino}-6-({[(8S,11S,14S)-14-[(tert-butoxycarbonyl)amino]-11-{3-[(tert-butoxycarbonyl)amino]propyl}-9-ethyl-5,17-dihydroxy-10,13-dioxo-9,12-diazatricyclo[14.3.1.1$^{2,6}$]henicosa-1(20),2(21),3,5,16,18-hexaen-8-yl]carbonyl}amino)hexanoyl]amino}ethyl)carbamate (Example 176A) are dissolved in 3 ml of ethanol. 15 mg of palladium on activated carbon (10%) are added thereto, and the mixture is then hydrogenated under atmospheric pressure for 15 h. The reaction mixture is filtered through prewashed kieselguhr, and the filtrate is concentrated on a rotary evaporator in vacuo. The crude product is reacted without further purification.

Yield: 8 mg (73% of theory).
LC-MS (Method 19): R$_t$=1.59 min.
MS (EI): m/z=855 (M+H)$^+$.

Example 205A tert-Butyl{3-[(8S,11S,14S)-8-[({(1S)-4-amino-1-[({(4S)-4-amino-6-[(2-aminoethyl)amino]-6-oxohexyl}amino)carbonyl]butyl}amino)carbonyl]-14-[(tert-butoxycarbonyl)amino]-5,17-dihydroxy-10,13-dioxo-9,12-diazatricyclo[14.3.1.1$^{2,6}$]henicosa-1(20),2(21),3,5,16,18-hexaen-11-yl]propyl}carbamate tris(hydroacetate)

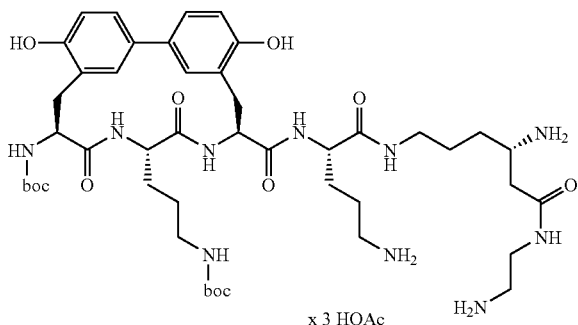

9 mg (0.007 mmol) of benzyl((1S)-4-{[(2S)-5-{[(benzyloxy)carbonyl]amino}-2-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)pentanoyl]amino}-1-{2-[(2-{[(benzyloxy)carbonyl]amino}ethyl)amino]-2-oxoethyl}butyl)carbamate (Example 189A) are added into 8 ml of a 4:1:1 acetic acid/water/ethanol mixture. 1 mg of palladium on activated carbon (10%) is added thereto, and the mixture is then hydrogenated at RT under atmospheric pressure for 15 h. The reaction mixture is filtered through prewashed kieselguhr and washed with ethanol, and the filtrate is concentrated on a rotary evaporator in vacuo.

Yieid: quant.
LC-MS (Method 17): R$_t$=1.33 min.
MS (EI): m/z=941 (M−3HOAc+H)$^+$

Example 206A tert-Butyl{3-[(8S,11S,14S)-8-[({(4S)-4-amino-6-[(2-aminoethyl)amino]-6-oxohexyl}amino)carbonyl]-14-[(tert-butoxycarbonyl)amino]-5,17-dihydroxy-10,13-dioxo-9,12-diazatricyclo[14.3.1.1$^{2,6}$]henicosa-1(20),2(21),3,5,16,18-hexaen-11-yl]propyl}carbamate bis(hydroacetate)

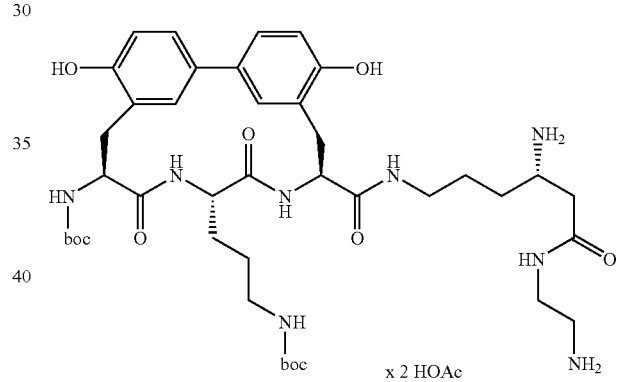

12 mg (0.011 mmol) of benzyl(2-{[(3S)-3-{[(benzyloxy)carbonyl]amino}-6-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)hexanoyl]amino}ethyl)carbamate (Example 190A) are added into 3 ml of a 4:1:1 acetic acid/water/ethanol mixture. 1.5 mg of palladium on activated carbon (10%) are added thereto, and the mixture is then hydrogenated at RT under atmospheric pressure for 15 h. The reaction mixture is filtered through prewashed kieselguhr and washed with ethanol, and the filtrate is concentrated on a rotary evaporator in vacuo.

Yieid: quant.
LC-MS (Method 17): R$_t$=1.48 min.
MS (EI): m/z=827 (M−2HOAc+H)$^+$

Example 207A tert-Butyl{3-[(8S,11S,14S)-8-{[((1S)-3-amino-1-{[(2-aminoethyl)amino]carbonyl}propyl)amino]carbonyl}-14-[(tert-butoxycarbonyl)amino]-5,17-dihydroxy-10,13-dioxo-9,12-diazatricyclo-[14.3.1.1$^{2,6}$]henicosa-1(20),2(21),3,5,16,18-hexaen-11-yl]propyl}carbamate bis(hydroacetate)

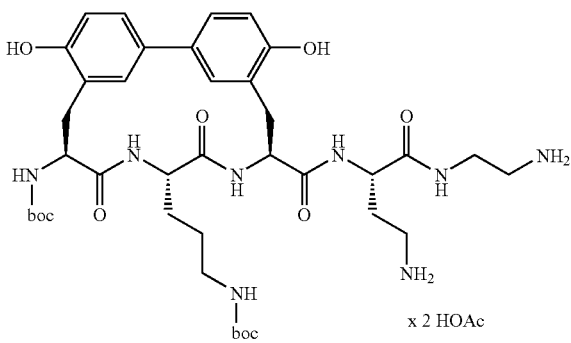

29 mg (0.027 mmol) of benzyl(2-{[(2S)-4-{[(benzyloxy)carbonyl]amino}-2-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)butanoyl]amino}ethyl)carbamate (Example 191A) are added into 8 ml of a 4:1:1 acetic acid/water/ethanol mixture. 2.5 mg of palladium on activated carbon (10%) are added thereto, and the mixture is then hydrogenated at RT under atmospheric pressure for 15 h. The reaction mixture is filtered through prewashed kieselguhr and washed with ethanol, and the filtrate is concentrated on a rotary evaporator in vacuo.

Yield: 16 mg (74% of theory)
LC-MS (Method 19): R$_t$=1.48 min.
MS (EI): m/z=799 (M−2HOAc+H)$^+$

Example 208A tert-Butyl{3-[(8S,11S,14S)-8-{[((1S)-4-amino-1-{[((1S)-3-amino-1-{[(2-aminoethyl)amino]carbonyl}propyl)amino]carbonyl}butyl)amino]carbonyl}-14-[(tert-butoxycarbonyl)amino]-5,17-dihydroxy-10,13-dioxo-9,12-diazatricyclo[14.3.1.1$^{2,6}$]henicosa-1(20),2(21),3,5,16,18-hexaen-11-yl]propyl}carbamate tris(hydroacetate)

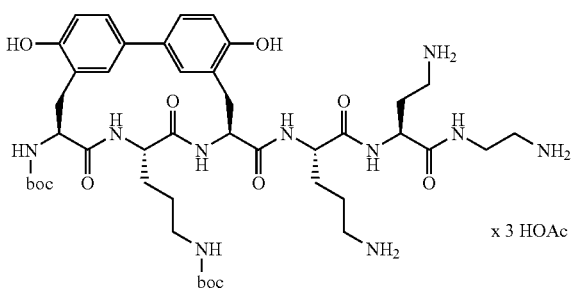

12 mg (0.009 mmol) of benzyl{(3S)-3-{[(2S)-5-{[(benzyloxy)carbonyl]amino}-2-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^2$]henicosa-1(20),2(21),3,5,16,18-hexaen-8-yl]carbonyl}amino)pentanoyl]amino}-4-[(2-{[(benzyloxy)carbonyl]amino}ethyl)amino]-4-oxobutyl}carbamate (Example 192A) are added into 8 ml of a 4:1:1 acetic acid/water/ethanol mixture. 1 mg of palladium on activated carbon (10%) is added thereto, and the mixture is then hydrogenated at RT under atmospheric pressure for 15 h. The reaction mixture is filtered through prewashed kieselguhr and washed with ethanol, and the filtrate is concentrated on a rotary evaporator in vacuo.

Yield: 7 mg (84% of theory)
LC-MS (Method 17): R$_t$=1.31 min.
MS (EI): m/z=913 (M−3HOAc+H)$^+$

Example 209A tert-Butyl{3-[(8S,11S,14S)-8-{[((1S)-1-{[(2-aminoethyl)amino]carbonyl}-4-{[amino(imino)methyl]amino}butyl)amino]carbonyl}-14-[(tert-butoxycarbonyl)amino]-5,17-dihydroxy-10,13-dioxo-9,12-diazatricyclo[14.3.1.1$^{2,6}$]henicosa-1(20),2(21),3,5,16,18-hexaen-11-yl]propyl}carbamate di(hydrotrifluoroacetate)

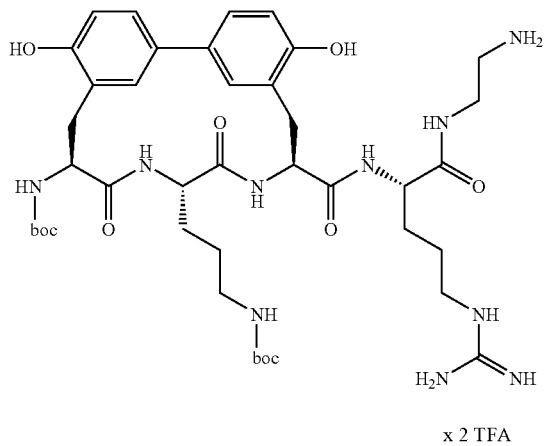

13.4 mg (0.012 mmol) of benzyl[(6S)-6-({[(8S,11S,14S)-14-[(tert-butoxycarbonyl)amino]-1-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)-7,12-dioxo-14-phenyl-13-oxa-2,8,11-triazatetradecane-1-imidoyl]carbamate (Example 194A) are added into 5 ml of a 4:1:1 acetic acid/water/ethanol mixture. 1 mg of palladium on activated carbon (10%) is added thereto, and the mixture is then hydrogenated at RT under atmospheric pressure for 15 h. The reaction mixture is filtered through prewashed kieselguhr and washed with ethanol, and the filtrate is concentrated on a rotary evaporator in vacuo. The target product is purified and converted into the di(hydrotrifluoroacetate) by preparative HPLC (Kromasil, mobile phase acetonitrile/0.2% aqueous trifluoroacetic acid 5:95→95:5).

Yield: 5.3 mg (41% of theory)
LC-MS (Method 12): R$_t$=1.19 min.
MS (EI): m/z=855 (M−2TFA+H)$^+$

Example 210A

N²-{[(8S,11S,14S)-14-[(tert-Butoxycarbonyl)amino]-11-{3-[(tert-butoxycarbonyl)amino]propyl}-5,17-dihydroxy-10,13-dioxo-9,12-diazatricyclo[14.3.1.1²,⁶]henicosa-1(20),2(21),3,5,16,18-hexaen-8-yl]carbonyl}-L-ornithyl-N-(2-aminoethyl)-L-ornithinamide tris(hydroacetate)

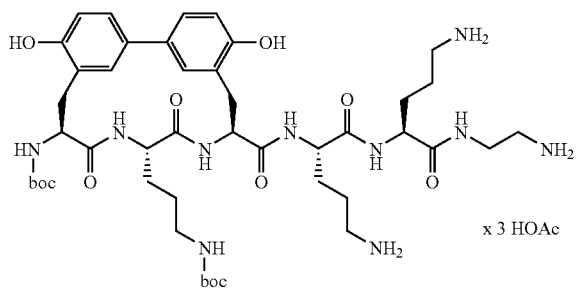

25 mg (0.02 mmol) of the compound from Example 181A are added into 8 ml of a 4:1:1 acetic acid/water/ethanol mixture. 3 mg of palladium on activated carbon (10%) are added thereto, and the mixture is then hydrogenated at RT under atmospheric pressure for 48 h. The reaction mixture is filtered through prewashed kieselguhr and washed with ethanol, and the filtrate is evaporated to dryness in vacuo.

Yield: 8.5 mg (41% of theory)

LC-MS (Method 20): $R_t$=2.63 min.

MS (EI): m/z=927 (M−3HOAc+H)⁺

Examples 211A to 215A listed in the following table are prepared from the appropriate starting materials in analogy to the method of Example 166A.

| Example No. | Starting material example | Structure | Analytical data |
|---|---|---|---|
| 211A | 29A and 159A | 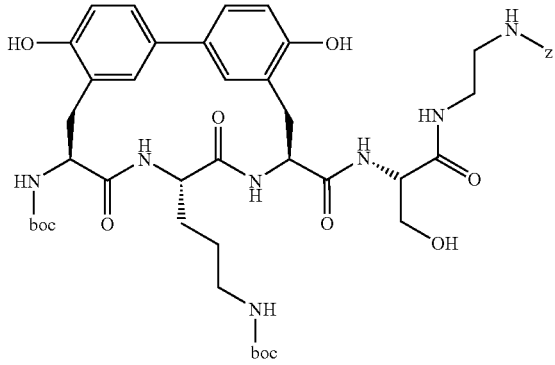 | LC-MS (Method 17): $R_t$ = 2.21 min. MS (EI): m/z = 920 (M + H)⁺ |
| 212A | 29A and 109A | 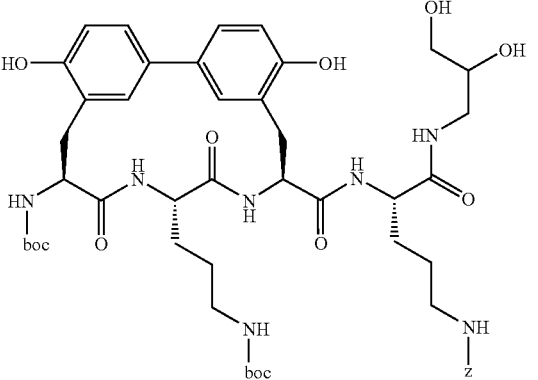 | LC-MS (Method 17): $R_t$ = 2.17 min. MS (EI): m/z = 978 (M + H)⁺ |

-continued

| Example No. | Starting material example | Structure | Analytical data |
|---|---|---|---|
| 213A | 29A and 165A | 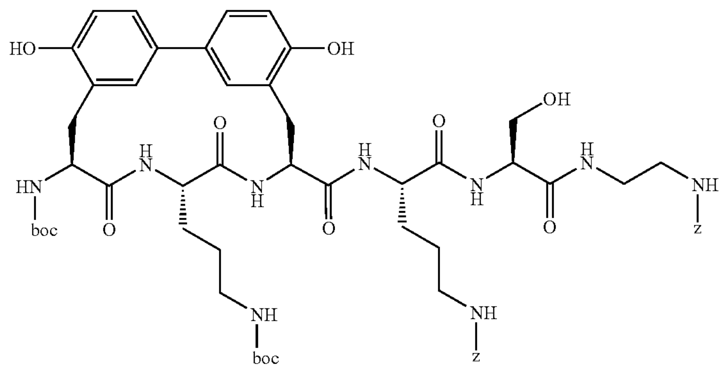 | LC-MS (Method 19): R_t = 2.42 min. MS (EI): m/z = 1168 (M + H)+ |
| 214A | 29A and 161A | 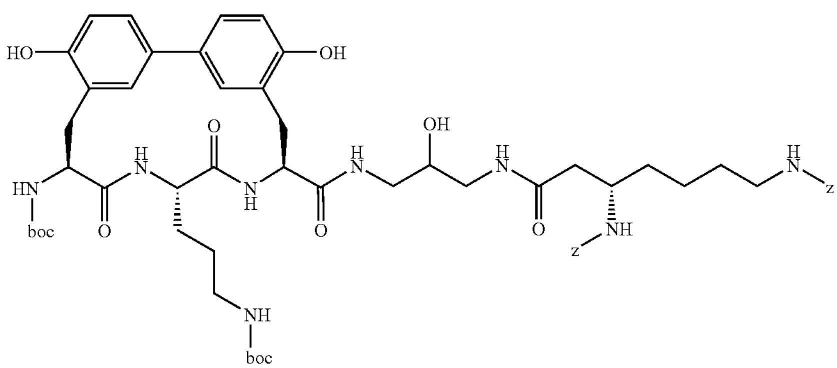 | LC-MS (Method 19): R_t = 2.48 min. MS (EI): m/z = 1139 (M + H)+ |
| 215A | 29A and 163A | 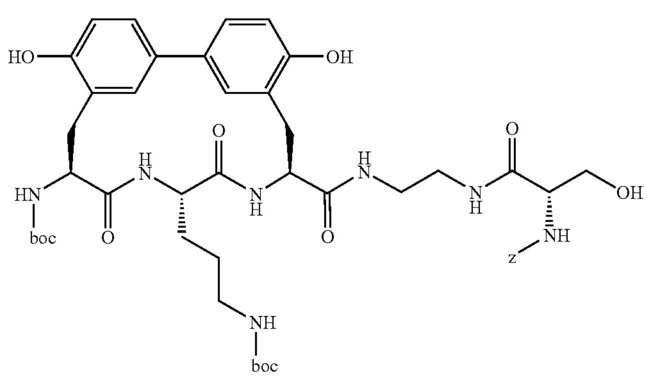 | LC-MS (Method 12): R_t = 1.98 min. MS (EI): m/z = 920 (M + H)+ |

Examples 216A to 220A listed in the following table are prepared from the appropriate starting materials in analogy to the method of Example 205A.

| Example No. | Starting material example | Structure | Analytical data |
|---|---|---|---|
| 216A | 211A | 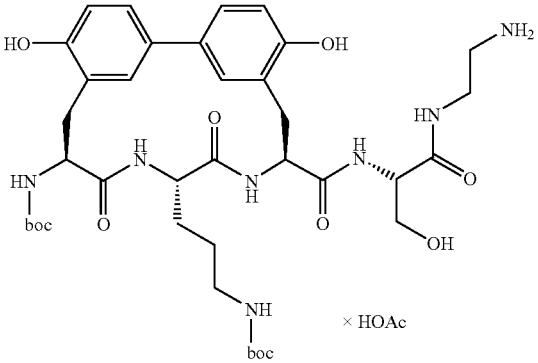 | LC-MS (Method 19): $R_t$ = 1.69 min. MS (EI): m/z = 786 (M − HOAc + H)$^+$ |
| 217A | 212A | 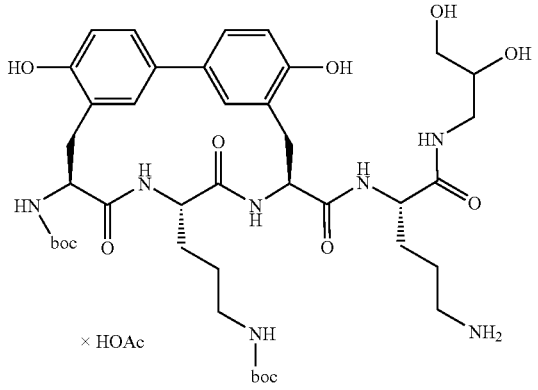 | LC-MS (Method 17): $R_t$ = 1.62 min. MS (EI): m/z = 844 (M − HOAc + H)$^+$ |
| 218A | 213A | 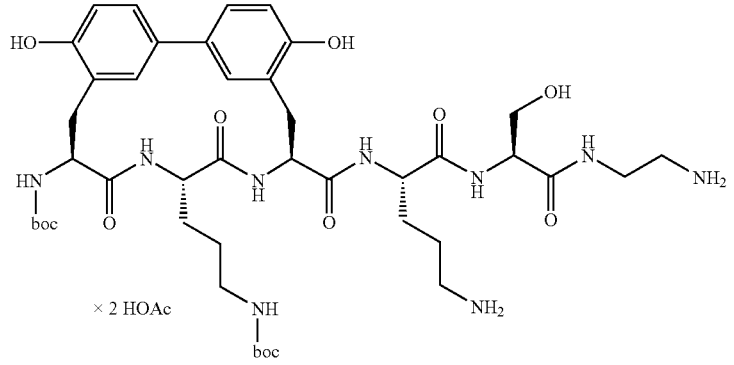 | LC-MS (Method 19): $R_t$ = 1.48 min. MS (EI): m/z = 899 (M − 2HOAc + H)$^+$ |
| 219A | 214A | 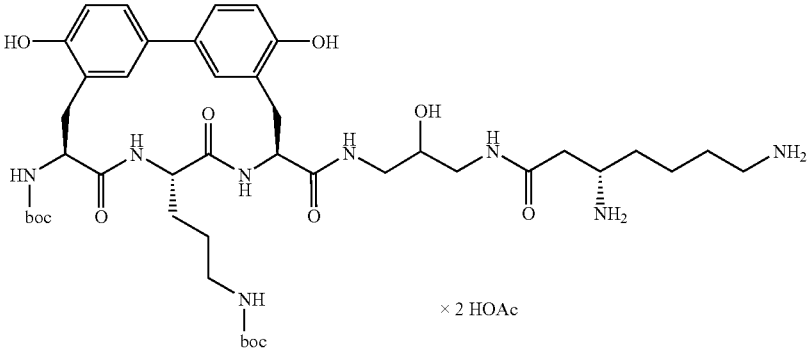 | LC-MS (Method 19): $R_t$ = 1.30 min. MS (EI): m/z = 869 (M − 2HOAc − H)$^-$ |

| Example No. | Starting material example | Structure | Analytical data |
|---|---|---|---|
| 220A | 215A | 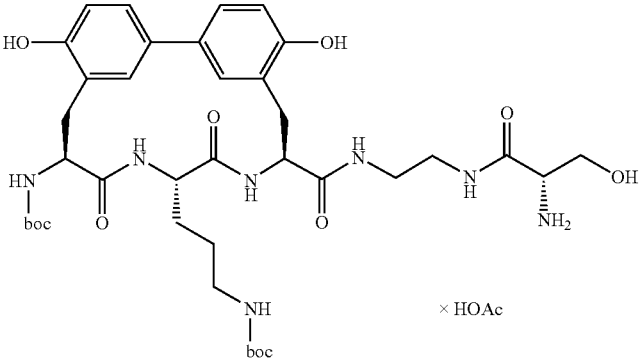 | LC-MS (Method 17):<br>$R_t$ = 1.69 min.<br>MS (EI): m/z = 786<br>(M − HOAc + H)$^+$ |

Example 221A tert-Butyl{3-[(8S,11S,14S)-8-[({2-[(2-aminoethyl)amino]-2-oxoethyl}amino)carbonyl]-14-[(tert-butoxycarbonyl)amino]-5,17-dihydroxy-10,13-dioxo-9,12-diazatricyclo[14.3.1.1$^{2,6}$]henicosa-1(20),2(21),3,5,16,18-hexaen-11-yl]propyl}carbamate hydrotrifluoroacetate

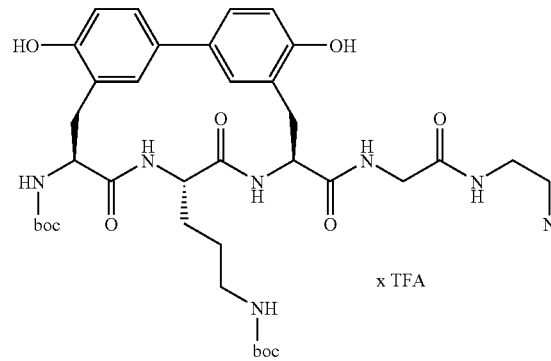

45 mg (0.057 mmol) of the compound from Example 183A are dissolved in 1 ml of ethane-1,2-diamine and, after the addition of 0.75 mg of potassium cyanide, stirred at RT for 12 h. The mixture is then diluted with 15 ml of water and extracted once with ethyl acetate. The organic phase is washed with water, and the combined aqueous phases are evaporated to dryness in vacuo. The residue is purified by RP-HPLC (Kromasil 100C18, mobile phase: acetonitrile/trifluoroacetic acid (0.2%) 5:95 to 95:5).

Yield: 6.4 mg (15% of theory)
LC-MS (Method 19): $R_t$=1.69 min.
MS (EI): m/z=756 (M−TFA+H)$^+$

Example 222A

Benzyl tert-butyl-[(2S)-3-({(2S)-2,5-bis[(tert-butoxycarbonyl)amino]pentyl}amino)-3-oxopropan-1,2-diyl]biscarbamate

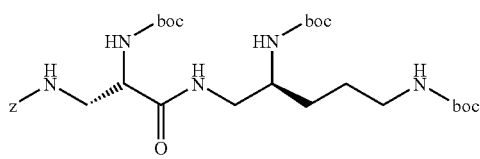

Under argon, 0.208 g (0.40 mmol) of 3-{[(benzyloxy)carbonyl]amino}-N-(tert-butoxycarbonyl)-L-alanine-N-cyclohexylcyclohexanamine (1:1), 126 mg (0.40 mmol) of tert-butyl{(4S)-5-amino-4-[(tert-butoxycarbonyl)amino]pentyl}carbamate (Example 86A) and 0.21 ml of triethylamine (1.48 mmol) are dissolved in 5 ml of dimethylformamide. Then, at 0° C. (ice bath), 130 mg (0.68 mmol) of EDC and 18 mg (0.13 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The crude product is purified by preparative HPLC (Kromasil, mobile phase acetonitrile/0.25% aqueous trifluoroacetic acid 5:95→95:5).

Yield: 88 mg (35% of theory)
LC-MS (Method 19): $R_t$=2.65 min.
MS (EI): m/z=638 (M+H)$^+$

Example 223A tert-Butyl{(4S)-5-({(2S)-3-amino-2-[(tert-butoxycarbonyl)amino]propanoyl}amino)-4-[(tert-butoxycarbonyl)amino]pentyl}carbamate hydroacetate

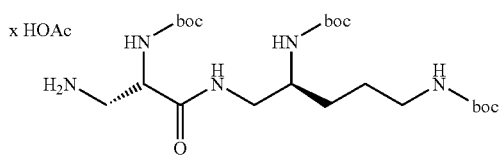

110 mg (0.172 mmol) of benzyl tert-butyl[(2S)-3-({(2S)-2,5-bis[(tert-butoxycarbonyl)amino]pentyl}amino)-3-oxo-propane-1,2-diyl]biscarbamate (Example 222A) is dissolved in 25 ml of a glacial acetic acid/water mixture (4:1). 20 mg of palladium on activated carbon (10%) are added thereto, and the mixture is then hydrogenated under atmospheric pressure for 15 h. The reaction mixture is filtered through prewashed kieselguhr and the filtrate is concentrated on a rotary evaporator in vacuo. The crude product is reacted without further purification.

Yield: 85 mg (93% of theory)
LC-MS (Method 17): $R_t$=1.67 min.
MS (EI): m/z=503 (M−HOAc+H)$^+$ Example 224A Benzyl[(5S)-5-[(tert-butoxycarbonyl)amino]-7-({2-[(tert-butoxycarbonyl)amino]ethyl}amino)-7-oxo-heptyl]carbamate

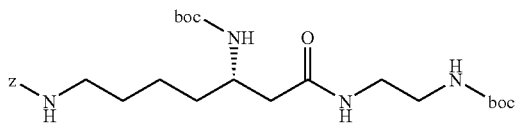

Under argon, 1 g (2.54 mmol) of (3S)-7-{[(benzyloxy)carbonyl]amino}-3-[(tert-butoxycarbonyl)amino]heptanoic acid, 406 mg (2.54 mmol) of tert-butyl (2-aminoethyl)carbamate and 0.96 ml of triethylamine (6.85 mmol) are dissolved in 20 ml of dimethylformamide. Then, at 0° C. (ice bath), 826 mg (4.3 mmol) of EDC and 113 mg (0.84 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is dried under high vacuum.

Yield: quant.
LC-MS (Method 12): $R_t$=2.21 min.
MS (EI): m/z=537 (M+H)$^+$

Example 225A tert-Butyl((1S)-5-amino-1-{2-[(2-{[(benzyloxy)carbonyl]amino}ethyl)amino]-2-oxoethyl}pentyl)carbamate hydroacetate bock

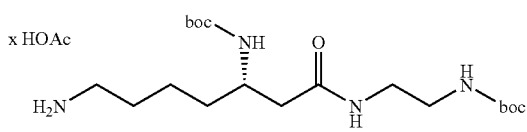

1.3 g (2.42 mmol) of benzyl[(5S)-5-[(tert-butoxycarbonyl)amino]-7-({2-[(tert-butoxycarbonyl)amino]ethyl}amino)-7-oxoheptyl]carbamate (Example 224A) are dissolved in 100 ml of a glacial acetic acid/water mixture (4:1). 70 mg of palladium on activated carbon (10%) are added thereto, and the mixture is then hydrogenated under atmospheric pressure for 15 h. The reaction mixture is filtered through prewashed kieselguhr and the filtrate is concentrated on a rotary evaporator in vacuo. The crude product is reacted without further purification.

Yield: quant.
LC-MS (Method 19): $R_t$=1.35 min.
MS (EI): m/z=403 (M−HOAc+H)$^+$ Example 226A Benzyl((1S,8S)-8-[(tert-butoxycarbonyl)amino]-1-{3-[(tert-butoxycarbonyl)amino]propyl}-17,17-dimethyl-2,10,15-trioxo-16-oxa-3,11,14-triazaoctadec-1-yl)carbamate

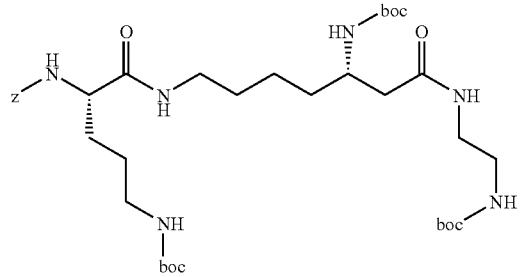

Under argon, 0.397 g (1.08 mmol) of $N^2$-[(benzyloxy)carbonyl]-$N^5$-(tert-butoxycarbonyl)-L-ornithine, 0.500 g (1.08 mmol) of tert-butyl((1S)-5-amino-1-{2-[(2-{[(benzyloxy)carbonyl]amino}ethyl)amino]-2-oxoethyl}pentyl)carbamate (Example 225A) and 0.56 ml of triethylamine (4.0 mmol) are dissolved in 10 ml of dimethylformamide. Then, at 0° C. (ice bath), 352 mg (1.84 mmol) of EDC and 48.2 mg (0.36 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is purified by preparative HPLC (Kromasil, mobile phase: acetonitrile/0.25% aqueous trifluoroacetic acid 5:95→95:5).

Yield: 290 mg (36% of theory)
LC-MS (Method 19): $R_t$=2.30 min.
MS (EI): m/z=751 (M+H)$^+$ Example 227A tert-Butyl{(4S,11S)-4-amino-11-[(tert-butoxycarbonyl)amino]-20,20-dimethyl-5,13,18-trioxo-19-oxa-6,14,17-triazahenicos-1-yl}carbamate hydroacetate

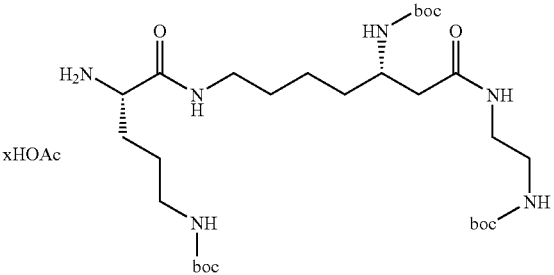

290 mg (0.390 mmol) of benzyl((1S,8S)-8-[(tert-butoxycarbonyl)amino]-1-{3-[(tert-butoxycarbonyl)amino]propyl}-17,17-dimethyl-2,10,15-trioxo-16-oxa-3,11,14-triazaoctadec-1-yl)carbamate (Example 226A) are dissolved in 10 ml of a 4/1 glacial acetic acid/water mixture. 75 mg of palladium on activated carbon (10%) are added thereto, and the mixture is then hydrogenated under atmospheric pressure for 15 h. The reaction mixture is filtered through a Millipore filter and the filtrate is concentrated and dried under high vacuum. The crude product is reacted without further purification.

Yield: quant.
LC-MS (Method 17): $R_t$=1.72 min.
MS (EI): m/z=617 (M−HOAc+H)$^+$ Example 228A N$^5$—[N$^2$-[(Benzyloxy)carbonyl]-N$^5$-(tert-butoxycarbonyl)-D-ornithyl]-N$^2$-(tert-butoxycarbonyl)-N-{2-[(tert-butoxycarbonyl)amino]ethyl}-L-ornithinamide

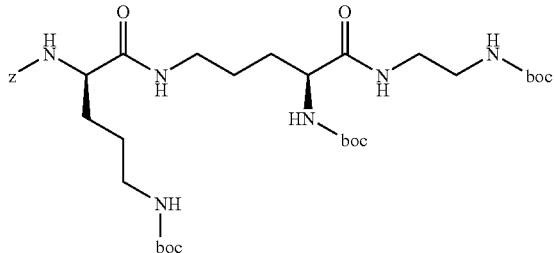

Under argon, 286 mg (0.78 mmol) of N$^2$-[(benzyloxy)carbonyl]-N$^5$-(tert-butoxycarbonyl)-D-ornithine and 439 mg (0.17 mmol) of the compound from Example 143A are dissolved in 16 ml of dimethylformamide. Then, at 0° C. (ice bath), 255 mg (1.33 mmol) of EDC and 106 mg (0.78 mmol) of HOBt are added. The mixture is slowly warmed to RT and stirred at RT for 48 h. The solution is concentrated in vacuo and the residue is taken up in dichloromethane and washed with a saturated aqueous sodium bicarbonate solution, 0.1N hydrochloric acid and water. The combined organic phases are concentrated in vacuo and the solid obtained in this way is reacted further without purification.

Yield: 0.58 g (quant.)
LC-MS (Method 17): $R_t$=2.59 min.
MS (EI): m/z=723 (M+H)$^+$ Example 229A N$^5$-[N$^5$-(tert-Butoxycarbonyl)-D-ornithyl]-N$^2$-(tert-butoxycarbonyl)-N-{2-[(tert-butoxycarbonyl)amino]ethyl}-L-ornithinamide

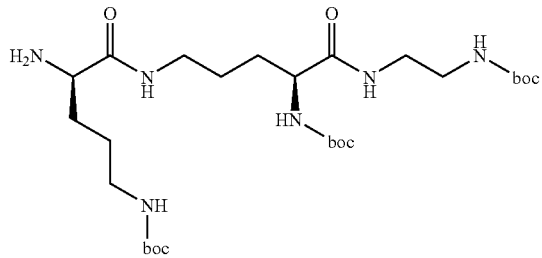

0.58 g (0.80 mmol) of the compound from Example 228A are dissolved in 27 ml of ethanol, and 0.06 g (0.06 mmol) of Pd/C are added. The mixture is hydrogenated under atmospheric pressure for 12 h and, after filtration through celite, the filtrate is concentrated in vacuo. The solid obtained in this way is reacted further without purification.

Yield: 0.47 g (97% of theory)
LC-MS (Method 19): $R_t$=1.61 min.
MS (EI): m/z=589 (M+H)$^+$ Example 230A Benzyl{(4S)-6-({(2S)-2,5-bis[(tert-butoxycarbonyl)amino]pentyl}amino)-4-[(tert-butoxycarbonyl)amino]-6-oxohexyl}carbamate

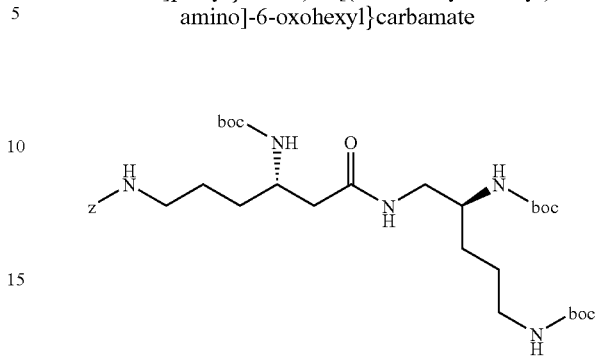

Under argon, 0.1 g (0.263 mmol) of (3S)-6-{[(benzyloxy)carbonyl]amino}-3-[(tert-butoxycarbonyl)amino]hexanoic acid (*Bioorg. Med. Chem. Lett.* (1998) 8:1477-1482) and 0.108 g (0.342 mmol) of tert-butyl{(4S)-5-amino-4-[(tert-butoxycarbonyl)amino]pentyl}carbamate (Example 86A) are dissolved in 6 ml of dimethylformamide. Then, at 0° C. (ice bath), 0.066 g (0.342 mmol) of EDC and 0.011 g (0.079 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is dried to constant weight under high vacuum.

Yield: 0.127 g (71% of theory)
LC-MS (Method 19): $R_t$=2.36 min.
MS (EI): m/z=680 (M+H)$^+$ Example 231A tert-Butyl{(1S)-4-amino-1-[2-({(2S)-2,5-bis[(tert-butoxycarbonyl)amino]pentyl}amino)-2-oxoethyl]butyl}carbamate

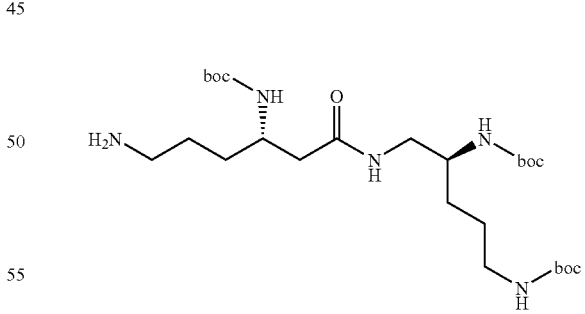

20 mg of palladium on activated carbon (10%) are added to a mixture of 0.127 g (0.19 mmol) of the compound from Example 230A in 10 ml of ethanol, and the mixture is then hydrogenated under atmospheric pressure for 12 h. The reaction mixture is filtered through kieselguhr, and the filtrate is concentrated in vacuo and dried under high vacuum. The crude product is reacted without further purification.

Yield: quant.
MS (EI): m/z=546 (M+H)$^+$

Example 232A

Benzyl tert-butyl[(2S)-3-({(2S)-2,5-bis[(tert-butoxycarbonyl)amino]pentyl}amino)-3-oxopropane-1,2-diyl]biscarbamate

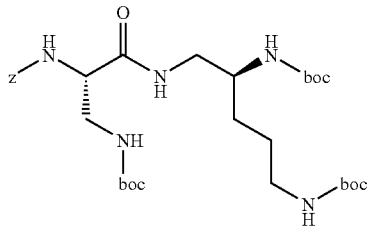

Under argon, 0.127 g (0.37 mmol) of N-[(benzyloxy)carbonyl]-3-[(tert-butoxycarbonyl)amino]-L-alanine and 0.193 g (0.49 mmol) of tert-butyl{(4S)-5-amino-4-[(tert-butoxycarbonyl)amino]pentyl}carbamate (Example 86A) are dissolved in 6 ml of dimethylformamide. Then, at 0° C. (ice bath), 0.093 g (0.49 mmol) of EDC and 0.015 g (0.11 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is purified by preparative HPLC (Kromasil, mobile phase acetonitrile/0.25% aqueous trifluoroacetic acid 5:95→95:5).

Yield: 0.126 g (53% of theory)
LC-MS (Method 19): $R_t$=2.65 min.
MS (EI): m/z=638 (M+H)$^+$

Example 233A tert-Butyl[(2S)-2-amino-3-({(2S)-2,5-bis[(tert-butoxycarbonyl)amino]pentyl}amino)-3-oxopropyl]carbamate

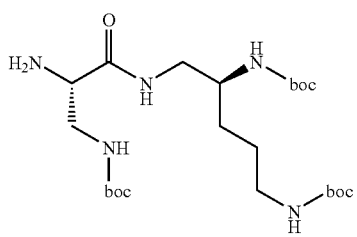

20 mg of palladium on activated carbon (10%) are added to a mixture of 0.122 g (0.19 mmol) of the compound from Example 232A in 50 ml of ethanol, and the mixture is then hydrogenated under atmospheric pressure for 4 h. The reaction mixture is filtered through kieselguhr, and the filtrate is concentrated in vacuo and dried under high vacuum. The crude product is reacted without further purification.

Yield: quant.
MS (EI): m/z=504 (M+H)$^+$

Example 234A

Benzyl{(1S)-1-[2-({(2S)-2,5-bis[(tert-butoxycarbonyl)amino]pentyl}amino)-2-oxoethyl]-4-[(tert-butoxycarbonyl)amino]butyl}carbamate

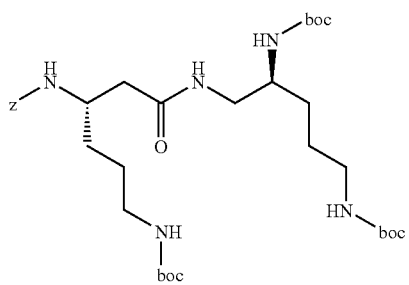

Under argon, 0.1 g (0.26 mmol) of (3S)-3-{[(benzyloxy)carbonyl]amino}-6-[(tert-butoxycarbonyl)amino]hexanoic acid (*J. Med. Chem.* (2002) 45:4246-4253) and 0.11 g (0.34 mmol) of tert-butyl{(4S)-5-amino-4-[(tert-butoxycarbonyl)amino]pentyl}carbamate (Example 86A) are dissolved in 6 ml of dimethylformamide. Then, at 0° C. (ice bath), 0.065 g (0.34 mmol) of EDC and 0.011 g (0.079 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is dried to constant weight under high vacuum.

Yield: 0.146 g (82% of theory)
LC-MS (Method 12): $R_t$=2.5 min.
MS (EI): m/z=680 (M+H)$^+$

Example 235A tert-Butyl[(4S)-4-amino-6-({(2S)-2,5-bis[(tert-butoxycarbonyl)amino]pentyl}amino)-6-oxohexyl]carbamate

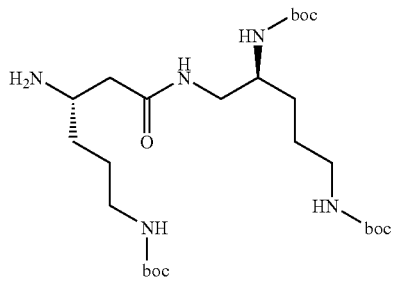

22 mg of palladium on activated carbon (10%) are added to a mixture of 0.146 g (0.22 mmol) of the compound from Example 234A in 10 ml of ethanol, and the mixture is then hydrogenated under atmospheric pressure for 12 h. The reaction mixture is filtered through kieselguhr, and the filtrate is concentrated in vacuo and dried under high vacuum. The crude product is reacted without further purification.

Yield: quant.
MS (EI): m/z=546 (M+H)$^+$

Example 236A

Benzyl{(3S)-3-[(tert-butoxycarbonyl)amino]-4-hydroxybutyl}carbamate

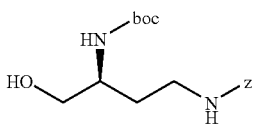

Preparation takes place in analogy to Example 83A from 300 mg (0.85 mmol) of (2S)-4-{[(benzyloxy)carbonyl]amino}-2-[(tert-butoxycarbonyl)amino]butanoic acid in 10 ml of tetrahydrofuran with 86 mg (0.85 mmol) of 4-methylmorpholine, 92 mg (0.85 mmol) of ethyl chloroformate and 1.7 ml (1.70 mmol) of a 1M solution of lithium aluminum hydride in tetrahydrofuran. The product is reacted without further purification.

Yield: 238 mg (82% of theory)
LC-MS (Method 12): $R_t$=1.83 min.
MS (EI): m/z=339 (M+H)$^+$

Example 237A tert-Butyl[(1S)-3-amino-1-(hydroxymethyl)propyl]carbamate

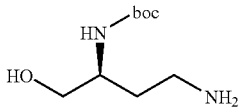

Preparation takes place in analogy to Example 81A from 237 mg (0.7 mmol) of benzyl{(3S)-3-[(tert-butoxycarbonyl)amino]-4-hydroxybutyl}carbamate (Example 236A) in 50 ml of ethanol with the addition of 23 mg of palladium on activated carbon (10%).

Yield: 177 mg (quant.)
MS (ESI): m/z=205 (M+H)$^+$.

Example 238A

Benzyl{(1S)-4-[(tert-butoxycarbonyl)amino]-1-[({(3S)-3-[(tert-butoxycarbonyl)amino]-4-hydroxybutyl}amino)carbonyl]butyl}carbamate

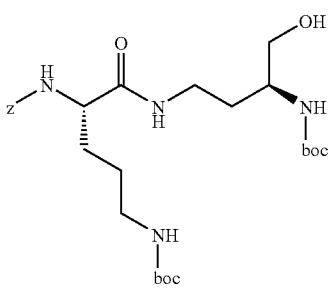

Under argon, 0.082 g (0.22 mmol) of N$^2$-[(benzyloxy)carbonyl]-N$^5$-(tert-butoxycarbonyl)-L-ornithine and 0.059 g (0.29 mmol) of benzyl{(3S)-3-[(tert-butoxycarbonyl)amino]-4-hydroxybutyl}carbamate (Example 237A) are dissolved in 6 ml of dimethylformamide. Then, at 0° C. (ice bath), 0.056 g (0.29 mmol) of EDC and 0.009 g (0.067 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is dried to constant weight under high vacuum.

Yield: 0.088 g, (72% of theory)
LC-MS (Method 12): $R_t$=2.04 min.
MS (EI): m/z=553 (M+H)$^+$

Example 239A

N$^5$-(tert-Butoxycarbonyl)-N-{(3S)-3-[(tert-butoxycarbonyl)amino]-4-hydroxybutyl}-L-ornithinamide

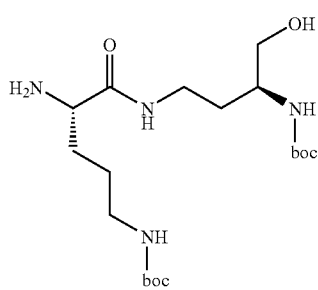

17 mg of palladium on activated carbon (10%) are added to a mixture of 0.088 g (0.16 mmol) of the compound from Example 238A in 10 ml of ethanol, and the mixture is then hydrogenated under atmospheric pressure for 12 h. The reaction mixture is filtered through kieselguhr, and the filtrate is concentrated in vacuo and dried under high vacuum. The crude product is reacted without further purification.

Yield: 0.064 g (96% of theory)
MS (EI): m/z=419 (M+H)$^+$

Example 240A

Benzyl tert-butyl-[5-({2-[(tert-butoxycarbonyl)amino]ethyl}amino)-5-oxopentane-1,3-diyl]biscarbamate

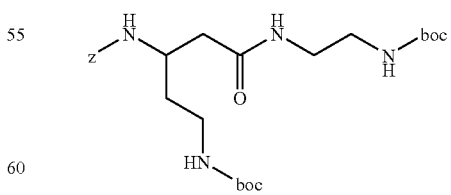

Under argon, 0.20 g (0.55 mmol) of 3-{[(benzyloxy)carbonyl]amino}-5-[(tert-butoxycarbonyl)amino]pentanoic acid (Bioorg. Chem. Med. Lett. (2003) 13:241-246) and 0.114 g (0.71 mmol) of tert-butyl(2-aminoethyl)carbamate are dissolved in 6 ml of dimethylformamide. Then, at 0° C. (ice bath), 0.136 g (0.71 mmol) of EDC and 0.022 g (0.164 mmol) of HOBt are added. The mixture is warmed slowly to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is purified by preparative HPLC (Kromasil, mobile phase acetonitrile/0.25% aqueous trifluoroacetic acid 5:95→95:5).

Yieid: 0.074 g (27% of theory)
LC-MS (Method 17): $R_t$=2.37 min.
MS (EI): m/z=509 (M+H)⁺

Example 241A tert-Butyl[3-amino-5-({2-[(tert-butoxycarbonyl)amino]ethyl}amino)-5-oxopentyl]carbamate

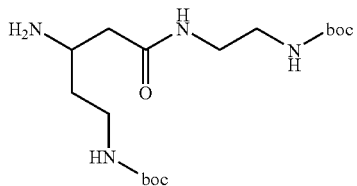

15 mg of palladium on activated carbon (10%) are added to a mixture of 0.074 g (0.15 mmol) of the compound from Example 240A in 10 ml of ethanol, and the mixture is then hydrogenated under atmospheric pressure for 12 h. The reaction mixture is filtered through kieselguhr, and the filtrate is concentrated in vacuo and dried under high vacuum. The crude product is reacted without further purification.

Yieid: 0.050 g (92% of theory)
MS (EI): m/z=375 (M+H)⁺

Example 242A

Benzyl[3-({(2S)-2,5-bis[(tert-butoxycarbonyl)amino]pentyl}amino)-3-oxopropyl]carbamate

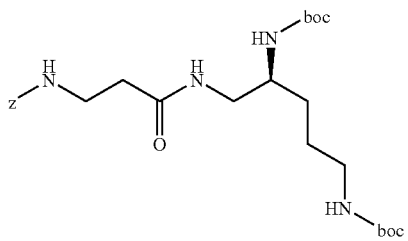

Under argon, 0.10 g (0.45 mmol) of N-[(benzyloxy)carbonyl]beta-alanine and 0.185 g (0.58 mmol) of tert-butyl{(4S)-5-amino-4-[(tert-butoxycarbonyl)amino]pentyl}carbamate (Example 86A) are dissolved in 6 ml of dimethylformamide. Then, at 0° C. (ice bath), 0.112 g (0.58 mmol) of EDC and 0.018 g (0.134 mmol) of HOBt are added. The mixture is warmed slowly to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is dried to constant weight under high vacuum.

Yieid: 0.215 g (92% of theory)
LC-MS (Method 12): $R_t$=2.19 min.
MS (EI): m/z=523 (M+H)⁺

Example 243A tert-Butyl{(4S)-5-[(3-aminopropanoyl)amino]-4-[(tert-butoxycarbonyl)amino]pentyl}carbamate

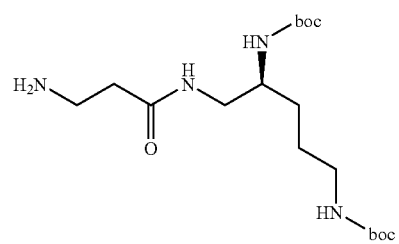

40 mg of palladium on activated carbon (10%) are added to a mixture of 0.215 g (0.41 mmol) of the compound from Example 242A in 10 ml of ethanol, and the mixture is then hydrogenated under atmospheric pressure for 12 h. The reaction mixture is filtered through kieselguhr, and the filtrate is concentrated in vacuo and dried under high vacuum. The crude product is reacted without further purification.

Yield: 0.160 g (quant.)
MS (EI): m/z=389 (M+H)⁺

Example 244A

Benzyl tert-butyl-[5-({(2S)-2,5-bis[(tert-butoxycarbonyl)amino]pentyl}amino)-5-oxopentane-1,3-diyl]biscarbamate

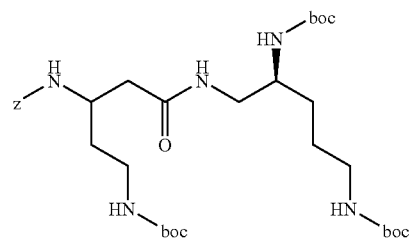

Under argon, 0.146 g (0.40 mmol) of 3-{[(benzyloxy)carbonyl]amino}-5-[(tert-butoxycarbonyl)amino]pentanoic acid and 0.164 g (0.52 mmol) of tert-butyl{(4S)-5-amino-4-[(tert-butoxycarbonyl)amino]pentyl}carbamate (Example 86A) are dissolved in 8 ml of dimethylformamide. Then, at 0° C. (ice bath), 0.10 g (0.52 mmol) of EDC and 0.009 g (0.12 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is dried to constant weight under high vacuum.

Yield: 0.232 g, (87% of theory)
LC-MS (Method 17): $R_t$=2.73 min.
MS (EI): m/z=666 (M+H)⁺

Example 245A tert-Butyl[3-amino-5-({(2S)-2,5-bis[(tert-butoxycarbonyl)amino]pentyl}amino)-5-oxopentyl]carbamate

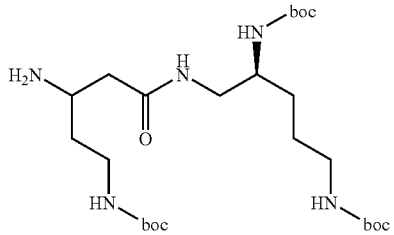

35 mg of palladium on activated carbon (10%) are added to a mixture of 0.232 g (0.35 mmol) of the compound from Example 244A in 10 ml of ethanol, and the mixture is then hydrogenated under atmospheric pressure for 12 h. The reaction mixture is filtered through kieselguhr, and the filtrate is concentrated in vacuo and dried under high vacuum. The crude product is reacted without further purification.

Yield: 0.175 g (94% of theory)
LC-MS (Method 17): $R_t$=1.8 min.
MS (EI): m/z=532 (M+H)$^+$

Example 246A

Benzyl{(4S)-4-[(tert-butoxycarbonyl)amino]-5-hydroxypentyl}carbamate

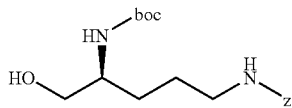

Preparation takes place in analogy to Example 83A from 1.0 g (2.73 mmol) of N$^5$-[(benzyloxy)carbonyl]-N$^2$-(tert-butoxycarbonyl)-L-ornithine in 35 ml of tetrahydrofuran with 0.276 g (2.73 mmol) of 4-methylmorpholine, 0.296 g (2.73 mmol) of ethyl chloroformate and 5.5 ml (5.5 mmol) of a 1M solution of lithium aluminum hydride in tetrahydrofuran. The product is purified by preparative HPLC (Kromasil, mobile phase acetonitrile/0.25% aqueous trifluoroacetic acid 5:95→95:5).

Yield: 0.398 g (41% of theory)
LC-MS (Method 12): $R_t$=1.84 min.
MS (EI): m/z=354 (M+H)$^+$

Example 247A tert-Butyl[(1S)-4-amino-1-(hydroxymethyl)butyl]carbamate

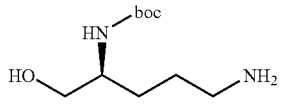

Preparation takes place in analogy to Example 81A from 0.232 g (0.66 mmol) of benzyl{(4S)-4-[(tert-butoxycarbonyl)amino]-5-hydroxypentyl}carbamate (Example 246A) in 50 ml of ethanol with the addition of 23 mg of palladium on activated carbon (10%).

Yield: 135 mg (94% of theory)
MS (ESI): m/z=219 (M+H)$^+$.

Example 248A

Benzyl{(1S)-4-[(tert-butoxycarbonyl)amino]-1-[({(4S)-4-[(tert-butoxycarbonyl)amino]-5-hydroxypentyl}amino)carbonyl]butyl}carbamate

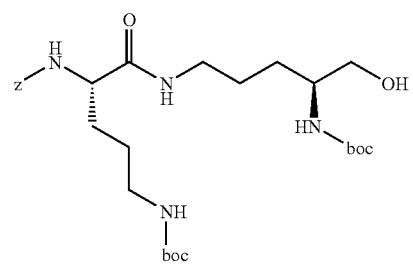

Under argon, 0.155 g (0.42 mmol) of N$^2$-[(benzyloxy)carbonyl]-N$^5$-(tert-butoxycarbonyl)-L-ornithine and 0.12 g (0.55 mmol) of tert-butyl[(1S)-4-amino-1-(hydroxymethyl)butyl]carbamate (Example 247A) are dissolved in 6 ml of dimethylformamide. Then, at 0° C. (ice bath), 0.105 g (0.55 mmol) of EDC and 0.017 g (0.13 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is purified by preparative HPLC (Kromasil, mobile phase acetonitrile/0.25% aqueous trifluoroacetic acid 5:95→95:5).

Yield: 0.164 g (69% of theory)
LC-MS (Method 12): $R_t$=2.05 min.
MS (EI): m/z=567 (M+H)$^+$

Example 249A

N$^5$-(tert-Butoxycarbonyl)-N-{(4S)-4-[(tert-butoxycarbonyl)amino]-5-hydroxypentyl}-L-ornithinamide

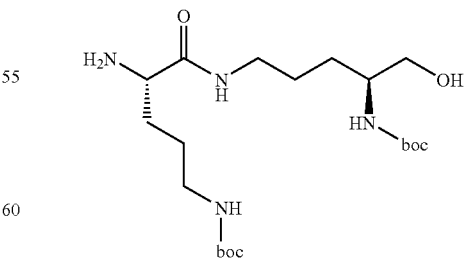

30 mg of palladium on activated carbon (10%) are added to a mixture of 0.164 g (0.29 mmol) of the compound from Example 248A in 10 ml of ethanol, and the mixture is then hydrogenated under atmospheric pressure for 12 h. The reaction mixture is filtered through kieselguhr, and the filtrate is concentrated in vacuo and dried under high vacuum. The crude product is reacted without further purification.

Yield: 0.125 g (quant.)
MS (EI): m/z=433 (M+H)+

Example 250A

Benzyl tert-butyl-[(2S)-3-hydroxypropane-1,2-diyl]biscarbamate

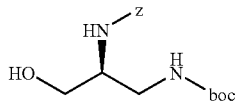

Preparation takes place in analogy to Example 83A from 0.40 g (0.18 mmol) of N-[(benzyloxy)carbonyl]-3-[(tert-butoxycarbonyl)amino]-L-alanine in 20 ml of tetrahydrofuran with 0.12 g (1.18 mmol) of 4-methylmorpholine, 0.13 g (1.18 mmol) of ethyl chloroformate and 2.4 ml (2.4 mmol) of a 1M solution of lithium aluminum hydride in tetrahydrofuran. The product is purified by preparative HPLC (Kromasil, mobile phase acetonitrile/0.25% aqueous trifluoroacetic acid 5:95→95:5).

Yield: 0.193 g (50% of theory)
LC-MS (Method 12): $R_t$=1.79 min.
MS (EI): m/z=325 (M+H)+

Example 251A tert-Butyl[(2S)-2-amino-3-hydroxypropyl]carbamate

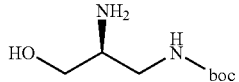

Preparation takes place in analogy to Example 81A from 0.193 g (0.59 mmol) of benzyl tert-butyl-[(2S)-3-hydroxypropane-1,2-diyl]biscarbamate (Example 250A) in 10 ml of ethanol with the addition of 23 mg of palladium on activated carbon (10%).

Yield: 112 mg (99% of theory)
MS (ESI): m/z=191 (M+H)+.

Example 252A

Benzyl[(1S)-4-[(tert-butoxycarbonyl)amino]-1-({[(1S)-2-[(tert-butoxycarbonyl)amino]-1-(hydroxymethyl)ethyl]amino}carbonyl)butyl]carbamate

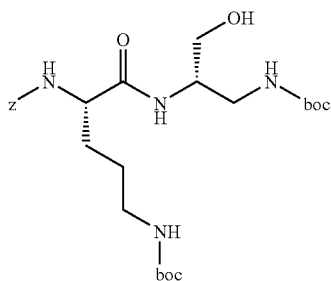

Under argon, 0.18 g (0.49 mmol) of N²-[(benzyloxy)carbonyl]-N⁵-(tert-butoxycarbonyl)-L-ornithine and 0.122 g (0.64 mmol) of tert-butyl[(2S)-2-amino-3-hydroxypropyl]carbamate (Example 251A) are dissolved in 6 ml of dimethylformamide. Then, at 0° C. (ice bath), 0.123 g (0.64 mmol) of EDC and 0.02 g (0.15 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is purified by preparative HPLC (Kromasil, mobile phase acetonitrile/0.25% aqueous trifluoroacetic acid 5:95→95:5).

Yield: 0.216 g (81% of theory)
LC-MS (Method 12): $R_t$=2.07 min.
MS (EI): m/z=539 (M+H)+

Example 253A $N^5$-(tert-Butoxycarbonyl)-N-[(1S)-2-[(tert-butoxycarbonyl)amino]-1-(hydroxymethyl)ethyl]-L-ornithinamide

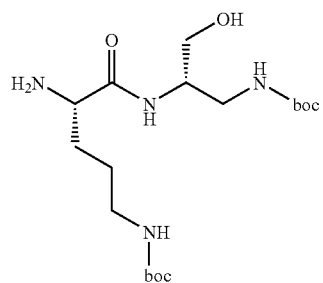

40 mg of palladium on activated carbon (10%) are added to a mixture of 0.216 g (0.40 mmol) of the compound from Example 252A in 10 ml of ethanol, and the mixture is then hydrogenated under atmospheric pressure for 12 h. The reaction mixture is filtered through kieselguhr, and the filtrate is concentrated in vacuo and dried under high vacuum. The crude product is reacted without further purification.

Yield: quant.
MS (EI): m/z=405 (M+H)+

Example 254A

Benzyl[3-({2-[(tert-butoxycarbonyl)amino]ethyl}amino)-3-oxopropyl]carbamate

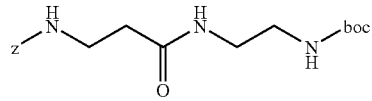

Under argon, 0.20 g (0.90 mmol) of N-[(benzyloxy)carbonyl]-beta-alanine and 0.187 g (1.17 mmol) of tert-butyl(2-aminoethyl)carbamate are dissolved in 6 ml of dimethylformamide. Then, at 0° C. (ice bath), 0.223 g (1.17 mmol) of EDC and 0.036 g (0.27 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solu-

Example 255A

N-{2-[(tert-Butoxycarbonyl)amino]ethyl}-beta-alaninamide

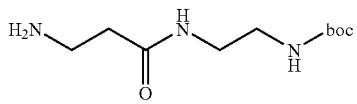

80 mg of palladium on activated carbon (10%) are added to a mixture of 0.30 g (0.82 mmol) of the compound from Example 254A in 10 ml of ethanol, and the mixture is then hydrogenated under atmospheric pressure for 12 h. The reaction mixture is filtered through kieselguhr, and the filtrate is concentrated in vacuo and dried under high vacuum. The crude product is reacted without further purification.

Yield: 0.190 g (quant.)
MS (EI): m/z=232 (M+H)$^+$

Example 256A di-tert-Butyl((6S)-6-{[(benzyloxy)carbonyl]amino}-10-hydroxy-15,15-dimethyl-7,13-dioxo-14-oxa-2,8,12-triazahexadecane-1-imidoyl)imidodicarbonate

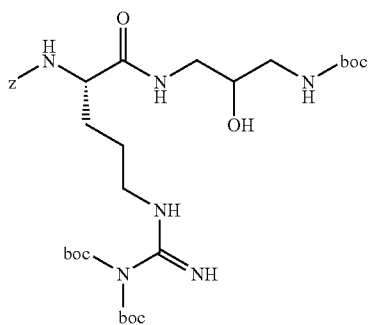

Under argon, 0.30 g (0.49 mmol) of N$^2$-[(benzyloxy)carbonyl]-N$^5$-[[bis(tert-butoxycarbonyl)amino](imino)methyl]-L-ornithine-cyclohexanamine (1:1) and 0.12 g (0.64 mmol) of tert-butyl(3-amino-2-hydroxypropyl)carbamate are dissolved in 6 ml of dimethylformamide. Then, at 0° C. (ice bath), 0.123 g (0.64 mmol) of EDC and 0.02 g (0.15 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is purified by preparative HPLC (Kromasil, mobile phase acetonitrile/0.25% aqueous trifluoroacetic acid 5:95→95:5).

Yield: 0.183 g (54% of theory)
LC-MS (Method 12): R$_t$=2.58 min.
MS (EI): m/z=681 (M+H)$^+$

Example 257A

N$^5$-[[bis(tert-Butoxycarbonyl)amino](imino)methyl]-N-{3-[(tert-butoxycarbonyl)amino]-2-hydroxypropyl}-L-ornithinamide

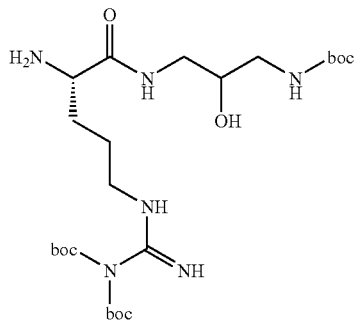

28 mg of palladium on activated carbon (10%) are added to a mixture of 0.182 g (0.27 mmol) of the compound from Example 256A in 10 ml of ethanol, and the mixture is then hydrogenated under atmospheric pressure for 12 h. The reaction mixture is filtered through kieselguhr, and the filtrate is concentrated in vacuo and dried under high vacuum. The crude product is reacted without further purification.

Yield: 0.138 g (94% of theory)
MS (EI): m/z=547 (M+H)$^+$

Example 258A

Benzyl{(1S)-4-{[(benzyloxy)carbonyl]amino}-1-[({3-[(tert-butoxycarbonyl)amino]-2-hydroxypropyl}amino)carbonyl]butyl}carbamate

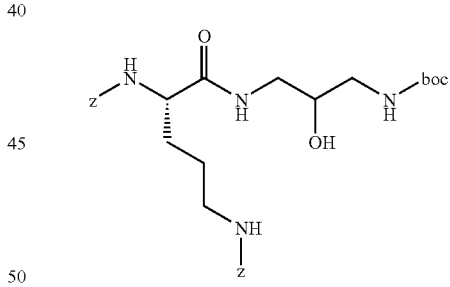

Under argon, 0.20 g (0.50 mmol) of N$^2$,N$^5$-bis[(benzyloxy)carbonyl]-L-ornithine and 0.124 g (0.65 mmol) of tert-butyl(3-amino-2-hydroxypropyl)carbamate are dissolved in 6 ml of dimethylformamide. Then, at 0° C. (ice bath), 0.124 g (0.65 mmol) of EDC and 0.02 g (0.15 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is dried to constant weight under high vacuum.

Yield: 0.245 g (86% of theory)
LC-MS (Method 12): R$_t$=2.15 min.
MS (EI): m/z=573 (M+H)$^+$ (continued from previous page)
tions, dried over magnesium sulfate and evaporated in vacuo. The remaining solid is dried to constant weight under high vacuum.
Yield: 0.30 g (82% of theory)
LC-MS (Method 19): R$_t$=1.93 min.
MS (EI): m/z=366 (M+H)$^+$

Example 259A

Benzyl((4S)-5-[(3-amino-2-hydroxypropyl)amino]-4-{[(benzyloxy)carbonyl]amino}-5-oxopentyl)carbamate hydrochloride

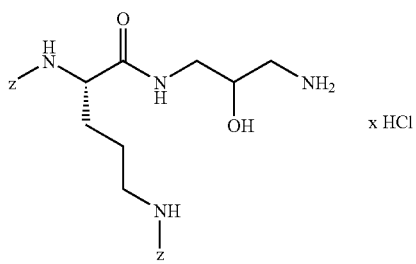

6.8 ml of a 4N solution of hydrogen chloride in dioxane are added to a solution of 0.263 g (0.46 mmol) of the compound from Example 258A in 1 ml of dioxane at 0° C. After 2 h at RT, the reaction solution is concentrated in vacuo and coevaporated with dichloromethane several times. The remaining solid is dried to constant weight under high vacuum.

Yield: 0.205 g (88% of theory)
LC-MS (Method 12): $R_t$=1.47 min.
MS (EI): m/z=473 (M−HCl+H)$^+$

Example 260A

Benzyl[(2S)-2-[(tert-butoxycarbonyl)amino]-3-({2-[(tert-butoxycarbonyl)amino]ethyl}amino)-3-oxopropyl]carbamate

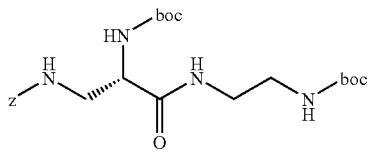

Under argon, 0.50 g (0.96 mmol) of 3-{[(benzyloxy)carbonyl]amino}-N-(tert-butoxycarbonyl)-L-alanine-N-cyclohexylcyclohexanamine (1:1) and 0.154 g (0.96 mmol) of tert-butyl(2-aminoethyl)carbamate are dissolved in 10 ml of dimethylformamide and 0.5 ml of triethylamine. Then, at 0° C. (ice bath), 0.314 g (1.64 mmol) of EDC and 0.043 g (0.32 mmol) of HOBt are added. The mixture is slowly warmed to RT and stirred at RT for 12 h. The solution is concentrated in vacuo and the residue is taken up with ethyl acetate. The organic phase is washed successively with saturated sodium bicarbonate and sodium chloride solutions, dried over magnesium sulfate and evaporated in vacuo. The remaining solid is dried to constant weight under high vacuum.

Yield: 0.41 g (88% of theory)
LC-MS (Method 12): $R_t$=2.17 min.
MS (EI): m/z=481 (M+H)$^+$

Example 261A

3-Amino-$N^2$-(tert-butoxycarbonyl)-N-{2-[(tert-butoxycarbonyl)amino]ethyl}-L-alaninamide hydroacetate

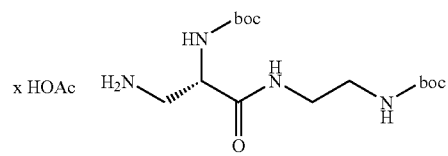

50 mg of palladium on activated carbon (10%) are added to a mixture of 0.41 g (0.847 mmol) of the compound from Example 260A in 80 ml of acetic acid/ethanol/water (4:1:1), and the mixture is then hydrogenated under atmospheric pressure for 12 h. The reaction mixture is filtered through kieselguhr, and the filtrate is concentrated in vacuo and dried under high vacuum. The crude product is reacted without further purification.

Yield: quant.
LC-MS (Method 12): $R_t$=1.09 min.
MS (EI): m/z=347 (M−HOAc+H)$^+$

Example 262A tert-Butyl{3-[(8S,11S,14S)-8-{(6S,11S)-6,11-bis[(tert-butoxycarbonyl)amino]-18,18-dimethyl-8,16-dioxo-17-oxa-2,9,15-triazanonadecan-1-oyl}-14-[(tert-butoxycarbonyl)amino]-5,17-dihydroxy-10,13-dioxo-9,12-diazatricyclo[14.3.1.1$^{2,6}$]henicosa-1(20),2(21),3,5,16,18-hexaen-11-yl]propyl}carbamate

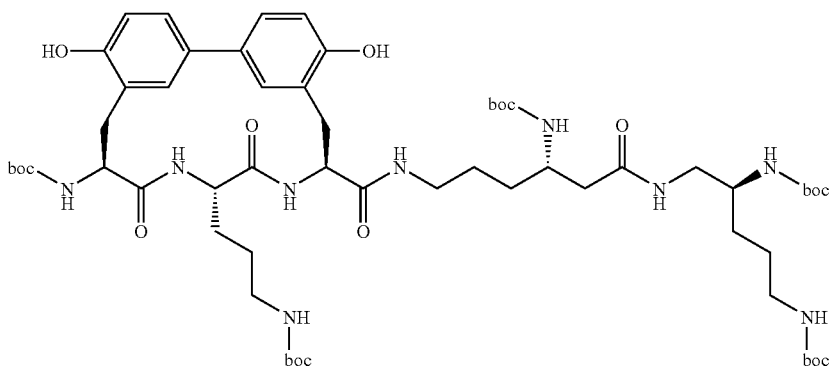

Under argon, 20 mg (0.03 mmol) of the compound from Example 29A and 22 mg (0.04 mmol) of tert-butyl{(1S)-4-amino-1-[2-({(2S)-2,5-bis[(tert-butoxycarbonyl)amino]pentyl}amino)-2-oxo-ethyl]butyl}carbamate (Example 231A) are dissolved in 1 ml of dimethylformamide. Then, at 0° C. (ice bath), 7.6 mg (0.04 mmol) of EDC and 1.24 mg (0.009 mmol) of HOBt are added. The mixture is slowly warmed to RT and stirred at RT for 12 h. The solution is concentrated in vacuo and the residue is stirred with water. The remaining solid is collected by suction filtration and purified by chromatography (Sephadex LH20, mobile phase: methanol/acetic acid (0.25%)).

Yield: 25.4 mg (70% of theory)
LC-MS (Method 17): $R_t$=2.81 min.
MS (EI): m/z=1184 (M+H)$^+$ Example 263A $N^5$-{N-[(Benzyloxy)carbonyl]glycyl}-$N^2$-(tert-butoxycarbonyl)-N-{2-[(tert-butoxycarbonyl)amino]ethyl}-L-ornithinamide

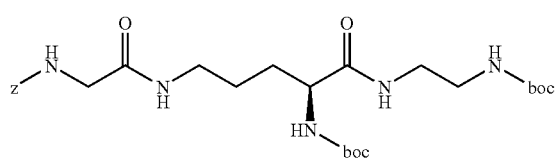

Under argon, 300 mg (1.43 mmol) of N-[(benzyloxy)carbonyl]glycine and 830 mg (2.15 mmol) of the compound from Example 143A are dissolved in 28 ml of dimethylformamide. Then, at 0° C. (ice bath), 467 mg (2.44 mmol) of EDC and 194 mg (1.43 mmol) of HOBt are added. The mixture is slowly warmed to RT and stirred at RT for 48 h. The solution is concentrated in vacuo and the residue is taken up with dichloromethane and washed with a saturated sodium bicarbonate solution, 0.1 N hydrochloric acid and water. The combined organic phases are concentrated in vacuo, and the solid obtained in this way is reacted further without purification.

Yield: quant.
LC-MS (Method 12): $R_t$=1.98 min.
MS (EI): m/z=566 (M+H)$^+$

Example 264A $N^5$-Glycyl-$N^2$-(tert-butoxycarbonyl)-N-{2-[(tert-butoxycarbonyl)amino]ethyl}-L-ornithinamide

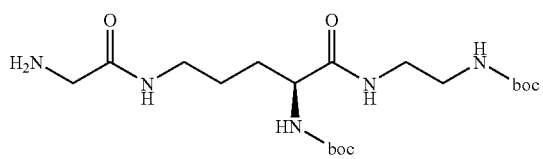

1030 mg (1.82 mmol) of the compound from Example 263A are dissolved in 60 ml of ethanol, and 100 mg (0.09 mmol) of Pd/C (10%) are added. The mixture is hydrogenated under atmospheric pressure overnight and, after filtration through celite, the filtrate is concentrated in vacuo. The solid obtained in this way is reacted further without purification.

Yield: 693 mg (84% of theory)
LC-MS (Method 17): $R_t$=1.41 min.
MS (EI): m/z=432 (M+H)$^+$ Example 265A $N^5$—[$N^2$-[(Benzyloxy)carbonyl]-N-(tert-butoxycarbonyl)-L-ornithyl]-$N^2$-(tert-butoxycarbonyl)-N-{2-[(tert-butoxycarbonyl)amino]ethyl}-L-ornithinamide

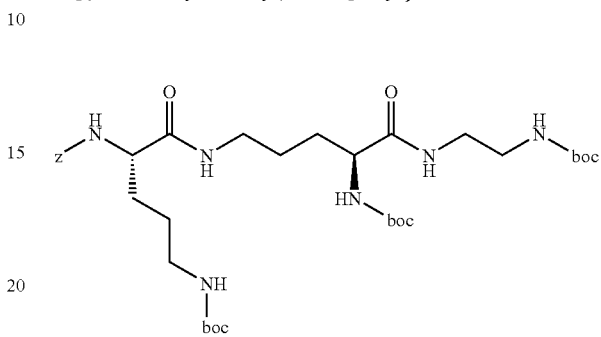

Under argon, 1.95 g (5.31 mmol) $N^2$-[(benzyloxy)carbonyl]-$N^5$-(tert-butoxycarbonyl)-L-ornithine and 3.12 g (7.97 mmol) of the compound from Example 143A are dissolved in 100 ml of dimethylformamide. Then, at 0° C. (ice bath), 1.73 g (9.03 mmol) of EDC and 0.72 g (5.31 mmol) of HOBt are added. The mixture is slowly warmed to RT and stirred at RT for 48 h. The solution is concentrated in vacuo and the residue is taken up with dichloromethane and washed with a saturated aqueous sodium bicarbonate solution, 0.1 N hydrochloric acid and water. The combined organic phases are concentrated in vacuo, and the solid obtained in this way is reacted further without purification.

Yield: 4.23 g (96% of theory)
LC-MS (Method 19): $R_t$=2.19 min.
MS (EI): m/z=723 (M+H)$^+$ Example 266A $N^5$—[$N^5$-(tert-Butoxycarbonyl)-L-ornithyl]-$N^2$-(tert-butoxycarbonyl)-N-{2-[(tert-butoxycarbonyl)amino]ethyl}-L-ornithinamide

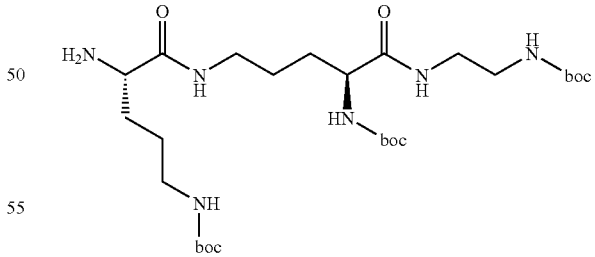

4.23 g (5.09 mmol) of the compound from Example 265A are dissolved in 250 ml of ethanol, and 0.42 g (0.39 mmol) of Pd/C (10%) are added. The mixture is hydrogenated under atmospheric pressure for 6 h and, after filtration through celite, the filtrate is concentrated in vacuo. The solid obtained in this way is reacted further without purification.

Yield: 2.4 g (72% of theory)
LC-MS (Method 12): $R_t$=1.31 min.
MS (EI): m/z=589 (M+H)$^+$

Example 267A

Benzyl((1S,7S)-7-[(tert-butoxycarbonyl)amino]-1-{2-[(tert-butoxycarbonyl)amino]ethyl}-15,15-dimethyl-2,8,13-trioxo-14-oxa-3,9,12-triazahexadec-1-yl)carbamate

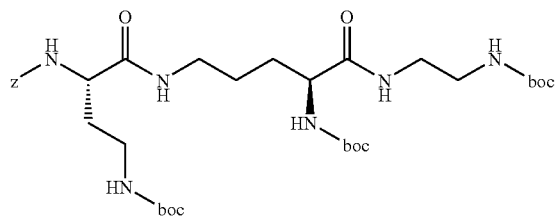

Under argon, 250 mg (0.71 mmol) of (2S)-2-{[(benzyloxy)carbonyl]amino}-4-[(tert-butoxycarbonyl)amino]butanoic acid and 410 mg (1.06 mmol) of the compound from Example 143A are dissolved in 14 ml of dimethylformamide. Then, at 0° C. (ice bath), 231 mg (1.21 mmol) of EDC and 96 mg (0.71 mmol) of HOBt are added. The mixture is slowly warmed to RT and stirred at RT for 48 h. The solution is concentrated in vacuo and the residue is taken up with dichloromethane and washed with a saturated sodium bicarbonate solution, 0.1 N hydrochloric acid and water. The combined organic phases are concentrated in vacuo, and the solid obtained in this way is reacted further without purification.

Yield: 355 mg (66% of theory)
LC-MS (Method 12): $R_t$=2.32 min.
MS (EI): m/z=709 (M+H)$^+$

Example 268A $N^5$-{(2S)-2-Amino-4-[(tert-butoxycarbonyl)amino]butanoyl}-$N^2$-(tert-butoxycarbonyl)-N-{2-[(tert-butoxycarbonyl)amino]ethyl}-L-ornithinamide

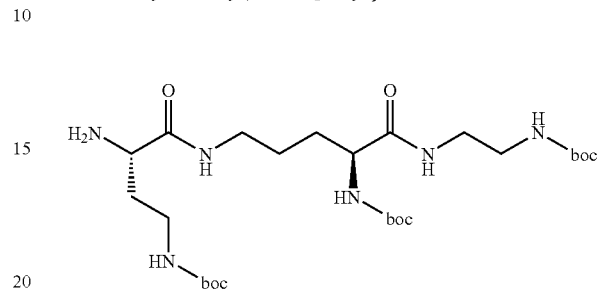

355 mg (0.5 mmol) of the compound from Example 267A are dissolved in 17 ml of ethanol, and 36 mg (0.03 mmol) of Pd/C (10%) are added. The mixture is hydrogenated under atmospheric pressure overnight and, after filtration through celite, the filtrate is concentrated in vacuo. The solid obtained in this way is reacted further without purification.

Yield: 304 mg (82% of theory)
LC-MS (Method 17): $R_t$=1.64 min.
MS (EI): m/z=575 (M+H)$^+$ Examples 269A to 286A listed in the following table are prepared in analogy to the method of Example 262A.

| Example No. | Precursor example | Structure | Analytical data |
|---|---|---|---|
| 269A | 233A + 29A | 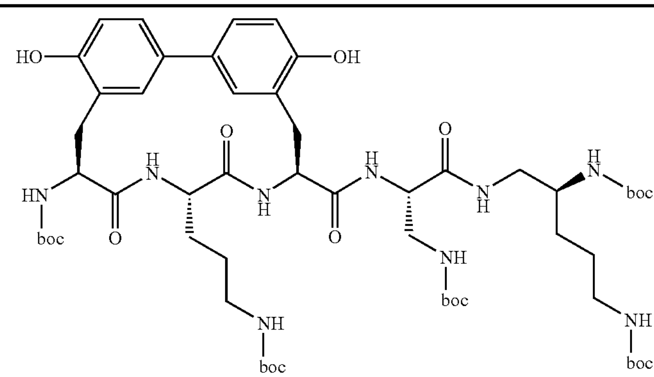 | LC-MS (Method 19): $R_t$ = 2.69 min. MS (EI): m/z = 1142 (M + H)$^+$. |
| 270A | 235A + 29A | 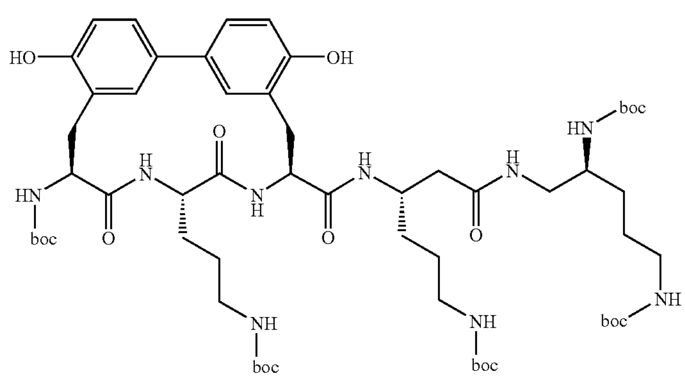 | LC-MS (Method 12): $R_t$ = 2.55 min. MS (EI): m/z = 1184 (M + H)$^+$. |

-continued
| Example No. | Precursor example | Structure | Analytical data |
|---|---|---|---|
| 271A | 81A + 65A | 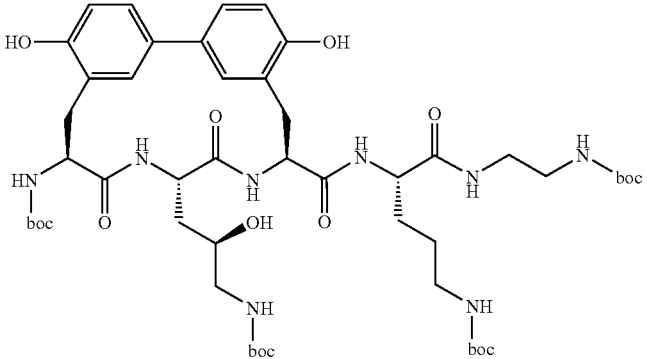 | LC-MS (Method 17): $R_t$ = 2.52 min. MS (EI): m/z = 1029 $(M + H)^+$. |
| 272A | 239A + 29A | 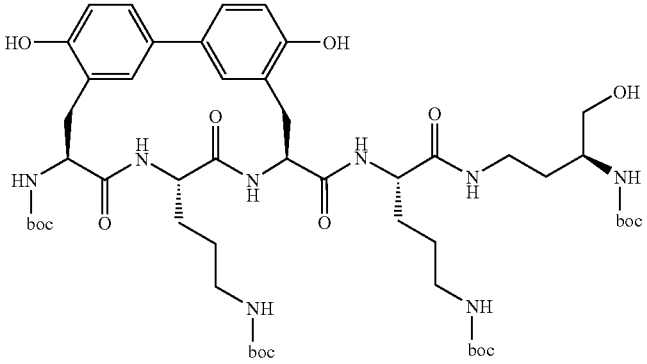 | LC-MS (Method 19): $R_t$ = 2.32 min. MS (EI): m/z = 1057 $(M + H)^+$. |
| 273A | 241A + 29A | 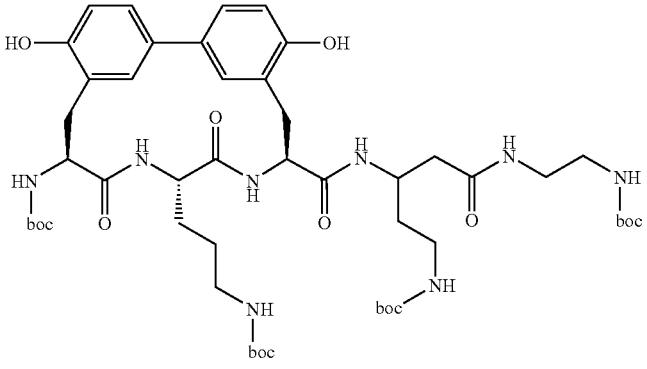 | LC-MS (Method 12): $R_t$ = 2.28 min. MS (EI): m/z = 1013 $(M + H)^+$. |
| 274A | 243A + 29A | 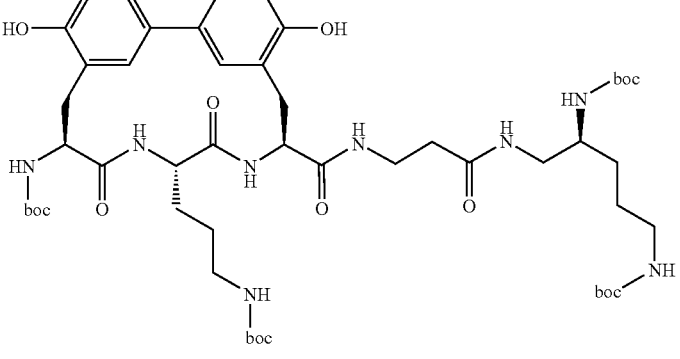 | LC-MS (Method 12): $R_t$ = 2.31 min. MS (EI): m/z = 1027 $(M + H)^+$. |

-continued
| Example No. | Precursor example | Structure | Analytical data |
|---|---|---|---|
| 275A | 245A + 29A | 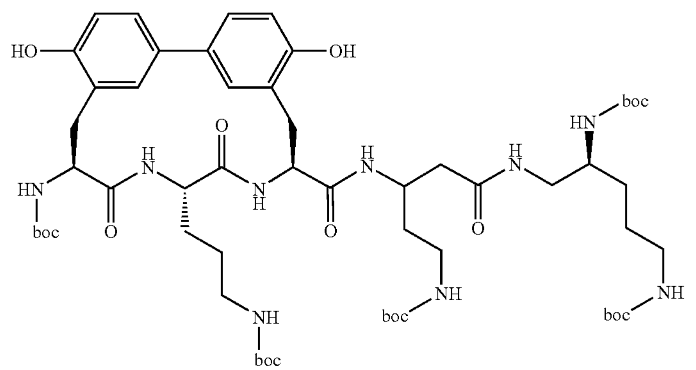 | LC-MS (Method 19): R$_t$ = 2.36 min. MS (EI): m/z = 1170 (M + H)$^+$. |
| 276A | 249A + 29A | 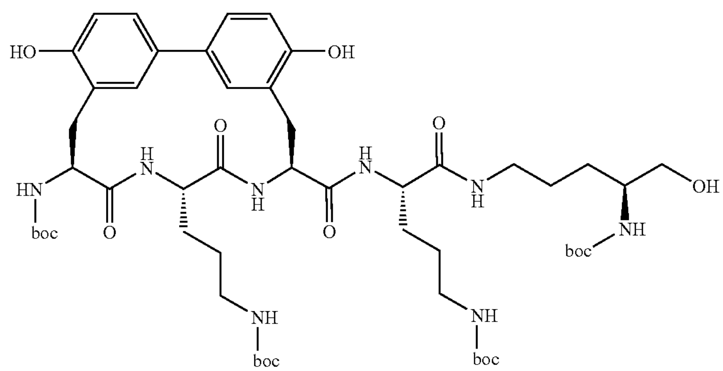 | LC-MS (Method 19): R$_t$ = 2.30 min. MS (EI): m/z = 1171 (M + H)$^+$. |
| 277A | 253A + 29A | 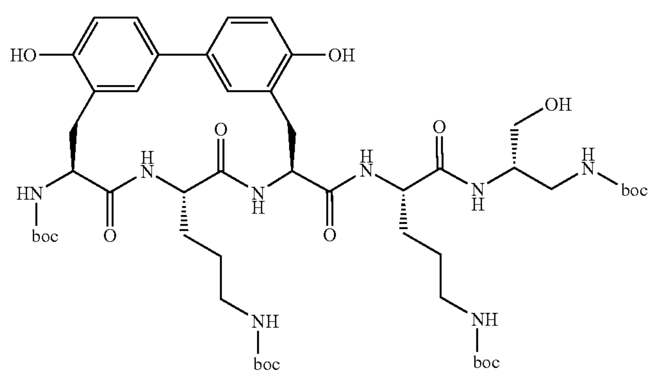 | LC-MS (Method 19): R$_t$ = 2.14 min. MS (EI): m/z = 1043 (M + H)$^+$. |
| 278A | 120A + 65A | 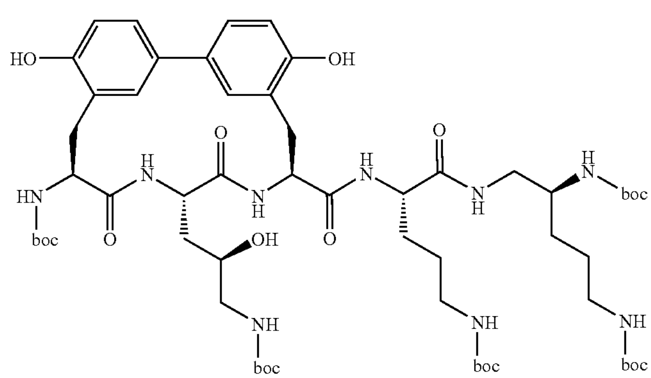 | LC-MS (Method 12): R$_t$ = 2.51 min. MS (EI): m/z = 1186 (M + H)$^+$. |

-continued

| Example No. | Precursor example | Structure | Analytical data |
|---|---|---|---|
| 279A | 255A + 29A | 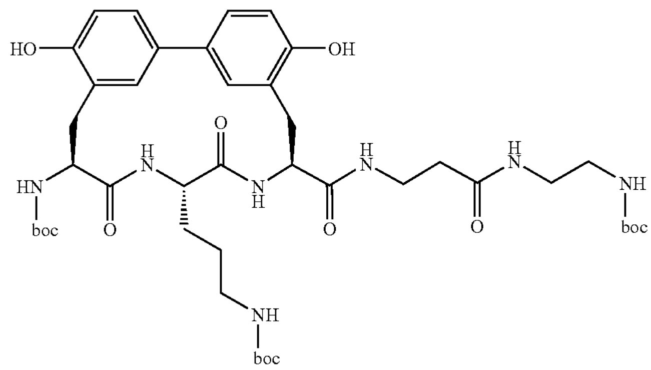 | LC-MS (Method 12): $R_t$ = 2.04 min. MS (EI): m/z = 870 (M + H)$^+$. |
| 280A | 257A + 29A | 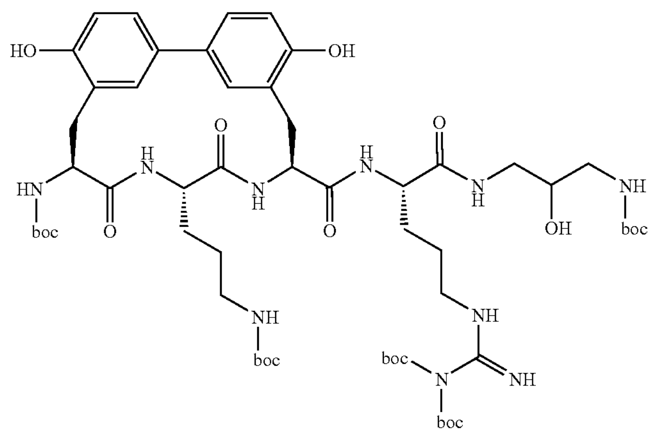 | LC-MS (Method 12): $R_t$ = 2.64 min. MS (EI): m/z = 1185 (M + H)$^+$. |
| 281A | 259A + 29A | 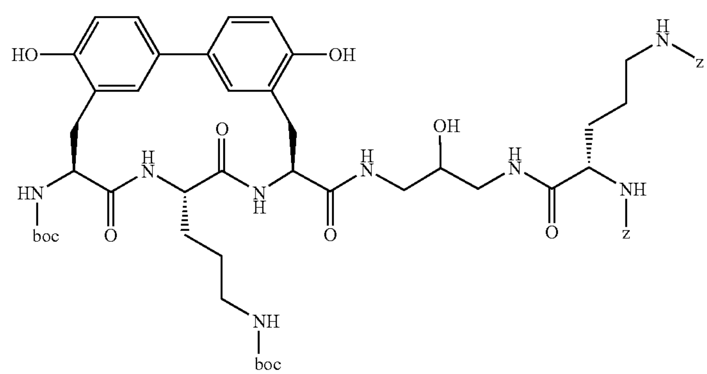 | LC-MS (Method 17): $R_t$ = 2.62 min. MS (EI): m/z = 1111 (M + H)$^+$. |
| 282A | 253A + 65A | 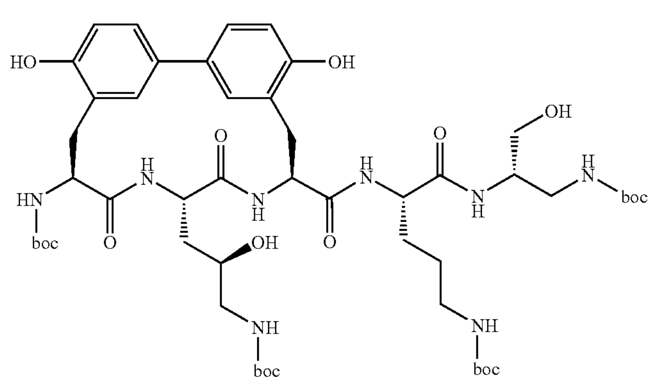 | LC-MS (Method 19): $R_t$ = 2.25 min. MS (EI): m/z = 1059 (M + H)$^+$. |

| Example No. | Precursor example | Structure | Analytical data |
|---|---|---|---|
| 283A | 29A + 264A | 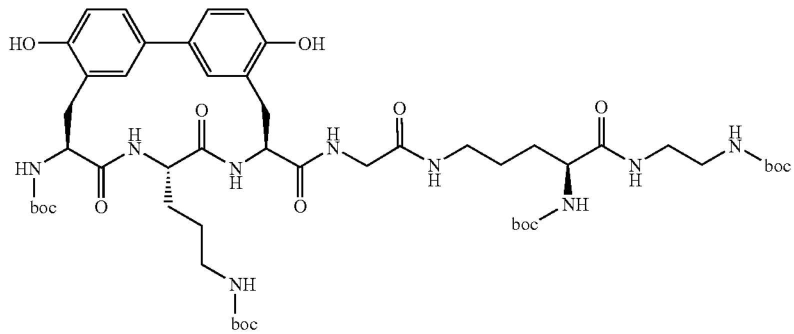 | LC-MS (Method 17): $R_t$ = 2.46 min. MS (EI): m/z = 1070 (M + H)$^+$. |
| 284A | 29A + 266A | 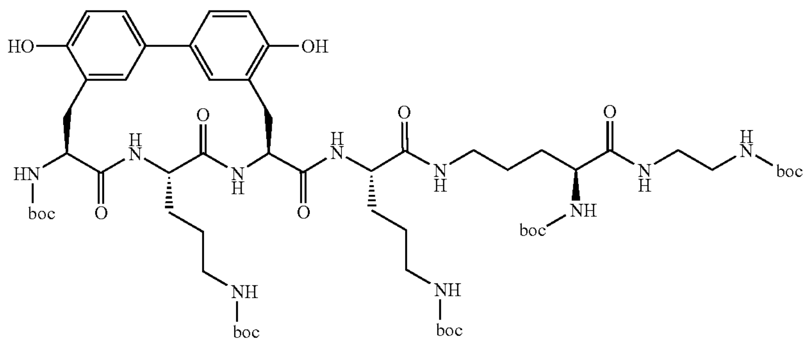 | LC-MS (Method 17): $R_t$ = 2.64 min. MS (EI): m/z = 1227 (M + H)$^+$. |
| 285A | 29A + 268A | 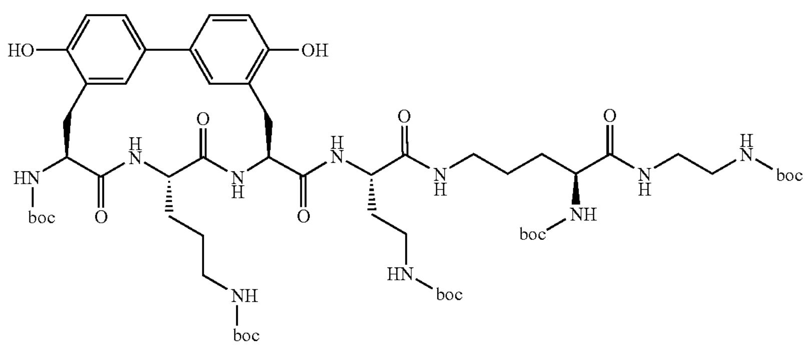 | LC-MS (Method 17): $R_t$ = 2.68 min. MS (EI): m/z = 1213 (M + H)$^+$. |
| 286A | 29A + 268A | 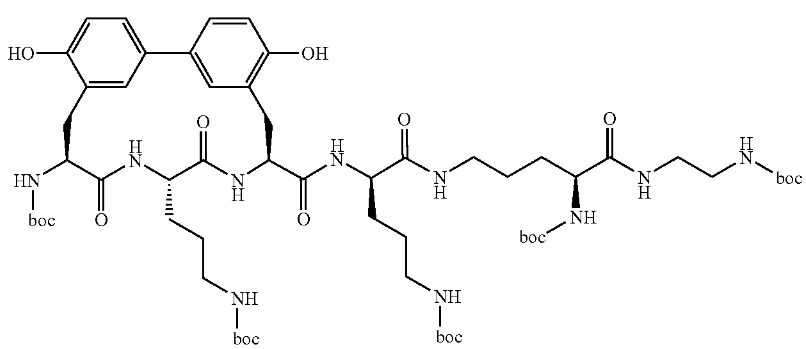 | LC-MS (Method 17): $R_t$ = 2.66 min. MS (EI): m/z = 1227 (M + H)$^+$. |

Examples 287A to 293A listed in the following table are prepared in analogy to the method of Example 178A.

| Example No. | Precursor example | Structure | Analytical data |
|---|---|---|---|
| 287A | 170A + 81A | 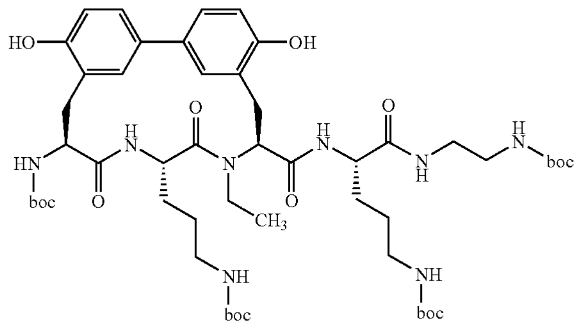 | LC-MS (Method 17): $R_t$ = 2.69 min. MS (EI): m/z = 1041 $(M + H)^+$. |
| 288A | 29A + 225A | 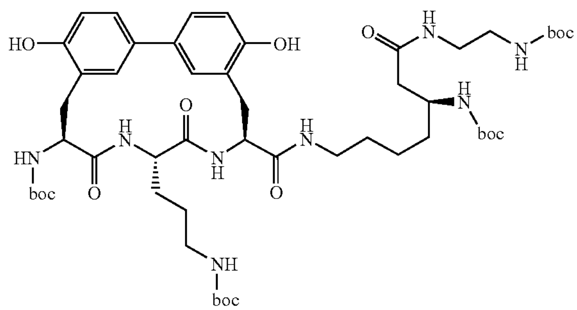 | LC-MS (Method 17): $R_t$ = 2.50 min. MS (EI): m/z = 1041 $(M + H)^+$. |
| 289A | 143A + 65A | 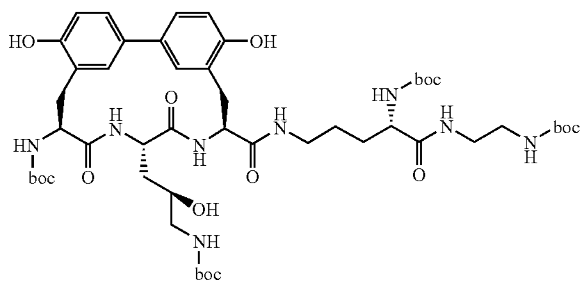 | LC-MS (Method 17): $R_t$ = 2.39 min. |
| 290A | 52A + 223A | 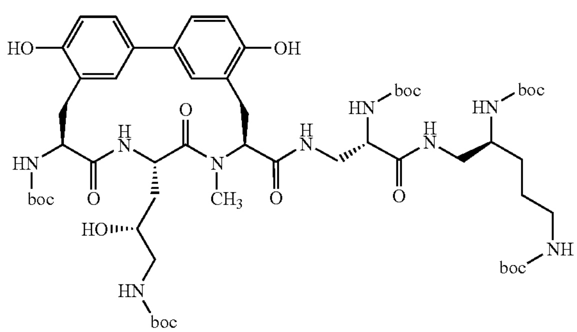 | LC-MS (Method 17): $R_t$ = 2.73 min. MS (EI): m/z = 1173 $(M + H)^+$. |
| 291A | 29A + 223A | 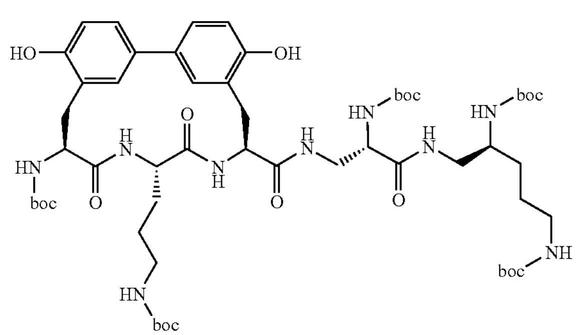 | LC-MS (Method 17): $R_t$ = 2.71 min. MS (EI): m/z = 1142 $(M + H)^+$. |

-continued

| Example No. | Precursor example | Structure | Analytical data |
|---|---|---|---|
| 292A | 261A + 52A | 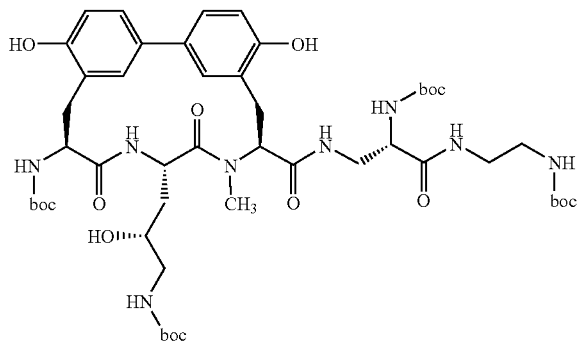 | LC-MS (Method 19): R_t = 2.42 min. MS (EI): m/z = 1015 (M + H)+. |
| 293A | 261A + 29A | 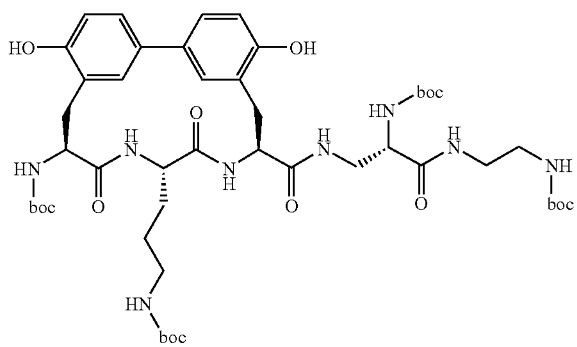 | LC-MS (Method 19): R_t = 2.42 min. MS (EI): m/z = 985 (M + H)+. |

Examples 294A to 297A listed in the following table are prepared in analogy to the method of Example 171A.

| Example No. | Precursor example | Structure | Analytical data |
|---|---|---|---|
| 294A | 227A + 29A | 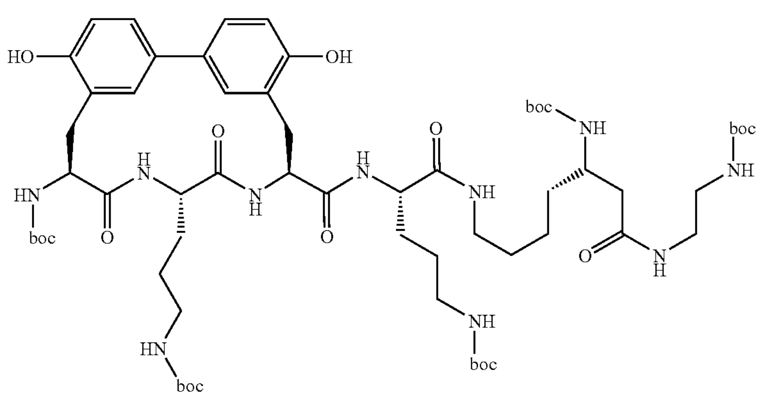 | LC-MS (Method 12): R_t = 2.47 min. MS (EI): m/z = 1255 (M + H)+. |

-continued
| Example No. | Precursor example | Structure | Analytical data |
|---|---|---|---|
| 295A | 52A + 225A | 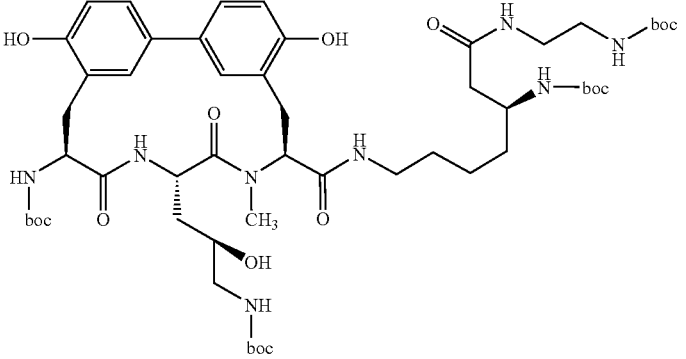 | LC-MS (Method 12): $R_t$ = 2.26 min. MS (EI): m/z = 1071 $(M + H)^+$. |
| 296A | 52A + 227A | 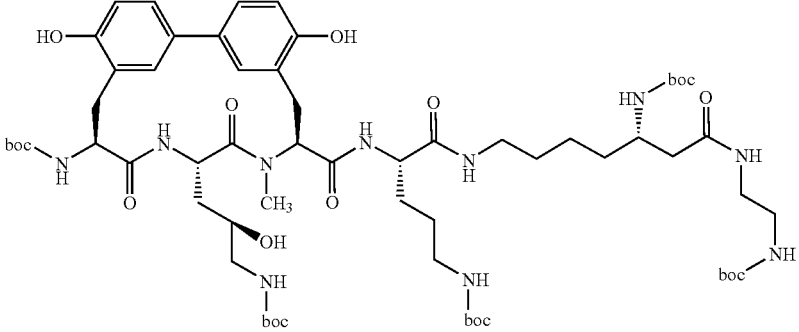 | LC-MS (Method 12): $R_t$ = 2.46 min. MS (EI): m/z = 1285 $(M + H)^+$. |
| 297A | 52A + 81A | 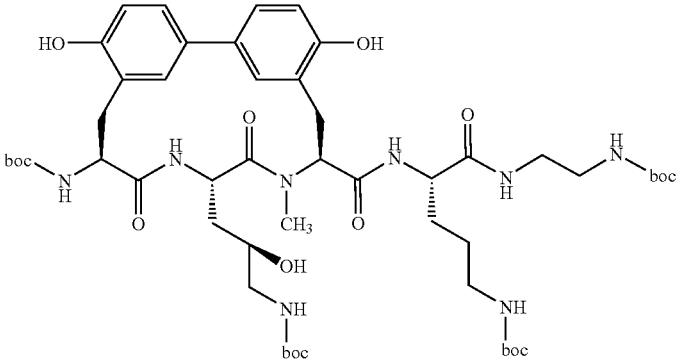 | LC-MS (Method 12): $R_t$ = 2.33 min. MS (EI): m/z = 1043 $(M + H)^+$. |
Example 298A detailed in the following table are prepared in analogy to the method of Example 205A.

| Example No. | Precursor example | Structure | Analytical data |
|---|---|---|---|
| 298A | 281A | 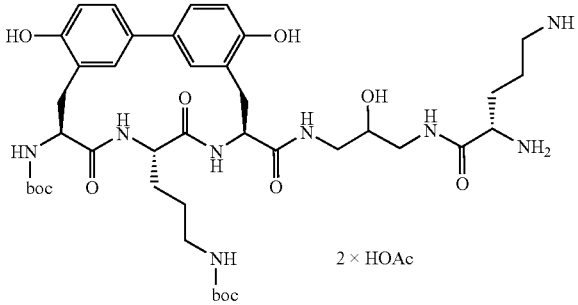 2 × HOAc | LC-MS (Method 12): $R_t$ = 1.14 min. MS (EI): m/z = 843 $(M - 2HOAc + H)^+$. |

Exemplary Embodiments

Exemplary embodiments can be synthesized starting from partially protected biphenomycin derivatives (such as, for example, 29A).

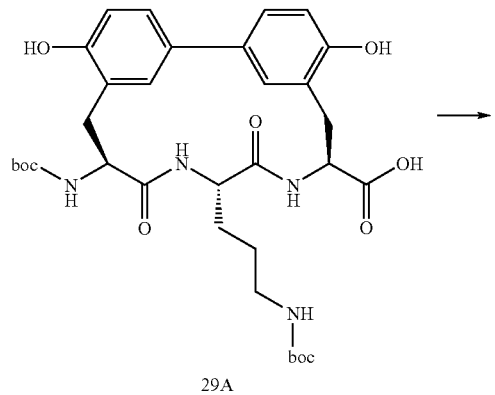

29A

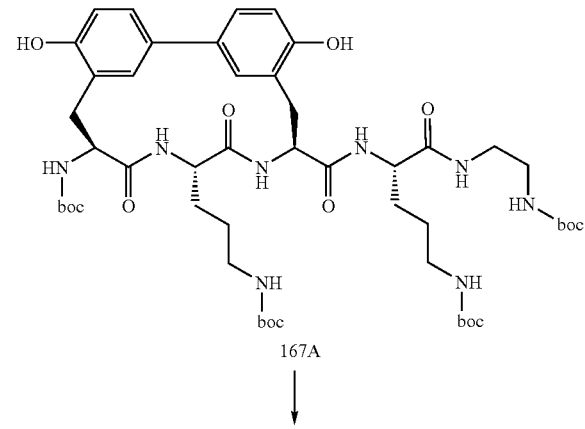

167A

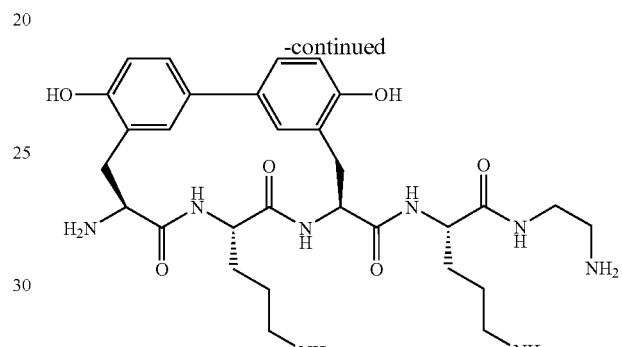

2

Example 1

(8S,11S,14S)-14-Amino-N-((1S)-4-amino-1-{[(3-amino-2-hydroxypropyl)amino]carbonyl}butyl)-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

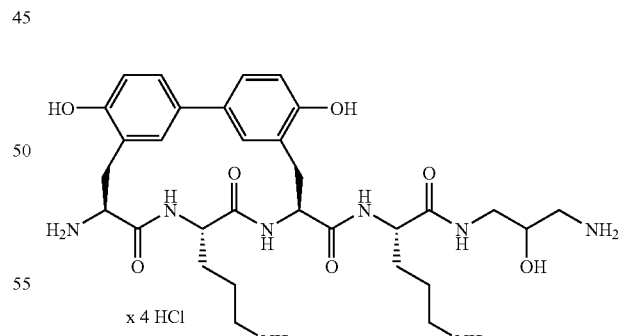

x 4 HCl 36 mg (0.035 mmol) of tert-butyl(3-{[(2S)-5-[(tert-butoxycarbonyl)amino]-2-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)pentanoyl]amino}-2-hydroxypropyl)carbamate (Example 166A) are dissolved in 3.0 ml of 4N hydrogen chloride in dioxane and stirred at room temperature for 2 h. The solvent is evaporated in vacuo and the remaining solid is dried to constant weight under high vacuum.

Yield: 25 mg (92% of theory).

MS (ESI): m/z=643 (M−4HCl+H)+.

$^1$H-NMR (400 MHz, D$_2$O): δ=1.55-2.05 (m, 8H), 2.75-3.15 (m, 8H), 3.17-3.45 (m, 3H), 3.54 (m$_c$, 1H), 3.73 (m$_c$, 1H), 3.87-4.0 (m, 2H), 4.23 (m$_c$, 1H), 4.41 (m$_c$, 1H), 4.82 (m$_c$, 1H), 6.83-6.92 (m, 2H), 6.96 (s, 1H), 7.25 (s, 1H), 7.36 (d, 1H), 7.42 (d, 1H).

The tetrahydrochloride salt is converted by preparative HPLC (Reprosil ODS-A, mobile phase acetonitrile/0.2% aqueous trifluoroacetic acid 5:95→95:5) into the tetra(hydrotrifluoroacetate).

Example 2

(8S,11S,14S)-14-Amino-N-((1S)-4-amino-1-{[(2-aminoethyl)amino]carbonyl}butyl)-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide tetra(hydrotrifluoroacetate)

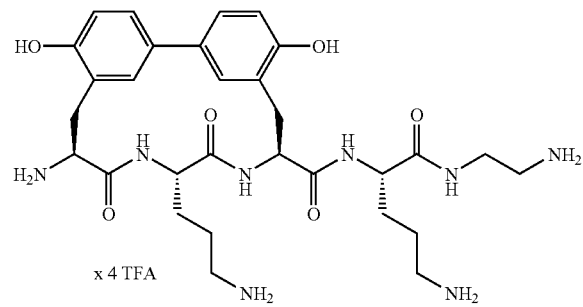

29.7 mg (0.029 mmol) of tert-butyl(2-{[(2S)-5-[(tert-butoxycarbonyl)amino]-2-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)pentanoyl]amino}ethyl)carbamate (Example 167A) are dissolved in 3.0 ml of 4N hydrogen chloride in dioxane and stirred at room temperature for 2 h. The solvent is evaporated in vacuo and the remaining solid is converted by preparative HPLC (Reprosil ODS-A, mobile phase acetonitrile/0.2% aqueous trifluoroacetic acid 5:95→95:5) into the tetra(hydrotrifluoroacetate).

Yield: 20 mg (64% of theory).

MS (ESI): m/z=613 (M−4TFA+H)+.

$^1$H-NMR (400 MHz, D$_2$O): δ=1.53-1.93 (m, 8H), 2.32 (m$_c$, 1H), 2.93 (m$_c$, 4H), 3.02 (m$_c$, 1H), 3.08 (m$_c$, 2H), 3.23 (m$_c$, 1H), 3.35-3.60 (m, 3H), 4.23 (m$_c$, 2H), 4.40 (m$_c$, 1H), 4.82 (m$_c$, 1H), 6.82-6.93 (m, 2H), 6.97 (s, 1H), 7.25 (s, 1H), 7.36 (d, 1H), 7.43 (d, 1H).

Example 3

(8S,11S,14S)-14-Amino-N-((4S)-4-amino-5-{[(1S)-3-amino-1-(hydroxymethyl)propyl]amino}-5-oxopentyl)-11-(3-aminopropyl)-5,17-dihydroxy-10,13-dioxo-9,12-diazatricyclo[14.3.1.1$^{2,6}$]-henicosa-1(20),2(21),3,5,16,18-hexaene-8-carboxamide tetrahydrochloride

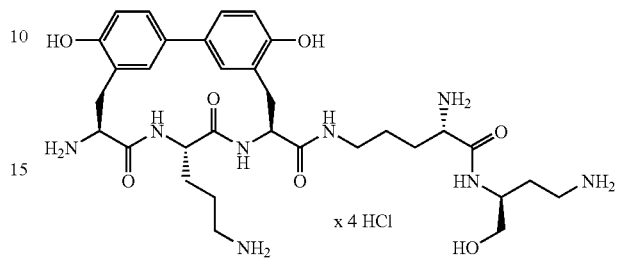

24.9 mg (0.024 mmol) of tert-butyl((3S)-3-{[(2S)-2-[(tert-butoxycarbonyl)amino]-5-({[(8S,11S,14S)-14-[(tert-butoxycarbonyl)amino]-1-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)pentanoyl]amino}-4-hydroxybutyl)carbamate (Example 168A) are dissolved in 3.0 ml of 4N hydrogen chloride in dioxane and stirred at room temperature for 2 h. The solvent is evaporated in vacuo and the remaining solid is dried to constant weight under high vacuum.

Yield: 17 mg (90% of theory).

MS (ESI): m/z=657 (M−4HCl+H)+.

$^1$H-NMR (400 MHz, D$_2$O): δ=1.5-1.95 (m, 10H), 2.75-3.05 (m, 7H), 3.08-3.18 (m, 2H), 3.3 (m$_c$, 1H), 3.43-3.61 (m, 3H), 3.87-3.97 (m, 2H), 4.41 (m$_c$, 1H), 4.82 (m$_c$, 1H), 6.83-6.92 (m, 2H), 6.96 (s, 1H), 7.25 (s, 1H), 7.34 (d, 1H), 7.42 (d, 1H).

The tetrahydrochloride salt is converted by preparative HPLC (Reprosil ODS-A, mobile phase acetonitrile/0.2% aqueous trifluoroacetic acid 5:95→95:5) into the tetra(hydrotrifluoroacetate).

Example 4

(8S,11S,14S)-14-Amino-N-((1S,3R)-4-amino-1-{[(2-aminoethyl)amino]carbonyl}-3-hydroxybutyl)-11-[(2R)-3-amino-2-hydroxypropyl]-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

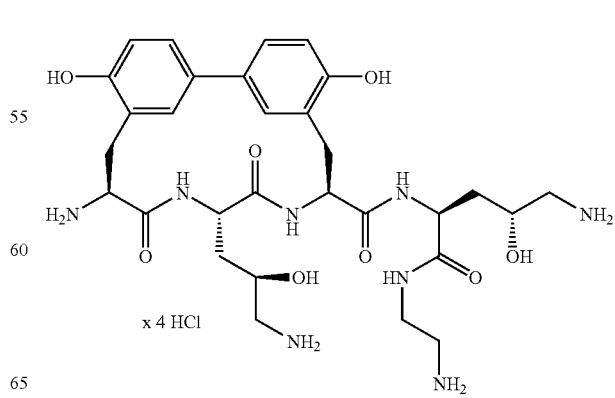

16 mg (0.02 mmol) of the compound from Example 172A are provided in 0.5 ml of dioxane and cooled to 0° C., and 1 ml of 4N hydrogen chloride in dioxane is added. The mixture is allowed to warm to room temperature and is stirred for 1 h. The mixture is then concentrated in vacuo and the residue is dried under high vacuum. Stirring with acetonitrile and collecting the precipitate which has separated out by filtration results in the title compound as a solid.

Yieid: 8 mg (42% of theory).
LC-MS (Method 20): $R_t$=1.03 min.
MS (EI): m/z=645 (M–4HCl+H)$^+$.

Example 5

(8S,11S,14S)-14-Amino-N-((1S)-3-amino-1-{[(3-amino-2-hydroxypropyl)amino]carbonyl}propyl)-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

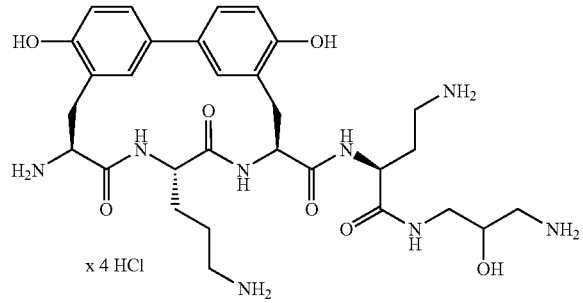

9 mg (0.01 mmol) of the compound from Example 173A are cooled to 0° C. and 1 ml of 4N hydrogen chloride in dioxane is added. After 1 h, the mixture is concentrated in vacuo. The residue is taken up in acetonitrile and again concentrated.

Yieid: 7 mg (98% of theory).
LC-MS (Method 20): $R_t$=0.95 min.
MS (EI): m/z=629 (M–4HCl+H)$^+$.

Example 6

(8S,11S,14S)-14-Amino-N-((1S,3R)-4-amino-1-{[(2-aminoethyl)amino]carbonyl}-3-hydroxybutyl)-11-[3-aminopropyl]-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

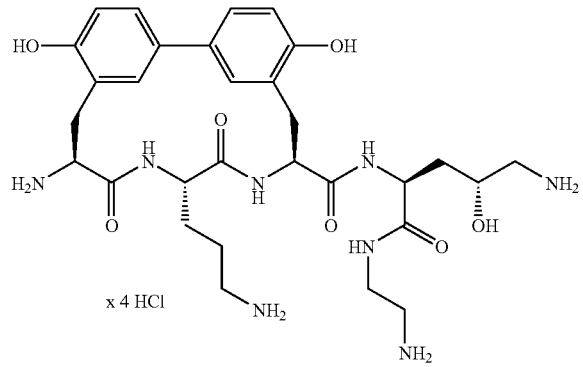

8 mg (0.01 mmol) of the compound from Example 175A are mixed at 0° C. with 0.5 ml of 4N hydrogen chloride in dioxane. The mixture is allowed to warm to room temperature and is stirred for 1 h. The mixture is then concentrated in vacuo, and the residue is dried under high vacuum. Stirring with acetonitrile and collecting the precipitate which has separated out by filtration results in the title compound as a solid.

Yieid: 7 mg (59% of theory).
LC-MS (Method 20): $R_t$=0.90 min.
MS (EI): m/z=630 (M–4HCl+H)$^+$.

Example 7

(8S,11S,14S)-14-Amino-N-{(4S)-4-amino-6-[(2-aminoethyl)amino]-6-oxohexyl}-11-(3-aminopropyl)-9-ethyl-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

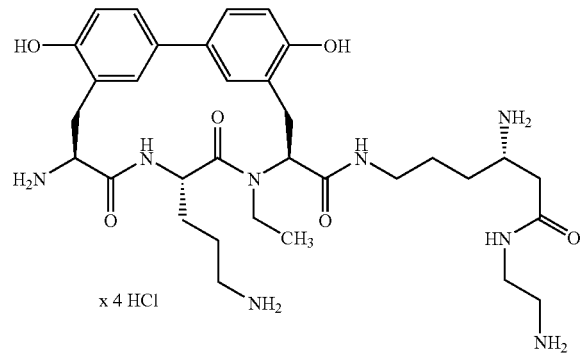

0.1 ml of 4M solution of hydrogen chloride in dioxane is added to a solution of 7.5 mg (0.009 mmol) of tert-butyl{3-[(8S,11S,14S)-8-[({(4S)-4-amino-6-[(2-aminoethyl)amino]-6-oxohexyl}amino)carbonyl]-14-[(tert-butoxycarbonyl)amino]-9-ethyl-5,17-dihydroxy-10,13-dioxo-9,12-diazatricyclo[14.3.1.1$^{2,6}$]henicosa-1(20),2(21),3,5,16,18-hexaen-11-yl]propyl}carbamate (Example 204A) in 0.1 ml of dioxane at 0° C. After 2 h at RT, the reaction solution is concentrated in vacuo, coevaporated with dichloromethane several times and dried under high vacuum. The residue is mixed with diethyl ether and concentrated.

Yield: 4.9 mg (70% of theory)

$^1$H-NMR (400 MHz, D$_2$O): δ=0.87 (m, 3H), 1.10-1.27 (m, 2H), 1.5-1.9 (m, 8H), 2.53-3.80 (m, 14H), 4.47 (m, 1H), 4.96 (m, 1H), 5.65 (m, 1H), 6.90 (d, 2H), 7.06 (s, 1H), 7.21 (s, 1H), 7.45 (d, 1H), 7.53 (d, 1H).

Example 8

(8S,11S,14S)-14-Amino-N-[(1S)-2-[(3-amino-2-hydroxypropyl)amino]-1-(hydroxymethyl)-2-oxoethyl]-1-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide trihydrochloride

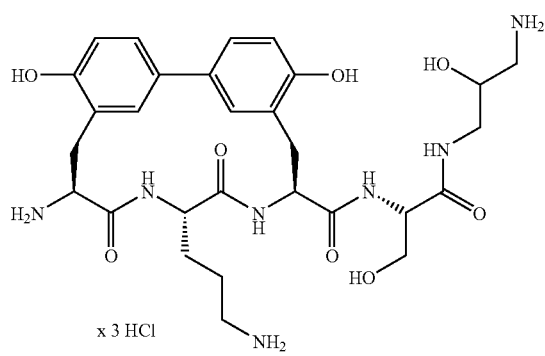

x 3 HCl

A mixture of 12.7 mg (0.014 mmol) of tert-butyl(3-{[(2S)-2-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)-3-hydroxypropanoyl]amino}-2-hydroxypropyl)carbamate (Example 188A) in 1 ml of a 4M solution of hydrogen chloride in dioxane is stirred at RT for 20 min. The reaction solution is concentrated, coevaporated with dichloromethane several times and dried under high vacuum.

Yield: 9.1 mg (90% of theory)
LC-MS (Method 20): R$_t$=1.83 min.
MS (EI): m/z=616 (M−3HCl+H)$^+$
$^1$H-NMR (400 MHz, D$_2$O): δ=1.56-1.90 (m, 4H), 2.78-3.82 (m, 14H), 3.96 (m, 1H), 4.42 (m, 1H), 4.88 (m, 1H), 6.91 (d, 2H), 6.97 (s, 1H), 7.27 (s, 1H), 7.36 (d, 1H), 7.43 (d, 1H).

Example 9

(8S,11S,14S)-14-Amino-N-((1S)-4-amino-1-{2-[(2-aminoethyl)amino]-2-oxoethyl}butyl)-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

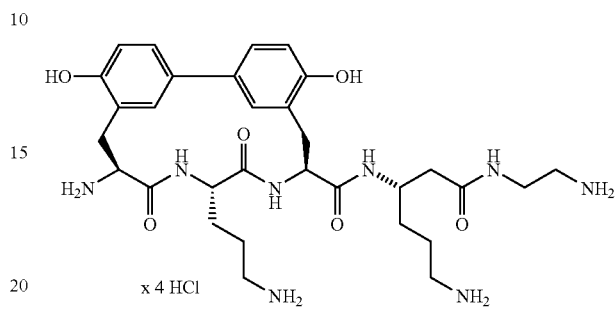

x 4 HCl

A mixture of 30 mg (0.029 mmol) of tert-butyl(2-{[(3S)-6-[(tert-butoxycarbonyl)amino]-3-({[(8S,11S,14S)-14-[(tert-butoxycarbonyl)amino]-11-{3-[(tert-butoxycarbonyl)amino]propyl}-5,17-dihydroxy-10,13-dioxo-9,12-diazatricyclo[14.3.1.1$^{2,6}$]henicosa-1(20),2(21),3,5,16,18-hexaen-8-yl]carbonyl}amino)hexanoyl]amino}ethyl)carbamate (Example 193A) in 2 ml of a 4M solution of hydrogen chloride in dioxane is stirred at RT for 20 min. The reaction solution is concentrated, coevaporated with dichloromethane several times and dried under high vacuum.

Yield: quant.
$^1$H-NMR (400 MHz, D$_2$O): δ=1.5-2.0 (m, 8H), 2.18-3.53 (m, 20H), 4.25 (m, 1H), 4.45 (m, 1H), 6.69 (d, 2H), 6.76 (s, 1H), 7.07 (s, 1H), 7.15 (s, 1H), 7.22 (d, 1H), 7.63 (s, 1H).

Example 10

(8S,11S,14S)-14-Amino-N-{(1S)-4-amino-1-[({(4R)-4-amino-6-[(2-aminoethyl)amino]-6-oxohexyl}amino)carbonyl]butyl}-1-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide pentahydrochloride

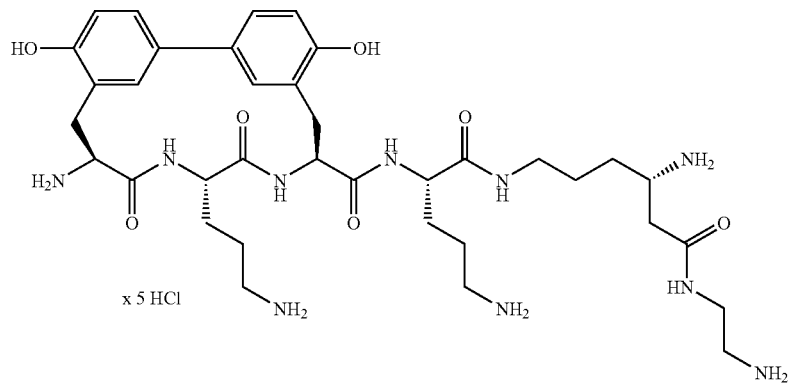

x 5 HCl 6 mg (0.006 mmol) of tert-butyl{3-[(8S,11S,14S)-8-({[(1S)-4-amino-1-({[(4S)-4,8-diamino-6-oxooctyl]amino}carbonyl)butyl]amino}carbonyl)-14-[(tert-butoxycarbonyl)amino]-5,17-dihydroxy-10,13-dioxo-9,12-diazatricyclo-[14.3.1.1$^{2,6}$]henicosa-1(20),2(21),3,5,16,18-hexaen-11-yl]propyl}carbamate tris(hydroacetate) (Example 205A) are added into 0.3 ml of a 4N solution of hydrogen chloride in dioxane and stirred at RT for 30 min. The reaction solution is concentrated, coevaporated with dichloromethane several times and dried under high vacuum.

Yield: 5 mg (85% of theory)

$^1$H-NMR (400 MHz, D$_2$O): δ=1.5-1.7 (m, 13H), 2.52-3.75 (m, 17H), 4.22 (m, 1H), 4.45 (m, 1H), 4.50 (m, 1H), 4.83 (m, 1H), 6.91 (d, 2H), 6.97 (s, 1H), 7.27 (s, 1H), 7.36 (d, 1H), 7.43 (d, 1H).

Example 11

(8S,11S,14S)-14-Amino-N-{(4S)-4-amino-6-[(2-aminoethyl)amino]-6-oxohexyl}-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

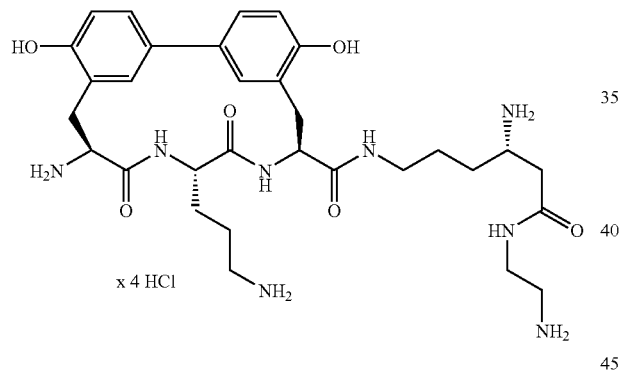

8 mg (0.010 mmol) of tert-butyl{3-[(8S,11S,14S)-8-[({(4S)-4-amino-6-[(2-aminoethyl)amino]-6-oxohexyl}amino)carbonyl]-14-[(tert-butoxycarbonyl)amino]-5,17-dihydroxy-10,13-dioxo-9,12-diazatricyclo[14.3.1.1$^{2,6}$]henicosa-1(20),2(21),3,5,16,18-hexaen-11-yl]propyl}carbamate bis(hydroacetate) (Example 206A) are added into 0.4 ml of a 4N solution of hydrogen in dioxane chloride and stirred at RT for 30 min. The reaction solution is concentrated, coevaporated with dichloromethane several times and dried under high vacuum.

Yield: quant.

LC-MS (Method 12): R$_t$=0.20 min.

MS (EI): m/z=627 (M+−4HCl+H)$^+$ $^1$H-NMR (400 MHz, D$_2$O): δ=1.19 (m, 1H), 1.25 (m, 2H), 1.5-1.9 (m, 8H), 2.53-2.71 (m, 1H), 2.79-3.64 (m, 15H), 4.44 (m, 1H), 6.90 (d, 2H), 6.97 (s, 1H), 7.27 (s, 1H), 7.36 (d, 1H), 7.43 (d, 1H).

Example 12

(8S,11S,14S)-14-Amino-N-((1S)-3-amino-1-{[(2-aminoethyl)amino]carbonyl}propyl)-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

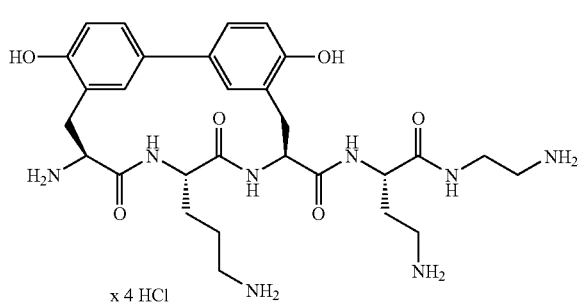

15 mg (0.019 mmol) of tert-butyl{3-[(8S,11S,14S)-8-{[((1S)-3-amino-1-{[(2-aminoethyl)amino]carbonyl}propyl)amino]carbonyl}-14-[(tert-butoxycarbonyl)amino]-5,17-dihydroxy-10,13-dioxo-9,12-diazatricyclo[14.3.1.1$^{2,6}$]henicosa-1(20),2(21),3,5,16,18-hexaen-11-yl]propyl}carbamate bis(hydroacetate) (Example 207A) are added into 1 ml of a 4N solution of hydrogen chloride in dioxane and stirred at RT for 20 min. The reaction solution is concentrated, coevaporated with dichloromethane several times and dried under high vacuum.

Yield: 12 mg (86% of theory)

$^1$H-NMR (400 MHz, D$_2$O): δ=1.6-2.0 (m, 5H), 2.07-2.30 (m, 2H), 2.84-3.23 (m, 10H), 3.33 (m, 1H), 3.51-3.83 (m, 4H), 4.50 (m, 1H), 4.90 (m, 1H), 6.98 (d, 2H), 7.06 (s, 1H), 7.35 (s, 1H), 7.45 (d, 1H), 7.52 (d, 1H).

Example 13

(8S,11S,14S)-14-Amino-N-((1S)-4-amino-1-{[((1S)-3-amino-1-{[(2-aminoethyl)amino]carbonyl}propyl)amino]carbonyl}butyl)-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide pentahydrochloride

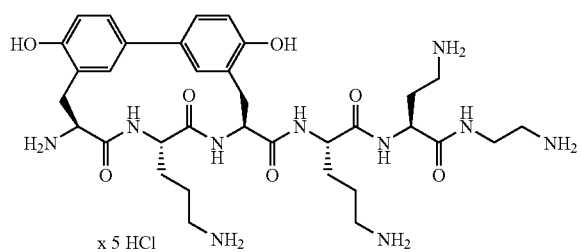

7 mg (0.008 mmol) of tert-butyl{3-[(8S,11S,14S)-8-{[((1S)-4-amino-1-{[((1S)-3-amino-1-{[(2-aminoethyl)amino]carbonyl}propyl)amino]carbonyl}butyl)amino]carbonyl}-14-[(tert-butoxycarbonyl)amino]-5,17-dihydroxy-10,13-dioxo-9,12-diazatricyclo[14.3.1.1$^{2,6}$]henicosa-1(20),2(21),3,5,16,18-hexaen-11-yl]propyl}carbamate tris(hydroacetate) (Example 208A) are added into 0.6 ml of a 4N solution of hydrogen chloride in dioxane and stirred at RT for 30 min. The reaction solution is concentrated, coevaporated with dichloromethane several times and dried under high vacuum.

Yield: 6.1 mg (89% of theory)

$^1$H-NMR (400 MHz, D$_2$O): δ=1.5-2.3 (m, 11H), 2.80-3.70 (m, 14H), 4.29-4.48 (m, 3H), 4.85 (m, 1H), 6.91 (d, 2H), 6.97 (s, 1H), 7.27 (s, 1H), 7.36 (d, 1H), 7.44 (d, 1H).

Example 14

(8S,11S,14S)-14-Amino-N-((1S)-1-{[(2-aminoethyl)amino]carbonyl}-4-{[amino(imino)methyl]amino}butyl)-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide pentahydrochloride

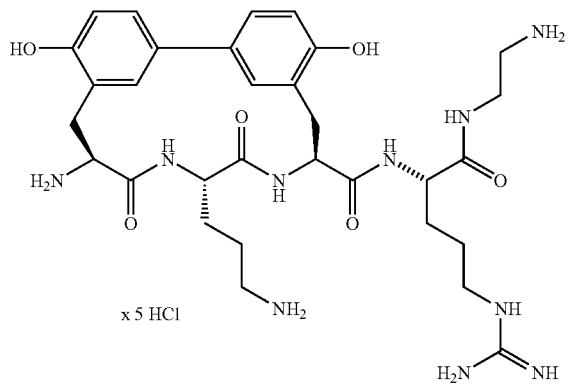

5.3 mg (0.005 mmol) of tert-butyl{3-[(8S,11S,14S)-8-{[((1S)-1-{[(2-aminoethyl)amino]carbonyl}-4-{[amino(imino)methyl]amino}butyl)amino]carbonyl}-14-[(tert-butoxycarbonyl)amino]-5,17-dihydroxy-10,13-dioxo-9,12-diazatricyclo[14.3.1.1$^{2,6}$]henicosa-1(20),2(21),3,5,16,18-hexaen-11-yl]propyl}carbamate di(hydrotrifluoroacetate) (Example 209A) are added into 0.4 ml of a 4N solution of hydrogen chloride in dioxane and stirred at RT for 30 min. The reaction solution is concentrated, coevaporated with dichloromethane several times and dried under high vacuum.

Yield: quant.

LC-MS (Method 20): R$_t$=1.75 min.

MS (EI): m/z=655 (M−5HCl+H)$^+$ $^1$H-NMR (400 MHz, D$_2$O): δ=1.5-1.9 (m, 8H), 2.81-3.75 (m, 13H), 4.25 (m, 1H), 4.44 (m, 1H), 4.84 (m, 1H), 6.86 (d, 1H), 6.90 (d, 2H), 6.97 (s, 1H), 7.28 (s, 1H), 7.36 (d, 1H), 7.45 (m, 2H).

Example 15

N$^2$-{[(8S,11S,14S)-14-Amino-1-(3-aminopropyl)-5,17-dihydroxy-10,13-dioxo-9,12-diazatricyclo[14.3.1.1$^{2,6}$]henicosa-1(20),2(21),3,5,16,18-hexaen-8-yl]carbonyl}-N$^1$-[(2S)-2,5-diaminopentyl]-L-glutamamide tetrahydrochloride

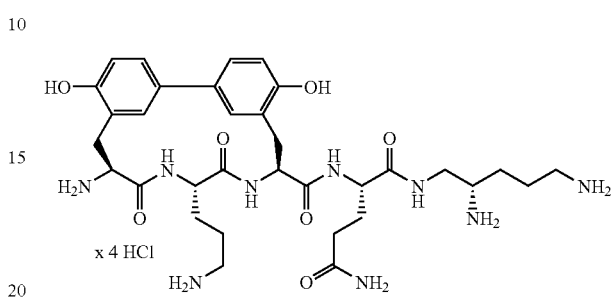

7 mg (0.01 mmol) of the compound from Example 180A are mixed with 0.1 ml of 4N hydrogen chloride in dioxane. The mixture is stirred at RT for 4 h. The mixture is then concentrated in vacuo, and the residue is dried under high vacuum.

Yield: 4.2 mg (78% of theory).

MS (ESI): m/z=684 (M−4HCl+H)$^+$.

Example 16

(8S,11S,14S)-14-Amino-N-[(1S)-4-amino-1-({[(2S)-2,5-diaminopentyl]amino}carbonyl)butyl]-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

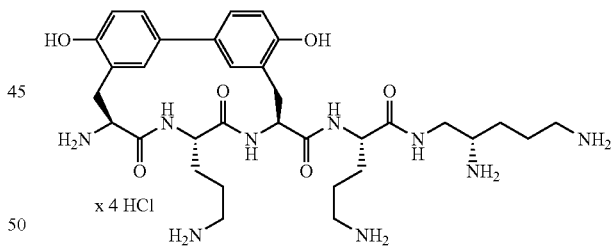

40 mg (0.034 mmol) of the compound from Example 177A are dissolved at 0° C. in 1 ml of dioxane. Then 0.5 ml of a 4N hydrogen chloride solution in dioxane are added and the mixture is stirred at RT for 2 h. The mixture is evaporated to dryness in vacuo and the residue is dried to constant weight under high vacuum.

Yield: 26 mg (88% of theory).

MS (ESI): m/z=670 (M−4HCl+H)$^+$.

$^1$H-NMR (400 MHz, D$_2$O): δ=1.45-1.95 (m, 12H), 2.8-3.05 (m, 6H), 3.1-3.4 (m, 4H), 3.42 (m$_c$, 2H), 3.54 (m$_c$, 1H), 3.97 (m$_c$, 1H), 4.41 (m$_c$, 1H), 4.6-4.8 (m, 2H, under D$_2$O), 6.83-6.9 (m, 2H), 6.95 (s, 1H), 7.24 (s, 1H), 7.32 (d, 1H), 7.4 (d, 1H).

Example 17

(8S,11S,14S)-14-Amino-11-(3-aminopropyl)-N-(2-{[(2S)-2,5-diaminopentyl]amino}-2-oxoethyl)-5,17-dihydroxy-10,13-dioxo-9,12-diazatricyclo[14.3.1.1²,⁶]henicosa-1(20),2(21),3,5,16,18-hexaene-8-carboxamide tetrahydrochloride

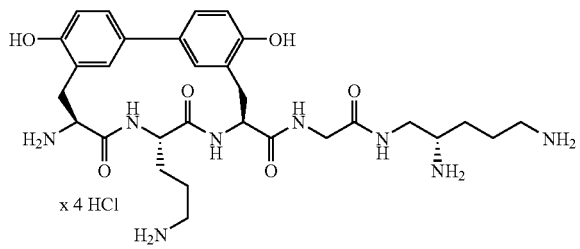

11.5 mg (0.011 mmol) of the compound from Example 178A are dissolved at 0° C. in 1 ml of dioxane. Then, 0.2 ml of a 4N hydrogen chloride solution in dioxane are added and the mixture is stirred at RT for 2 h. The mixture is evaporated to dryness in vacuo, and the residue is dried to constant weight under high vacuum.

Yield: 8.5 mg (99% of theory).

MS (ESI): m/z=613 (M−4HCl+H)⁺.

¹H-NMR (400 MHz, D₂O): δ=1.5-1.9 (m, 8H), 2.75-3.05 (m, 6H), 3.24 (m$_c$, 1H), 3.3-3.43 (m, 2H), 3.45-3.55 (m, 2H), 3.87-3.97 (m, 2H), 4.41 (m$_c$, 1H), 4.7 (m, 1H, under D₂O), 4.83 (m$_c$, 1H), 6.83-6.9 (m, 2H), 6.95 (s, 1H), 7.23 (s, 1H), 7.3 (d, 1H), 7.4 (d, 1H).

Example 18

(8S,11S,14S)-14-Amino-11-(3-aminopropyl)-N-[(1S)-2-{[(2S)-2,5-diaminopentyl]amino}-1-(hydroxymethyl)-2-oxoethyl]-5,17-dihydroxy-10,13-dioxo-9,12-diazatricyclo[14.3.1.1²,⁶]henicosa-1(20),2(21),3,5,16,18-hexaene-8-carboxamide tetrahydrochloride

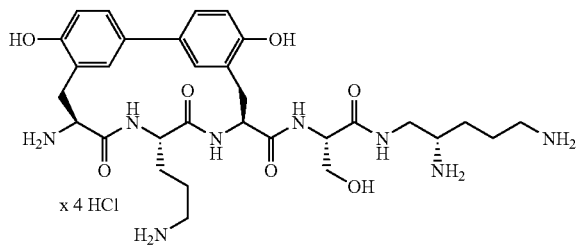

18.4 mg (0.018 mmol) of the compound from Example 179A are dissolved at 0° C. in 1 ml of dioxane. Then 0.26 ml of a 4N hydrogen chloride solution in dioxane are added and the mixture is stirred at RT for 4 h. The mixture is evaporated to dryness in vacuo, and the residue is dried to constant weight under high vacuum.

Yield: 13 mg (93% of theory).

MS (ESI): m/z=643 (M−4HCl+H)⁺.

¹H-NMR (400 MHz, D₂O): δ=1.4-1.85 (m, 8H), 2.75-3.05 (m, 6H), 3.26 (m$_c$, 1H), 3.35-3.85 (m, 7H), 4.41 (m$_c$, 1H), 4.7 (m, 1H, under D₂O), 4.87 (m$_c$, 1H), 6.85-6.92 (m, 2H), 6.96 (s, 1H), 7.22 (s, 1H), 7.32 (d, 1H), 7.4 (d, 1H).

Example 19

N²-{[(8S,11S,14S)-14-Amino-1-(3-aminopropyl)-5,17-dihydroxy-10,13-dioxo-9,12-diazatricyclo[14.3.1.1²,⁶]henicosa-1(20),2(21),3,5,16,18-hexaen-8-yl]carbonyl}-L-ornithyl-N-(2-aminoethyl)-L-ornithinamide pentahydrochloride

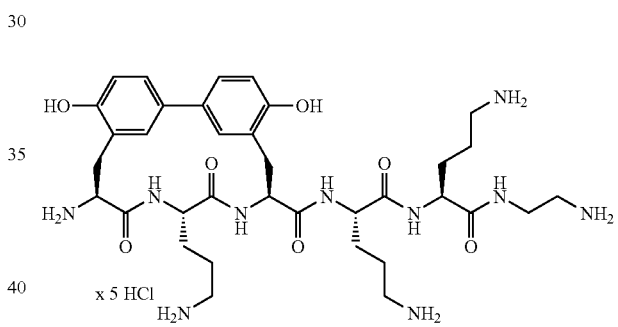

8.5 mg (0.008 mmol) of the compound from Example 210A are mixed with 0.2 ml of a 4N hydrogen chloride solution in dioxane and stirred at RT for 3 h. The mixture is evaporated to dryness in vacuo, and the residue is dried to constant weight under high vacuum.

Yield: quant.

MS (ESI): m/z=727 (M−5HCl+H)⁺.

¹H-NMR (400 MHz, D₂O): δ=1.55-1.95 (m, 12H), 2.75-3.15 (m, 10H), 3.25 (m$_c$, 1H), 3.35-3.75 (m, 3H), 4.25-4.35 (m, 2H), 4.41 (m$_c$, 1H), 4.7-4.9 (m, 2H, under D₂O), 6.91 (m$_c$, 2H), 6.98 (s, 1H), 7.28 (s, 1H), 7.38 (d, 1H), 7.45 (d, 1H).

Examples 20 to 39 listed in the following table are prepared in analogy to the method of Example 1 as hydrochloride or hydrotrifluoroacetate salt according to the respective method of isolation.

| Example No. | Precursor example | Structure | Analytical data |
|---|---|---|---|
| 20 | 221A | 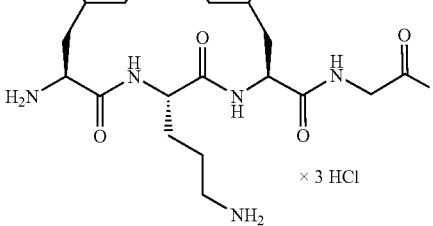 ×3 HCl | LC-MS (Method 20): $R_t$ =1.87 min. MS (EI): m/z = 556 $(M - 3HCl + H)^+$. $^1$H-NMR (400 MHz, D$_2$O): δ = 1.55-1.90 (m, 4 H), 2.8-2.97 (m, 3 H), 3.0-3.15 (m, 3 H), 3.27 ($m_c$, 1 H), 3.45-3.75 (m, 5 H), 4.40 ($m_c$, 1 H), 4.8 ($m_c$, 1 H, under D$_2$O), 4.72 ($m_c$, 1 H), 6.8-6.9 (m, 2 H), 6.94 (s, 1 H), 7.23 (s, 1 H), 7.34 (d, 1 H), 7.42 (d, 1 H). |
| 21 | 184A | 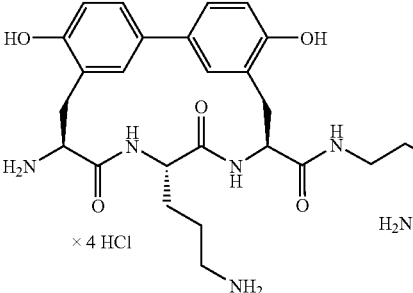 ×4 HCl | MS (EI): m/z = 613 $(M - 4HCl + H)^+$ $^1$H-NMR (400 MHz, D$_2$O): δ = 1.45-1.95 (m, 6 H), 2.82-3.2 (m, 8 H), 3.25-3.45 (m, 2 H), 3.47-3.75 (m, 4 H), 3.94 ($m_c$, 1 H), 4.42 ($M_c$, 1 H), 4.68 (m, 1 H, under D$_2$O), 4.77 ($m_c$, 1 H) 6.83-6.92 (m, 2 H), 6.97 (s, 1 H), 7.25 (s, 1 H), 7.36 (d, 1 H), 7.43 (d, 1 H). |
| 22 | 185A | 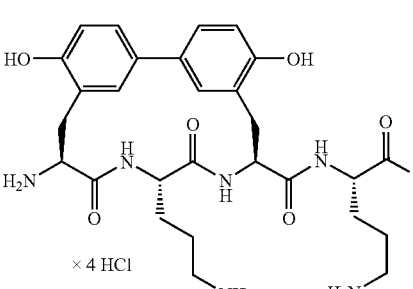 ×4 HCl | LC-MS (Method 20): $R_t$ =1.83 min. MS (EI): m/z = 685 $(M - 4HCl + H)^+$. $^1$H-NMR (400 MHz, D$_2$O): δ = 1.2-1.9 (m, 14 H), 2.7-3.1 (m, 5 H), 3.1-3.3 (m, 4 H), 3.5-3.6 (m, 2 H), 3.72 ($m_c$, 2 H), 3.88 ($m_c$, 2 H), 4.18 ($m_c$, 1 H), 4.41 ($m_c$, 1 H), 4.78 ($m_c$, 1 H), 6.83-6.92 (m, 2 H), 6.97 (s, 1 H), 7.25 (s, 1 H), 7.36 (d, 1 H), 7.43 (d, 1 H). |
| 23 | 186A | 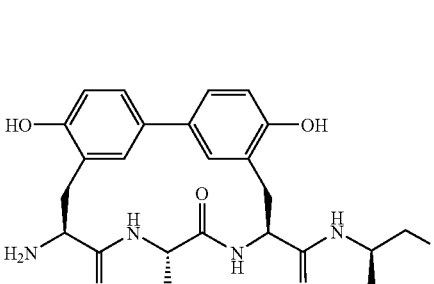 ×4 HCl | MS (EI): m/z = 643 $(M - 4HCl + H)^+$. $^1$H-NMR (400 MHz, D$_2$O): δ = 1.5-2.0 (m, 8 H), 2.7-3.1 (m, 6 H), 3.22 ($m_c$, 1 H), 3.3-3.8 (m, 5 H), 3.9-4.05 (m, 2 H), 4.4 ($m_c$, 1 H), 4.6-4.8 (m, 2 H under D$_2$O), 6.8-6.93 (m, 2H), 6.96 (s, 1 H), 7.23 (s, 1 H), 7.34 (d, 1 H), 7.42 (d, 1 H). |

-continued

| Example No. | Precursor example | Structure | Analytical data |
|---|---|---|---|
| 24 | 187A | (structure) × 3 HCl | LC-MS (Method 12): R$_t$ =0.238 min. MS (EI): m/z = 613 (M − 3HCl + H)$^+$ |
| 25 | 216A | (structure) × 3 HCl | LC-MS (Method 20): R$_t$ =2.17 min. MS (EI): m/z = 586 (M − 3HCl + H)$^+$ |
| 26 | 217A | (structure) × 3 HCl | LC-MS (Method 20): R$_t$ =2.03 min. MS (EI): m/z = 644 (M − 3HCl + H)$^+$ $^1$H-NMR (400 MHz, D$_2$O): δ = 1.6-1.7 (m, 7 H), 2.80-3.78 (m, 15 H), 4.24 (m, 1 H), 4.43 (m, 1 H), 4.80 (m, 1 H), 6.90 (d, 2 H), 6-97 (s, 1 H), 7.28 (s, 1 H), 7.36 (d, 1 H), 7.43 (d, 1 H). |
| 27 | 218A | (structure) × 4 HCl | LC-MS (Method 17): R$_t$ =0.24 min. MS (EI): m/z = 700 (M − 4HCl + H)$^+$ $^1$H-NMR (400 MHz, D$_2$O): δ = 1.5-1.9 (m, 9 H), 2.81-3.83 (m, 20 H), 4.32-4.39 (m, 2 H), 4.44 (m, 1 H), 4.84 (m, 1 H), 6.90 (d, 2 H), 6.97 (s, 1 H), 7.28 (s, 1 H), 7.36 (d, 1 H), 7.44 (d, 1 H). |

| Example No. | Precursor example | Structure | Analytical data |
|---|---|---|---|
| 28 | 219A | 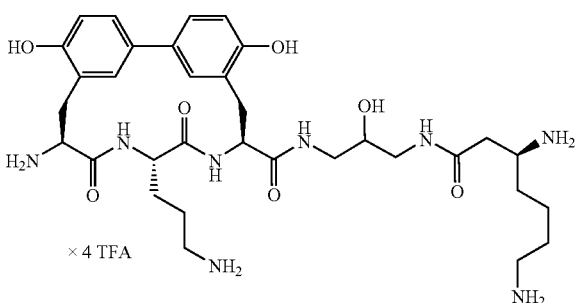<br>× 4 TFA | LC-MS (Method 20):<br>R$_t$ =1.82 min.<br>MS (EI): m/z = 671<br>(M − 4TFA + H)$^+$ |
| 29 | 195A | 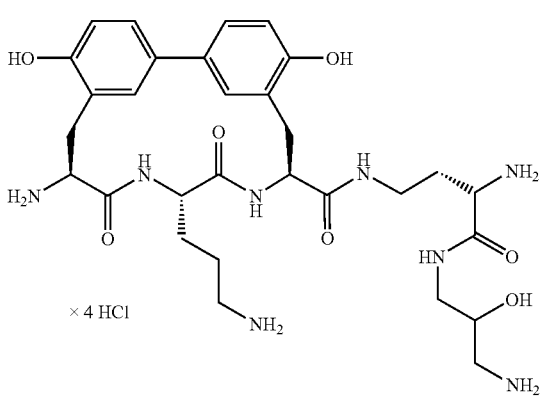<br>× 4 HCl | $^1$H-NMR (400 MHz, D$_2$O):<br>δ = 1.58-1.89 (m, 4 H), 2.02-2.16 (m, 2 H), 2.80-3.75 (m, 15 H), 3.97 (m, 2 H), 4.44 (m, 1 H), 6.90 (d, 2 H), 6.98 (s, 1 H), 7.26 (s, 1 H), 7.37 (d, 1 H), 7.44 (d, 1 H). |
| 30 | 196A | 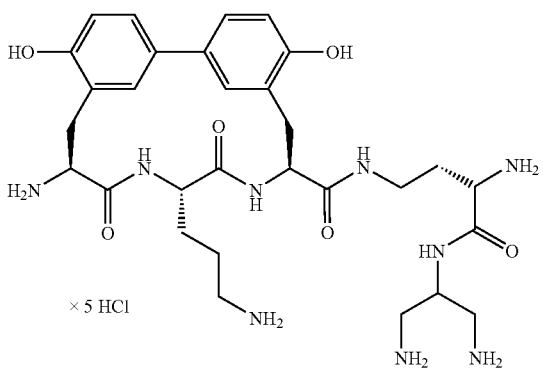<br>× 5 HCl | LC-MS (Method 20):<br>R$_t$ =0.45 min.<br>MS (EI): m/z = 628<br>(M − 5HCl + H)$^+$<br>$^1$H-NMR (400 MHz, D$_2$O):<br>δ = 1.57-1.87 (m, 4 H), 2.09 (m, 1 H), 2.20 (m, 1 H), 2.85-3.76 (m, 15 H), 4.01 (m, 1 H), 4.45 (s, 1 H), 4.50 (m, 1 H), 6.90 (d, 2 H), 6.98 (s, 1 H), 7.26 (s, 1 H), 7.37 (d, 1 H), 7.44 (d, 1 H). |
| 31 | 220A | 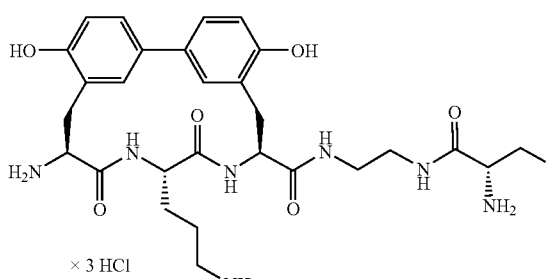<br>× 3 HCl | LC-MS (Method 20):<br>R$_t$ =1.80 min.<br>MS (EI): m/z = 585<br>(M − 3HCl + H)$^+$<br>$^1$H-NMR (400 MHz, D$_2$O):<br>δ = 1.53-1.89 (m, 4 H), 2.81-3.46 (m, 10 H), 3.56 (m, 1 H), 3.67 (s, 2 H), 3.84-3.93 (m, 2 H), 4.05 (m, 1 H), 4.44 (m, 1 H), 6.90 (d, 2 H), 6.97 (s, 1 H), 7.27 (s, 1 H), 7.36 (d, 1 H), 7.43 (d, 1 H). |

-continued

| Example No. | Precursor example | Structure | Analytical data |
|---|---|---|---|
| 32 | 182A | 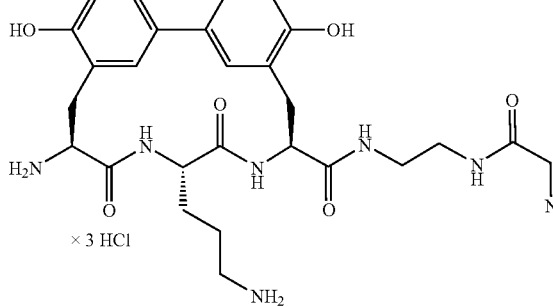 | LC-MS (Method 20): $R_t$ =1.68 min. MS (EI): m/z = 556 $(M - 3HCl + H)^+$ $^1$H-NMR (400 MHz, $D_2O$): δ = 1.55-1.85 (m, 4 H), 2.81-3.05 (m, 4 H), 3.15-3.7 (m, 9 H), 4.42 ($m_c$, 1 H), 4.6-4.8 (m, 2 H, under $D_2O$), 6.88 (d, 2 H), 6.95 (s, 1 H), 7.26 (s, 1 H), 7.35 (d, 1 H), 7.41 (d, 1 H). |
| 33 | 199A | 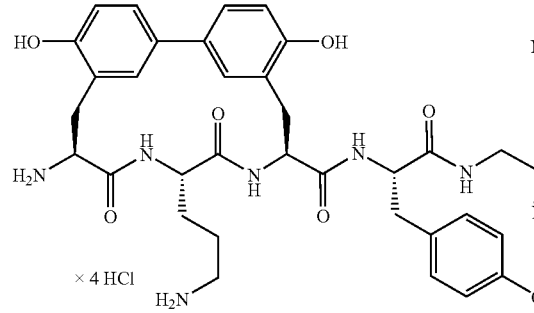 | MS (EI): m/z = 719 $(M - 4HCl + H)^+$ $^1$H-NMR (400 MHz, $D_2O$): δ = 1.45-1.75 (m, 8 H), 2.7-3.05 (m, 6 H), 3.15 ($m_c$, 1 H), 3.26 ($m_c$, 1 H), 3.45 ($m_c$, 2 H), 3.55 ($m_c$, 1 H), 4.42 ($m_c$, 1 H), 4.48 ($m_c$, 1 H), 4.6-4.8 (m, 2 H, under $D_2O$), 6.75 (d, 2 H), 6.88 (d, 2 H), 6.94 (s, 1 H), 7.07 (d, 2 H), 7.2 (s, 1 H), 7.33 (d, 1 H), 7.42 (d, 1 H). |
| 34 | 197A | 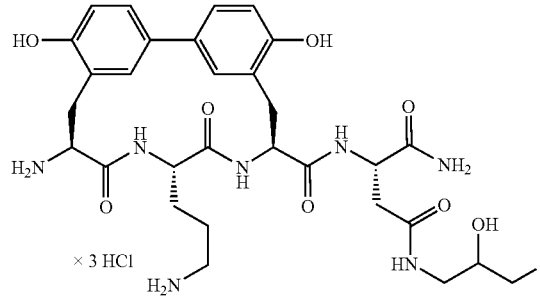 | LC-MS (Method 20): $R_t$ =1.72 min. MS (EI): m/z = 643 $(M - 3HCl + H)^+$ $^1$H-NMR (400 MHz, $D_2O$): δ = 1.55-1.85 (m, 4 H), 2.6-3.35 (m, 11 H), 3.5-3.75 (m, 2 H), 3.92 ($m_c$, 1 H), 4.41 ($m_c$, 1 H), 4.48($m_c$, 1 H), 4.7 (m, 1 H, under $D_2O$), 4.78 (d, 1 H), 6.87 (d, 2 H), 6.93 (s, 1 H), 7.23 (s, 1 H), 7.32 (d, 1 H), 7.4 (d, 1 H). |
| 35 | 198A | 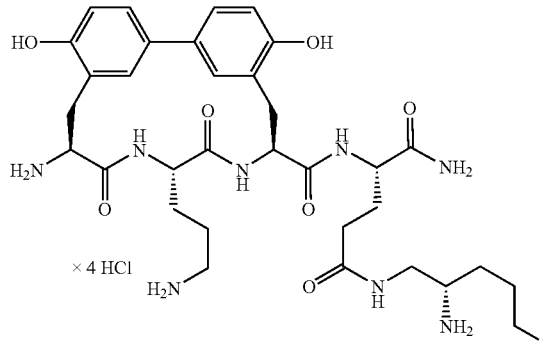 | MS (EI): m/z = 684 $(M - 4HCl + H)^+$ |

| Example No. | Precursor example | Structure | Analytical data |
|---|---|---|---|
| 36 | 200A | 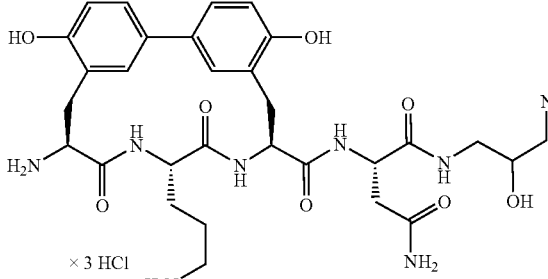 | LC-MS (Method 20): R$_t$ =1.74 min. MS (EI): m/z = 643 (M − 3HCl + H)$^+$ $^1$H-NMR (400 MHz, D$_2$O): δ = 1.45-1.85 (m, 4 H), 2.65-3.1 (m, 7 H), 3.2-3.4 (m, 4 H), 3.5-3.75 (m, 2 H), 3.92 (m$_c$, 1 H), 4.41 (m$_c$, 1 H), 4.48 (m$_c$, 1 H), 4.7 (m, 1 H, under D$_2$O), 4.78 (d, 1 H), 6.87 (d, 2 H), 6.93 (s, 1 H), 7.23 (s, 1 H), 7.32 (d, 1 H), 7.4 (d, 1 H). |
| 37 | 201A | 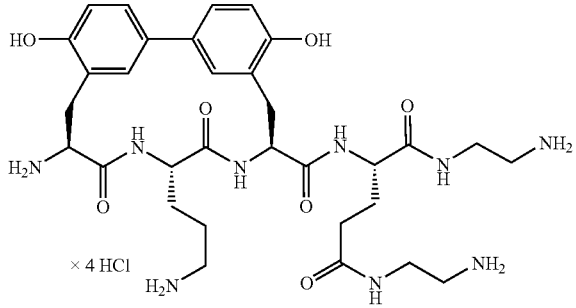 | MS (EI): m/z = 670 (M − 4HCl + H)$^+$ |
| 38 | 202A | 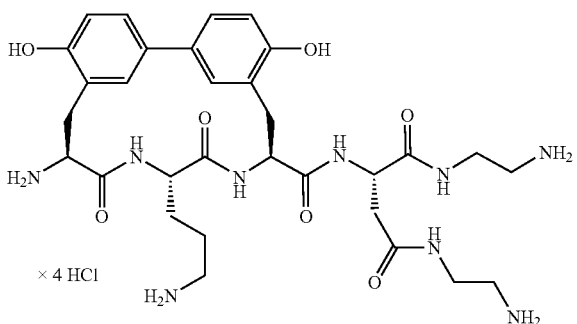 | MS (EI): m/z = 656 (M − 4HCl + H)$^+$ |
| 39 | 203A | 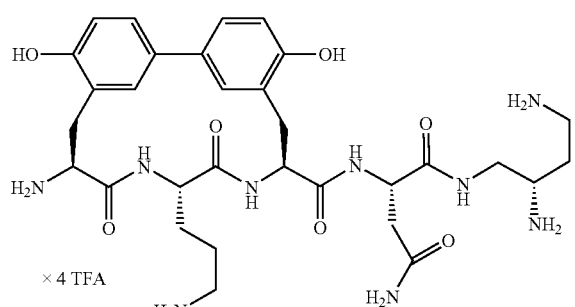 | MS (EI): m/z = 656 (M − 4TFA + H)$^+$ |

Example 40

(8S,11S,14S)-14-Amino-N-((4S)-4-amino-6-{[(2S)-2,5-diaminopentyl]amino}-6-oxohexyl)-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide pentahydrochloride

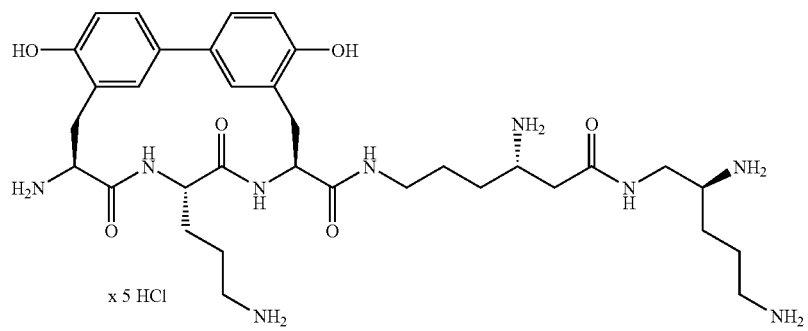

0.32 ml of a 4N solution of hydrogen chloride in dioxane are added to a solution of 25 mg (0.021 mmol) of the compound from Example 262A in 1 ml of dioxane at 0° C. After 2 h at RT, the reaction solution is concentrated in vacuo and coevaporated with dichloromethane several times. The remaining solid is dried to constant weight under high vacuum.

Yield: 17.8 mg (96% of theory)

MS (ESI): m/z=684 (M−5HCl+H)$^+$.

$^1$H-NMR (400 MHz, D$_2$O): δ=1.4-1.9 (m, 12H), 2.5-3.2 (m, 10H), 3.3-3.7 (m, 6H), 4.41 (m$_c$, 1H), 4.7-4.9 (m, 2H, under D$_2$O), 6.85-6.92 (m, 2H), 6.96 (s, 1H), 7.28 (s, 1H), 7.38 (d, 1H), 7.44 (d, 1H).

Example 41

(8S,11S,14S)-14-Amino-N-((1S)-1-(aminomethyl)-2-{[(2S)-2,5-diaminopentyl]amino}-2-oxoethyl)-11-(3-aminopropyl)-5,17-dihydroxy-10,13-dioxo-9,12-diazatricyclo[14.3.1.1$^{2,6}$]henicosa-1(20),2(21),3,5,16,18-hexaene-8 carboxamide pentahydrochloride

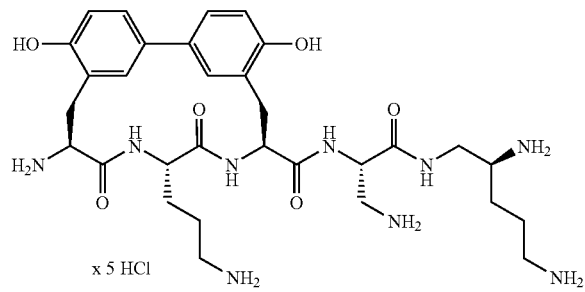

0.62 ml of a 4N solution of hydrogen chloride in dioxane are added to a solution of 47 mg (0.021 mmol) of the compound from Example 269A in 1 ml of dioxane at 0° C. After 3 h at RT, the reaction solution is concentrated in vacuo and coevaporated with dichloromethane several times. The remaining solid is dried to constant weight under high vacuum.

Yield: 33 mg (98% of theory)

MS (ESI): m/z=642 (M−5HCl+H)$^+$.

$^1$H-NMR (400 MHz, D$_2$O): δ=1.5-1.9 (m, 8H), 2.8-3.1 (m, 6H), 3.2-3.7 (m, 8H), 4.41 (m$_c$, 1H), 4.7-4.9 (m, 2H, under D$_2$O), 6.91 (m$_c$, 2H), 7.0 (s, 1H), 7.27 (s, 1H), 7.38 (d, 1H), 7.45 (d, 1H).

Example 42

(8S,11S,14S)-14-Amino-N-[(1S)-4-amino-1-(2-{[(2S)-2,5-diaminopentyl]amino}-2-oxoethyl)butyl]-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide pentahydrochloride

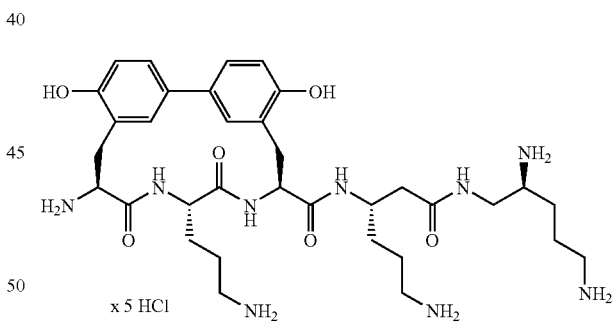

0.22 ml of a 4N solution of hydrogen chloride in dioxane are added to a solution of 17 mg (0.014 mmol) of the compound from Example 270A in 1 ml of dioxane at 0° C. After 3 h at RT, the reaction solution is concentrated in vacuo and coevaporated with dichloromethane several times. The remaining solid is dried to constant weight under high vacuum.

Yield: 12 mg (99% of theory)

MS (ESI): m/z=684 (M−5HCl+H)$^+$.

$^1$H-NMR (400 MHz, D$_2$O): δ=1.4-1.9 (m, 12H), 2.37 (m$_c$, 1H), 2.55 (m$_c$, 1H), 2.7-3.2 (m, 7H), 3.2-3.7 (m, 6H), 4.22 (m$_c$, 1H), 4.42 (m$_c$, 1H), 4.7-4.9 (m, 2H, under D$_2$O), 6.89 (m$_c$, 2H), 6.96 (s, 1H), 7.27 (s, 1H), 7.36 (d, 1H), 7.42 (d, 1H).

Example 43

(8S,11S,14S)-14-Amino-N-((1S)-4-amino-1-{[(2-aminoethyl)amino]carbonyl}butyl)-11-[(2R)-3-amino-2-hydroxypropyl]-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

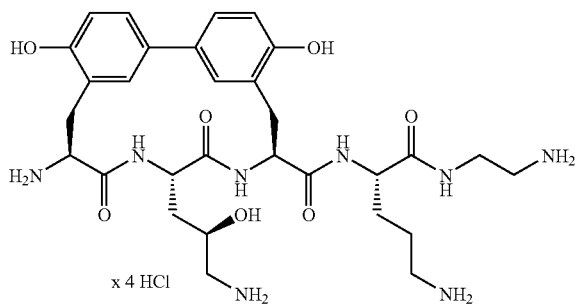

0.83 ml of a 4N solution of hydrogen chloride in dioxane are added to 57 mg (0.014 mmol) of the compound from Example 271A at 0° C. After 3 h at RT, the reaction solution is concentrated in vacuo and coevaporated with dichloromethane several times. The remaining solid is dried to constant weight under high vacuum.

Yield: 44 mg (99% of theory)

MS (ESI): m/z=629 (M−4HCl+H)$^+$.

$^1$H-NMR (400 MHz, D$_2$O): δ=1.5-2.1 (m, 6H), 2.7-3.2 (m, 8H), 3.28 (m$_c$, 1H), 3.37-3.62 (m, 3H), 3.86 (m$_c$, 1H), 4.27 (m$_c$, 1H), 4.42 (m$_c$, 1H), 4.7-4.9 (m, 2H, under D$_2$O), 6.91 (m$_c$, 2H), 6.99 (s, 1H), 7.29 (s, 1H), 7.38 (d, 1H), 7.44 (d, 1H).

Example 44

(8S,11S,14S)-14-Amino-N-[(1S)-4-amino-1-({[(3S)-3-amino-4-hydroxybutyl]amino}carbonyl)butyl]-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

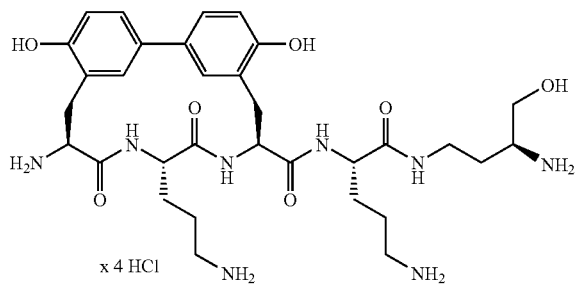

0.27 ml of a 4N solution of hydrogen chloride in dioxane are added to 19 mg (0.018 mmol) of the compound from Example 272A at 0° C. After 3 h at RT, the reaction solution is concentrated in vacuo and coevaporated with dichloromethane several times. The remaining solid is dried to constant weight under high vacuum.

Yield: 14 mg (97% of theory)

MS (ESI): m/z=657 (M−4HCl+H)$^+$.

$^1$H-NMR (400 MHz, D$_2$O): δ=1.55-1.95 (m, 10H), 2.75-3.1 (m, 4H), 3.2-3.4 (m, 4H), 3.5-3.6 (m, 2H), 3.7-3.8 (m, 2H), 3.93 (m$_c$, 1H), 4.21 (m$_c$, 1H), 4.45 (m$_c$, 1H), 4.7-4.9 (m, 2H, under D$_2$O), 6.91 (m$_c$, 2H), 6.98 (s, 1H), 7.28 (s, 1H), 7.38 (d, 1H), 7.44 (d, 1H).

Example 45

(8S,11S,14S)-14-Amino-N-{1-(2-aminoethyl)-3-[(2-aminoethyl)amino]-3-oxopropyl}-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

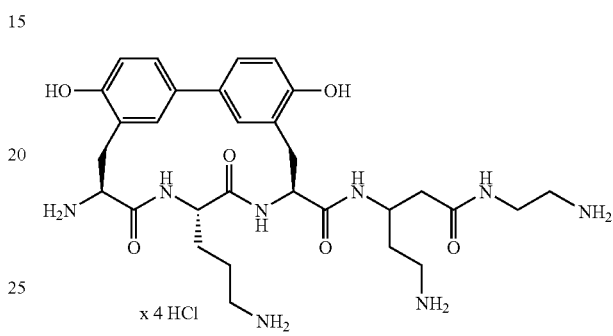

0.41 ml of a 4N solution of hydrogen chloride in dioxane are added to a solution of 28 mg (0.028 mmol) of the compound from Example 273A in 1 ml of dioxane at 0° C. After 3 h at RT, the reaction solution is concentrated in vacuo and coevaporated with dichloromethane several times. The remaining solid is dried to constant weight under high vacuum.

Yield: 12 mg (58% of theory)

MS (ESI): m/z=627 (M−4HCl+H)$^+$.

$^1$H-NMR (400 MHz, D$_2$O): δ=1.5-2.0 (m, 6H), 2.3-2.65 (m, 2H), 2.7-3.2 (m, 8H), 3.3-3.8 (m, 4H), 4.28 (m$_c$, 1H), 4.42 (m$_c$, 1H), 4.7-4.9 (m, 2H, under D$_2$O), 6.90 (m$_c$, 2H), 6.96 (s, 1H), 7.27 (s, 1H), 7.36 (d, 1H), 7.43 (d, 1H).

Example 46

(8S,11S,14S)-14-Amino-11-(3-aminopropyl)-N-(3-{[(2S)-2,5-diaminopentyl]amino}-3-oxopropyl)-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

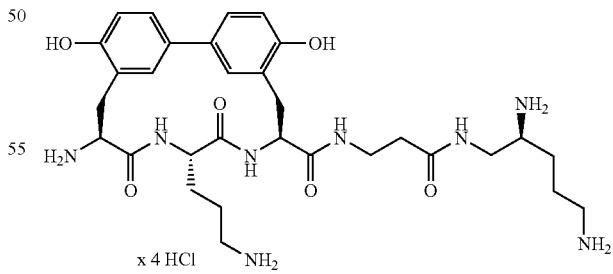

0.30 ml of a 4N solution of hydrogen chloride in dioxane are added to a solution of 20.7 mg (0.020 mmol) of the compound from Example 274A in 1 ml of dioxane at 0° C. After 3 h at RT, the reaction solution is concentrated in vacuo and coevaporated with dichloromethane several times. The remaining solid is dried to constant weight under high vacuum.

Yield: 15 mg (98% of theory)
MS (ESI): m/z=627 (M−4HCl+H)+.
1H-NMR (400 MHz, D2O): δ=1.5-1.9 (m, 8H), 2.35-2.55 (m, 2H), 2.7-3.2 (m, 7H), 3.3-3.7 (m, 6H), 4.42 (m$_c$, 1H), 4.7-4.9 (m, 2H, under D2O), 6.90 (m$_c$, 2H), 6.96 (s, 1H), 7.25 (s, 1H), 7.35 (d, 1H), 7.42 (d, 1H).

Example 47

(8S,11S,14S)-14-Amino-N-(1-(2-aminoethyl)-3-{ [(2S)-2,5-diaminopentyl]amino}-3-oxopropyl)-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide pentahydrochloride

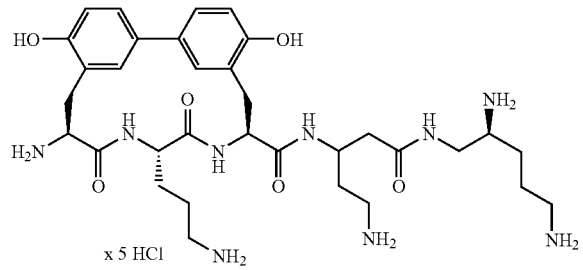

0.355 ml of a 4N solution of hydrogen chloride in dioxane are added to a solution of 27.7 mg (0.024 mmol) of the compound from Example 275A in 1 ml of dioxane at 0° C. After 3 h at RT, the reaction solution is concentrated in vacuo and coevaporated with dichloromethane several times. The remaining solid is dried to constant weight under high vacuum.

Yield: 20 mg (99% of theory)
MS (ESI): m/z=670 (M−5HCl+H)+.
1H-NMR (400 MHz, D2O): δ=1.5-1.9 (m, 10H), 2.3-2.7 (m, 2H), 2.7-3.7 (m, 13H), 4.24 (m$_c$, 1H), 4.42 (m$_c$, 1H), 4.7-4.9 (m, 2H, under D2O), 6.90 (m$_c$, 2H), 6.96 (s, 1H), 7.26 (s, 1H), 7.36 (d, 1H), 7.43 (d, 1H).

Example 48

(8S,11S,14S)-14-Amino-N-[(1S)-4-amino-1-({[(4S)-4-amino-5-hydroxypentyl]amino}carbonyl)butyl]-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

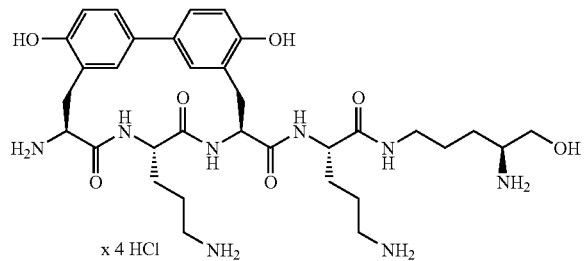

0.11 ml of a 4N solution of hydrogen chloride in dioxane are added to 7.8 mg (0.007 mmol) of the compound from Example 276A at 0° C. After 3 h at RT, the reaction solution is concentrated in vacuo and coevaporated with dichloromethane several times. The remaining solid is dried to constant weight under high vacuum.

Yield: 5.8 mg (99% of theory)
MS (ESI): m/z=671 (M−4HCl+H)+.
1H-NMR (400 MHz, D2O): δ=1.4-1.95 (m, 12H), 2.75-3.4 (m, 10H), 3.5-3.8 (m, 3H), 4.20 (m$_c$, 1H), 4.44 (m$_c$, 1H), 4.7-4.9 (m, 2H, under D2O), 6.91 (m$_c$, 2H), 6.98 (s, 1H), 7.28 (s, 1H), 7.38 (d, 1H), 7.45 (d, 1H).

Example 49

(8S,11S,14S)-14-Amino-N-[(1S)-4-amino-1-({[(S)-2-amino-1-(hydroxymethyl)ethyl]amino}carbonyl)butyl]-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

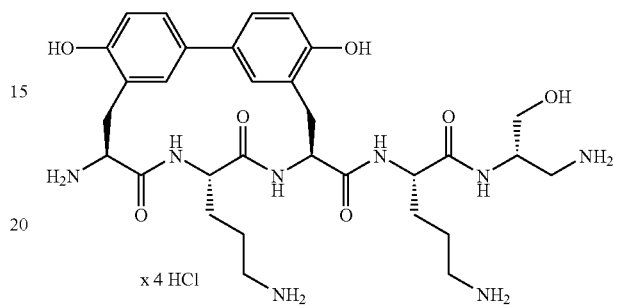

0.56 ml of a 4N solution of hydrogen chloride in dioxane are added to a solution of 39 mg (0.037 mmol) of the compound from Example 277A in 1 ml of dioxane at 0° C. After 3 h at RT, the reaction solution is concentrated in vacuo and coevaporated with dichloromethane several times. The remaining solid is dried to constant weight under high vacuum.

Yield: 25 mg (85% of theory)
MS (ESI): m/z=643 (M−4HCl+H)+.
1H-NMR (400 MHz, D2O): δ=1.5-1.9 (m, 8H), 2.83 (m$_c$, 1H), 2.9-3.1 (m, 6H), 3.15-3.3 (m, 2H), 4.19 (m$_c$, 1H), 4.29 (m$_c$, 1H), 4.43 (m$_c$, 1H), 4.7-4.9 (m, 2H, under D2O), 6.89 (m$_c$, 2H), 6.96 (s, 1H), 7.26 (s, 1H), 7.36 (d, 1H), 7.43 (d, 1H).

Example 50

(8S,11S,14S)-14-Amino-N-[(1S)-4-amino-1-({[(2S)-2,5-diaminopentyl]amino}carbonyl)butyl]-11-[(2R)-3-amino-2-hydroxypropyl]-5,17-dihydroxy-10,13-dioxo-9,12-diazatricyclo[14.3.1.1$^{2,6}$]henicosa-1(20),2(21),3,5,16,18-hexaene-8-carboxamide pentahydrochloride

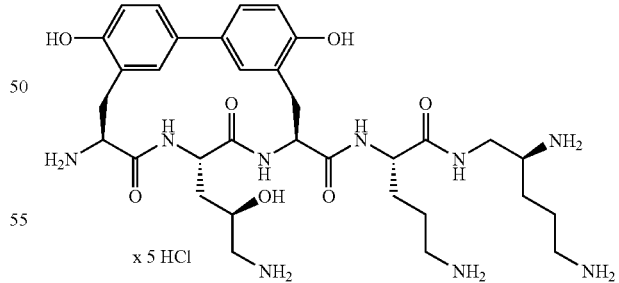

0.30 ml of a 4N solution of hydrogen chloride in dioxane are added to a solution of 24 mg (0.02 mmol) of the compound from Example 278A in 1 ml of dioxane at 0° C. After 3 h at RT, the reaction solution is concentrated in vacuo and coevaporated with dichloromethane several times. The remaining solid is dried to constant weight under high vacuum.

Yield: 17 mg (97% of theory)
MS (ESI): m/z=686 (M−5HCl+H)+.

¹H-NMR (400 MHz, D₂O): δ=1.3-1.9 (m, 10H), 2.5-2.95 (m, 7H), 2.95-3.25 (m, 3H), 3.3-3.5 (m, 2H), 3.62 (m_c, 1H), 4.06 (m_c, 1H), 4.18 (m_c, 1H), 4.7-4.9 (m, 2H, under D₂O), 6.67 (m_c, 2H), 6.75 (s, 1H), 7.05 (s, 1H), 7.14 (d, 1H), 7.21 (d, 1H).

Example 51

(8S,11S,14S)-14-Amino-N-{3-[(2-aminoethyl)amino]-3-oxopropyl}-11-(3-aminopropyl)-5,17-dihydroxy-10,13-dioxo-9,12-diazatricyclo[14.3.1.1²,⁶]henicosa-1(20),2(21),3,5,16,18-hexaene-8-carboxamide trihydrochloride

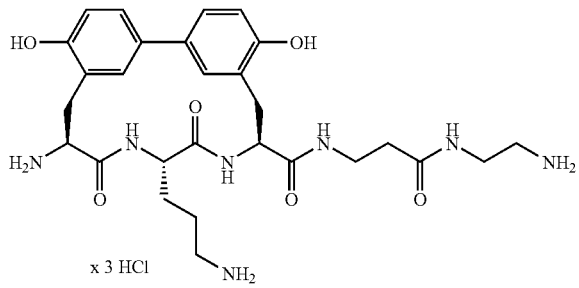

0.36 ml of a 4N solution of hydrogen chloride in dioxane are added to a solution of 21 mg (0.024 mmol) of the compound from Example 279A in 1 ml of dioxane at 0° C. After 3 h at RT, the reaction solution is concentrated in vacuo and coevaporated with dichloromethane several times. The remaining solid is dried to constant weight under high vacuum.

Yield: 16 mg (98% of theory)

LC-MS (Method 23): R_t=1.84 min.

MS (ESI): m/z=570 (M−3HCl+H)⁺.

¹H-NMR (400 MHz, D₂O): δ=1.5-1.9 (m, 4H), 2.3-2.6 (m, 2H), 2.7-3.2 (m, 7H), 3.3-3.7 (m, 5H), 4.42 (m_c, 1H), 4.7-4.9 (m, 2H, under D₂O), 6.89 (m_c, 2H), 6.95 (s, 1H), 7.25 (s, 1H), 7.34 (d, 1H), 7.42 (d, 1H).

Example 52 rel-(8S,11S,14S)-14-Amino-N-((1S)-1-{[(3-amino-2-hydroxypropyl)amino]carbonyl}-4-{[amino(imino)methyl]amino}butyl)-11-(3-aminopropyl)-5,17-dihydroxy-10,13-dioxo-9,12-diazatricyclo[14.3.1.1²,⁶]henicosa-1(20),2(21),3,5,16,18-hexaene-8-carboxamide tetrahydrochloride

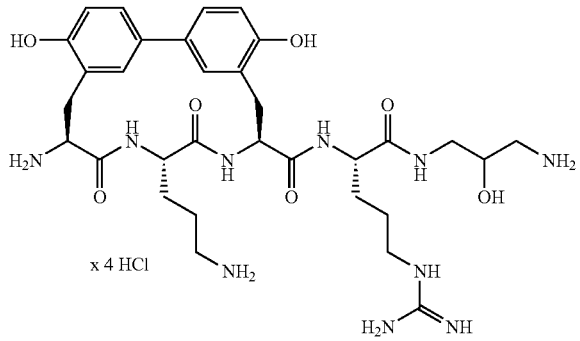

0.52 ml of a 4N solution of hydrogen chloride in dioxane are added to a solution of 41 mg (0.035 mmol) of the compound from Example 280A in 1 ml of dioxane at 0° C. After 3 h at RT, the reaction solution is concentrated in vacuo and coevaporated with dichloromethane several times. The remaining solid is dried to constant weight under high vacuum.

Yield: 28.5 mg (99% of theory)

MS (ESI): m/z=685 (M−4HCl+H)⁺.

¹H-NMR (400 MHz, D₂O): δ=1.5-1.9 (m, 8H), 2.7-3.4 (m, 11H), 3.5-3.7 (m, 1H), 3.97 (m_c, 1H), 4.28 (m_c, 1H), 4.47 (m_c, 1H), 4.7-4.9 (m, 2H, under D₂O), 6.94 (m_c, 2H), 7.01 (s, 1H), 7.31 (s, 1H), 7.40 (d, 1H), 7.48 (d, 1H).

Example 53 rel-(8S,11S,14S)-14-Amino-11-(3-aminopropyl)-5,17-dihydroxy-N-[2-hydroxy-3-(L-ornithylamino)propyl]-10,13-dioxo-9,12-diazatricyclo[14.3.1.1²,⁶]henicosa-1(20),2(21),3,5,16,18-hexaene-8-carboxamide tetrahydrotrifluoroacetate

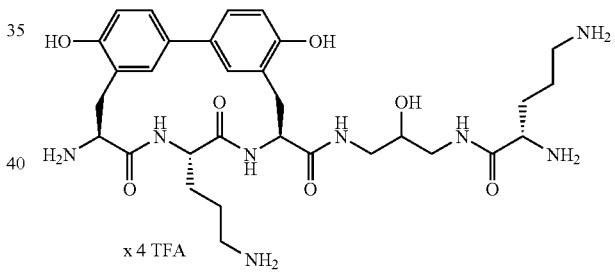

1.52 ml of a 4N solution of hydrogen chloride in dioxane are added to a solution of 98 mg (0.101 mmol) of the compound from Example 281A in 1 ml of dioxane at 0° C. After 3 h at RT, the reaction solution is concentrated in vacuo and coevaporated with dichloromethane several times. The remaining solid is converted by preparative HPLC (Reprosil ODS-A, mobile phase acetonitrile/0.2% aqueous trifluoroacetic acid 5:95→95:5) into the tetra(hydrotrifluoroacetate).

Yield: 24.6 mg (22% of theory)

MS (ESI): m/z=643 (M−4TFA+H)⁺.

¹H-NMR (400 MHz, D₂O): δ=1.55-2.0 (m, 8H), 2.8-3.5 (m, 11H), 3.56 (m_c, 1H), 3.86 (m_c, 1H), 3.97 (m_c, 1H), 4.43 (m_c, 1H), 4.7-4.9 (m, 2H, under D₂O), 6.91 (m_c, 2H), 6.98 (s, 1H), 7.27 (s, 1H), 7.36 (d, 1H), 7.44 (d, 1H).

Example 54

(8S,11S,14S)-14-Amino-N-[(1S)-4-amino-1-({[(1S)-2-amino-1-(hydroxymethyl)ethyl]amino}carbonyl)butyl]-11-[(2R)-3-amino-2-hydroxypropyl]-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

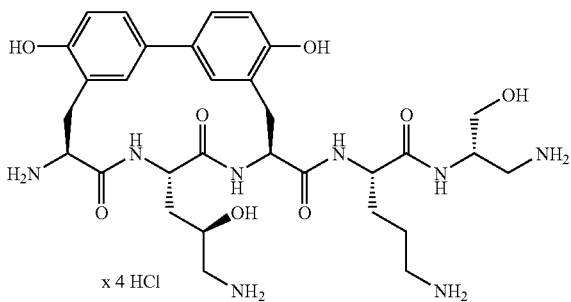

0.31 ml of a 4N solution of hydrogen chloride in dioxane are added to a solution of 22 mg (0.021 mmol) of the compound from Example 282A in 1 ml of dioxane at 0° C. After 3 h at RT, the reaction solution is concentrated in vacuo and coevaporated with dichloromethane several times. The remaining solid is dried to constant weight under high vacuum.

Yield: 16 mg (98% of theory)

MS (ESI): m/z=659 (M−4HCl+H)$^+$.

$^1$H-NMR (400 MHz, D$_2$O): δ=1.6-2.05 (m, 6H), 2.8-3.15 (m, 6H), 3.2-3.35 (m, 2H), 3.5-3.7 (m, 3H), 3.87 (m$_c$, 1H), 4.21 (m$_c$, 1H), 4.31 (m$_c$, 1H), 4.43 (m$_c$, 1H), 4.7-4.9 (m, 2H, under D$_2$O), 6.92 (m$_c$, 2H), 6.99 (s, 1H), 7.29 (s, 1H), 7.38 (d, 1H), 7.45 (d, 1H).

Example 55

(8S,11S,14S)-14-Amino-N-{(2S)-2-amino-3-[(2-aminoethyl)amino]-3-oxopropyl}-11-[(2R)-3-amino-2-hydroxypropyl]-5,17-dihydroxy-9-methyl-10,13-dioxo-9,12-diazatricyclo[14.3.1.1$^{2,6}$]henicosa-1(20),2(21),3,5,16,18-hexaene-8-carboxamide tetrahydrochloride

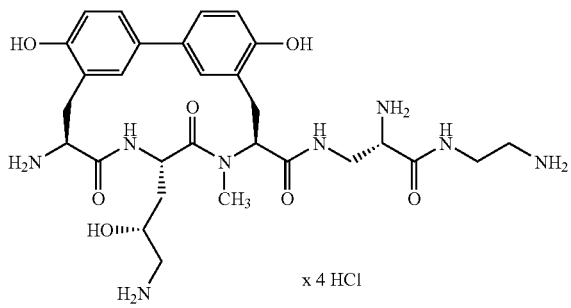

2 ml of a 4N solution of hydrogen chloride in dioxane are added to a solution of 19.4 mg (0.019 mmol) of the compound from Example 292A in 1 ml of dioxane at 0° C. After 3 h at RT, the reaction solution is concentrated in vacuo and coevaporated with dichloromethane several times. The remaining solid is dried to constant weight under high vacuum.

Yield: 12 mg (81% of theory)

LC-MS (Method 23): R$_t$=0.47 min.

MS (ESI): m/z=615 (M−4HCl+H)$^+$.

$^1$H-NMR (400 MHz, D$_2$O): δ=1.92-2.12 (m, 2H), 2.9-3.3 (m, 8H), 3.4-3.9 (m, 7H), 4.0 (m$_c$, 1H), 4.17 (m$_c$, 1H), 4.51 (m$_c$, 1H), 5.15 (m$_c$, 1H), 5.70 (m$_c$, 1H), 6.97 (m$_c$, 2H), 7.03 (s, 1H), 7.10 (s, 1H), 7.49 (d, 1H), 7.56 (d, 1H).

Example 56

(8S,11S,14S)-14-Amino-N-{(2S)-2-amino-3-[(2-aminoethyl)amino]-3-oxopropyl}-11-(3-aminopropyl)-5,17-dihydroxy-10,13-dioxo-9,12-diazatricyclo[14.3.1.1$^{2,6}$]henicosa-1(20),2(21),3,5,16,18-hexaene-8-carboxamide tetrahydrochloride

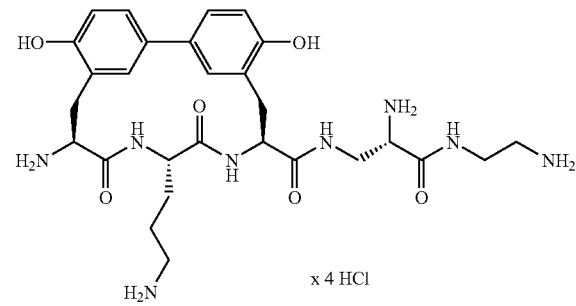

2 ml of a 4N solution of hydrogen chloride in dioxane are added to a solution of 18.2 mg (0.018 mmol) of the compound from Example 293A in 1 ml of dioxane at 0° C. After 3 h at RT, the reaction solution is concentrated in vacuo and coevaporated with dichloromethane several times. The remaining solid is dried to constant weight under high vacuum.

Yield: 13 mg (98% of theory)

LC-MS (Method 23): R$_t$=0.43 min.

MS (ESI): m/z=585 (M−4HCl+H)$^+$.

$^1$H-NMR (400 MHz, D$_2$O): δ=1.5-1.9 (m, 4H), 2.8-3.3 (m, 7H), 3.4-3.9 (m, 5H), 4.12 (m$_c$, 1H), 4.45 (m$_c$, 1H), 4.7-4.9 (m, 2H, under D$_2$O), 6.91 (m$_c$, 2H), 6.98 (s, 1H), 7.25 (s, 1H), 7.37 (d, 1H), 7.44 (d, 1H).

Examples 57 to 69 listed in the following table are prepared in analogy to the method of Example 56.

| Example No. | Precursor example | Structure | Analytical data |
|---|---|---|---|
| 57 | 287A | 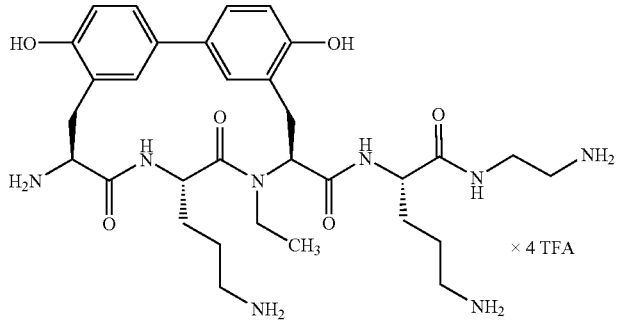 × 4 TFA | LC-MS (Method 23): $R_t$ = 0.90 min. MS (EI): m/z = 640 (M − 4TFA + H)$^+$. |
| 58 | 288A | 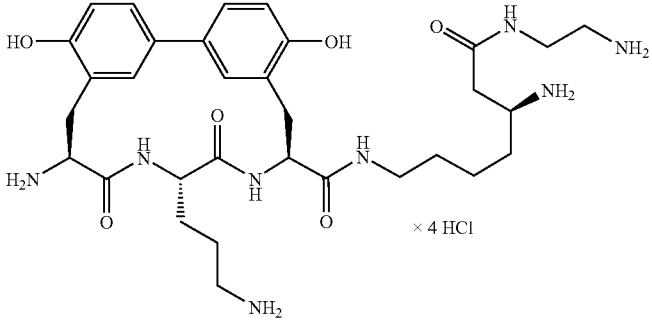 × 4 HCl | LC-MS (Method 17): $R_t$ = 0.33 min. MS (EI): m/z = 641 (M − 4HCl + H)$^+$. |
| 59 | 295A | 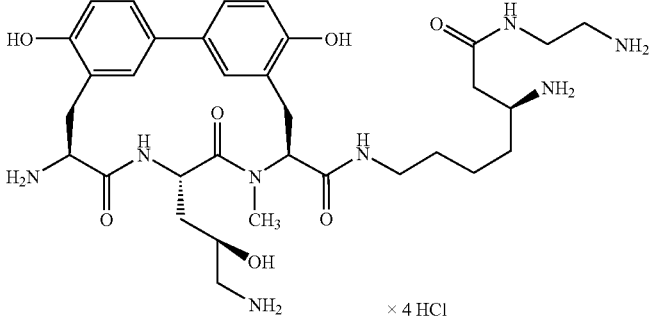 × 4 HCl | LC-MS (Method 23): $R_t$ = 1.86 min. MS (EI): m/z = 671 (M − 4HCl + H)$^+$. |
| 60 | 296A | 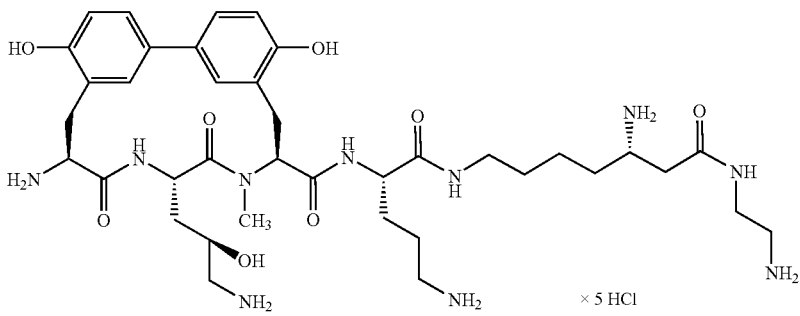 × 5 HCl | LC-MS (Method 23): $R_t$ = 1.74 min. MS (EI): m/z = 785 (M − 5HCl + H)$^+$. |

-continued
| Example No. | Precursor example | Structure | Analytical data |
|---|---|---|---|
| 61 | 294A | 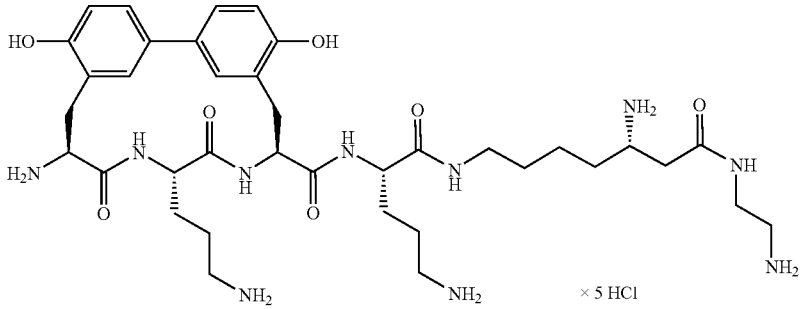 | LC-MS (Method 23): $R_t$ = 0.46 min. MS (EI): m/z = 755 (M − 5HCl + H)$^+$. |
| 62 | 297A | 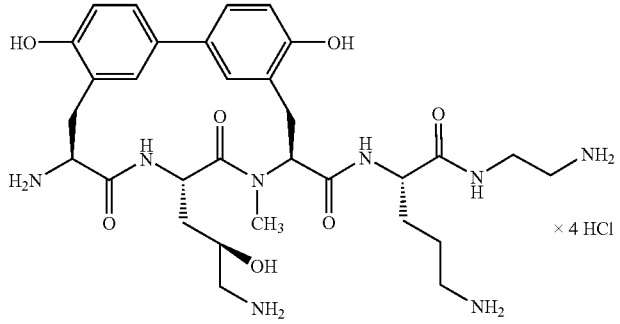 | LC-MS (Method 23): $R_t$ = 1.73 min. MS (EI): m/z = 643 (M − 4HCl + H)$^+$. |
| 63 | 289A | 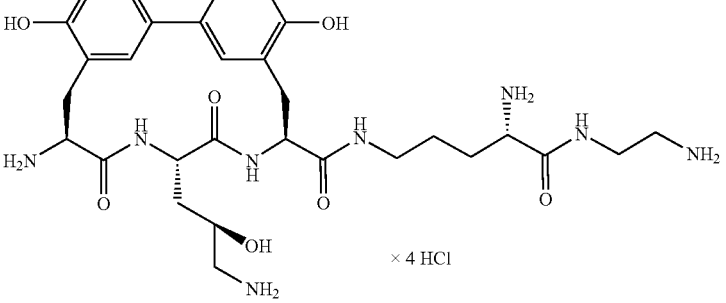 | LC-MS (Method 19): $R_t$ = 0.22 min. MS (EI): m/z = 629 (M − 4HCl + H)$^+$. |
| 64 | 283A | 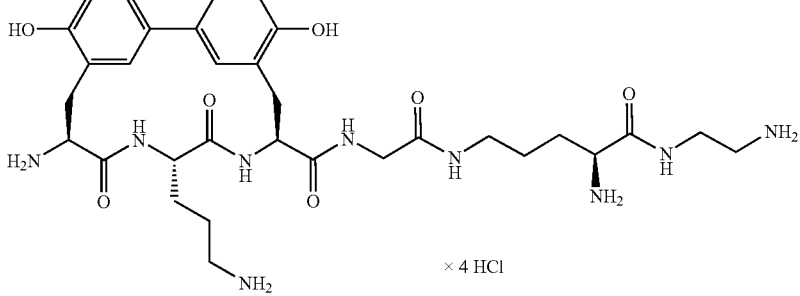 | LC-MS (Method 23): $R_t$ = 0.51 min. MS (EI): m/z = 670 (M − 4HCl + H)$^+$. |

-continued

| Example No. | Precursor example | Structure | Analytical data |
|---|---|---|---|
| 65 | 284A | 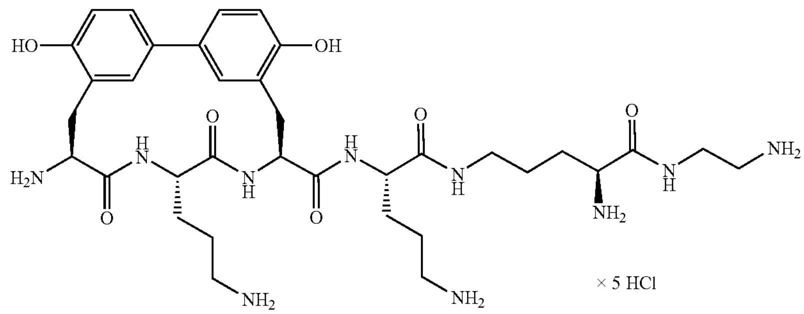 | LC-MS (Method 23): R$_t$ = 0.37 min. MS (EI): m/z = 727 (M − 5HCl + H)$^+$. |
| 66 | 286A | 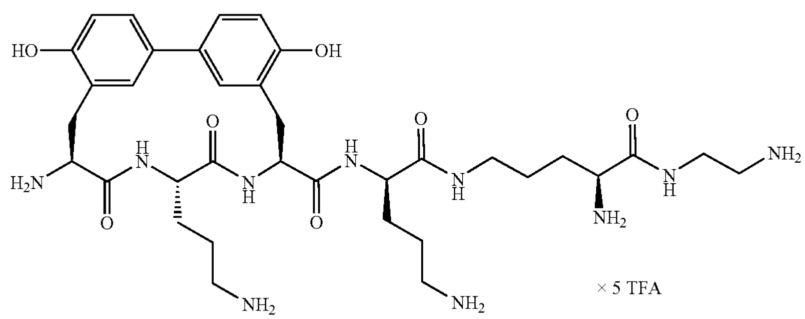 | LC-MS (Method 23): R$_t$ = 0.37 min. MS (EI): m/z = 727 (M − 5TFA + H)$^+$. |
| 67 | 285A | 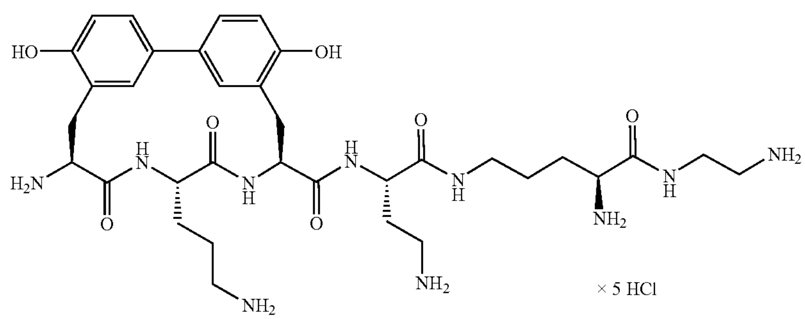 | LC-MS (Method 23): R$_t$ = 0.37 min. MS (EI): m/z = 713 (M − 5HCl + H)$^+$. |
| 68 | 290A | 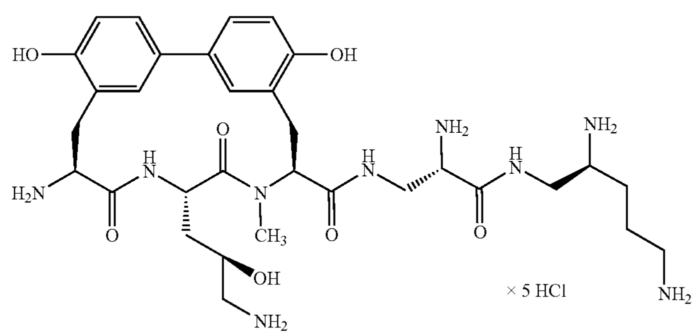 | LC-MS (Method 23): R$_t$ = 0.37 min. MS (EI): m/z = 672 (M − 5HCl + H)$^+$. |

-continued

| Example No. | Precursor example | Structure | Analytical data |
|---|---|---|---|
| 69 | 291A | 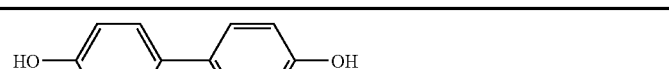 | LC-MS (Method 23): $R_t = 0.35$ min. MS (EI): m/z = 642 $(M - 5HCl + H)^+$. |

B. Assessment of the Physiological Activity

Abbreviations Used:
AMP adenosine monophosphate
ATP adenosine triphosphate
BHI mediumbrain heart infusion medium
CoA coenzyme A
DMSO dimethylsulfoxide
DTT dithiothreitol
EDTA ethylenediaminetetraacetic acid
KCl potassium chloride
$KH_2PO_4$ potassium dihydrogen phosphate
$MgSO_4$ magnesium sulfate
MIC minimum inhibitory concentration
MTP microtiter plate
NaCl sodium chloride
$Na_2HPO_4$ disodium hydrogen phosphate
NHbCl ammonium chloride
NTP nucleotide triphosphate
PBS phosphate-buffered saline
PCR polymerase chain reaction
PEG polyethylene glycol
PEP phosphoenolpyruvate
Tris tris[hydroxymethyl]aminomethane The in vitro effect of the compounds of the invention can be shown in the following assays:

In Vitro Transcription-Translation with *E. coli* Extracts

In order to prepare an S30 extract logarithmically growing *Escherichia coli* MRE 600 (M. Müller; Freiburg University) are harvested, washed and employed as described for the in vitro transcription-translation assay (Müller, M. and Blobel, G., *Proc Natl Acad Sci USA* (1984) 81:7421-7425).

1 µl of cAMP (11.25 mg/ml) are additionally added per 50l of reaction mix to the reaction mix for the in vitro transcription-translation assay. The assay mixture amounts to 105 µl, with 5 µl of the substance to be tested being provided in 5% DMSO. 1 µg/100 µl of mixture of the plasmid pBESTluc (Promega, Germany) are used as transcription templates. After incubation at 30° C. for 60 min, 50l of luciferin solution (20 mM tricine, 2.67 mM $MgSO_4$, 0.1 mM EDTA, 33.3 mM DTT pH 7.8, 270 µM CoA, 470 µM luciferin, 530 µM ATP) are added, and the resulting bioluminescence is measured in a luminometer for 1 minute. The concentration of an inhibitor which leads to a 50% inhibition of the translation of firefly luciferase is given as the $IC_{50}$.

In Vitro Transcription-Translation with *S. aureus* Extracts

Construction of an *S. aureus* Luciferase Reporter Plasmid

For the construction of a reporter plasmid which can be used in an in vitro transcription-translation assay from *S. aureus* the plasmid pBESTluc (Promega Corporation, USA) is used. The *E. coli* tac promoter present in this plasmid in front of the firefly luciferase is replaced by the capA1 promoter with appropriate Shine-Dalgarno sequence from *S. aureus*. The primers CAPFor 5'-CGGCCAAGCTTACTCG-GATCCAG AGTTTGCAAAATATACAGGGGAT-TATATATAATGGAAAACAAGAAAGGAAAATAG GAG-GTTTATATGGAAGACGCCA-3' and CAPRev 5'-GTCATCGTCGGGAAGACCTG-3' are used for this. The primer CAPFor contains the capA1 promoter, the ribosome binding site and the 5' region of the luciferase gene. After PCR using pBESTluc as template it is possible to isolate a PCR product which contains the firefly luciferase gene with the fused capA1 promoter. This is, after restriction with ClaI and HindIII, ligated into the vector pBESTluc which has likewise been digested with ClaI and HindIII. The resulting plasmid p1a is able to replicate in *E. coli* and be used as template in the *S. aureus* in vitro transcription-translation assay.

Preparation of S30 Extracts from *S. aureus*

Six liters of BHI medium are inoculated with a 250 ml overnight culture of an *S. aureus* strain and allowed to grow at 37° C. until the OD600 nm is 2-4. The cells are harvested by centrifugation and washed in 500 ml of cold buffer A (10 mM Tris acetate, pH 8.0, 14 mM magnesium acetate, 1 mM DTT, 1 M KCl). After renewed centrifugation, the cells are washed in 250 ml of cold buffer A with 50 mM KCl, and the resulting pellets are frozen at −20° C. for 60 min. The pellets are thawed on ice in 30 to 60 min and taken up in buffer B (10 mM Tris acetate, pH 8.0, 20 mM magnesium acetate, 1 mM DTT, 50 mM KCl) up to a total volume of 99 ml. 1.5 ml portions of lysostaphin (0.8 mg/ml) in buffer B are introduced into 3 precooled centrifuge cups and each is mixed with 33 ml of the cell suspension. The samples are incubated at 37° C., shaking occasionally, for 45 to 60 min, before 150 µl of a 0.5 M DTT solution are added. The lysed cells are centrifuged at 30 000×g and 4° C. for 30 min. The cell pellet is taken up in buffer B and then centrifuged again under the same conditions, and the collected supernatants are combined. The supernatants are centrifuged again under the same conditions, and 0.25 volumes of buffer C (670 mM Tris acetate, pH 8.0, 20 mM magnesium acetate, 7 mM $Na_3$ phosphoenolpyruvate, 7 mM DTT, 5.5 mM ATP, 70 µM amino acids (complete from Promega), 75 µg of pyruvate kinase (Sigma, Germany))/ml are added to the upper ⅔ of the supernatant. The samples are incubated at 37° C. for 30 min. The supernatants are dialysed against 2l of dialysis buffer (10 mM Tris acetate, pH 8.0, 14 mM magnesium acetate, 1 mM DTT, 60 mM potassium acetate) in a dialysis tube with a 3500 Da cut-off with one buffer change at 4° C. overnight. The dialysate is concentrated to a protein concentration of about 10 mg/ml by covering the dialysis tube with cold PEG 8000 powder (Sigma, Germany) at 4° C. The S30 extracts can be stored in aliquots at −70° C.

Determination of the $IC_{50}$ in the *S. aureus* In Vitro Transcription-Translation Assay Inhibition of protein biosynthesis of the compounds can be shown in an in vitro transcription-translation assay. The assay is based on the cell-free transcription and translation of firefly luciferase using the reporter plasmid p1a as template and cell-free S30 extracts obtained from *S. aureus*. The activity of the resulting luciferase can be detected by luminescence measurement.

The amount of S30 extract or plasmid p1a respectively to be employed must be tested anew for each preparation in order to ensure an optimal concentration in the assay. 3 µl of the substance to be tested, dissolved in 5% DMSO, are introduced into an MTP. Then 10 µl of a suitably concentrated plasmid solution p1a are added. Then 46 µl of a mixture of 23 µl of premix (500 mM potassium acetate, 87.5 mM Tris acetate, pH 8.0, 67.5 mM ammonium acetate, 5 mM DTT, 50 µg of folic acid/ml, 87.5 mg of PEG 8000/ml, 5 mM ATP, 1.25 mM each NTP, 20 µM each amino acid, 50 mM PEP ($Na_3$ salt), 2.5 mM cAMP, 250 µg each *E. coli* tRNA/ml) and 23 µl of a suitable amount of *S. aureus* S30 extract are added and mixed. After incubation at 30° C. for 60 min, 50 µl of luciferin solution (20 mM tricine, 2.67 mM $MgSO_4$, 0.1 mM EDTA, 33.3 mM DTT pH 7.8, 270 µM CoA, 470 µM luciferin, 530 µM ATP) are added, and the resulting bioluminescence is measured in a luminometer for 1 min. The concentration of an inhibitor which leads to a 50% inhibition of the translation of firefly luciferase is given as the $IC_{50}$.

Determination of the Minimum Inhibitory Concentration (MIC)

The minimum inhibitory concentration (MIC) is the minimum concentration of an antibiotic with which the growth of a test microbe is inhibited over 18-24 h. The inhibitor concentration can in these cases be determined by standard microbiological methods (see, for example, The National Committee for Clinical Laboratory Standards. Methods for dilution antimicrobial susceptibility tests for bacteria that grow aerobically; approved standard-fifth edition. NCCLS document M7-A5 [ISBN 1-56238-394-9]. NCCLS, 940 West Valley Road, Suite 1400, Wayne, Pa. 19087-1898 USA, 2000). The MIC of the compounds of the invention is determined in the liquid dilution test on the 96-well microtitre plate scale. The bacterial microbes are cultivated in a minimal medium (18.5 mM $Na_2HPO_4$, 5.7 mM $KH_2PO_4$, 9.3 mM $NH_4Cl$, 2.8 mM $MgSO_4$, 17.1 mM NaCl, 0.033 µg/ml thiamine hydrochloride, 1.2 µg/ml nicotinic acid, 0.003 µg/ml biotin, 1% glucose, 25 µg/ml of each proteinogenic amino acid with the exception of phenylalanine; [H.-P. Kroll; unpublished]) with the addition of 0.4% BH broth (test medium). In the case of *Enterococcus facium* L4001, heat-inactivated fetal calf serum (FCS; GibcoBRL, Germany) is added to the test medium in a final concentration of 10%. Overnight cultures of the test microbes are diluted to an $OD_{578}$ of 0.001 (to 0.01 in the case of enterococci) in fresh test medium, and incubated 1:1 with dilutions of the test substances (1:2 dilution steps) in test medium (200 µl final volume). The cultures are incubated at 37° C. for 18-24 hours; enterococci in the presence of 5% $CO_2$.

The lowest substance concentration in each case at which no visible bacterial growth occurred any more is defined as the MIC.

Alternative Method for Determining the Minimum Inhibitory Concentration (MIC)

The minimum inhibitory concentration (MIC) is the minimum concentration of an antibiotic with which the growth of a test microbe is inhibited over 18-24 h. The inhibitor concentration can in these cases be determined by standard microbiological methods with modified medium in an agar dilution test (see, for example, The National Committee for Clinical Laboratory Standards. Methods for dilution antimicrobial susceptibility tests for bacteria that grow aerobically; approved standard-fifth edition. NCCLS document M7-A5 [ISBN 1-56238-394-9]. NCCLS, 940 West Valley Road, Suite 1400, Wayne, Pa. 19087-1898 USA, 2000). The bacterial microbes are cultivated on 1.5% agar plates which contain 20% defibrinated horse blood. The test microbes, which are incubated overnight on Columbia blood agar plates (Becton-Dickinson), are diluted in PBS, adjusted to a microbe count of about 5×10 microbe/ml and placed dropwise (1-3 µl) on test plates. The test substances comprise different dilutions of the test substances (1:2 dilution steps). The cultures are incubated at 37° C. in the presence of 5% $CO_2$ for 18-24 hours.

The lowest substance concentration in each case at which no visible bacterial growth occurred any more is defined as the MIC and is reported in µg/ml.

TABLE 1

(with comparative example 20A (biphenomycin B))

| Ex. No. | MIC S. aureus 133 | MIC S. aureus T17 | MIC E. faecium L4001 | $IC_{50}$ S. aureus 133 translation |
|---|---|---|---|---|
| 6 | 1 | 2 | 8 | 0.1 |
| 10 | 0.5 | 0.5 | 8 | 0.07 |
| 13 | 0.5 | 0.5 | 16 | 0.06 |
| 14 | 1 | 2 | 4 | 0.07 |
| 16 | 2 | 2 | >32 | 0.1 |
| 23 | 0.5 | 1 | 4 | 0.32 |
| 20A | <0.03 | >32 | 0.5 | 1.5 |

Concentration data: MIC in µg/ml; $IC_{50}$ in µM.

Systemic Infection with *S. aureus* 133

The suitability of the compounds of the invention for the treatment of bacterial infections can be shown in various animal models. For this purpose, the animals are generally infected with a suitable virulent microbe and then treated with the compound to be tested, which is in a formulation which is adapted to the particular therapy model. The suitability of the compounds of the invention can be demonstrated specifically for the treatment of bacterial infections in a mouse sepsis model after infection with *S. aureus*.

For this purpose, *S. aureus* 133 cells are cultured overnight in BH broth (Oxoid, Germany). The overnight culture was diluted 1:100 in fresh BH broth and expanded for 3 hours. The bacteria which are in the logarithmic phase of growth are centrifuged and washed twice with buffered physiological saline solution. A cell suspension in saline solution with an extinction of 50 units is then adjusted in a photometer (Dr Lange LP 2W). After a dilution step (1:15), this suspension is mixed 1:1 with a 10% mucine suspension. 0.2 ml of this infection solution is administered i.p. per 20 g of mouse. This corresponds to a cell count of about 1-2×10⁶ microbes/ mouse. The i.v. therapy takes place 30 minutes after the infection. Female CFW1 mice are used for the infection test. The survival of the animals is recorded over 6 days. The animal model is adjusted so that untreated animals die within 24 h after the infection. It was possible to demonstrate in this model a therapeutic effect of $ED_{100}$=1.25 mg/kg for the compound of Example 2.

Determination of the Rates of Spontaneous Resistance to S. aureus

The spontaneous resistance rates for the compounds of the invention are determined as follows: the bacterial microbes are cultivated in 30 ml of a minimal medium (18.5 mM $Na_2HPO_4$, 5.7 mM $KH_2PO_4$, 9.3 mM $NH_4Cl$, 2.8 mM $MgSO_4$, 17.1 mM NaCl, 0.033 µg/ml thiamine hydrochloride, 1.2 µg/ml nicotinic acid, 0.003 µg/ml biotin, 1% glucose, 25 µg/ml of each proteinogenic amino acid with the addition of 0.4% BH broth) at 37° C. overnight, centrifuged at 6000×g for 10 min and resuspended in 2 ml of phosphate-buffered physiological NaCl solution (about $2 \times 10^9$ microbes/ml). 100 µl of this cell suspension, and 1:10 and 1:100 dilutions, are plated out on predried agar plates (1.5% agar, 20% defibrinated horse blood, or 1.5% agar, 20% bovine serum in 1/10 Müller-Hinton medium diluted with PBS) which contain the compound of the invention to be tested in a concentration equivalent to 5×MIC or 10×MIC respectively, and incubated at 37° C. for 48 h. The resulting colonies (cfu) are counted.

Isolation of the Biphenomycin-Resistant S. aureus Strains $RN4220Bi^R$ and T17

The S. aureus strain $RN4220Bi^R$ is isolated in vitro. For this purpose, 100 µl portions of an S. aureus RN4220 cell suspension (about $1.2 \times 10^8$ cfu/ml) are plated out on an antibiotics-free agar plate (18.5 mM $Na_2HPO_4$, 5.7 mM $KH_2PO_4$, 9.3 mM $NH_4Cl$, 2.8 mM $MgSO_4$, 17.1 mM NaCl, 0.033 µg/ml thiamine hydrochloride, 1.2 µg/ml nicotinic acid, 0.003 µg/ml biotin, 1% glucose, 25 µg/ml of each proteinogenic amino acid with the addition of 0.4% BH broth and 1% agarose) and on an agar plate containing 2 µg/ml biphenomycin B (10× MIC), and incubated at 37° C. overnight. Whereas about $1 \times 10^9$ cells grow on the antibiotics-free plate, about 100 colonies grow on the antibiotics-containing plate, corresponding to a resistance rate of $1 \times 10^{-5}$. Some of the colonies grown on the antibiotics-containing plate are tested for the biphenomycin B MIC. One colony with an MIC of >50 µM is selected for further use, and the strain is referred to as $RN4220Bi^R$.

The S. aureus strain T17 is isolated in vivo. CFW1 mice are infected intraperitoneally with $4 \times 10^7$ S. aureus 133 cells per mouse. 0.5 h after the infection, the animals are treated intravenously with 50 mg/kg biphenomycin B. The kidneys are removed from the surviving animals on day 3 after the infection. After homogenization of the organs, the homogenates are plated out as described for $RN4220Bi^R$ on antibiotics-free and antibiotics-containing agar plates and incubated at 37° C. overnight. About half the colonies isolated from the kidney show growth on the antibiotics-containing plates ($2.2 \times 10^6$ colonies), demonstrating the accumulation of biphenomycin B-resistant S. aureus cells in the kidney of the treated animals. About 20 of these colonies are tested for the biphenomycin B MIC, and a colony with an MIC of >50 µM is selected for further cultivation, and the strain is referred to as T17.

C. Exemplary Embodiments of Pharmaceutical Compositions

The compounds of the invention can be converted into pharmaceutical preparations in the following way:

Solution which can be Administered Intravenously:
Composition:

1 mg of the compound of Example 1, 15 g of polyethylene glycol 400 and 250 g of water for injections.

Preparation:

The compound of the invention is dissolved together with polyethylene glycol 400 in the water with stirring. The solution is sterilized by filtration (pore diameter 0.22 µm) and dispensed under aseptic conditions into heat-sterilized infusion bottles. These are closed with infusion stoppers and crimped caps.

What is claimed is:
1. A compound of formula

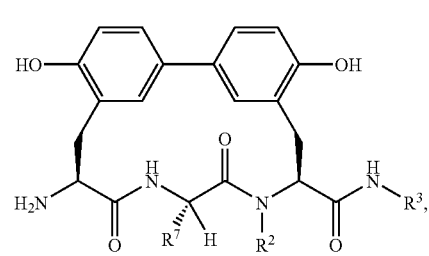

(I)

in which
$R^7$ represents a group of formula

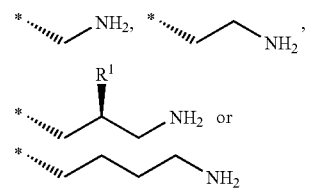

whereby
$R^1$ is hydrogen or hydroxy,
* is the linkage site to the carbon atom,
$R^2$ represents hydrogen, methyl or ethyl,
$R^3$ represents a group of formula

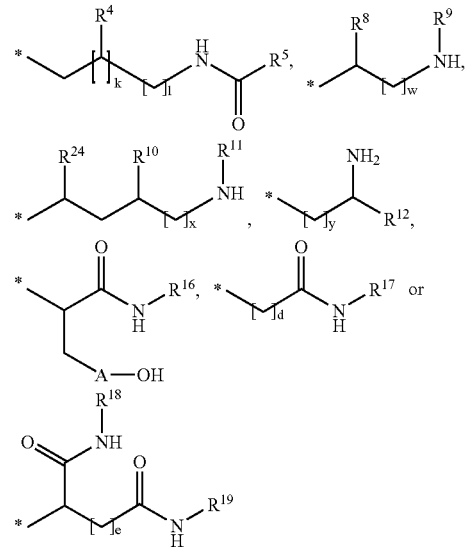

whereby
* is the linkage site to the nitrogen atom,
A represents a bond or phenyl,
R$^4$ represents hydrogen, amino or hydroxy,
R$^5$ represents a group of formula

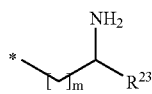

wherein
* is the linkage site to the carbon atom,
R$^{23}$ represents hydrogen or a group of formula *—(CH$_2$)$_n$—OH or *—(CH$_2$)$_o$—NH$_2$,
wherein
* is the linkage site to the carbon atom,
n and o independently of one another are a number 1, 2, 3 or 4,
m is a number 0 or 1,
R$^8$ and R$^{12}$ independently of one another represent a group of formula *—CONHR$^{14}$ or *—CH$_2$CONHR$^{15}$,
wherein
* is the linkage site to the carbon atom,
R$^{14}$ and R$^{15}$ independently of one another represent a group of formula

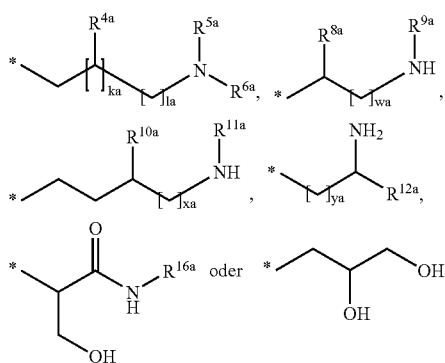

wherein
* is the linkage site to the nitrogen atom,
R$^{4a}$ represents hydrogen, amino or hydroxy,
R$^{5a}$ represents hydrogen, methyl or aminoethyl,
R$^{6a}$ represents hydrogen or aminoethyl, or
R$^{5a}$ and R$^{6a}$ together with the nitrogen atom to which they are bonded form a piperazine ring,
R$^{8a}$ and R$^{12a}$ independently of one another represent
*—(CH$_2$)$_{Z1a}$—OH, *—(CH$_2$)$_{Z2a}$—NHR$^{13a}$,
*—CONHR$^{14a}$ or *—CH$_2$CONHR$^{15a}$,
wherein
* is the linkage site to the carbon atom,
Z1a and Z2a independently of one another are a number 1, 2 or 3,
R$^{13a}$ represents hydrogen or methyl, and
R$^{14a}$ or R$^{15a}$ independently of one another represent a group of formula

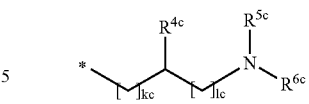

in which
* is the linkage site to the nitrogen atom,
R$^{4c}$ represents hydrogen, amino or hydroxy,
R$^{5c}$ represents hydrogen, methyl or aminoethyl,
R$^{6c}$ represents hydrogen or aminoethyl,
kc is a number 0 or 1, and
lc is a number 1, 2, 3 or 4,
R$^{9a}$ and R$^{11a}$ independently of one another represent hydrogen or methyl,
R$^{10a}$ represents amino or hydroxy,
R$^{16a}$ represents a group of formula

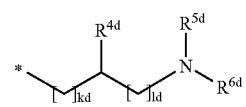

wherein
* is the linkage site to the nitrogen atom,
R$^{4d}$ represents hydrogen, amino or hydroxy,
R$^{5d}$ represents hydrogen, methyl or aminoethyl,
R$^{6d}$ represents hydrogen or aminoethyl,
kd is a number 0 or 1, and
ld is a number 1, 2, 3 or 4,
ka is a number 0 or 1, and
la, wa, xa and ya independently of one another are a number 1, 2, 3 or 4,
R$^9$ and R$^{11}$ independently of one another represent hydrogen, methyl, *—C(NH$_2$)=NH or a group of formula

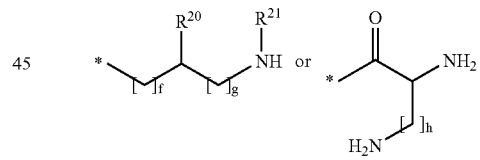

wherein
* is the linkage site to the nitrogen atom,
R$^{20}$ represents hydrogen or *—(CH$_2$)$_i$—NHR$^{22}$,
wherein
R$^{22}$ represents hydrogen or methyl, and
i is a number 1, 2 or 3,
R$^{21}$ represents hydrogen or methyl,
f is a number 0, 1, 2 or 3,
g is a number 1, 2 or 3, and
h is a number 1, 2, 3 or 4, or
R$^8$ represents *—(CH$_2$)$_{Z1}$—OH,
wherein
* is the linkage site to the carbon atom,
Z1 is a number 1, 2 or 3, and
R$^9$ represents a group of formula

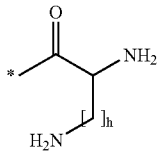

wherein
* is the linkage site to the nitrogen atom, and
h is a number 1, 2, 3 or 4,
$R^{10}$ represents amino or hydroxy,
$R^{16}$ and $R^{17}$ independently of one another represent a group of formula

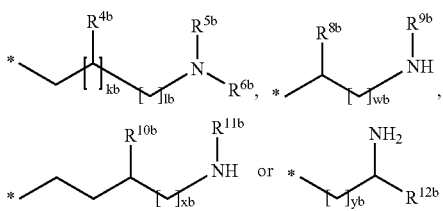

wherein
* is the linkage site to the nitrogen atom,
$R^{4b}$ represents hydrogen, amino or hydroxy,
$R^{5b}$ represents hydrogen, methyl or aminoethyl,
$R^{6b}$ represents hydrogen or aminoethyl, or
$R^{5b}$ and $R^{6b}$ together with the nitrogen atom to which they are bonded form a piperazine ring,
$R^{8b}$ and $R^{12b}$ independently of one another represent
*—$(CH_2)_{Z1b}$—OH, *—$(CH_2)_{Z2b}$—$NHR^{13b}$,
*—$CONHR^{14b}$ or *—$CH_2CONHR^{15b}$,
wherein
* is the linkage site to the carbon atom,
$R^{13b}$ represents hydrogen or methyl, and
Z1b and Z2b independently of one another are a number 1, 2 or 3, and
$R^{14b}$ and $R^{15b}$ independently of one another represent a group of formula

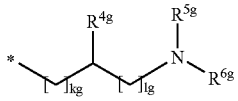

wherein
* is the linkage site to the nitrogen atom,
$R^{4g}$ represents hydrogen, amino or hydroxy,
$R^{5g}$ represents hydrogen, methyl or aminoethyl,
$R^{6g}$ represents hydrogen or aminoethyl,
kg is a number 0 or 1, and
lg is a number 1, 2, 3 or 4,
$R^{9b}$ and $R^{11b}$ independently of one another represent hydrogen or methyl,
$R^{10b}$ represents amino or hydroxy,
kb is a number 0 or 1,
lb, wb, xb and yb independently of one another are a number 1, 2, 3 or 4,
$R^{18}$ and $R^{19}$ independently of one another represent hydrogen or a group of formula

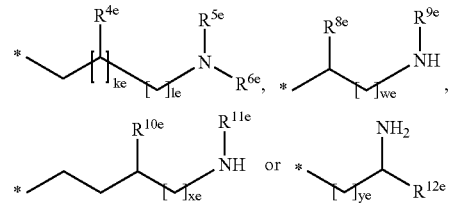

wherein
* is the linkage site to the nitrogen atom,
$R^{4e}$ represents hydrogen, amino or hydroxy,
$R^{5e}$ represents hydrogen, methyl or aminoethyl,
$R^{6e}$ represents hydrogen or aminoethyl, or
$R^{5e}$ and $R^{6e}$ together with the nitrogen atom to which they are bonded form a piperazine ring,
$R^{8e}$ and $R^{12e}$ independently of one another represent
*—$(CH_2)_{Z1e}$—OH or *—$(CH_2)_{Z2e}$—$NHR^{13e}$,
wherein
* is the linkage site to the carbon atom,
$R^{13e}$ represents hydrogen or methyl, and
Z1e and Z2e independently of one another are a number 1, 2 or 3,
$R^{9e}$ and $R^{11e}$ independently of one another represent hydrogen or methyl,
$R^{10e}$ represents amino or hydroxy,
ke is a number 0 or 1, and
le, we, xe and ye independently of one another are a number 1, 2, 3 or 4,
whereby $R^{18}$ and $R^{19}$ are not simultaneously hydrogen,
$R^{24}$ represents a group of formula *—$CONHR^{25}$,
wherein
* is the linkage site to the carbon atom,
$R^{25}$ represents a group of formula

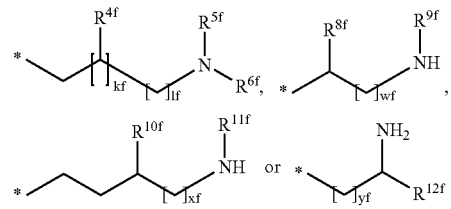

wherein
* is the point of linkage to the nitrogen atom,
$R^{4f}$ represents hydrogen, amino or hydroxy,
$R^{5f}$ represents hydrogen, methyl or aminoethyl,
$R^{6f}$ represents hydrogen or aminoethyl, or
$R^{5f}$ and $R^{6f}$ together with the nitrogen atom to which they are bonded form a piperazine ring,
$R^{8f}$ and $R^{12f}$ independently of one another represent
*—$(CH_2)_{Z1f}$—OH or *—$(CH_2)_{Z2f}$—$NHR^{13f}$,
wherein
* is the linkage site to the carbon atom,
$R^{13f}$ represents hydrogen or methyl, and
Z1f and Z2f independently of one another are a number 1, 2 or 3,
$R^{9f}$ and $R^{11f}$ independently of one another represent hydrogen or methyl,
$R^{10f}$ represents amino or hydroxy,
kf is a number 0 or 1, and lf, wf, xf and yf independently of one another are a number 1, 2, 3 or 4,
d and e independently of one another are a number 1, 2 or 3,
k is a number 0 or 1,
l, w, x and y independently of one another are a number 1, 2, 3 or 4,

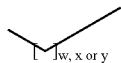

independently of one another may when w, x or y equals 3 carry a hydroxy group,
or one of its salts.

2. The compound of claim 1, corresponding to formula

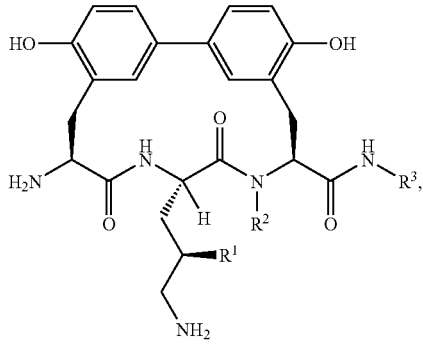

(Ia)

in which
$R^1$ represents hydrogen or hydroxy,
$R^2$ represents hydrogen, methyl or ethyl,
$R^3$ is as defined in claim 1,
or one of its salts.

3. The compound of claim 1, whereby
$R^3$ represents a group of formula

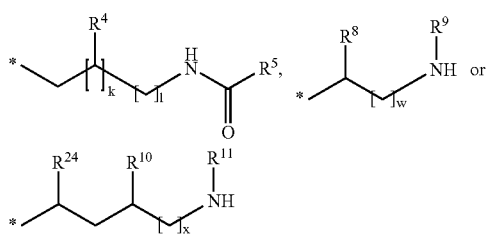

whereby
* is the linkage site to the nitrogen atom,
$R^4$ represents hydrogen, amino or hydroxy,
$R^5$ represents a group of formula

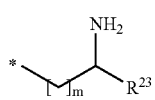

wherein
* is the linkage site to the carbon atom, $R^{23}$ represents hydrogen or a group of formula *—$(CH_2)_n$—OH or *—$(CH_2)_o$—$NH_2$,
wherein
* is the linkage site to the carbon atom,
n and o independently of one another are a number 1, 2, 3 or 4,
m is a number 0 or 1,
$R^8$ represents a group of formula *—$CONHR^{14}$ or *—$CH_2CONHR^{15}$,
wherein
* is the linkage site to the carbon atom,
$R^{14}$ and $R^{15}$ independently of one another represent a group of formula

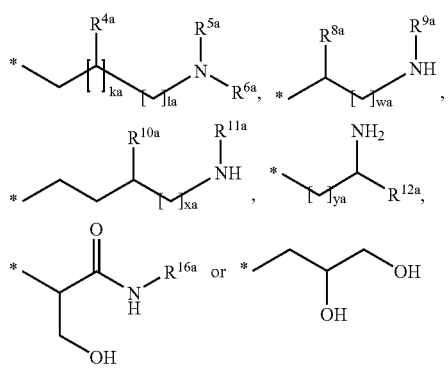

wherein
* is the linkage site to the nitrogen atom,
$R^{4a}$ represents hydrogen, amino or hydroxy,
$R^{5a}$ represents hydrogen, methyl or aminoethyl,
$R^{6a}$ represents hydrogen or aminoethyl, or
$R^{5a}$ and $R^{6a}$ together with the nitrogen atom to which they are bonded form a piperazine ring,
$R^{8a}$ and $R^{12a}$ independently of one another represent *—$(CH_2)_{Z1a_{44a}}$—OH, *—$(CH_2)_{Z2a}$—$NHR^{13a}$, *—$CONHR^{14a}$ or *—$CH_2CONHR^{15a}$,
wherein
* is the linkage site to the carbon atom,
Z1a and Z2a independently of one another are a number 1, 2 or 3,
$R^{13a}$ represents hydrogen or methyl, and
$R^{14a}$ and $R^{15a}$ independently of one another represent a group of formula

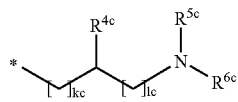

wherein
* is the linkage site to the nitrogen atom,
$R^{4c}$ represents hydrogen, amino or hydroxy,
$R^{5c}$ represents hydrogen, methyl or aminoethyl,
$R^{6c}$ represents hydrogen or aminoethyl,
kc is a number 0 or 1, and
lc is a number 1, 2, 3 or 4,
$R^{9a}$ and $R^{11a}$ independently of one another represent hydrogen or methyl,
$R^{10a}$ represents amino or hydroxy,
$R^{16a}$ represents a group of formula

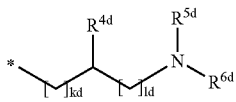

wherein
* is the linkage site to the nitrogen atom,
$R^{4d}$ represents hydrogen, amino or hydroxy,
$R^{5d}$ represents hydrogen, methyl or aminoethyl,
$R^{6d}$ represents hydrogen or aminoethyl,
kd is a number 0 or 1, and
ld is a number 1, 2, 3 or 4,
ka is a number 0 or 1, and
la, wa, xa and ya independently of one another are a number 1, 2, 3 or 4,
$R^9$ and $R^{11}$ independently or one another represent hydrogen, methyl, *—C(NH$_2$)=NH or a group of formula

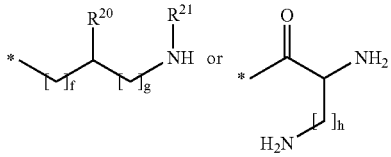

wherein
* is the linkage site to the nitrogen atom,
$R^{20}$ represents hydrogen or *—(CH$_2$)$_i$—NHR$^{22}$,
wherein
$R^{22}$ represents hydrogen or methyl, and
i is a number 1, 2 or 3,
$R^{21}$ represents hydrogen or methyl,
f is a number 0, 1, 2 or 3,
g is a number 1, 2 or 3, and
h is a number 1, 2, 3 or 4, or
$R^8$ represents *—(CH$_2$)$_{Z1}$—OH
wherein
* is the linkage site to the carbon atom,
Z1 is a number 1, 2 or 3, and
$R^9$ represents a group of formula

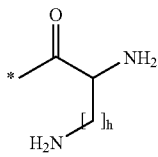

wherein
* is the linkage site to the nitrogen atom, and
h is a number 1, 2, 3 or 4,
$R^{10}$ represents amino or hydroxy,
$R^{24}$ represents a group of formula *—CONHR$^{25}$,
wherein
* is the linkage site to the carbon atom,
$R^{25}$ is a group of formula

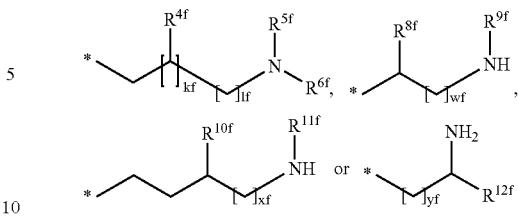

wherein
* is the linkage site to the nitrogen atom,
$R^{4f}$ represents hydrogen, amino or hydroxy,
$R^{5f}$ represents hydrogen, methyl or aminoethyl,
$R^{6f}$ represents hydrogen or aminoethyl, or
$R^{5f}$ and $R^{6f}$ together with the nitrogen atom to which they are bonded form a piperazine ring,
$R^{8f}$ and $R^{12f}$ independently of one another represent *—(CH$_2$)$_{Z1f}$—OH or *—(CH$_2$)$_{Z2f}$—NHR$^{13f}$,
wherein
* is the linkage site to the carbon atom,
$R^{13f}$ represents hydrogen or methyl, and
Z1f and Z2f independently of one another are a number 1, 2 or 3,
$R^{9f}$ and $R^{11f}$ independently of one another represent hydrogen or methyl,
$R^{10f}$ represents amino or hydroxy,
kf is a number 0 or 1, and
lf, wf, xf and yf independently of one another are a number 1, 2, 3 or 4,
k is a number 0 or 1,
lf, w and x independently of one another are a number 1, 2, 3 or 4,

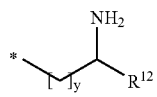

independently of one another may when w or x equals 3 carry a hydroxy group,
or one of its salts.
4. The compound of claim 1, whereby
$R^3$ represents a group of formula

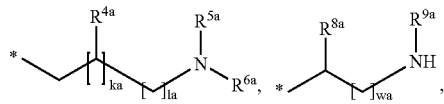

whereby
* is the linkage site to the nitrogen atom,
$R^{12}$ represents a group of formula *—CONHR$^{14}$ or *—CH$_2$CONHR$^{15}$,
wherein
* is the linkage site to the carbon atom,
$R^{14}$ and $R^{15}$ independently of one another represent a group of formula -continued

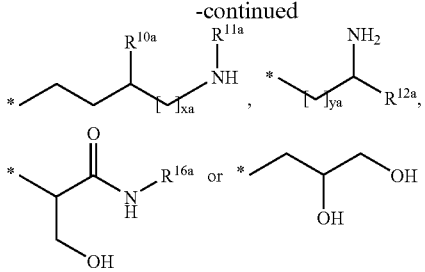

wherein
* is the linkage site to the nitrogen atom,
$R^{4a}$ represents hydrogen, amino or hydroxy,
$R^{5a}$ represents hydrogen, methyl or aminoethyl,
$R^{6a}$ represents hydrogen or aminoethyl, or
$R^{5a}$ and $R^{6a}$ together with the nitrogen atom to which they are bonded form a piperazine ring,
$R^{8a}$ and $R^{12a}$ independently of one another represent
*—$(CH_2)_{Z1a}$—OH, *—$(CH_2)_{Z2a}$—$NHR^{13a}$,
*—$CONHR^{14a}$ or *—$CH_2CONHR^{15a}$,
wherein
* is the linkage site to the carbon atom,
Z1a and Z2a independently of one another are a number 1, 2 or 3,
$R^{13a}$ represents hydrogen or methyl, and
$R^{14a}$ and $R^{15a}$ independently of one another represent a group of formula

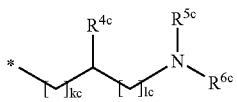

wherein
* is the linkage site to the nitrogen atom,
$R^{4c}$ represents hydrogen, amino or hydroxy,
$R^{5c}$ represents hydrogen, methyl or aminoethyl,
$R^{6c}$ represents hydrogen or aminoethyl,
kc is a number 0 or 1, and
lc is a number 1, 2, 3 or 4,
$R^{9a}$ and $R^{11a}$ independently of one another represent hydrogen or methyl,
$R^{10a}$ represents amino or hydroxy,
$R^{16a}$ represents a group of formula

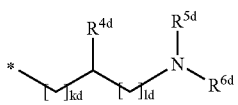

wherein
* is the linkage site to the nitrogen atom,
$R^{4d}$ represents hydrogen, amino or hydroxy,
$R^{5d}$ represents hydrogen, methyl or aminoethyl,
$R^{6d}$ represents hydrogen or aminoethyl,
kd is a number 0 or 1, and
ld is a number 1, 2, 3 or 4,
ka is a number 0 or 1, and
la, wa, xa and ya independently of one another are a number 1, 2, 3 or 4,
y is a number 1, 2, 3 or 4,

may when y equals 3 carry a hydroxy group,
or one of its salts.

5. The compound of claim 1, whereby
$R^3$ represents a group of formula

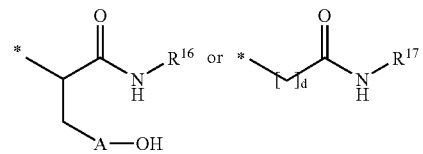

whereby
* is the linkage site to the nitrogen atom,
A represents a bond or phenyl,
$R^{16}$ and $R^{17}$ independently of one another represent a group of formula

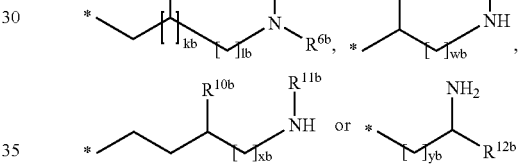

wherein
* is the linkage site to the nitrogen atom,
$R^{4b}$ represents hydrogen, amino or hydroxy,
$R^{5b}$ represents hydrogen, methyl or aminoethyl,
$R^{6b}$ represents hydrogen or aminoethyl, or
$R^{5b}$ and $R^{6b}$ together with the nitrogen atom to which they are bonded form a piperazine ring,
$R^{8b}$ and $R^{12b}$ independently of one another represent
*—$(CH_2)_{Z1b}$—OH or *—$(CH_2)_{Z2b}$—$NHR^{13b}$,
wherein
* is the linkage site to the carbon atom,
$R^{13b}$ represents hydrogen or methyl, and
Z1b and Z2b independently of one another are a number 1, 2 or 3,
$R^{9b}$ and $R^{11b}$ independently of one another represent hydrogen or methyl,
$R^{10b}$ represents amino or hydroxy,
kb is a number 0 or 1,
lb, wb, xb and yb independently of one another are a number 1, 2, 3 or 4,
d is a number 1, 2 or 3,
or one of its salts.

6. The compound of claim 1, whereby
$R^3$ represents a group of formula

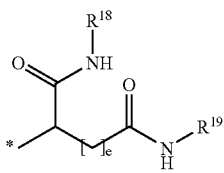

whereby
* is the linkage site to the nitrogen atom,
$R^{18}$ and $R^{19}$ independently of one another represent hydrogen or a group of formula

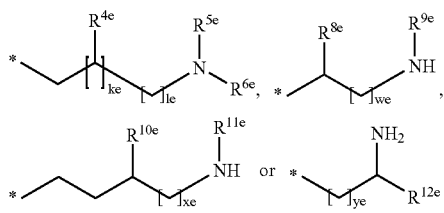

wherein
* is the linkage site to the nitrogen atom,
$R^{4e}$ represents hydrogen, amino or hydroxy,
$R^{5e}$ represents hydrogen, methyl or aminoethyl,
$R^{6e}$ represents hydrogen or aminoethyl, or
$R^{5e}$ and $R^{6e}$ together with the nitrogen atom to which they are bonded form a piperazine ring,
$R^{8e}$ and $R^{12e}$ independently of one another represent *—$(CH_2)_{Z1e}$—OH or *—$(CH_2)_{Z2e}$—$NHR^{13e}$,
wherein
* is the linkage site to the carbon atom,
$R^{13e}$ represents hydrogen or methyl, and
Z1e and Z2e independently of one another are a number 1, 2 or 3,
$R^{9e}$ and $R^{11e}$ independently of one another represent hydrogen or methyl,
$R^{10e}$ represents amino or hydroxy,
ke is a number 0 or 1, and
le, we, xe and ye independently of one another are a number 1, 2, 3 or 4,
whereby $R^{18}$ and $R^{19}$ are not simultaneously hydrogen,
e is a number 1, 2 or 3,
or one of its salts.

7. A process for preparing a compound of formula (I) of claim 1 or one of its salts, whereby
[A] a compound of formula

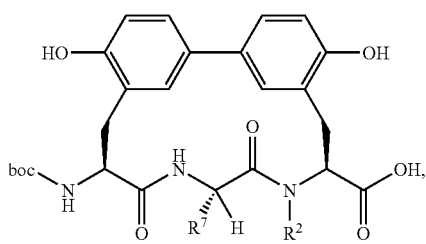

wherein $R^2$ and $R^7$ have the meaning indicated in claim 1, and boc represents tert-butoxycarbonyl, is reacted in a two-stage process firstly in the presence of one or more dehydrating reagents with a compound of formula $$H_2NR^3 \qquad (III),$$

wherein $R^3$ has the meaning indicated in claim 1, and subsequently with an acid and/or by hydrogenolysis, or

[B] a compound of formula

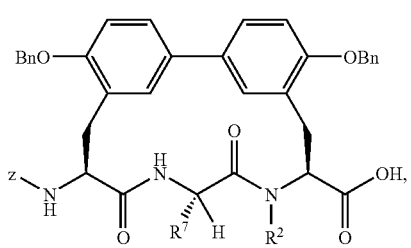

wherein $R^2$ and $R^7$ have the meaning indicated in claim 1, and Z represents benzyloxycarbonyl, is reacted in a two-stage process firstly in the presence of one or more dehydrating reagents with a compound of formula $$H_2NR^3 \qquad (III),$$

wherein $R^3$ has the meaning indicated in claim 1, and subsequently with an acid or by hydrogenolysis.

8. A process for preparing a compound of formula (I) of claim 1, whereby a salt of the compound is converted into the compound by chromatography with the addition of a base.

9. A method for the manufacture of a medicament comprising mixing a compound of formula (I) as claimed in claim 1 and at least one pharmaceutically acceptable excipient.

10. A medicament comprising at least one compound of claim 1 in combination with at least one inert, non-toxic, pharmaceutically acceptable excipient.

11. A method for treating bacterial infections with gram-positive bacteria in humans and animals by administration of an antibacterially effective amount of at least one compound of claim 1.

12. A method for treating bacterial infections with gram-positive bacteria in humans and animals by administration of a medicament of claim 10.

* * * * *